United States Patent
Han et al.

(10) Patent No.: US 10,882,867 B2
(45) Date of Patent: Jan. 5, 2021

(54) FORMS AND COMPOSITIONS OF A MK2 INHIBITOR

(71) Applicant: Celgene CAR LLC, Pembroke (BM)

(72) Inventors: Jianxin Han, Green Brook, NJ (US); Lianfeng Huang, Basking Ridge, NJ (US); Uday Jain, Plainsboro, NJ (US); Ying Li, Millburn, NJ (US); John Malona, Brookline, MA (US); Kevin Molter, Summit, NJ (US); Chittari Pabba, Slingerlands, NY (US); Alexander L. Ruchelman, Cream Ridge, NJ (US); Jean Xu, Warren, NJ (US); Daozhong Zou, Raritan, NJ (US)

(73) Assignee: Celgene CAR LLC, Pembroke (BM)

( * ) Notice: Subject to any disclaimer, the term of this patent is extended or adjusted under 35 U.S.C. 154(b) by 0 days.

(21) Appl. No.: 16/494,725

(22) PCT Filed: Mar. 15, 2018

(86) PCT No.: PCT/US2018/022543
§ 371 (c)(1),
(2) Date: Sep. 16, 2019

(87) PCT Pub. No.: WO2018/170199
PCT Pub. Date: Sep. 20, 2018

(65) Prior Publication Data
US 2020/0148701 A1    May 14, 2020

Related U.S. Application Data

(60) Provisional application No. 62/472,015, filed on Mar. 16, 2017.

(51) Int. Cl.
| *A61K 31/4353* | (2006.01) |
| *A61K 31/551* | (2006.01) |
| *C07D 495/14* | (2006.01) |
| *C07D 513/14* | (2006.01) |
| *A61K 38/00* | (2006.01) |

(52) U.S. Cl.
CPC .......... *C07D 495/14* (2013.01); *A61K 38/005* (2013.01)

(58) Field of Classification Search
CPC ................ C07D 495/14; C07D 513/14; A61K 31/4353; A61K 31/551
See application file for complete search history.

(56) References Cited

U.S. PATENT DOCUMENTS

| 7,838,674 | B2 | 11/2010 | Schlapbach et al. |
| 9,458,175 | B2 | 10/2016 | Alexander et al. |
| 9,790,235 | B2 | 10/2017 | Alexander et al. |
| 10,138,256 | B2 | 11/2018 | Alexander et al. |
| 10,253,040 | B1 | 4/2019 | Alexander et al. |
| 10,577,380 | B2 | 3/2020 | Alexander et al. |
| 2012/0022030 | A1 | 1/2012 | Schlapbach et al. |
| 2013/0137708 | A1 | 5/2013 | Garske et al. |
| 2014/0018343 | A1 | 1/2014 | Romero et al. |
| 2016/0200782 | A1 | 7/2016 | Lander et al. |
| 2019/0375762 | A1 | 12/2019 | Alexander et al. |
| 2020/0102325 | A1 | 4/2020 | Guo et al. |
| 2020/0102326 | A1 | 4/2020 | Feigelson et al. |
| 2020/0102327 | A1 | 4/2020 | Malona et al. |

FOREIGN PATENT DOCUMENTS

| WO | WO-2004/058762 A1 | 7/2004 |
| WO | WO-2005/105814 A1 | 11/2005 |
| WO | WO-2009/010488 A1 | 1/2009 |
| WO | WO-2014/149164 A1 | 9/2014 |
| WO | WO-2016/032882 A1 | 3/2016 |
| WO | WO-2016/044463 A2 | 3/2016 |
| WO | WO-2018/170199 A1 | 9/2018 |
| WO | WO-2018/170200 A1 | 9/2018 |
| WO | WO-2018/170201 A1 | 9/2018 |
| WO | WO-2018/170203 A1 | 9/2018 |
| WO | WO-2018/170204 A1 | 9/2018 |

OTHER PUBLICATIONS

International Search Report for PCT/US2015/050495, 2 pages (dated Dec. 11, 2015).
International Search Report for PCT/US2018/022543, 3 pages (dated May 7, 2018).

*Primary Examiner* — Bruck Kifle
(74) *Attorney, Agent, or Firm* — Choate, Hall and Stewart LLP; Kristen C. Buteau; Nicholas J. Pace

(57) ABSTRACT

The present invention provides solid forms of an MK2 inhibitor, compositions thereof, and methods of using the same.

23 Claims, 91 Drawing Sheets

| | Target | Change In Mass (%) - ref | | |
|---|---|---|---|---|
| | % P/Po | Sorption | Desorption | Hysteresis |
| Cycle 1 | 0.0 | -0.001 | -0.189 | |
| | 10.0 | 0.102 | -0.065 | -0.168 |
| | 20.0 | 0.180 | 0.052 | -0.127 |
| | 30.0 | 0.245 | 0.178 | -0.067 |
| | 40.0 | 0.329 | 0.295 | -0.034 |
| | 50.0 | 0.408 | 0.450 | 0.042 |
| | 60.0 | 0.448 | 0.688 | 0.240 |
| | 70.0 | 0.564 | 1.026 | 0.461 |
| | 80.0 | 0.916 | 1.396 | 0.480 |
| | 90.0 | 2.338 | 2.338 | |

|  | Target % P/Po | Change In Mass (%) - ref | | |
|---|---|---|---|---|
|  |  | Sorption | Desorption | Hysteresis |
| Cycle 1 | 0.0 | 0.000 | -0.217 |  |
|  | 10.0 | 0.162 | 0.125 | -0.037 |
|  | 20.0 | 0.790 | 0.884 | 0.095 |
|  | 30.0 | 1.067 | 1.185 | 0.117 |
|  | 40.0 | 1.431 | 1.547 | 0.116 |
|  | 50.0 | 1.862 | 2.086 | 0.224 |
|  | 60.0 | 2.324 | 2.717 | 0.393 |
|  | 70.0 | 2.840 | 3.271 | 0.431 |
|  | 80.0 | 3.441 | 3.680 | 0.238 |
|  | 90.0 | 4.081 | 4.081 |  |

| Conversion | Representative Conditions |
|---|---|
| B → A | slurry in acetone; long period of storage at ambient |
| C → A | slurry in acetone |
| C → E | slurry in THF/water (5:95); compression; DVS humidity cycle |
| D → A | slurry in acetone |
| D → E | slurry in THF/water (5:95) |
| E → A | slurry in acetone; slurry in THF/water (5:95) |
| H → A | slurry in THF/water (5:95) |
| H → I | slurry in water for 4 days |
| I → A | slurry in acetone |

FORMS AND COMPOSITIONS OF A MK2 INHIBITOR

CROSS-REFERENCE TO RELATED APPLICATIONS

The present application claims priority to U.S. Provisional Patent Application No. 62/472,015, filed on Mar. 16, 2017, the entirety of which is hereby incorporated by reference.

FIELD OF THE INVENTION

The present invention provides solid forms of a compound useful as inhibitors of MK2 kinases. The invention also provides pharmaceutically acceptable compositions comprising solid forms of the present invention and methods of using said compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

Mitogen-activated protein kinase-activated protein kinase 2 (MAPKAP K2 or MK2) mediates multiple p38 MAPK-dependent cellular responses. MK2 is an important intracellular regulator of the production of cytokines, such as tumor necrosis factor alpha (TNF-α), interleukin 6 (IL-6) and interferon gamma (IFNγ), that are involved in many acute and chronic inflammatory diseases, e.g. rheumatoid arthritis and inflammatory bowel disease. MK2 resides in the nucleus of non-stimulated cells and upon stimulation, it translocates to the cytoplasm and phosphorylates and activates tuberin and HSP27. MK2 is also implicated in heart failure, brain ischemic injury, the regulation of stress resistance and the production of TNF-α. (see Deak et al., *EMBO.* 17:4426-4441 (1998); Shi et al., *Biol. Chem.* 383:1519-1536 (2002); Staklatvala, *Curr. Opin. Pharmacol.* 4:372-377 (2004), and Shiroto et al., *J. Mol. Cardiol.* 38:93-97 (2005)).

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there remains a need to find protein kinase inhibitors useful as therapeutic agents.

SUMMARY OF THE INVENTION

It has now been found that novel solid forms of the present invention, and compositions thereof, are useful as inhibitors of one or more protein kinases and exhibit desirable characteristics for the same. In general, salt forms, freebase forms, and/or complex forms, and pharmaceutically acceptable compositions thereof, are useful for treating or lessening the severity of a variety of diseases or disorders as described in detail herein.

DETAILED DESCRIPTION OF THE INVENTION

Figure 1:
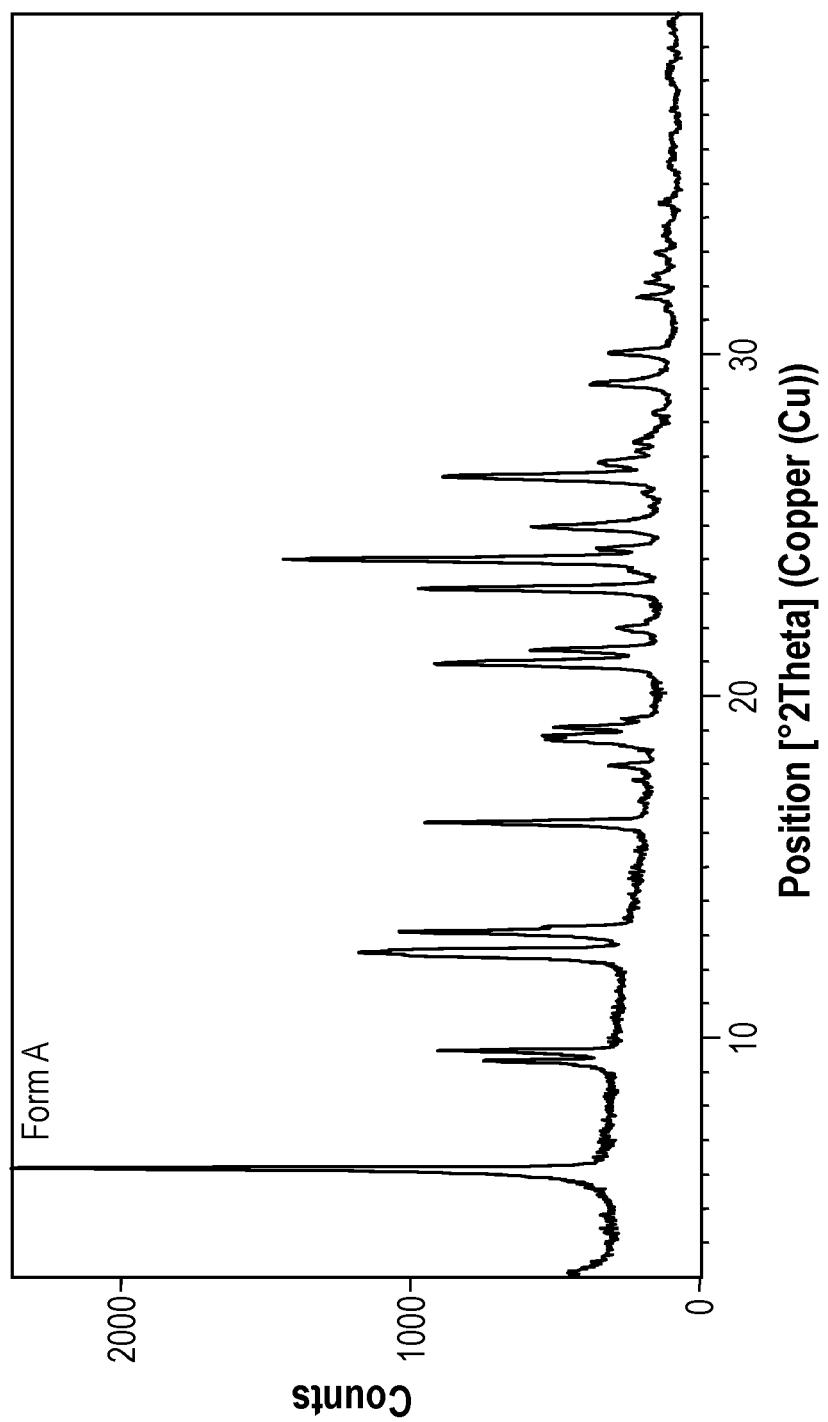
FIG. 1 depicts an XRPD pattern of Form A of Compound 1.

General Description of Certain Aspects of the Invention

PCT patent application PCT/US2015/050495, filed Sep. 16, 2015 and published as WO 2016/044463 on Mar. 24, 2016 ("the '463 application," the entirety of which is hereby incorporated herein by reference), describes certain compounds which covalently and/or irreversibly inhibit the activity MK2. Such compounds include Compound 1:

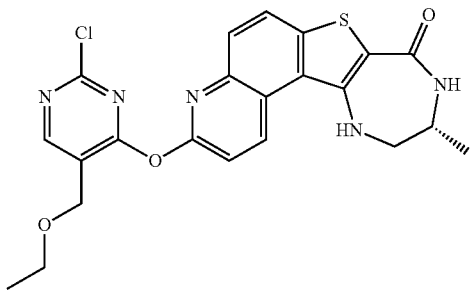

Compound 1 ((R)-3-((2-chloro-5-(ethoxymethyl)pyrimidin-4-yl)oxy)-10-methyl-9,10,11,12-tetrahydro-8H-[1,4]diazepino[5',6':4,5]thieno[3,2-f]quinolin-8-one) is designated as compound I-82 in the '463 application and the synthesis of Compound 1 is described in detail at Example 82 therein.

Compound 1 is active in a variety of assays and therapeutic models demonstrating covalent, irreversible inhibition of MK2 kinase (in enzymatic and cellular assays). Notably, Compound 1 was found to inhibit MK2 in Thp-1 human acute monocytic leukemia cells. Accordingly, Compound 1 is useful for treating one or more disorders associated with activity of, or mediated by, MK2 kinase.

A crystalline form of Compound 1, as compared to amorphous Compound 1, imparts or may impart characteristics such as improved aqueous solubility, stability and ease of formulation. Accordingly, the present invention provides several crystalline forms of Compound 1.

According to one embodiment, the present invention provides Compound 1 in an amorphous form, a crystalline form, or a mixture thereof. Exemplary crystalline forms of Compound 1 are described in more detail below.

In other embodiments, the present invention provides Compound 1 substantially free of impurities. As used herein, the term "substantially free of impurities" means that the compound contains no significant amount of extraneous matter. Such extraneous matter may include starting materials, residual solvents, or any other impurities that may result from the preparation of, and/or isolation of, Compound 1. In certain embodiments, at least about 90% by weight of Compound 1 is present. In certain embodiments, at least about 95% by weight of Compound 1 is present. In still other embodiments of the invention, at least about 99% by weight of Compound 1 is present.

According to one embodiment, Compound 1 is present in an amount of at least about 95, 97, 97.5, 98.0, 98.5, 99, 99.5, 99.8 weight percent where the percentages are based on the total weight of the composition. According to another embodiment, Compound 1 contains no more than about 5.0 area percent HPLC of total organic impurities and, in certain embodiments, no more than about 3.0 area percent HPLC of total organic impurities and, in certain embodiments, no more than about 1.5 area percent HPLC total organic impurities relative to the total area of the HPLC chromatogram. In other embodiments, Compound 1 contains no more than about 1.0 area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for Compound 1 is also meant to include all tautomeric forms of Compound 1. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

Crystalline Forms of Compound 1:

It has been found that Compound 1 can exist in a variety of crystalline forms. The crystalline forms can be solvates, hydrates and unsolvated forms of Compound 1. All such forms are contemplated by the present invention. In certain embodiments, the present invention provides Compound 1 as a mixture of one or more crystalline forms.

As used herein, the term "polymorph" refers to the different crystal structures (of solvated or unsolvated forms) in which a compound can crystallize.

As used herein, the term "solvate" refers to a solid form with either a stoichiometric or non-stoichiometric amount of solvent (e.g., a channel solvate). For polymorphs, the solvent is incorporated into the crystal structure. Similarly, the term "hydrate" refers to a solid form with either a stoichiometric or non-stoichiometric amount of water. For polymorphs, the water is incorporated into the crystal structure.

As used herein, the term "about", when used in reference to a degree 2-theta value refers to the stated value±0.3 degree 2-theta. In certain embodiments, "about" refers to ±0.2 degree 2-theta or ±0.1 degree 2-theta.

In certain embodiments, Compound 1 is a crystalline solid. In other embodiments, Compound 1 is a crystalline solid substantially free of amorphous Compound 1. As used herein, the term "substantially free of amorphous Compound 1" means that the compound contains no significant amount of amorphous Compound 1. In certain embodiments, at least about 90% by weight of crystalline Compound 1 is present, or at least about 95% by weight of crystalline Compound 1 is present. In still other embodiments of the invention, at least about 97%, 98% or 99% by weight of crystalline compound 1 is present.

In certain embodiments, Compound 1 is a neat or unsolvated crystal form and thus does not have any water or solvent incorporated into the crystal structure. It has been found that Compound 1 can exist in at least three distinct neat (i.e., anhydrous) crystal forms, or polymorphs. In some embodiments, the present invention provides an anhydrous polymorphic (i.e., crystalline) form of Compound 1 referred to herein as Form A. In other embodiments, the present invention provides an anhydrous polymorphic (i.e., crystalline) form of Compound 1 referred to herein as Form B. In other embodiments, the present invention provides an anhydrous polymorphic (i.e., crystalline) form of Compound 1 referred to herein as Form D.

It has been found that Compound 1 can exist in at least two distinct hydrate crystal forms, or polymorphs. In some embodiments, the present invention provides a hydrate polymorphic (i.e., crystalline) form of Compound 1 referred to herein as Form C. In other embodiments, the present invention provides a hydrate polymorphic (i.e., crystalline) form of Compound 1 referred to herein as Form E.

Compound 1 can also exist in at least four distinct solvate crystal forms, or polymorphs. In some embodiments, the present invention provides a solvate polymorphic (i.e., crystalline) form of Compound 1 referred to herein as Form F. In some embodiments, the present invention provides a solvate polymorphic (i.e., crystalline) form of Compound 1 referred to herein as Form G. In some embodiments, the present invention provides a solvate polymorphic (i.e., crystalline) form of Compound 1 referred to herein as Form H. In some embodiments, the present invention provides a solvate polymorphic (i.e., crystalline) form of Compound 1 referred to herein as Form I. In some embodiments, the present invention provides a mixture of various polymorphic (i.e., crystalline) forms of Compound 1. For example, in some embodiments, the present invention provides a mixture of Form A of Compound 1 and one or more forms selected from Form B, Form C, Form D, Form E, Form F, Form G, Form H and Form I.

In certain embodiments, the present invention provides Form A of Compound 1. According to one embodiment, Form A of Compound 1 is characterized by one or more peaks in its powder X-ray diffraction pattern selected from those at about 6.19, about 9.33, about 9.64, about 12.39, about 12.49, about 12.59, about 13.11, about 13.25, about 16.31, about 18.70, about 18.84, about 19.09, about 20.92, about 21.35, about 23.17, about 24.02, about 24.94, about 26.44, about 29.14, and about 30.04 degrees 2-theta.

In some embodiments, Form A of Compound 1 is characterized by a powder X-ray diffraction pattern having peaks at about 9.33, about 9.64, and about 16.31 degrees 2-theta. In some embodiments, Form A of Compound 1 is characterized by a powder X-ray diffraction pattern having peaks at about 6.19, about 9.33, about 9.64, and about 16.31 degrees 2-theta. In some embodiments, Form A of Compound 1 is characterized by a powder X-ray diffraction pattern having peaks at about 6.19, about 9.33, about 9.64, about 16.31, and about 24.02 degrees 2-theta. In an exemplary embodiment, Form A of Compound 1 is characterized by substantially all of the peaks in its X-ray powder diffraction pattern at about

| Position [°2θ] | d-spacing [Å] | Relative Intensity [%] |
|---|---|---|
| 6.19 | 14.2764 | 100.0 |
| 9.33 | 9.4795 | 22.7 |
| 9.64 | 9.1797 | 30.0 |
| 12.39 | 7.1437 | 36.9 |
| 12.49 | 7.0879 | 44.9 |
| 12.59 | 7.0322 | 37.8 |
| 13.11 | 6.7559 | 39.2 |
| 13.25 | 6.6815 | 14.3 |
| 16.31 | 5.4343 | 37.3 |
| 18.70 | 4.7453 | 17.0 |
| 18.84 | 4.7095 | 18.7 |
| 19.09 | 4.6482 | 16.6 |
| 20.92 | 4.2456 | 35.3 |
| 21.35 | 4.1618 | 21.3 |
| 23.17 | 3.8397 | 38.8 |
| 24.02 | 3.7054 | 58.8 |
| 24.94 | 3.5701 | 20.2 |
| 26.44 | 3.3708 | 36.6 |
| 29.14 | 3.0646 | 12.8 |
| 30.04 | 2.9745 | 10.2 |

In certain embodiments, the present invention provides Form B of Compound 1. According to one embodiment, Form B of Compound 1 is characterized by one or more peaks in its powder X-ray diffraction pattern selected from those at about 6.19, about 7.04, about 9.30, about 9.58, about 9.64, about 12.54, about 18.69, about 19.33, about 21.34, about 27.52, and about 29.18 degrees 2-theta.

In some embodiments, Form B of Compound 1 is characterized by a powder X-ray diffraction pattern having peaks at about 7.04, about 12.54, and about 21.34 degrees 2-theta. In some embodiments, Form B of Compound 1 is characterized by a powder X-ray diffraction pattern having peaks at about 6.19, about 7.04, about 12.54, and about 21.34 degrees 2-theta. In an exemplary embodiment, Form B of Compound 1 is characterized by substantially all of the peaks in its X-ray powder diffraction pattern at about

| Position [°2θ] | d-spacing [Å] | Relative Intensity [%] |
|---|---|---|
| 6.19 | 14.2879 | 21.7 |
| 7.04 | 12.5629 | 100.0 |
| 9.30 | 9.5103 | 19.7 |
| 9.58 | 9.2284 | 25.9 |
| 9.64 | 9.1760 | 27.6 |
| 12.54 | 7.0607 | 57.5 |
| 18.69 | 4.7487 | 12.0 |
| 19.33 | 4.5922 | 6.4 |
| 21.34 | 4.1645 | 18.1 |
| 27.52 | 3.2415 | 8.5 |
| 29.18 | 3.0601 | 4.9 |

In certain embodiments, the present invention provides Form C of Compound 1. According to one embodiment, Form C of Compound 1 is characterized by one or more peaks in its powder X-ray diffraction pattern selected from those at about 7.03, about 13.54, about 13.91, about 14.13, about 21.25, about 21.51, about 24.73, and 25.77 degrees 2-theta.

In some embodiments, Form C of Compound 1 is characterized by a powder X-ray diffraction pattern having peaks at about 7.03, about 13.54, about 13.91, and about 14.13 degrees 2-theta. In some embodiments, Form C of Compound 1 is characterized by one or more peaks in its powder X-ray diffraction pattern selected from those at about 7.03, about 13.54, about 13.91, about 14.13, and about 25.77 degrees 2-theta. In an exemplary embodiment, Form C of Compound 1 is characterized by substantially all of the peaks in its X-ray powder diffraction pattern at about

| Position [°2θ] | d-spacing [Å] | Relative Intensity [%] |
| --- | --- | --- |
| 7.03 | 12.5770 | 100.0 |
| 13.54 | 6.5377 | 3.5 |
| 13.91 | 6.3652 | 4.7 |
| 14.13 | 6.2694 | 5.9 |
| 21.25 | 4.1804 | 7.0 |
| 21.51 | 4.1308 | 3.6 |
| 24.73 | 3.5998 | 4.2 |
| 25.77 | 3.4575 | 3.8 |

In certain embodiments, the present invention provides Form D of Compound 1. According to one embodiment, Form D of Compound 1 is characterized by one or more peaks in its powder X-ray diffraction pattern selected from those at about 4.89, about 6.01, about 6.10, about 9.83, about 12.06, about 20.55, about 20.98, about 25.75, and about 26.42 degrees 2-theta.

In some embodiments, Form D of Compound 1 is characterized by a powder X-ray diffraction pattern having peaks at about 4.89, about 6.01, and about 9.83 degrees 2-theta. In some embodiments, Form D of Compound 1 is characterized by a powder X-ray diffraction pattern having peaks at about 4.89, about 6.01, about 9.83, about 25.75, and about 26.42 degrees 2-theta. In an exemplary embodiment, Form D of Compound 1 is characterized by substantially all of the peaks in its X-ray powder diffraction pattern at about

| Position [°2θ] | d-spacing [Å] | Relative Intensity [%] |
| --- | --- | --- |
| 4.89 | 18.0774 | 100.0 |
| 6.01 | 14.6968 | 43.3 |
| 6.10 | 14.4888 | 34.3 |
| 9.83 | 8.9996 | 31.2 |
| 12.06 | 7.3416 | 15.8 |
| 20.55 | 4.3230 | 17.1 |
| 20.98 | 4.2353 | 16.1 |
| 25.75 | 3.4593 | 23.1 |
| 26.42 | 3.3731 | 13.6 |

In certain embodiments, the present invention provides Form E of Compound 1. According to one embodiment, Form E of Compound 1 is characterized by one or more peaks in its powder X-ray diffraction pattern selected from those at about 6.80, about 7.13, about 9.95, about 15.48, about 15.64, and about 21.44 degrees 2-theta. In some embodiments, Form E of Compound 1 is characterized by a powder X-ray diffraction pattern having peaks at about 6.80 and about 7.13 degrees 2-theta. In an exemplary embodiment, Form E of Compound 1 is characterized by substantially all of the peaks in its X-ray powder diffraction pattern at about

| Position [°2θ] | d-spacing [Å] | Relative Intensity [%] |
| --- | --- | --- |
| 6.80 | 12.9949 | 100.0 |
| 7.13 | 12.4033 | 94.5 |
| 9.95 | 8.8927 | 5.1 |
| 15.48 | 5.7228 | 4.7 |
| 15.64 | 5.6656 | 5.4 |
| 21.44 | 4.1447 | 5.2 |

In certain embodiments, the present invention provides Form F of Compound 1. According to one embodiment, Form F of Compound 1 is characterized by one or more peaks in its powder X-ray diffraction pattern selected from those at about 7.11, about 8.92, about 10.41, about 10.68, about 11.00, about 13.70, about 22.11, and about 23.73 degrees 2-theta. In some embodiments, Form F of Compound 1 is characterized by a powder X-ray diffraction pattern having peaks at about 7.11, about 8.92 and about 11.00 degrees 2-theta. In an exemplary embodiment, Form F of Compound 1 is characterized by substantially all of the peaks in its X-ray powder diffraction pattern at about

| Position [°2θ] | d-spacing [Å] | Relative Intensity [%] |
| --- | --- | --- |
| 7.11 | 12.4324 | 100.0 |
| 8.92 | 9.9089 | 22.2 |
| 10.41 | 8.4984 | 16.9 |
| 10.68 | 8.2860 | 13.8 |
| 11.00 | 8.0462 | 32.4 |
| 13.70 | 6.4641 | 11.6 |
| 22.11 | 4.0201 | 9.2 |
| 23.73 | 3.7491 | 9.2 |

In certain embodiments, the present invention provides Form G of Compound 1. According to one embodiment, Form G of Compound 1 is characterized by one or more peaks in its powder X-ray diffraction pattern selected from those at about 6.36, about 9.56, about 9.94, about 10.41, about 10.77, about 12.71, about 12.89, about 17.56, about 18.12, about 19.09, about 19.35, about 19.74, about 20.83, about 23.49, and about 24.08 degrees 2-theta. In some embodiments, Form G of Compound 1 is characterized by a powder X-ray diffraction pattern having peaks at about 6.36, about 12.71, and about 12.89 degrees 2-theta. In an exemplary embodiment, Form G of Compound 1 is characterized by substantially all of the peaks in its X-ray powder diffraction pattern at about

| Position [°2θ] | d-spacing [Å] | Relative Intensity [%] |
| --- | --- | --- |
| 6.36 | 13.8918 | 100.0 |
| 9.56 | 9.2509 | 30.2 |
| 9.94 | 8.8976 | 33.6 |
| 10.41 | 8.4973 | 44.9 |
| 10.77 | 8.2159 | 33.5 |
| 12.71 | 6.9634 | 65.6 |
| 12.89 | 6.8706 | 48.5 |
| 17.56 | 5.0511 | 26.2 |
| 18.12 | 4.8966 | 24.4 |
| 19.09 | 4.6503 | 33.1 |
| 19.35 | 4.5884 | 51.6 |
| 19.74 | 4.4968 | 27.5 |
| 20.83 | 4.2655 | 25.0 |
| 23.49 | 3.7873 | 20.9 |
| 24.08 | 3.6955 | 37.1 |

In certain embodiments, the present invention provides Form H of Compound 1. According to one embodiment, Form H of Compound 1 is characterized by one or more peaks in its powder X-ray diffraction pattern selected from those at about 10.37, about 12.81, about 19.31, about 19.75, and about 24.06 degrees 2-theta. In some embodiments, Form H of Compound 1 is characterized by a powder X-ray diffraction pattern having peaks at about 12.81, about 19.31, and about 24.06 degrees 2-theta. In an exemplary embodiment, Form H of Compound 1 is characterized by substantially all of the peaks in its X-ray powder diffraction pattern at about

| Position [°2θ] | d-spacing [Å] | Relative Intensity [%] |
| --- | --- | --- |
| 10.37 | 8.5341 | 78.8 |
| 12.81 | 6.9123 | 77.6 |

-continued

| Position [°2θ] | d-spacing [Å] | Relative Intensity [%] |
|---|---|---|
| 19.31 | 4.5967 | 100.0 |
| 19.75 | 4.4954 | 60.8 |
| 24.06 | 3.6989 | 97.3 |

In certain embodiments, the present invention provides Form I of Compound 1. According to one embodiment, Form I of Compound 1 is characterized by one or more peaks in its powder X-ray diffraction pattern selected from those at about 6.73, about 8.44, about 13.45, about 15.27, about 17.53, about 20.54, about 23.95, and about 24.49 degrees 2-theta. In some embodiments, Form I of Compound 1 is characterized by a powder X-ray diffraction pattern having peaks at about 6.73, about 8.44, and about 23.95 degrees 2-theta. In some embodiments, Form I of Compound 1 is characterized by a powder X-ray diffraction pattern having peaks at about 6.73, about 8.44, about 17.53, and about 23.95 degrees 2-theta. In some embodiments, Form I of Compound 1 is characterized by a powder X-ray diffraction pattern having peaks at about 6.73, about 8.44, about 15.27, about 17.53, and about 23.95 degrees 2-theta. In an exemplary embodiment, Form I of Compound 1 is characterized by substantially all of the peaks in its X-ray powder diffraction pattern at about

| Position [°2θ] | d-spacing [Å] | Relative Intensity [%] |
|---|---|---|
| 6.73 | 13.1420 | 100.0 |
| 8.44 | 10.4774 | 46.5 |
| 13.45 | 6.5817 | 18.7 |
| 15.27 | 5.8035 | 26.7 |
| 17.53 | 5.0587 | 34.7 |
| 20.54 | 4.3244 | 19.2 |
| 23.95 | 3.7160 | 50.0 |
| 24.49 | 3.6346 | 16.8 |

Complex Forms of Compound 1:

Compound 1 can also exist in a complex. The term "complex" is used herein to refer to a form comprising Compound 1 non-covalently associated with a co-former. Such non-covalent associations include, by way of example, ionic interactions, dipole-dipole interactions, π-stacking interactions, hydrogen bond interactions, etc. It will be appreciated that the term "complex", as used herein, encompasses salt forms resulting from an ionic interaction between Compound 1 and an acid, as well as non-ionic associations between Compound 1 and a neutral species. Accordingly, in some embodiments, a "complex" is an inclusion complex, a salt form, a co-crystal, a clathrate, or hydrates and/or solvates thereof, etc. In some embodiments, the term "complex" is used to refer to a 1:1 (i.e., stoichiometric) ratio of Compound 1 and co-former. In some embodiments, the term "complex" does not necessarily indicate any particular ratio of Compound 1 to co-former. In some embodiments, a complex is a salt form, or a hydrate or solvate thereof. In some embodiments, a complex is a co-crystal form, or a hydrate or solvate thereof. In some embodiments, a complex is an inclusion complex, or a hydrate or solvate thereof. In some embodiments, a complex is a clathrate, or a hydrate or solvate thereof. In some embodiments, a complex is an amorphous solid. In some embodiments, a complex is a crystalline solid. In some embodiments, a complex is in solution form.

In some embodiments, the present invention provides a complex comprising Compound 1 and a co-former. In some such embodiments, the co-former is selected from the group consisting of t-aconitic acid, L-ascorbic acid, aspartic acid, benzoic acid, citric acid, gentisic acid, glutaric acid, 1-hydroxy-2-naphthoic acid, isethionic acid, ketoglutaric acid, L-lysine, maleic acid, malonic acid, methanesulfonic acid, naphthalene-1,5-disulphonic acid, oxalic acid, phosphoric acid, saccharin, thiocyanic acid, p-toluenesulfonic acid, and vanillin.

Accordingly, in some embodiments, the present invention provides a complex comprising Compound 1 and a co-former X, wherein X is selected from the group consisting of t-aconitic acid, L-ascorbic acid, aspartic acid, benzoic acid, citric acid, gentisic acid, glutaric acid, 1-hydroxy-2-naphthoic acid, isethionic acid, ketoglutaric acid, L-lysine, maleic acid, malonic acid, methanesulfonic acid, naphthalene-1,5-disulphonic acid, oxalic acid, phosphoric acid, saccharin, thiocyanic acid, p-toluenesulfonic acid, and vanillin.

In some embodiments, a complex comprising Compound 1 and a co-former X is referred to herein as Compound 2. Accordingly, in some embodiments, Compound 2 comprises Compound 1 and a co-former X, wherein X is selected from the group consisting of t-aconitic acid, L-ascorbic acid, aspartic acid, benzoic acid, citric acid, gentisic acid, glutaric acid, 1-hydroxy-2-naphthoic acid, isethionic acid, ketoglutaric acid, L-lysine, maleic acid, malonic acid, methanesulfonic acid, naphthalene-1,5-disulphonic acid, oxalic acid, phosphoric acid, saccharin, thiocyanic acid, p-toluenesulfonic acid, and vanillin.

In some embodiments, Compound 2 is crystalline. In some such embodiments, a crystalline form of Compound 2 (i.e., a complex of Compound 1 and a co-former X), as compared to amorphous Compound 1 or amorphous Compound 2, imparts or may impart characteristics such as improved aqueous solubility, stability and ease of formulation.

According to one embodiment, the present invention provides Compound 2 in an amorphous form, a crystalline form, or a mixture thereof. In some embodiments, the present invention provides a mixture of Compound 1 and Compound 2. In some such embodiments, the mixture comprises Form A of Compound 1 and Compound 2. In some embodiments, the present invention provides a mixture of Compound 2 and co-former. In some embodiments, the present invention provides a mixture comprising Compound 1, Compound 2 and co-former. In some such embodiments, Compound 1 is Form A.

In other embodiments, the present invention provides Compound 2 substantially free of impurities such as starting materials, residual solvents, or any other impurities that may result from the preparation of, and/or isolation of, Compound 2. In certain embodiments, at least about 90% by weight of Compound 2 is present. In certain embodiments, at least about 95% by weight of Compound 2 is present. In still other embodiments of the invention, at least about 99% by weight of Compound 2 is present.

According to one embodiment, Compound 2 is present in an amount of at least about 95, 97, 97.5, 98.0, 98.5, 99, 99.5, 99.8 weight percent where the percentages are based on the total weight of the composition. According to another embodiment, Compound 2 contains no more than about 5.0 area percent HPLC of total organic impurities and, in certain embodiments, no more than about 3.0 area percent HPLC of total organic impurities and, in certain embodiments, no more than about 1.5 area percent HPLC total organic impurities relative to the total area of the HPLC chromatogram. In other embodiments, Compound 2 contains no more than about 1.0 area percent HPLC of any single impurity; no more than about 0.6 area percent HPLC of any single impurity, and, in certain embodiments, no more than about 0.5 area percent HPLC of any single impurity, relative to the total area of the HPLC chromatogram.

In some embodiments, the present invention provides Compound 2, wherein X is t-aconitic acid ("the t-aconitic acid complex"). In some embodiments, the t-aconitic acid complex is crystalline. In some such embodiments, the t-aconitic acid complex is characterized by one or more peaks in its powder X-ray diffraction pattern selected from those at about 3.91, about 7.81, about 10.98, about 23.58, about 23.90, about 24.54, and about 30.90 degrees 2-theta. In some embodiments, the t-aconitic acid complex is characterized by peaks in its powder X-ray diffraction pattern at about 3.91, about 7.81, about 10.98, and about 30.90 degrees 2-theta.

In some embodiments, the present invention provides Compound 2, wherein X is L-ascorbic acid ("the L-ascorbic acid complex"). In some embodiments, the L-ascorbic acid complex is crystalline. In some such embodiments, the L-ascorbic acid complex is characterized by one or more peaks in its powder X-ray diffraction pattern selected from those at about 6.79, about 14.06, about 24.76, and about 25.68 degrees 2-theta. In some embodiments, the L-ascorbic acid complex is characterized by peaks in its powder X-ray diffraction pattern at about 6.79, about 24.76, and about 25.68 degrees 2-theta.

In some embodiments, the present invention provides Compound 2, wherein X is aspartic acid ("the aspartic acid complex"). In some embodiments, the aspartic acid complex is crystalline. In some such embodiments, the aspartic acid complex is characterized by one or more peaks in its powder X-ray diffraction pattern selected from those at about 6.81, about 6.97, about 13.63, about 13.94, about 14.17, about 15.21, about 15.61, about 20.97, and about 24.03 degrees 2-theta. In some embodiments, the aspartic acid complex is characterized by peaks in its powder X-ray diffraction pattern at about 6.81, about 6.97, about 20.97, and about 24.03 degrees 2-theta.

In some embodiments, the present invention provides Compound 2, wherein X is benzoic acid ("the benzoic acid complex"). In some embodiments, the benzoic acid complex is crystalline. In some such embodiments, the benzoic acid complex is characterized by one or more peaks in its powder X-ray diffraction pattern selected from those at about 9.94, about 10.55, about 14.91, about 19.90, and about 20.38 degrees 2-theta. In some embodiments, the benzoic acid complex is characterized by peaks in its powder X-ray diffraction pattern at about 10.55, about 14.91, and about 19.90 degrees 2-theta.

In some embodiments, the present invention provides Compound 2, wherein X is citric acid ("the citric acid complex"). In some embodiments, the citric acid complex is crystalline. In some such embodiments, the citric acid complex is characterized by one or more peaks in its powder X-ray diffraction pattern selected from those at about 11.07, about 12.97, about 14.52, about 15.58, about 21.30, about 22.10, about 23.79, and about 24.09 degrees 2-theta. In some embodiments, the citric acid complex is characterized by a powder X-ray diffraction pattern having peaks at about 11.07, about 12.97, about 15.58, and about 21.30 degrees 2-theta. In an exemplary embodiment, the citric acid complex is characterized by substantially all of the peaks in its X-ray powder diffraction pattern at about 11.07, about 12.97, and about 15.58 degrees 2-theta.

In some embodiments, the present invention provides Compound 2, wherein X is gentisic acid ("the gentisic acid complex"). In some embodiments, the present invention provides Form 1 of the gentisic acid complex. In some embodiments, the Form 1 gentisic acid complex is crystalline. In some such embodiments, the Form 1 gentisic acid complex is characterized by one or more peaks in its powder X-ray diffraction pattern selected from those at about 6.65, about 13.10, about 13.30, about 13.49, about 14.01, about 14.96, about 20.03, about 24.79, and about 25.63 degrees 2-theta. In some embodiments, the Form 1 gentisic acid complex is characterized by a powder X-ray diffraction pattern having peaks at about 6.65, about 20.03, about 24.79, and about 25.63 degrees 2-theta.

In some embodiments, the present invention provides Form 2 of the gentisic acid complex. In some embodiments, the Form 2 gentisic acid complex is crystalline. In some such embodiments, Form 2 gentisic acid complex is characterized by one or more peaks in its powder X-ray diffraction pattern selected from those at about 8.42, about 9.80, about 24.74, and about 27.60 degrees 2-theta. In some embodiments, Form 2 gentisic acid complex is characterized by a powder X-ray diffraction pattern having peaks at about 8.42, about 9.80, about 24.74, and about 27.60 degrees 2-theta.

In some embodiments, the present invention provides Compound 2, wherein X is glutaric acid ("the glutaric acid complex"). In some embodiments, the glutaric acid complex is crystalline. In some such embodiments, the glutaric acid complex is characterized by one or more peaks in its powder X-ray diffraction pattern selected from those at about 4.59, about 7.15, about 11.97, about 16.78, about 17.49, about 37.25, and about 37.39 degrees 2-theta. In some embodiments, the glutaric acid complex is characterized by a powder X-ray diffraction pattern having peaks at about 4.59, about 7.15, about 11.97, and about 16.78 degrees 2-theta.

In some embodiments, the present invention provides Compound 2, wherein X is 1-hydroxy-2-naphthoic acid ("the 1-hydroxy-2-naphthoic acid complex"). In some embodiments, the present invention provides Form 1 of the 1-hydroxy-2-naphthoic acid complex. In some embodiments, the Form 1 1-hydroxy-2-naphthoic acid complex is crystalline. In some such embodiments, the Form 1 1-hydroxy-2-naphthoic acid complex is characterized by one or more peaks in its powder X-ray diffraction pattern selected from those at about 7.40, about 9.53, about 11.18, about 17.24, about 22.46, about 23.37, and about 25.99 degrees 2-theta. In some embodiments, the Form 1 1-hydroxy-2-naphthoic acid complex is characterized by powder X-ray diffraction pattern having peaks at about 7.40, about 9.53, about 11.18, and about 17.24 degrees 2-theta.

In some embodiments, the present invention provides Form 2 of the 1-hydroxy-2-naphthoic acid complex. In some embodiments, the Form 2 1-hydroxy-2-naphthoic acid complex is crystalline. In some such embodiments, the Form 2 1-hydroxy-2-naphthoic acid complex is characterized by one or more peaks in its powder X-ray diffraction pattern selected from those at about 5.09, about 7.62, about 10.15, about 12.12, about 12.37, about 17.46, about 19.46, and about 24.04 degrees 2-theta. In some embodiments, the Form 2 1-hydroxy-2-naphthoic acid complex is characterized by a powder X-ray diffraction pattern having peaks at about 5.09, about 7.62, about 12.12, about 12.37, about 19.46, and about 24.04 degrees 2-theta.

In some embodiments, the present invention provides Compound 2, wherein X is isethionic acid ("the isethionic acid complex"). In some embodiments, the isethionic acid complex is crystalline. In some such embodiments, the isethionic acid complex is characterized by one or more peaks in its powder X-ray diffraction pattern selected from those at about 5.07, about 5.77, about 6.84, about 18.24, about 26.72, and about 27.35 degrees 2-theta. In some embodiments, the isethionic acid complex is characterized by a powder X-ray diffraction pattern having peaks at about 5.07, about 5.77, about 6.84, about 26.72, and about 27.35 degrees 2-theta.

In some embodiments, the present invention provides Compound 2, wherein X is ketoglutaric acid ("the ketoglutaric acid complex"). In some embodiments, the ketoglutaric acid complex is crystalline. In some such embodiments, the ketoglutaric acid complex is characterized by one or more peaks in its powder X-ray diffraction pattern selected from those at about 8.31, about 9.25, about 11.23, about 20.08, about 25.50, about 32.44, about 33.12, about 33.74, and about 37.75 degrees 2-theta. In some embodiments, the ketoglutaric acid complex is characterized by peaks in its powder X-ray diffraction pattern at about 8.31, about 9.25, about 11.23, and about 20.08 degrees 2-theta. In some embodiments, the ketoglutaric acid complex is characterized by peaks in its powder X-ray diffraction pattern at about 8.31, about 9.25, about 11.23, about 20.08, and about 25.50 degrees 2-theta.

In some embodiments, the present invention provides Compound 2, wherein X is L-lysine ("the L-lysine complex"). In some embodiments, the L-lysine complex is crystalline. In some such embodiments, the L-lysine complex is characterized by one or more peaks in its powder X-ray diffraction pattern selected from those at about 7.04, about 7.64, about 14.05, about 22.69, about 24.58, and about 25.80 degrees 2-theta. In some embodiments, the L-lysine complex is characterized by peaks in its powder X-ray diffraction pattern at about 7.04, about 7.64, and about 22.69 degrees 2-theta.

In some embodiments, the present invention provides Compound 2, wherein X is maleic acid ("the maleic acid complex"). In some embodiments, the maleic acid complex is crystalline. In some such embodiments, the maleic acid complex is characterized by one or more peaks in its powder X-ray diffraction pattern selected from those at about 8.37, about 10.54, about 12.07, about 13.01, about 13.81, about 14.84, about 19.31, about 24.76, and about 25.27 degrees 2-theta. In some embodiments, the maleic acid complex is characterized by peaks in its powder X-ray diffraction pattern at about 8.37, about 10.54, about 12.07, about 13.01, and about 19.31 degrees 2-theta.

In some embodiments, the present invention provides Compound 2, wherein X is malonic acid ("the malonic acid complex"). In some embodiments, the malonic acid complex is crystalline. In some such embodiments, the malonic acid complex is characterized by one or more peaks in its powder X-ray diffraction pattern selected from those at about 7.26, about 8.51, about 11.63, about 14.52, about 15.52, about 15.82, about 19.71, about 23.38, and about 27.98 degrees 2-theta. In some embodiments, the malonic acid complex is characterized by peaks in its powder X-ray diffraction pattern at about 7.26, about 8.51, about 11.63, about 14.52, about 15.52, about 15.82, and about 19.71 degrees 2-theta.

In some embodiments, the present invention provides Compound 2, wherein X is methanesulfonic acid ("the methanesulfonic acid complex"). In some embodiments, the methanesulfonic acid complex is crystalline. In some such embodiments, the methanesulfonic acid complex is characterized by one or more peaks in its powder X-ray diffraction pattern selected from those at about 5.04, about 5.90, about 13.08, about 21.83, about 23.46, about 24.08, and about 26.02 degrees 2-theta. In some embodiments, the methanesulfonic acid complex is characterized by peaks in its powder X-ray diffraction pattern at about 5.04, about 5.90, about 13.08, and about 21.83 degrees 2-theta.

In some embodiments, the present invention provides Compound 2, wherein X is naphthalene-1,5-disulphonic acid ("the naphthalene-1,5-disulphonic acid complex"). In some embodiments, the naphthalene-1,5-disulphonic acid complex is crystalline. In some such embodiments, the naphthalene-1,5-disulphonic acid complex is characterized by one or more peaks in its powder X-ray diffraction pattern selected from those at about 12.02, about 20.61, about 20.98, about 21.25, about 22.49, and about 24.39 degrees 2-theta. In some embodiments, the naphthalene-1,5-disulphonic acid complex is characterized by peaks in its powder X-ray diffraction pattern at about 12.02, about 20.61, about 20.98, and about 21.25 degrees 2-theta.

In some embodiments, the present invention provides Compound 2, wherein X is oxalic acid ("the oxalic acid complex"). In some embodiments, the oxalic acid complex is crystalline. In some such embodiments, the oxalic acid complex is characterized by one or more peaks in its powder X-ray diffraction pattern selected from those at about 11.14, about 20.52, about 21.22, about 23.13, about 24.08, and about 24.67 degrees 2-theta. In some embodiments, the oxalic acid complex is characterized by a powder X-ray diffraction pattern having peaks at about 11.14, about 20.52, about 24.08, and about 24.67 degrees 2-theta. In an exemplary embodiment, the oxalic acid complex is characterized by substantially all of the peaks in its X-ray powder diffraction pattern at about 11.14, about 24.08, and about 24.67 degrees 2-theta.

In some embodiments, the present invention provides Compound 2, wherein X is phosphoric acid ("the phosphoric acid complex"). In some embodiments, the phosphoric acid complex is crystalline. In some such embodiments, the phosphoric acid complex is characterized by one or more peaks in its powder X-ray diffraction pattern selected from those at about 6.79, about 7.08, about 7.39, about 9.93, about 11.95, about 14.18, and about 14.88 degrees 2-theta. In some embodiments, the phosphoric acid complex is characterized by a powder X-ray diffraction pattern having peaks at about 6.79, about 7.08, about 7.39, about 9.93, and about 11.95 degrees 2-theta.

In some embodiments, the present invention provides Compound 2, wherein X is saccharin ("the saccharin complex"). In some embodiments, the saccharin complex is crystalline. In some such embodiments, the saccharin complex is characterized by one or more peaks in its powder X-ray diffraction pattern selected from those at about 6.82, about 10.24, about 20.53, and about 24.63 degrees 2-theta. In some embodiments, the saccharin complex is characterized by peaks in its powder X-ray diffraction pattern at about 6.82, about 10.24, and about 20.53 degrees 2-theta.

In some embodiments, the present invention provides Compound 2, wherein X is thiocyanic acid ("the thiocyanic acid complex"). In some embodiments, the thiocyanic acid complex is crystalline. In some such embodiments, the thiocyanic acid complex is characterized by one or more peaks in its powder X-ray diffraction pattern selected from those at about 6.86, about 6.95, about 14.17, about 25.80 degrees 2-theta.

In some embodiments, the present invention provides Compound 2, wherein X is p-toluenesulfonic acid ("the p-toluenesulfonic acid complex"). In some embodiments, the toluenesulfonic acid complex is crystalline. In some such embodiments, the p-toluenesulfonic acid complex is characterized by one or more peaks in its powder X-ray diffraction pattern selected from those at about 6.49, about 9.65, about 10.00, about 13.22, about 19.99, about 23.55, about 23.79, and about 27.56 degrees 2-theta. In some embodiments, the p-toluenesulfonic acid complex is characterized by peaks in its powder X-ray diffraction pattern at about 6.49, about 9.65, about 10.00, and about 13.22 degrees 2-theta.

In some embodiments, the present invention provides Compound 2, wherein X is vanillin ("the vanillin complex"). In some embodiments, the vanillin complex is crystalline. In some such embodiments, the vanillin complex is characterized by one or more peaks in its powder X-ray diffraction pattern selected from those at about 10.93, about 11.43, about 11.58, about 12.22, about 14.42, about 15.45, about 17.28, about 22.89, about 23.53, and about 23.77 degrees 2-theta. In some embodiments, the vanillin complex is characterized by a powder X-ray diffraction pattern having peaks at about 10.93, about 11.43, about 11.58, about 14.42, about 15.45, and about 17.28 degrees 2-theta. In an exemplary embodiment, the vanillin complex is characterized by substantially all of the peaks in its X-ray powder diffraction pattern at about 11.43, about 11.58, about 14.42, about 15.45, and about 17.28 degrees 2-theta.

General Methods of Providing Compound 1 and Compound 2:

Compound 1 is prepared according to the methods described in detail in the '463 application, the entirety of which is hereby incorporated herein by reference. The various crystalline forms of Compound 1 can be prepared by dissolving Compound 1 in various suitable solvents and then causing Compound 1 to return to the solid phase. Specific combinations of solvents and conditions under which Compound 1 returns to the solid phase are discussed in greater detail in the Examples.

A suitable solvent may solubilize Compound 1, either partially or completely. Examples of suitable solvents useful in the present invention are a protic solvent, a polar aprotic solvent, or mixtures thereof. In certain embodiments, suitable solvents include an ether, an ester, an alcohol, a ketone, or a mixture thereof. In certain embodiments, the suitable solvent is methanol, ethanol, isopropanol (IPA), or acetone wherein said solvent is anhydrous or in combination with water, methyl tert-butyl ether (MTBE) or heptane. In other embodiments, suitable solvents include methyl acetate, isopropyl acetate, toluene, tetrahydrofuran (THF), 1,4-dioxane, dimethylformamide (DMF), dimethylacetamide (DMA), dimethylsulfoxide (DMSO), glyme, diglyme, methyl ethyl ketone, N-methyl-2-pyrrolidone, 2-methyl tetrahydrofuran, methyl t-butyl ether, t-butanol, n-butanol, and acetonitrile.

According to one embodiment, the present invention provides a method for preparing a crystalline form of Compound 1, comprising the steps of dissolving Compound 1 in a suitable solvent, optionally heating to form a solution thereof, and isolating Compound 1. In some embodiments, Compound 1 is prepared by equilibration in a suitable solvent. In some such embodiments, Compound 1 is dissolved in a suitable solvent and the solution agitated at room temperature for a period of time, e.g., 1 day. In some embodiments, the sample is then gently heated (e.g., at 50° C.) for a period of time, e.g., 1 day. Compound 1 may then be isolated by removal of the supernatant by, e.g., filtration.

In some embodiments, Compound 1 is prepared by evaporation of a suitable solvent. In some embodiments, Compound 1 is dissolved in a suitable solvent and the solvent is allowed to evaporate. In some embodiments, the solvent is THF. In some embodiments, the solvent is THF/water. In some embodiments, the solvent is dichloromethane (DCM). In some embodiments, the solvent is ethanol. In some embodiments, the solvent is ethanol/water.

In some embodiments, Compound 1 is recrystallized in a solvent/anti-solvent system. In some embodiments, Compound 1 is dissolved in a suitable solvent and then the solution added to an anti-solvent. Anti-solvents useful in the recrystallization of Compound 1 include acetone, acetonitrile (ACN), isopropanol, heptane, methyl acetate, toluene and water. The mixture may be cooled and Compound 1 isolated by, e.g., filtration. In some embodiments, the solvent is DMSO and the anti-solvent is ACN. In some embodiments, the solvent is DMSO and the anti-solvent is IPA. In some embodiments, the solvent is DMSO and the anti-solvent is water.

As described generally above, Compound 1 is dissolved in a suitable solvent, optionally with heating. In certain embodiments, Compound 1 is dissolved at about 50 to about 60° C. In other embodiments, Compound 1 is dissolved at about 50 to about 55° C. In still other embodiments, Compound 1 is dissolved at the boiling temperature of the solvent. In other embodiments, Compound 1 is dissolved without heating (e.g., at ambient temperature, approximately 20-25° C.).

In some embodiments, the present invention provides processes for preparing a crystalline form of Compound 1, comprising dissolving Compound 1 in a suitable solvent, optionally heating to form a solution thereof, and isolating Compound 1. In some embodiments, a process for preparing a crystalline form of Compound 1 comprises (a) dissolving Compound 1 in a suitable solvent to form a mixture, (b) heating the mixture from step (a) to form a solution of Compound 1, (c) allowing the solution to cool, and (d) isolating a crystalline form of Compound 1.

In some embodiments, the present invention provides processes for preparing an anhydrate form of Compound 1, comprising dissolving Compound 1 in a suitable solvent in the presence of an anhydrate form of Compound 1, optionally heating to form a solution thereof, and isolating Compound 1.

In some embodiments, the present invention provides processes for preparing an anhydrate form of Compound 1, comprising dissolving a hydrate or solvate of Compound 1 in a suitable solvent in the presence of an anhydrate form of Compound 1, optionally heating to form a solution thereof, and isolating Compound 1.

In some embodiments, the present invention provides processes for preparing Form A of Compound 1, comprising dissolving a solvate of Compound 1 in a suitable solvent in the presence of Form A of Compound 1, optionally heating to form a solution thereof, and isolating Compound 1. In some embodiments, a process for preparing a crystalline form of Compound 1 comprises (a) dissolving Compound 1 in a suitable solvent, (b) heating the mixture from step (a) to form a solution of Compound 1, (c) contacting the solution with Form A of Compound 1, (d) allowing the solution to cool in the presence of Form A of Compound 1, and (e) isolating a crystalline form of Compound 1.

In some embodiments, the present invention provides processes for preparing Form A of Compound 1, comprising dissolving Form I of Compound 1 in a suitable solvent in the presence of Form A of Compound 1, optionally heating to form a solution thereof, and isolating Compound 1. In some embodiments, a process for preparing a crystalline form of Compound 1 comprises (a) dissolving Form I Compound 1 in a suitable solvent, (b) heating the mixture from step (a) to form a solution of Compound 1, (c) contacting the solution with Form A of Compound 1, (d) allowing the solution to cool in the presence of Form A of Compound 1, and (e) isolating Form A of Compound 1.

In some embodiments, the present invention provides a method for preparing Compound 2, comprising the steps of dissolving Compound 1 in a suitable solvent, adding a co-former to the solution, optionally heating to form a solution thereof, and isolating Compound 2.

In some embodiments, Compound 2 is prepared by dissolving Compound 1 in a suitable solvent, adding a co-former to the solution, and allowing the solvent to evaporate. In some embodiments, the solvent is allowed to evaporate at room temperature.

In some embodiments, Compound 2 is prepared by slurrying Compound 1 in a solution of a co-former in a suitable solvent, and isolating Compound 2. In some embodiments, Compound 2 is prepared by grinding Compound 1 in a solution of a co-former in a suitable solvent, and isolating Compound 2. In some embodiments, Compound 2 is prepared by dissolving Compound 1 in a suitable solvent, adding a co-former, cooling the solution, and isolating Compound 2.

In certain embodiments, Compound 1 or Compound 2 precipitates from the mixture. In another embodiment, Compound 1 or Compound 2 crystallizes from the mixture. In other embodiments, Compound 1 or Compound 2 crystallizes from solution following seeding of the solution (i.e., adding crystals of Compound 1 or Compound 2 to the solution).

Crystalline Compound 1 or Compound 2 can precipitate out of the reaction mixture, or be generated by removal of part or all of the solvent through methods such as evaporation, distillation, filtration (e.g., nanofiltration, ultrafiltration), reverse osmosis, absorption and reaction, by adding an anti-solvent (e.g., water, MTBE and/or heptane), by cooling (e.g., crash cooling) or by different combinations of these methods.

As described generally above, Compound 1 or Compound 2 is optionally isolated. It will be appreciated that Compound 1 or Compound 2 may be isolated by any suitable physical means known to one of ordinary skill in the art. In certain embodiments, precipitated solid Compound 1 or Compound 2 is separated from the supernatant by filtration. In other embodiments, precipitated solid Compound 1 or Compound 2 is separated from the supernatant by decanting the supernatant.

In certain embodiments, precipitated solid Compound 1 or Compound 2 is separated from the supernatant by filtration.

In certain embodiments, isolated Compound 1 or Compound 2 is dried in air. In other embodiments, isolated Compound 1 or Compound 2 is dried under reduced pressure, optionally at elevated temperature.

Uses, Formulation and Administration

Pharmaceutically Acceptable Compositions

According to another embodiment, the invention provides a composition comprising a compound of this invention or a pharmaceutically acceptable salt thereof and a pharmaceutically acceptable carrier, adjuvant, or vehicle. In certain embodiments, the amount of compound in compositions of this invention is such that it is effective to measurably inhibit MK2, or a mutant thereof, in a biological sample or in a patient. In certain embodiments, a composition of this invention is formulated for administration to a patient in need of such composition. In some embodiments, a composition of this invention is formulated for oral administration to a patient.

Compounds and compositions, according to method of the present invention, are administered using any amount and any route of administration effective for treating or lessening the severity of a disorder provided herein (i.e., an MK2-mediated disease or disorder). The exact amount required will vary from subject to subject, depending on the species, age, and general condition of the subject, the severity of the infection, the particular agent, its mode of administration, and the like. Compounds of the invention are preferably formulated in unit dosage form for ease of administration and uniformity of dosage.

Compositions of the present invention may be administered orally, parenterally, by inhalation spray, topically, rectally, nasally, buccally, vaginally, intraperitoneally, intracisternally or via an implanted reservoir. In some embodiments, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

In some embodiments, provided pharmaceutically acceptable compositions are formulated for oral administration. Such formulations may be administered with or without food. In some embodiments, pharmaceutically acceptable compositions of this invention are administered without food. In other embodiments, pharmaceutically acceptable compositions of this invention are administered with food.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and/or i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Uses of Compounds and Pharmaceutically Acceptable Compositions

Compounds and compositions described herein are generally useful for the inhibition of kinase activity of one or more enzymes. Examples of kinases that are inhibited by the compounds and compositions described herein and against which the methods described herein are useful include MK2, or a mutant thereof.

The activity of a compound utilized in this invention as an inhibitor of a MK2 kinase, or a mutant thereof, may be assayed in vitro, in vivo or in a cell line. In vitro assays include assays that determine inhibition of either the phosphorylation activity and/or the subsequent functional consequences, or ATPase activity of activated MK2 kinase, or a mutant thereof. Alternate in vitro assays quantitate the ability of the test compound to bind to MK2. Inhibitor binding may be measured by radiolabeling the test compound prior to binding, isolating the test compound/MK2 complex and determining the amount of radiolabel bound. Alternatively, inhibitor binding may be determined by running a competition experiment where test compounds are incubated with MK2 kinase bound to known radioligands. Detailed conditions for assaying a compound utilized in this invention as an inhibitor of MK2, or a mutant thereof, are detailed in Examples 136-138 of the '463 application.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting MK2 kinase, or a mutant thereof, activity in a biological sample comprising the step of contacting said biological sample with a compound of this invention, or a composition comprising said compound. In certain embodiments, the invention relates to a method of irreversibly inhibiting MK2 kinase, or a mutant thereof, activity in a biological sample comprising the step of contacting said biological sample with a compound of this invention, or a composition comprising said compound.

According to another embodiment, the invention relates to a method of inhibiting MK2 kinase, or a mutant thereof, activity in a patient comprising the step of administering to said patient a compound of the present invention, or a composition comprising said compound. According to certain embodiments, the invention relates to a method of irreversibly inhibiting MK2 kinase, or a mutant thereof, activity in a patient comprising the step of administering to said patient a compound of the present invention, or a composition comprising said compound. In other embodiments, the present invention provides a method for treating an MK2-mediated disease or disorder, in a patient in need thereof, comprising the step of administering to said patient a compound according to the present invention or pharmaceutically acceptable composition thereof. Such disorders are described in detail herein.

MK2 Kinase

MAP kinase-activated protein kinase 2 ("MK2") is an enzyme that in humans is encoded by the MAPKAPK2 gene. The MAPKAPK2 gene encodes a member of the Ser/Thr protein kinase family and two transcript variants encoding two different isoforms have been found. MK2 is regulated through direct phosphorylation by p38 MAP kinase.

MK2 is a multi-domain protein consisting of an N-terminal proline-rich domain, a catalytic domain, an autoinhibitory domain and at the C-terminus a nuclear export signal (NES) and nuclear localization signal (NLS). Two isoforms of human MK2 have been characterized. One isoform consists of 400 amino acids and the other isoform 370 residues which is thought to be a splice variant missing the C-terminal NLS.

MK2 is known to be involved in many cellular processes including stress and inflammatory responses, nuclear export, gene expression regulation and cell proliferation. Indeed, MK2 regulates, by a post-transcriptional mechanism, biosynthesis of tumor necrosis factor α (TNFα) that is over-produced in inflammatory diseases such as rheumatoid arthritis and inflammatory bowel disease. See Natesan et al., *J Med. Chem.* 2012, 55, 2035-2047.

Compounds of the present invention have been shown to inhibit phosphorylation of heat shock protein 27 (Hsp27). See Example 138 of the '463 application. Inhibition of Hsp27 phosphorylation occurs by inhibiting the formation of the p38 kinase-MK2-Hsp27 signaling complex. Phosphorylation of Hsp27 is the penultimate event in a complex signaling cascade that occurs in response to extracellular stimuli. See Zheng et al., *The Journal of Biological Chemistry*, vol. 281, no. 48, 37215-37226, Dec. 1, 2006. Hsp27 usually exists as oligomers and plays a role in regulation of many cellular functions such as inhibition of the death receptor-mediated apoptosis, promotion of proper refolding of denatured proteins by acting as a molecular chaperone, and regulation of cytoskeleton. The presence of MK2 is a necessary condition for the formation of p38 kinase-MK2-Hsp27 signaling complex in cells. See Zheng et al., *The Journal of Biological Chemistry*, vol. 281, no. 48, 37215-37226, Dec. 1, 2006.

Evidence suggests that many signaling proteins form multimeric complexes. See Zheng et al., *The Journal of Biological Chemistry*, vol. 281, no. 48, 37215-37226, Dec. 1, 2006. One such complex is the Hsp27/Akt (a serine/threonine kinase) dimer, which forms in the cytoplasm of a cell. Another complex is formed between MK2 and p38. See Ben-Levy et al., *Current Biology* 1998, 8:1049-1057; Natesan et al., *J Med. Chem.* 2012, 55, 2035-2047; Zheng et al., *The Journal of Biological Chemistry*, vol. 281, no. 48, 37215-37226, Dec. 1, 2006.

In unstimulated conditions, inactive p38 and unphosphorylated MK2 form such dimer in the nucleus of a cell. Upon activation, p38 phosphorylates MK2, thereby inducing a conformational change of the autoinhibitory domain of MK2 and exposing the active site for substrate binding. Once MK2 is phosphorylated, the p38-MK2 dimer is translocated to the cytoplasm, where it forms a quaternary complex with the Hsp27-Akt dimer. See Zheng et al., *The Journal of Biological Chemistry*, vol. 281, no. 48, 37215-37226, Dec. 1, 2006. Hsp27 is then phosphorylated by MK2, resulting in degradation of the quaternary complex and the release of p-Hsp27 monomers and dimers. Because inhibition of MK2 blocks phosphorylation of Hsp27, without wishing to be bound by theory, it is believed that inhibition of MK2 prevents degradation of the p38-MK2-Akt-Hsp27 quaternary complex, thereby altering downstream effects. Consequent to the inhibition of quaternary complex degradation, the amount of quaternary complex would thereby increase. Moreover, the equilibrium of p38 and MK2 between the cytoplasm and nucleus would be shifted towards the cytoplasm.

Interestingly, transport of the MK2/p38 complex out of the nucleus does not require catalytically active MK2, as the active site mutant, Asp207Ala, is still transported to the cytoplasm. Phosphorylation of human MK2 by p38 on residues T222, S272 and T334 is thought to activate the enzyme by inducing a conformational change of the autoinhibitory domain thus exposing the active site for substrate binding. Mutations of two autoinhibitory domain residues W332A and K326E in murine MK2 demonstrate an increase in basal activity and a C-terminal deletion of the autoinhibitory domain renders the enzyme constitutively active, providing additional evidence to the role of this domain in inhibition of MK2 activity.

Diseases or disorders associated with MK2 that are treated by compounds of the present invention include autoimmune disorders, chronic inflammatory disorders, acute inflammatory disorders, auto-inflammatory disorders, fibrotic disorders, metabolic disorders, neoplasias, or cardiovascular or cerebrovascular disorders. Thus, in some embodiments, the present invention provides a method for treating an MK2-mediated disease or disorder in a patient in need thereof, wherein said method comprises administering to said patient a therapeutically effective amount of a provided compound, or composition thereof. Such MK2-mediated diseases or disorders include, but are not limited to those described herein.

In some embodiments, the MK2-mediated disease or disorder is an autoimmune disorder, chronic and/or acute inflammatory disorder, and/or auto-inflammatory disorder. Exemplary autoimmune and/or inflammatory and/or auto-inflammatory disorders include: inflammatory bowel diseases (for example, ulcerative colitis or Crohn's disease), multiple sclerosis, psoriasis, arthritis, rheumatoid arthritis, osteoarthritis, juvenile arthritis, psoriatic arthritis, reactive arthritis, ankylosing spondylitis, cryopyrin associated periodic syndromes, Muckle-Wells syndrome, familial cold auto-inflammatory syndrome, neonatal-onset multisystem inflammatory disease, TNF receptor associated periodic syndrome, acute and chronic pancreatitis, atherosclerosis, gout, ankylosing spondylitis, fibrotic disorders (for example, hepatic fibrosis or idiopathic pulmonary fibrosis), nephropathy, sarcoidosis, scleroderma, anaphylaxis, diabetes (for example, diabetes mellitus type 1 or diabetes mellitus type 2), diabetic retinopathy, Still's disease, vasculitis, sarcoidosis, pulmonary inflammation, acute respiratory distress syndrome, wet and dry age-related macular degeneration, autoimmune hemolytic syndromes, autoimmune and inflammatory hepatitis, autoimmune neuropathy, autoimmune ovarian failure, autoimmune orchitis, autoimmune thrombocytopenia, silicone implant associated autoimmune disease, Sjogren's syndrome, familial Mediterranean fever, systemic lupus erythematosus, vasculitis syndromes (for example, temporal, Takayasu's and giant cell arteritis, Behcet's disease or Wegener's granulomatosis), vitiligo, secondary hematologic manifestation of autoimmune diseases (for example, anemias), drug-induced autoimmunity, Hashimoto's thyroiditis, hypophysitis, idiopathic thrombocytic pupura, metal-induced autoimmunity, myasthenia gravis, pemphigus, autoimmune deafness (for example, Meniere's disease), Goodpasture's syndrome, Graves' disease, HW-related autoimmune syndromes, Guillain-Barre disease, Addison's disease, anti-phospholipid syndrome, asthma, atopic dermatitis, Celiac disease, Cushing's syndrome, dermatomyositis, idiopathic adrenal adrenal atrophy, idiopathic thrombocytopenia, Kawasaki syndrome, Lambert-Eaton Syndrome, pernicious anemia, pollinosis, polyarteritis nodosa, primary biliary cirrhosis, primary sclerosing cholangitis, Raynaud's, Reiter's Syndrome, relapsing polychondritis, Schmidt's syndrome, thyrotoxidosis, sepsis, septic shock, endotoxic shock, exotoxin-induced toxic shock, gram negative sepsis, toxic shock syndrome, glomerulonephritis, peritonitis, interstitial cystitis, hyperoxia-induced inflammations, chronic obstructive pulmonary disease (COPD), vasculitis, graft vs. host reaction (for example, graft vs. host disease), allograft rejections (for example, acute allograft rejection or chronic allograft rejection), early transplantation rejection (for example, acute allograft rejection), reperfusion injury, pain (for example, acute pain, chronic pain, neuropathic pain, or fibromyalgia), chronic infections, meningitis, encephalitis, myocarditis, gingivitis, post surgical trauma, tissue injury, traumatic brain injury, enterocolitis, sinusitis, uveitis, ocular inflammation, optic neuritis, gastric ulcers, esophagitis, peritonitis, periodontitis, dermatomyositis, gastritis, myositis, polymyalgia, pneumonia and bronchitis.

In some embodiments, the MK2-mediated disease or disorder is a fibrotic disorder. Exemplary fibrotic disorders include systemic sclerosis/scleroderma, lupus nephritis, connective tissue disease, wound healing, surgical scarring, spinal cord injury, CNS scarring, acute lung injury, pulmonary fibrosis (for example, idiopathic pulmonary fibrosis or cystic fibrosis), chronic obstructive pulmonary disease, adult respiratory distress syndrome, acute lung injury, drug-induced lung injury, glomerulonephritis, chronic kidney disease (for example, diabetic nephropathy), hypertension-induced nephropathy, alimentary track or gastrointestinal fibrosis, renal fibrosis, hepatic or biliary fibrosis, liver fibrosis (for example, nonalcoholic steatohepatitis, hepatitis C, or hepatocellular carcinoma), cirrhosis (for example, primary biliary cirrhosis or cirrhosis due to fatty liver disease (for example, alcoholic and nonalcoholic steatosis)), radiation-induced fibrosis (for example, head and neck, gastrointestinal or pulmonary), primary sclerosing cholangitis, restenosis, cardiac fibrosis (for example, endomyocardial fibrosis or atrial fibrosis), opthalmic scarring, fibrosclerosis, fibrotic cancers, fibroids, fibroma, fibroadenomas, fibrosarcomas, transplant arteriopathy, keloid, mediastinal fibrosis, myelofibrosis, retroperitoneal fibrosis, progressive massive fibrosis, and nephrogenic systemic fibrosis.

In some embodiments, the MK2-mediated disease or disorder is a metabolic disorder. Exemplary metabolic disorders include obesity, steroid-resistance, glucose intolerance, and metabolic syndrome.

In some embodiments, the MK2-mediated disease or disorder is a neoplasia. Exemplary neoplasias include cancers. In some embodiments, exemplary neoplasias include angiogenesis disorders, multiple myeloma, leukemias (for example, acute lymphocytic leukemia, acute and chronic myelogenous leukemia, chronic lymphocytic leukemia, acute lymphoblastic leukemia, or promyelocytic leukemia), lymphomas (for example, B-cell lymphoma, T-cell lymphoma, mantle cell lymphoma, hairy cell lymphoma, Burkitt's lymphoma, mast cell tumors, Hodgkin's disease or non-Hodgkin's disease), myelodysplastic syndrome, fibrosarcoma, rhabdomyosarcoma; astrocytoma, neuroblastoma, glioma and schwannomas; melanoma, seminoma, teratocarcinoma, osteosarcoma, xenoderma pigmentosum, keratoctanthoma, thyroid follicular cancer, Kaposi's sarcoma, melanoma, teratoma, rhabdomyosarcoma, metastatic and bone disorders, as well as cancer of the bone, mouth/pharynx, esophagus, larynx, stomach, intestine, colon, rectum, lung (for example, non-small cell lung cancer or small cell lung cancer), liver, pancreas, nerve, brain (for example, glioma or glioblastoma multiforme), head and neck, throat, ovary, uterus, prostate, testis, bladder, kidney, breast, gall bladder, cervix, thyroid, prostate, and skin.

In some embodiments, the MK2-mediated disorder is a cardiovascular or cerebrovascular disorder. Exemplary cardiovascular disorders include atherosclerosis, restenosis of an atherosclerotic coronary artery, acute coronary syndrome, myocardial infarction, cardiac-allograft vasculopathy and stroke. Exemplary cerebrovascular diseases include central nervous system disorders with an inflammatory or apoptotic component, Alzheimer's disease, Parkinson's disease, Huntington's disease, amyotrophic lateral sclerosis, spinal cord injury, neuronal ischemia and peripheral neuropathy.

All features of each of the aspects of the invention apply to all other aspects mutatis mutandis.

In order that the invention described herein may be more fully understood, the following examples are set forth. It should be understood that these examples are for illustrative purposes only and are not to be construed as limiting this invention in any manner.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Example 1. Polymorph Screen of Compound 1

A preliminary polymorph screen of Compound 1 was performed to investigate whether different solid forms of Compound 1 could be generated under various conditions, such as different solvents, temperature and humidity changes. Nine unique crystalline forms (Forms A through I) of Compound 1 were identified during the screen, including three anhydrates (Forms A, B, and D) and two hydrates (Forms C and E). Characterization of the crystal forms produced during the screen was performed by X-ray powder diffraction (XRPD), differential scanning calorimetry (DSC), thermogravimetric analysis (TGA), dynamic vapor sorption (DVS), Karl Fischer (KF), and $^1$H-Nuclear Magnetic Resonance (NMR).

Solubility of Form A was approximated in the following solvents: acetonitrile (ACN), ACN/water (1:1), n-butanol (n-BuOH), absolute ethanol (EtOH), ethanol/water (1:1), methanol (MeOH), 2-propanol (IPA), ethyl acetate (EtOAc), methyl acetate (MeOAc), dichloromethane (DCM), methyl ethyl ketone (MEK), methyl t-butyl ether (MTBE), heptane, toluene, methyl acetate (MeOAc), isopropyl acetate (IPAc), methyl isobutyl ketone (MIBK), 2-methyltetrahydrofuran (2-MeTHF), 1,4-dioxane, tetrahydrofuran (THF), THF/water (1:1), water, dimethyl sufoxide (DMSO), dimethylacetamide (DMA, DMAc), and N-methylpyrrolidone (NMP). A weighed sample of Form A (about 50 mg) was treated with a known volume of a test solvent. The resulting mixture was agitated for 1 day at room temperature. If all of the solids appeared to be dissolved by visual inspection, the estimated solubility was calculated based on the total volume of solvent used to give a complete solution. If solids were present, a known volume of filtrate was evaporated to dryness and the weight of the residue was measured to estimate the solubility.

The results are summarized in Table 1. Form A was found to be most soluble (>50 mg/mL) in DMSO, DMA and NMP. Form A showed moderate solubility (8~16 mg/mL) in THF/water, THF, and DCM, and (>2 mg/mL) in acetone, 1,4-dioxane, and MEK. Form A showed low or very low solubility (<3 mg/mL) in all other solvents tested.

TABLE 1

Approximate Solubility of Compound 1 Form A at Room Temperature

| Solvent | Approximate Solubility (mg/mL) |
| --- | --- |
| acetone | <3 |
| ACN | <2 |
| ACN/water (1:1) | <1 |
| n-BuOH | <1 |
| EtOH | <2 |
| EtOH/water (1:1) | <1 |
| EtOAc | <1 |
| heptane | <1 |
| IPA | <1 |
| DCM | <9 |
| MeOAc | <2 |
| MeOH | <3 |
| MTBE | <1 |
| MEK | <3 |
| toluene | <1 |
| THF | <10 |
| THF/water (1:1) | <16 |
| water | <1 |
| 1,4-dioxane | <6 |
| MIBK | <1 |
| IPAc | <1 |
| 2-MeTHF | <2 |
| DMA | >50 |
| NMP | >50 |
| DMSO | >50 |

Equilibration/Slurry and Evaporation.

Equilibration and evaporation experiments at room temperature and 50° C. were carried out by adding an excess of Compound 1 solid to up to 1 mL of a test solvent. The resulting mixture was agitated for 1 day at room temperature and 1 day at 50° C. separately. Upon reaching equilibrium, the saturated supernatant solution was removed, filtered using 0.45 μm PTFE filters and allowed to evaporate in an open vial under nitrogen at room temperature and 50° C., respectively. The solid resulting from the equilibration was isolated and air-dried before analysis.

The results are summarized in Table 2. All equilibration experiments afforded Form A. Four unique crystalline solids were obtained from evaporation experiments. Solid from evaporation at 50° C. in EtOH/water was designated as Form B. Solid from evaporation at 50° C. in THF was designated as Form C. Solid from evaporation at 50° C. in DCM was designated as Form D. Solid from evaporation at 50° C. in THF/water sample was designated as Form E. Most other evaporation experiments didn't afford analyzable solid due to relatively low solubility.

TABLE 2

Summary of Equilibration (EQ) and Evaporation (EV) Results

| Solvent | Form Observed by XRPD | | | |
|---|---|---|---|---|
| | EQ at RT | EV at RT | EQ at 50° C. | EV at 50° C. |
| acetone | A | — | A | — |
| ACN | A | — | A | — |
| ACN/water | A | — | A | A |
| n-BuOH | A | — | A | — |
| EtOH | A | — | A | — |
| EtOH/water | A | — | A | B |
| EtOAc | A | — | A | — |
| heptane | A | — | A | — |
| IPA | A | — | A | — |
| DCM | A | D | A | D |
| MeOAc | A | — | A | — |
| MeOH | A | — | A | A |
| MTBE | A | — | A | — |
| MEK | A | — | A | — |
| toluene | A | — | A | — |
| THF | A | A | A | C |
| THF/water | A | A (diffuse) | A | E + A |
| water | A | — | A | — |
| 1,4-dioxane | A | — | A | A |
| MIBK | A | — | A | — |
| IPAc | A | — | A | — |
| 2-MeTHF | A | — | A | — |

—: not analyzable

Recrystallization.

For cooling recrystallization, each of the selected solvents was saturated with Compound 1 solid at 50° C. The solvents included THF/water (1:1), THF, and DCM. The solution was stirred for 60 minutes, filtered using a 0.45 μm PTFE syringe filter, and then cooled to −15° C. and 4° C. by placing the vials into a freezer or refrigerator. The solid resulting from the recrystallization was isolated and air-dried before analysis.

Cooling recrystallization experiments were performed using solvents DCM, THF/water (1:1) and THF. The results are summarized in Table 3. The solid obtained from DCM was confirmed to be Form D. No solid was obtained from THF and THF/water.

TABLE 3

Results from Cooling Recrystallization

| Solvent | Cooling Profile | Form Observed by XRPD |
|---|---|---|
| DCM | 60° C. to −15° C. | D |
| THF | 60° C. to −15° C. | — |
| THF/water (1:1) | 60° C. to 4° C. | — |
| DMSO | 100° C. to −15° C. | H (diffuse) |

—: no precipitation

For anti-solvent recrystallization, the selected solvent DMSO was saturated with Compound 1 material at the 50° C. Once the solid was completely dissolved, a portion of the solution was filtered into a vial containing a selected anti-solvent (acetone, ACN, IPA, heptane, MeOAc, toluene and water). The mixture was cooled to −15° C. or 4° C. by placing the vials into a freezer or a refrigerator. The solid resulting from the recrystallization was isolated and air-dried before analysis.

Recrystallizations with anti-solvents were performed using DMSO as the primary solvent. Acetone, ACN, IPA, heptane, MeOAc, toluene and water were used as anti-solvents. The results are summarized in Table 4. Three additional unique XRPD patterns were observed. Solid obtained from DMSO/ACN was designated as Form F. Solid obtained from DMSO/IPA was designated as Form G and solid obtained from DMSO/water was designated as Form H. Precipitation was not observed from experiments using heptane, MeOAc, acetone or toluene as anti-solvents.

TABLE 4

Results from Anti-Solvent Recrystallization

| Primary solvent | Anti-Solvent | Solvent Ratio | Cooling profile | Form Observed by XRPD |
|---|---|---|---|---|
| DMSO | ACN | 1:40 | 50° C. to −15° C. | F |
| DMSO | IPA | 1:40 | 50° C. to −15° C. | G |
| DMSO | heptane | 1:40 | 50° C. to −15° C. | — |
| DMSO | MeOAc | 1:40 | 50° C. to −15° C. | — |
| DMSO | toluene | 1:40 | 50° C. to −15° C. | — |
| DMSO | water | 1:40 | 50° C. to 4° C. | A (diffuse) |
| DMSO | acetone | 1:40 | 50° C. to −15° C. | — |

—: no precipitation

Additional experiments were performed to generate materials for further characterization, as detailed in Table 5. Forms C, D, and E were reproduced from these experiments.

TABLE 5

Experiments to Generate Materials for Characterization

| Solvent | Experimental Conditions | Form Observed by XRPD |
|---|---|---|
| EtOH/water (1:1) | Evaporation at 50° C. for 1 day | A* |
| THF | Evaporation at 50° C. for 1 day | C |
| DCM | Evaporation at 50° C. for 1 day | D |
| THF/water (1:1) | Evaporation at 50° C. for 1 day | E |

*Targeted Form B but generated Form A; repeated twice

Form conversion experiments were performed to determine interconversion among solid forms. The results are summarized in Table 6.

TABLE 6

Summary of Form Transfer Experiments

| Starting Form(s) | Solvent/Condition | Temperature/ Condition | Resulting Form(s) |
|---|---|---|---|
| A | slurry in THF/IPA (10:90) | RT, 5 days | A |
| B | compression | 2000 psi, RT, 1 min | B + A |
| B | heating in KF oven | 190° C., ~10 min | A |
| B | slurry in acetone | 50° C., 2 days | A |
| B | slurry in acetone | RT, 10 days | A |
| C | 0-90-0% RH cycle in DVS | 25° C. | E + C + peaks |
| C | compression | 2000 psi, RT, 1 min | E + C + peaks |
| C | heating in KF oven | 190° C., ~10 min | A + C (shifted) |
| C | slurry in acetone | 50° C., 2 days | A |
| C | slurry in acetone | RT, 10 days | A |
| C | slurry in THF/water (5:95) | RT, 5 days | A |
| D | compression | 2000 psi, RT, 1 min | D (+ A?) |
| D | heating in KF oven | 190° C., ~10 min | A |
| D | slurry in acetone | 50° C., 2 days | A |
| D | slurry in acetone | RT, 10 days | A |
| D | slurry in THF/water (5:95) | RT, 5 days | E |
| D | slurry in THF/water (5:95) | RT, 9 days | A |
| E | compression | 2000 psi, RT, 1 min | E |
| E | heating in KF oven | 190° C., ~10 min | E |
| E | slurry in acetone | 50° C., 2 days | A |
| E | slurry in acetone | RT, 10 days | A |
| E + A | slurry in THF/water (5:95) | RT, 5 days | A |
| H | slurry in water | RT, 4 days | I |
| H | slurry in THF/water (5:95) | RT, 8 days | A + I |
| I* | 0-90-0% RH cycle in DVS | 25° C. | A |
| I** | slurry in acetone | 50° C., 3 days | A |

Figure 48:
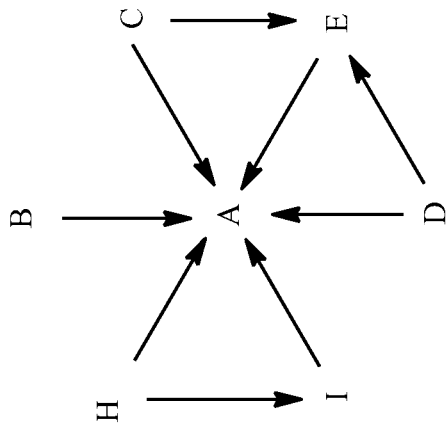
FIG. 48 is a schematic depicting inter-conversion among crystalline Forms of Compound 1.

*starting material: slurry of Form H in water
**starting material: Compound 1 recrystallized in THF/water The inter-conversion relationship between the forms was explored through form conversion experiments as summarized in Table 6. Slurry experiments of single and mixed forms in selected organic solvents or solvent/water mixtures were explored, and all solids converted to Form A as the final form. These results suggested that Form A is the most stable anhydrate form. This conclusion was further confirmed by additional results from heat and humidity stress experiments also summarized in Table 6. The schematic inter-conversion among crystalline forms of Compound 1 is depicted in FIG. 48.

Characterization of Crystalline Forms of Compound 1.

X-Ray Powder Diffraction (XRPD).

All of the solid samples generated in the polymorph screen were analyzed by XRPD. XRPD analysis was conducted on a PANalytical Empyrean X-ray powder diffractometer using Cu Kα radiation at 1.54 Å.

The PANalytical Empyrean instrument was equipped with a fine focus X-ray tube. The voltage and amperage of the X-ray generator were set at 45 kV and 40 mA, respectively. The divergence slits were set at 1/160 and 1/8°, and the receiving slit was set at 1/160. Diffracted radiation was measured using a Pixel 2D detector. A theta-two theta continuous scan was set at step size 0.013 or 0.026 from 3° to 400 2θ with sample spinning rate at 4. A sintered alumina standard was used to check the peak positions. FIGS. 1-9 depict the XRPD spectra for Forms A, B, C, D, E, F, G, H and I, respectively.

Differential Scanning Calorimetry (DSC).

DSC analyses were performed on a TA Discovery Differential Scanning Calorimeter. Indium was used as the calibration standard. Approximately 1-5 mg of sample was placed into a DSC pan. The sample was heated under nitrogen at a rate of 10° C./min, up to a final temperature of 300° C. Melting points were reported as the extrapolated onset temperatures. FIGS. 11-20 depict the DSC thermograms for Forms A, B, C, D, E, F, G, H and I.

Thermogravimetric Analysis (TGA).

TGA analyses were performed on a TA Discovery Thermogravimetric Analyzer. Approximately 2-10 mg of accurately weighed sample was placed on a pan and loaded into the TGA furnace. The sample was heated under nitrogen at a rate of 10° C./min, up to a final temperature of 300° C. FIGS. 21-28 depict the TGA thermograms for Forms A, B, C, D, E, H and I.

Dynamic Vapor Sorption (DVS).

Hygroscopicity was determined on a Surface Measurement Systems DVS. A sample size of 5-20 mg was loaded into the DVS instrument sample pan and the sample was analyzed on a DVS automated sorption analyzer at room temperature. The relative humidity was increased from 0% to 90% RH at 10% RH step, then decreased in a similar manner to accomplish a full adsorption/desorption cycle. FIGS. 29-33 depict the DVS isotherm plots of Forms A, C, D, E, and I.

Nuclear Magnetic Resonance (NMR).

$^1$H NMR spectra were obtained on a Bruker 300 MHz NMR spectrometer. Samples were dissolved in DMSO-$d_6$ and analyzed with 64 scans. FIGS. 34-41 depict the NMR spectra of Forms A, B, C, D, E, F, G, and I.

Karl Fischer (KF).

Water content was measured using a Metrohm KF coulometric oven titrator equipped with an oven sample processor. The oven temperature was set as 190° C.

Characterization data for crystalline forms of Compound 1 are summarized in Table 7.

TABLE 7

Summary of Characterization Data for Crystalline Forms of Compound 1

| Form | Description | Representative conditions | DSC peak (° C.) | TGA loss (wt %)/KF | DVS or other comments |
|---|---|---|---|---|---|
| A | anhydrate | equilibration in all selected solvents | 246 (onset) | ~0.2 (up to 190° C.) | DVS: ~2.5 wt % water uptake up to 90% RH; KF: 0.3 wt % water; NMR: DMSO present |
| B | anhydrate | evaporation from EtOH/water at 50° C. | 44, 242 (onset) | 0.0 (up to 190° C.) | KF: 0.5 wt % water; NMR: no residual EtOH |

TABLE 7-continued

Summary of Characterization Data for Crystalline Forms of Compound 1

| Form | Description | Representative conditions | DSC peak (° C.) | TGA loss (wt %)/KF | DVS or other comments |
|------|-------------|---------------------------|-----------------|---------------------|------------------------|
| C | hydrate | evaporation from THF at 50° C. | 62 (small), ^231, 246 | 0.3 (up to 190° C.) | DVS: ~4.1 wt % water uptake up to 90% RH; KF: 1.4 wt % water; NMR: no residual THF |
| D | anhydrate | evaporation from or recrystallization in DCM at RT or 50° C. | 154, ^171, 230 | 0.2 (up to 190° C.) | DVS: ~2.6 wt % water uptake up to 90% RH; KF: 0.4 wt % water; NMR: no residual DCM |
| E | hydrate | evaporation in THF/water at 50° C. | 66, 214, ^217, 230 | 0.3 (up to 190° C.) | DVS: ~7.5 wt % water uptake up to 90% RH; KF: 1.2 wt % water; NMR: no residual THF |
| F | solvate | Anti-solvent recrystallization in DMSO/ACN | 117, ^134, 238 | n/a | NMR: 6.5 wt % ACN, with DMSO present |
| G | solvate | Anti-solvent recrystallization in DMSO/IPA | 70, 119, ^122, 153, 236 | n/a | NMR: 14.3 wt % IPA, with DMSO present |
| H | solvate/ hydrate | recrystallization in DMSO | Multiple events | 18.7 (up to ~200° C.) | n/a |
| I | isostructural solvate/ hydrate | Form H slurry in water at RT or recrystallization in THF/water | 123, 231, ^233, 241; or 137, 247 (onset) | 13.1 or 10.5 (up to 150° C.) | n/a |

^exothermic peak in DSC thermogram
n/a: not available

Form A.

Form A was designated as the crystalline form of the starting material used for the polymorph screen. Form A has a crystalline XRPD pattern as shown in FIG. 1.

TABLE 8

Form A XRPD Peak List

| Position [°2θ] | d-spacing [Å] | Relative Intensity [%] |
|----------------|---------------|-------------------------|
| 6.19 | 14.2764 | 100.0 |
| 9.33 | 9.4795 | 22.7 |
| 9.64 | 9.1797 | 30.0 |
| 12.39 | 7.1437 | 36.9 |
| 12.49 | 7.0879 | 44.9 |
| 12.59 | 7.0322 | 37.8 |
| 13.11 | 6.7559 | 39.2 |
| 13.25 | 6.6815 | 14.3 |
| 16.31 | 5.4343 | 37.3 |
| 17.97 | 4.9360 | 7.0 |
| 18.70 | 4.7453 | 17.0 |
| 18.84 | 4.7095 | 18.7 |
| 19.09 | 4.6482 | 16.6 |
| 20.92 | 4.2456 | 35.3 |
| 21.35 | 4.1618 | 21.3 |
| 22.00 | 4.0407 | 7.2 |
| 23.17 | 3.8397 | 38.8 |
| 24.02 | 3.7054 | 58.8 |
| 24.34 | 3.6572 | 9.7 |
| 24.94 | 3.5701 | 20.2 |
| 26.44 | 3.3708 | 36.6 |
| 26.88 | 3.3168 | 9.8 |
| 29.14 | 3.0646 | 12.8 |
| 30.04 | 2.9745 | 10.2 |

Figure 11:
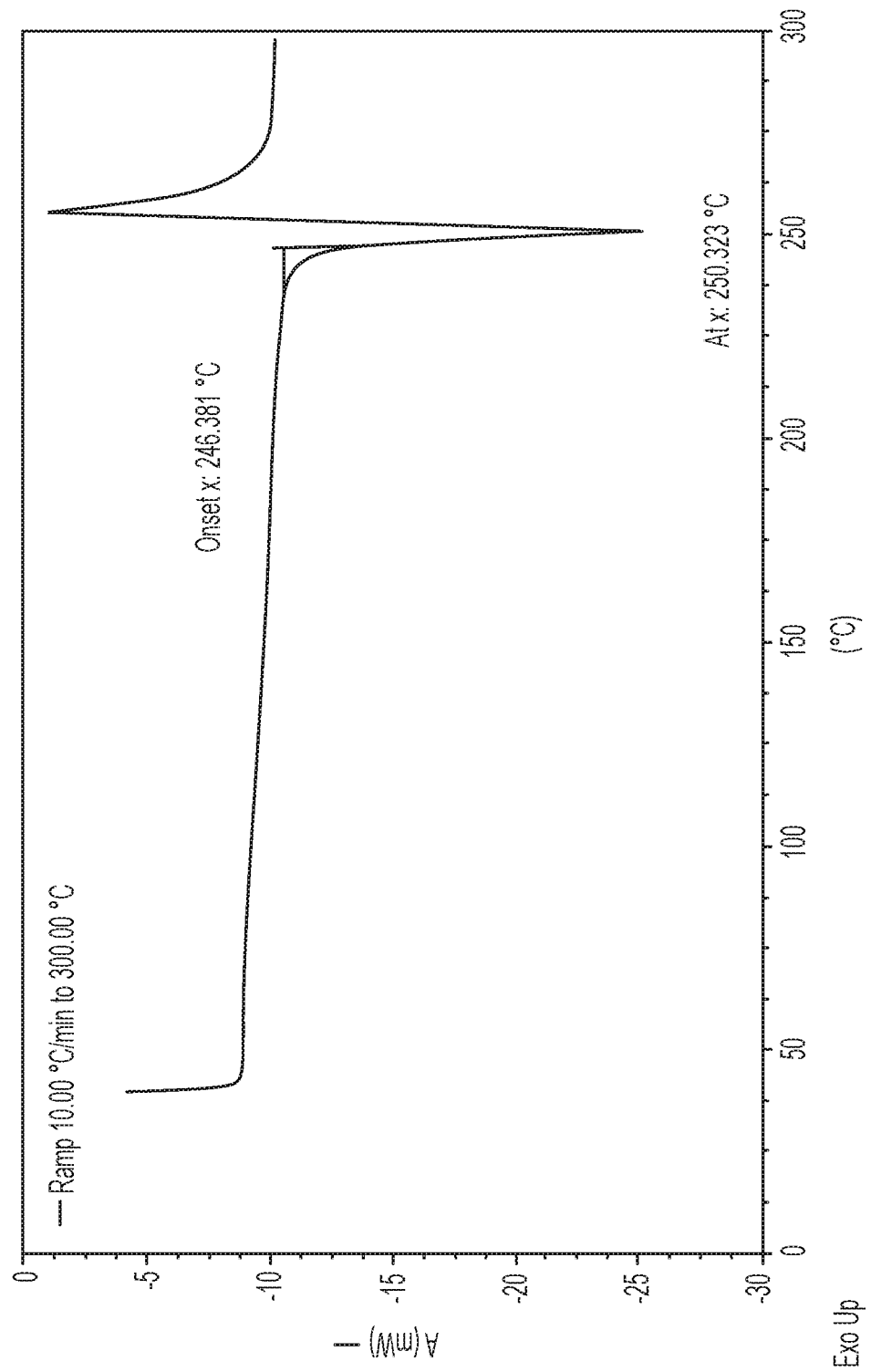
FIG. 11 depicts a DSC thermogram of Form A of Compound 1.
Figure 21:
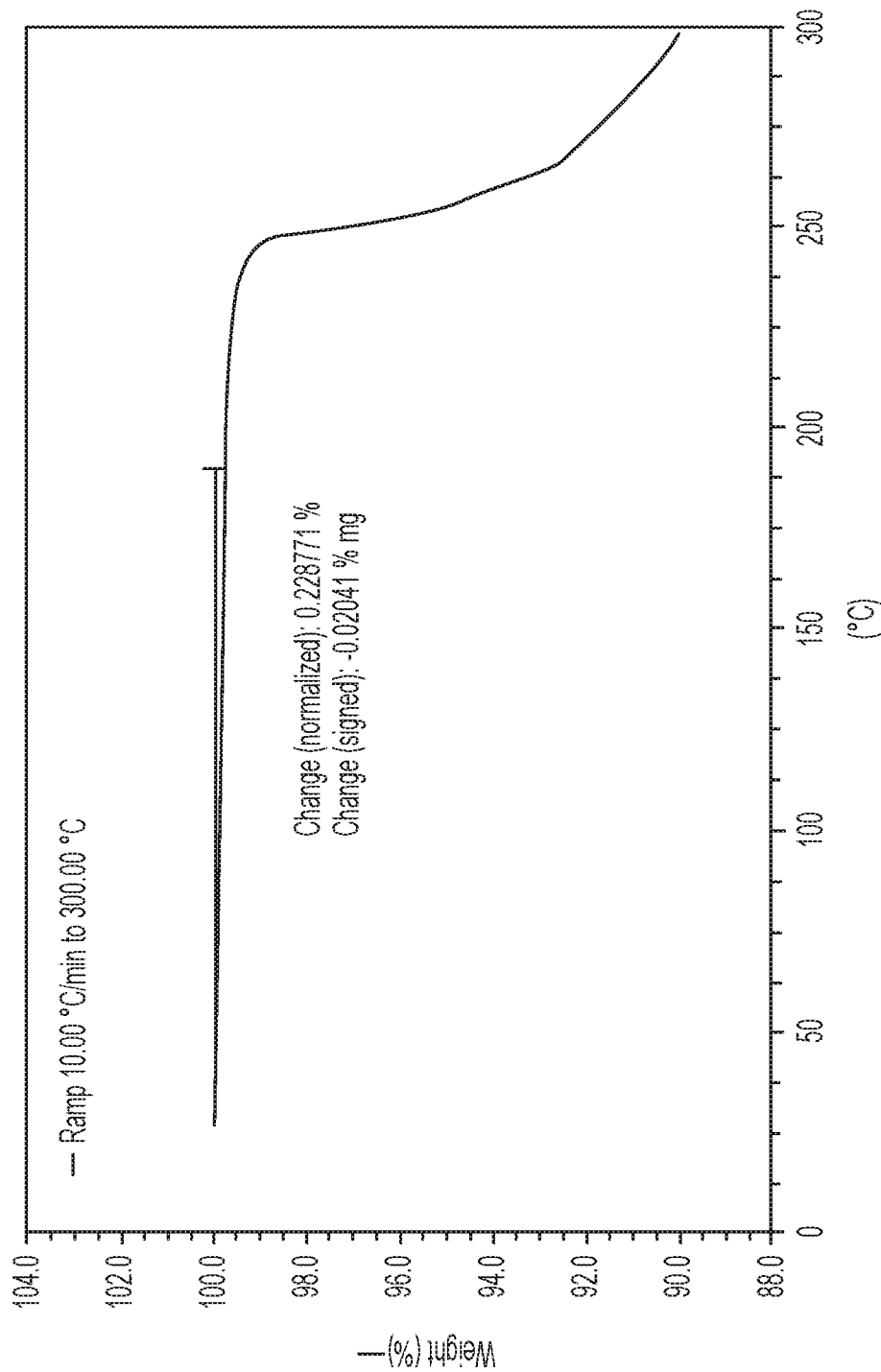
FIG. 21 depicts a TGA thermogram of Form A of Compound 1.
Figure 34:
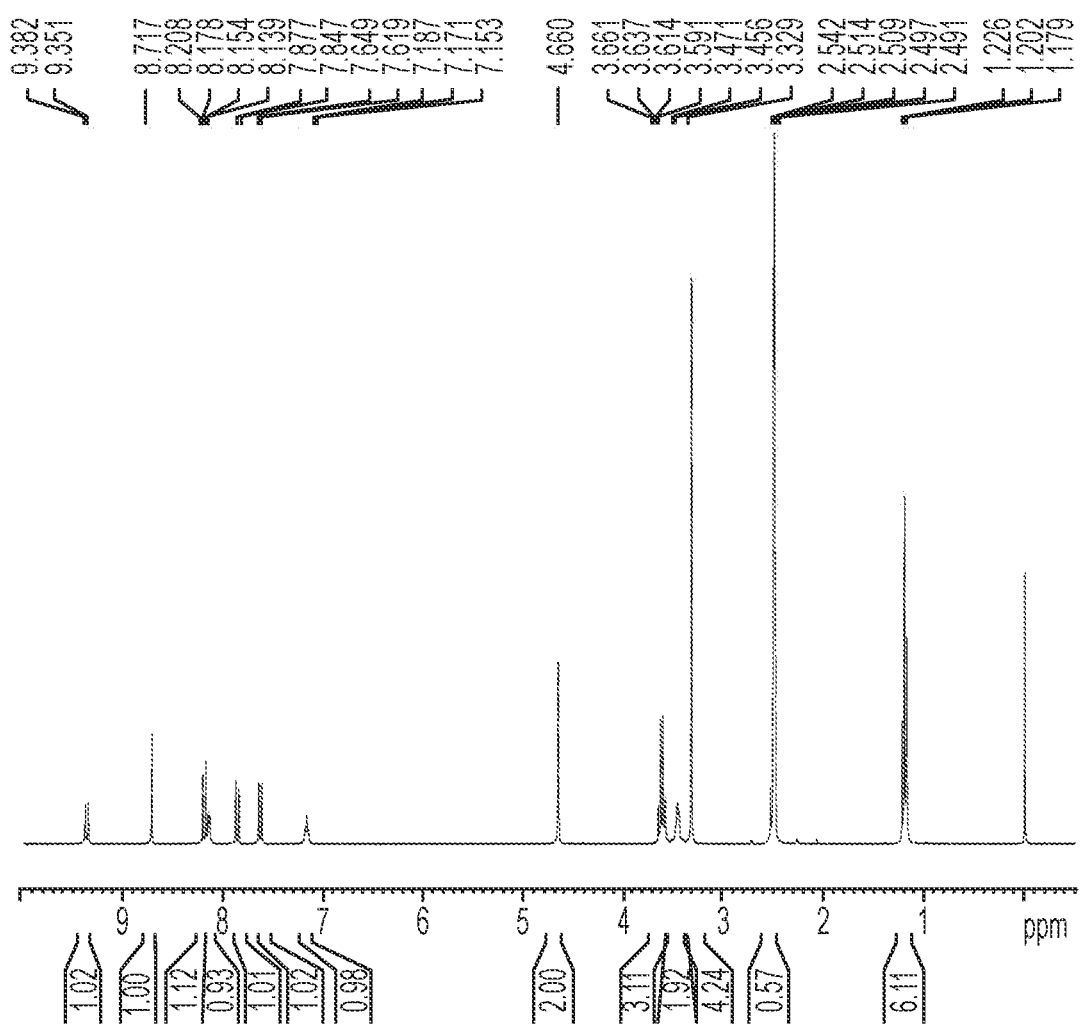
FIG. 34 depicts a $^1$H NMR spectrum of Form A of Compound 1.
Figure 42A:
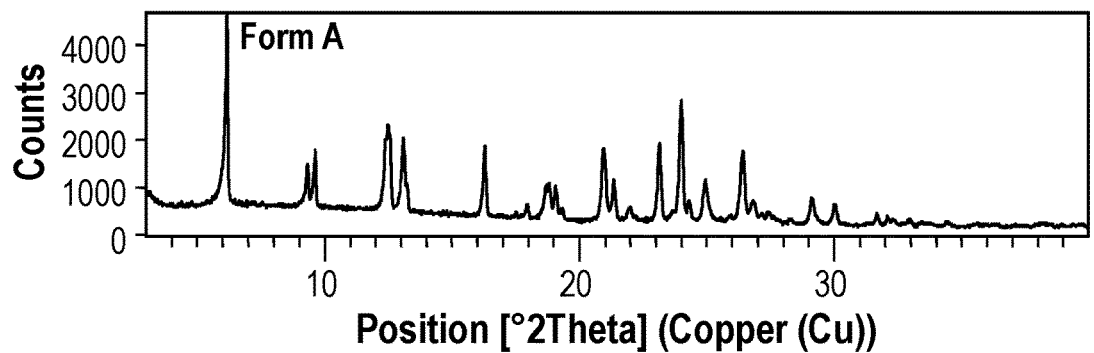
FIG. 42 depicts a comparison of XRPD patterns of Form A of Compound 1 (a) as-is, (b) after DVS, (c) after compression at 2000 psi, and (d) after heating at 190° C.
Figure 42B:
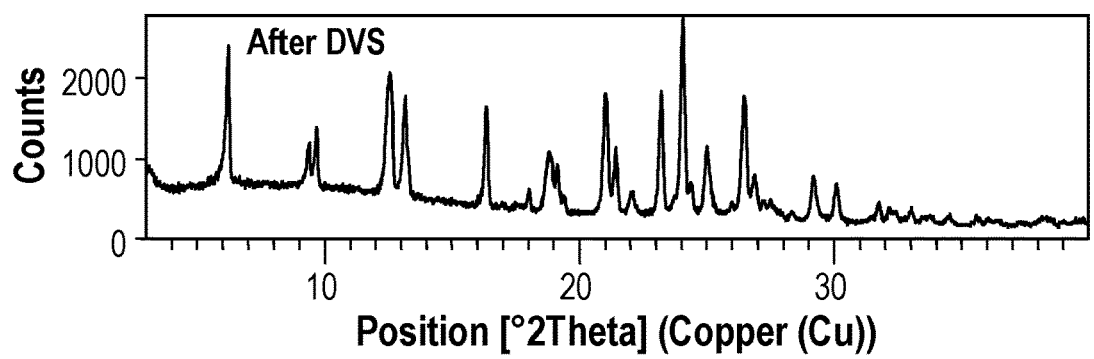

The DSC and TGA thermograms of Form A are shown in FIG. 11 and FIG. 21, respectively. The DSC thermogram showed a melting/decomposition event with an onset temperature of 246° C. TGA weight loss of approximately 0.2% was observed up to 190° C., with additional weight loss observed before decomposition. The $^1$H NMR spectrum of Form A is consistent with the structure of Compound 1, with some residual DMSO (FIG. 34). DMSO content was difficult to quantify due to overlapping signals, but seemed to correspond to the TGA weight loss observed at higher temperatures. The DVS isothermal plot of Form A in shown in FIG. 29. Form A is slightly hygroscopic, with about 2.5 wt % water uptake between 0 and 90% RH. No form change was observed by XRPD after DVS experiment (FIG. 42(b)). The KF result for Form A showed about 0.3 wt % of water. These results suggest Form A is an anhydrate of Compound 1.

Figure 42C:
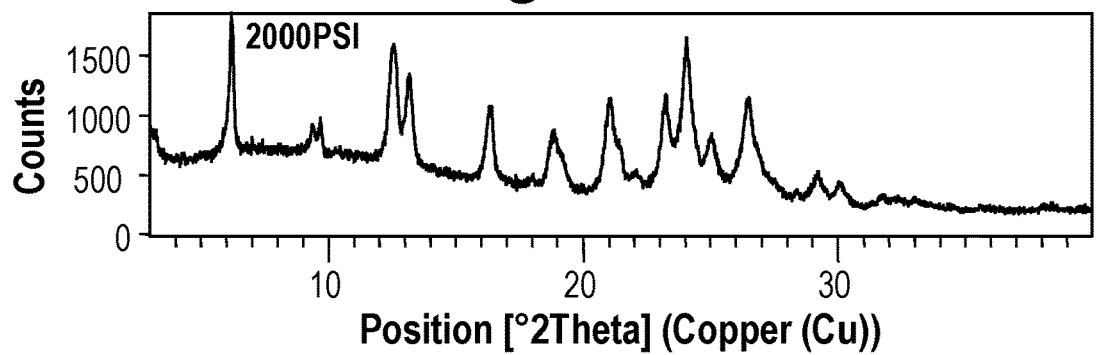
Figure 42D:
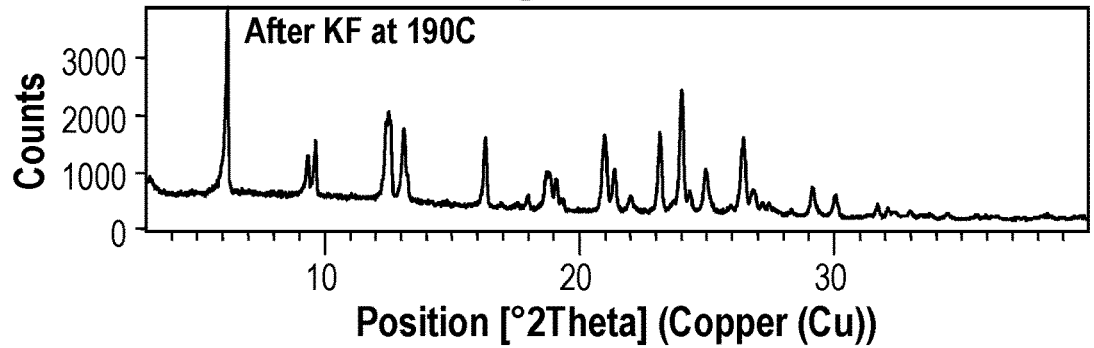

The stability of Form A was further characterized by compression test and form transfer experiments (Table 6). Upon application of 2000-psi pressure for about 1 minute, the material was still Form A, with broader diffraction peaks (FIG. 42(c)). The solid obtained upon heating in the KF oven at 190° C. was confirmed to be Form A (FIG. 42(d)). Results from solvent mediated transformation experiments further confirmed that Form A is the most stable anhydrous form of Compound 1.

Form B.

Figure 2:
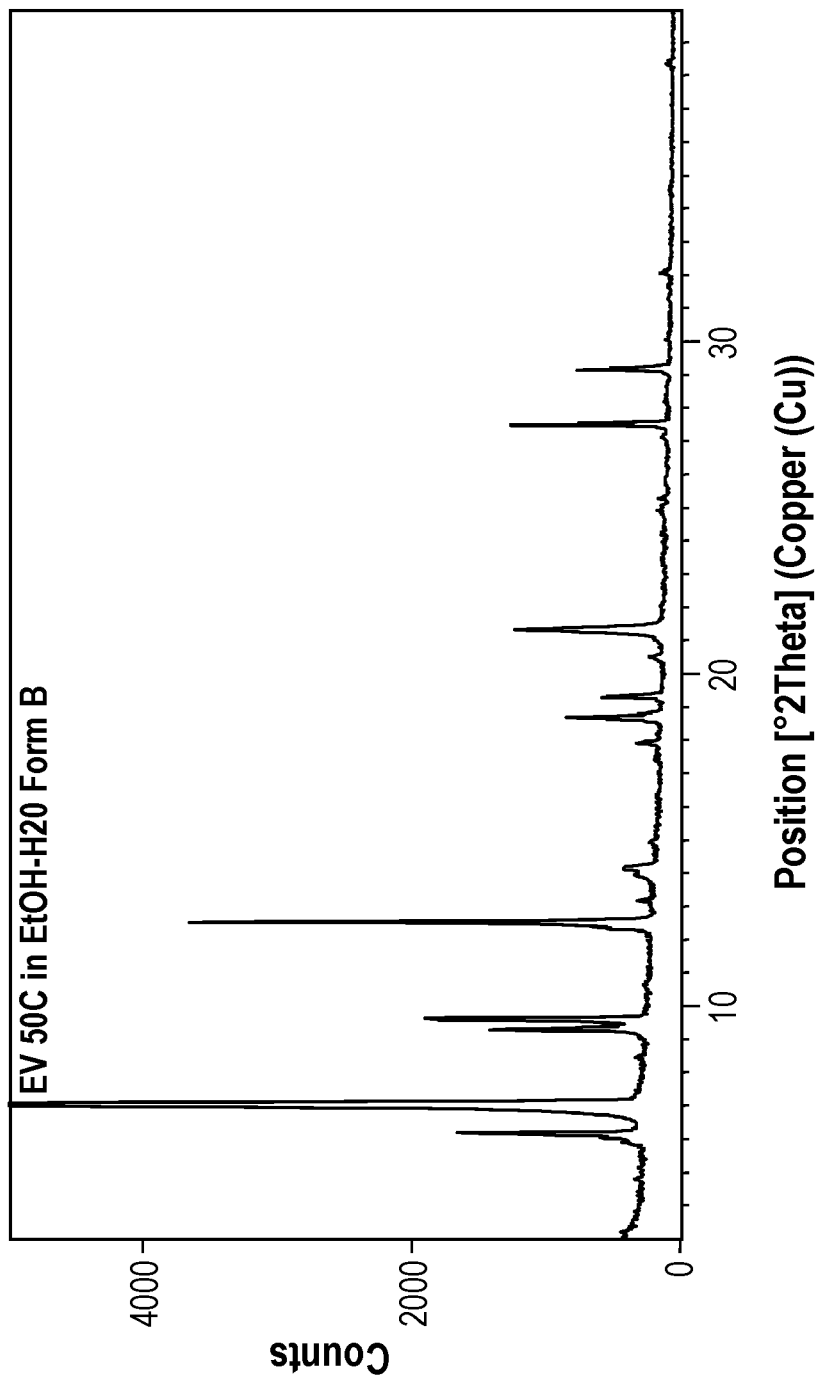
FIG. 2 depicts an XRPD pattern of Form B of Compound 1.

Form B was generated by evaporation experiment in EtOH/water (1:1) at 50° C. Form B has a crystalline XRPD pattern as shown in FIG. 2.

TABLE 9

Form B XRPD Peak List

| Position [°2θ] | d-spacing [Å] | Relative Intensity [%] |
|----------------|---------------|-------------------------|
| 6.19 | 14.2879 | 21.7 |
| 7.04 | 12.5629 | 100.0 |

TABLE 9-continued

Form B XRPD Peak List

| Position [°2θ] | d-spacing [Å] | Relative Intensity [%] |
|---|---|---|
| 9.30 | 9.5103 | 19.7 |
| 9.58 | 9.2284 | 25.9 |
| 9.64 | 9.1760 | 27.6 |
| 12.34 | 7.1720 | 5.6 |
| 12.54 | 7.0607 | 57.5 |
| 14.16 | 6.2557 | 4.1 |
| 17.92 | 4.9501 | 3.2 |
| 18.69 | 4.7487 | 12.0 |
| 19.33 | 4.5922 | 6.4 |
| 21.34 | 4.1645 | 18.1 |
| 27.52 | 3.2415 | 8.5 |
| 29.18 | 3.0601 | 4.9 |

Figure 12:
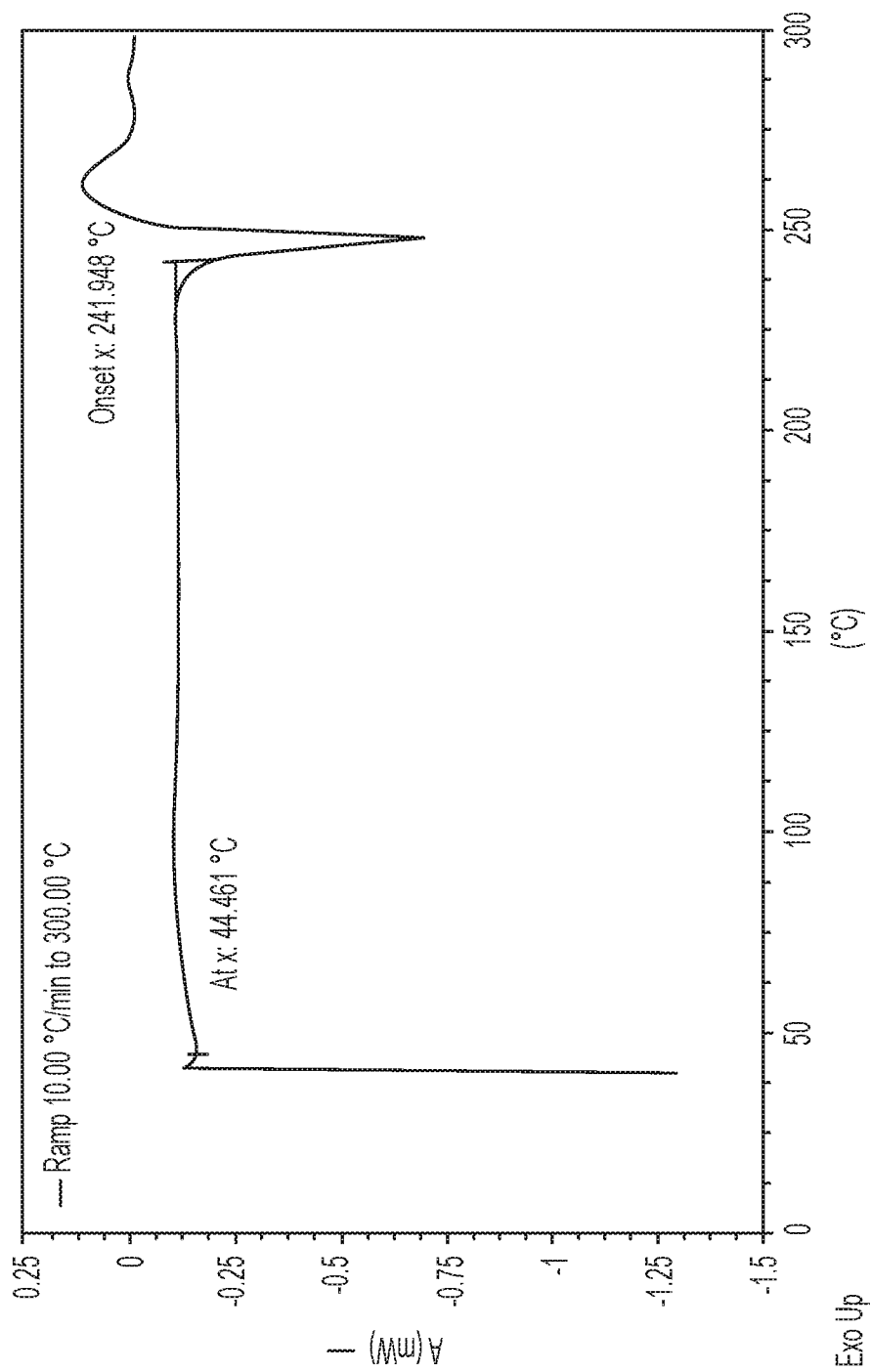
FIG. 12 depicts a DSC thermogram of Form B of Compound 1.
Figure 22:
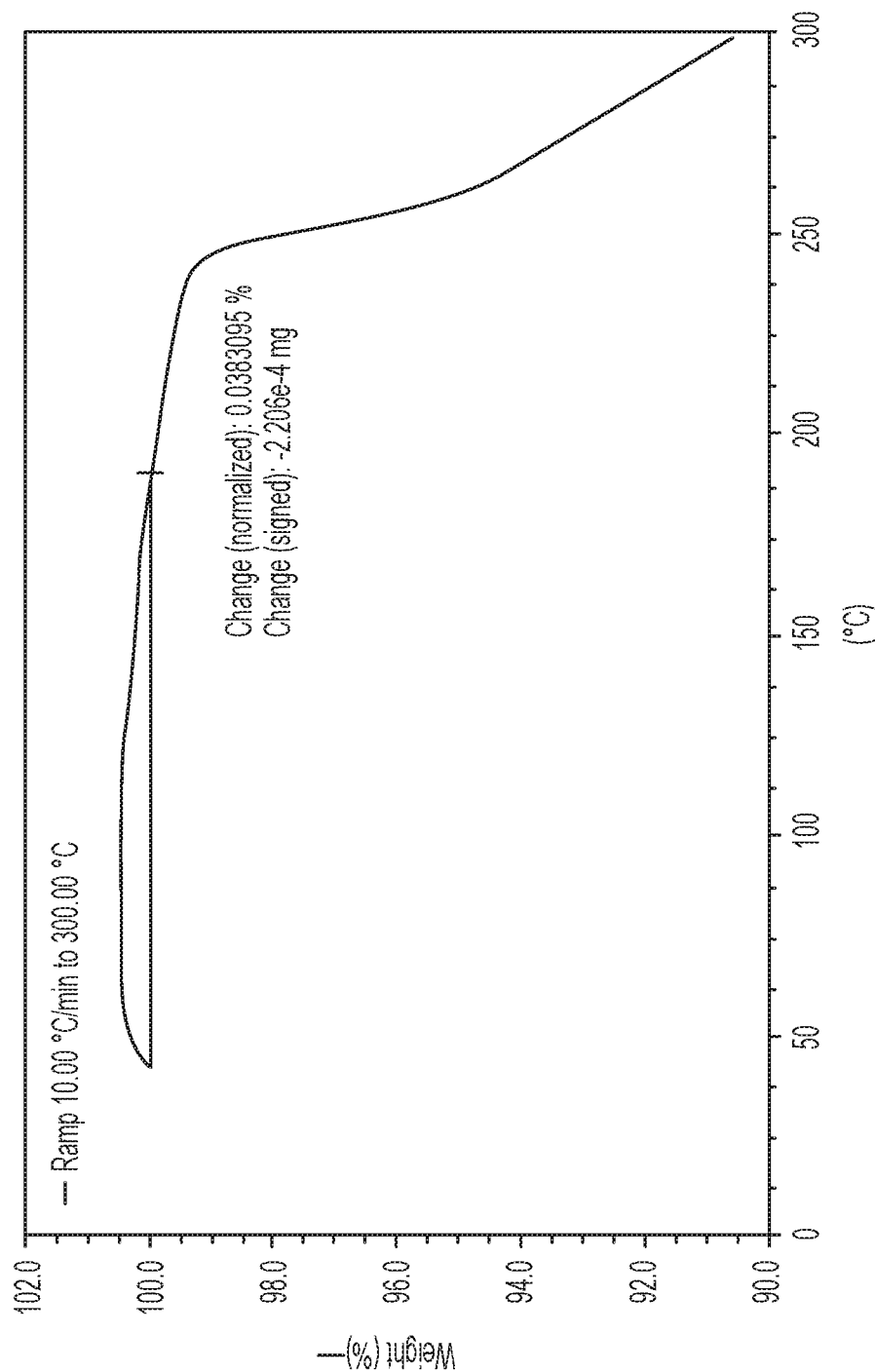
FIG. 22 depicts a TGA thermogram of Form B of Compound 1.
Figure 35:
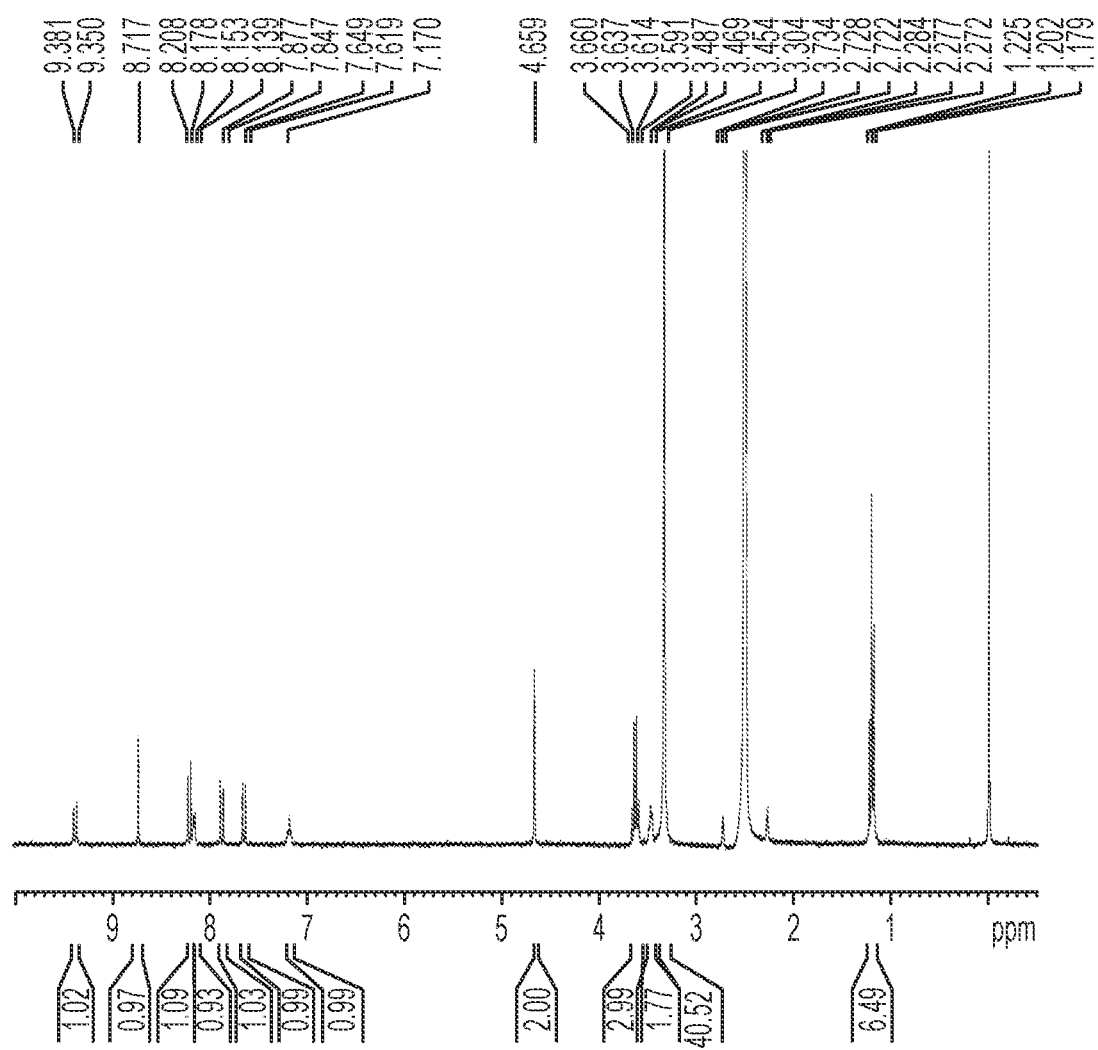
FIG. 35 depicts a $^1$H NMR spectrum of Form B of Compound 1.

The DSC and TGA thermograms of Form B are shown in FIG. 12 and FIG. 22, respectively. The DSC thermogram showed a melting/decomposition event with an onset temperature of 243° C. Minimal TGA weight loss was observed for Form B up to 190° C., with additional weight loss observed before decomposition. The $^1$H NMR spectrum for the Form B sample out evaporation in EtOH/water at 50° C. is consistent with the structure of Compound 1, without detectable residual EtOH (FIG. 35). The KF result for this Form B sample showed about 0.5 wt % of water. These observations suggested that Form B is an anhydrate.

Figure 43A:
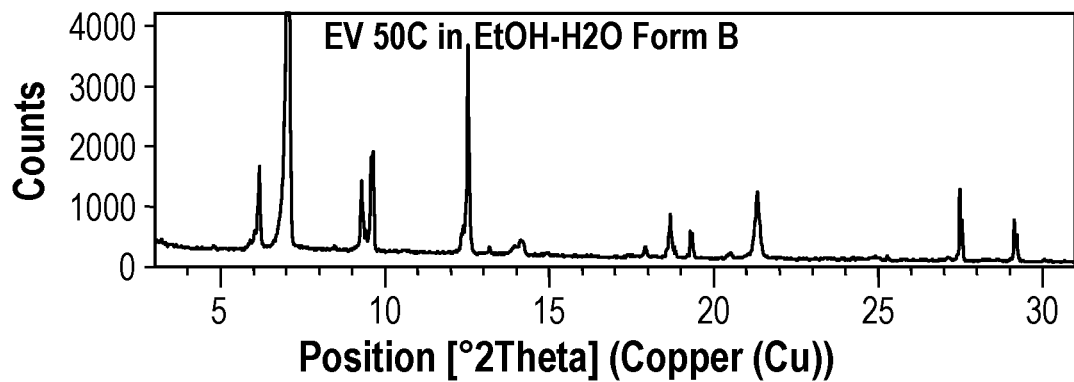
FIG. 43 depicts a comparison of XRPD patterns of Form B of Compound 1 (a) as-is, (b) after compression at 2000 psi, and (c) after heating at 190° C.
Figure 43B:
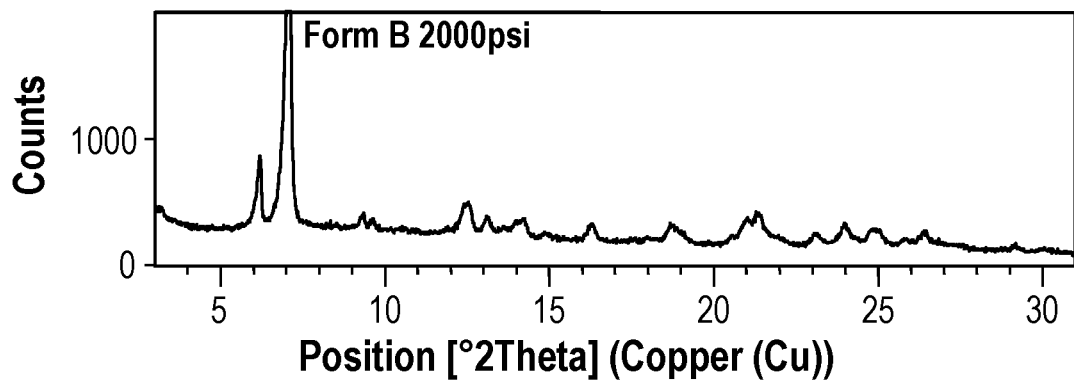
Figure 43C:
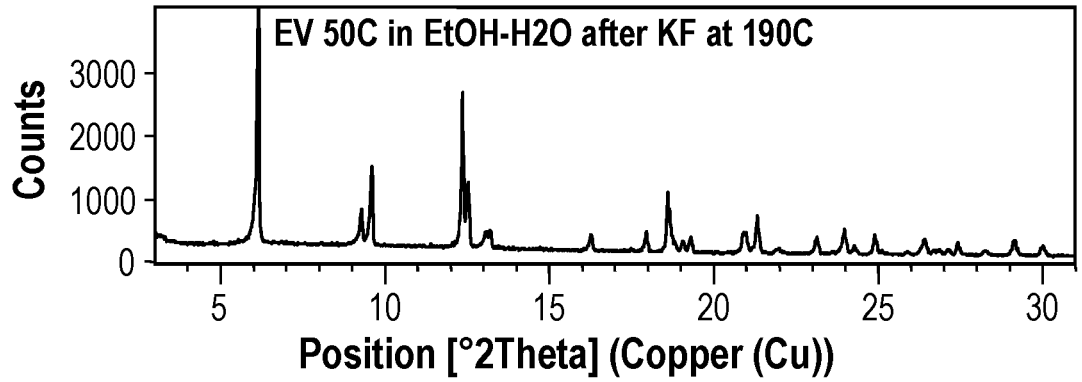

The stability of Form B was further characterized by compression test and form transfer experiments (Table 6). Upon application of 2000-psi pressure for about 1 minute, the material was shown to be mainly Form B, with a small amount of Form A (FIG. 43(b)). The solid obtained upon heating Form B in the KF oven at 190° C. was confirmed to be Form A (FIG. 43(c)). A couple of Form B samples were also observed to convert to Form A upon storage in vials. These results along with the solvent mediated transformation experiment confirmed that Form B is a metastable anhydrate.

Form C.

Figure 3:
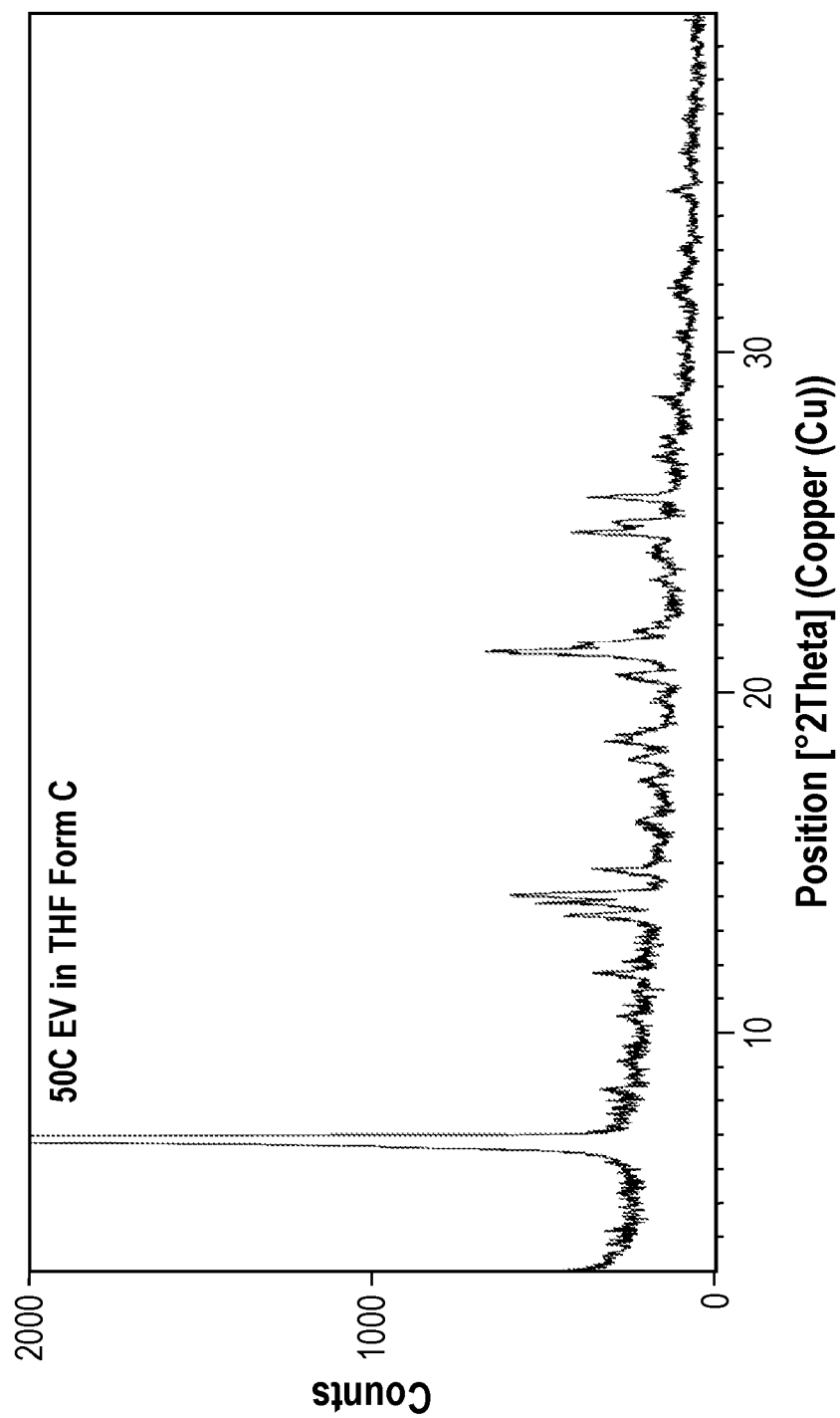
FIG. 3 depicts an XRPD pattern of Form C of Compound 1.

Form C was generated by evaporation experiment in THF at 50° C. Form C has a crystalline XRPD pattern as shown in FIG. 3.

TABLE 10

Form C XRPD Peak List

| Position [°2θ] | d-spacing [Å] | Relative Intensity [%] |
|---|---|---|
| 7.03 | 12.5770 | 100.0 |
| 13.54 | 6.5377 | 3.5 |
| 13.91 | 6.3652 | 4.7 |
| 14.13 | 6.2694 | 5.9 |
| 14.88 | 5.9550 | 2.2 |
| 18.63 | 4.7628 | 2.5 |
| 20.56 | 4.3205 | 2.1 |
| 21.25 | 4.1804 | 7.0 |
| 21.51 | 4.1308 | 3.6 |
| 24.73 | 3.5998 | 4.2 |
| 25.02 | 3.5587 | 2.6 |
| 25.77 | 3.4575 | 3.8 |

Figure 13:
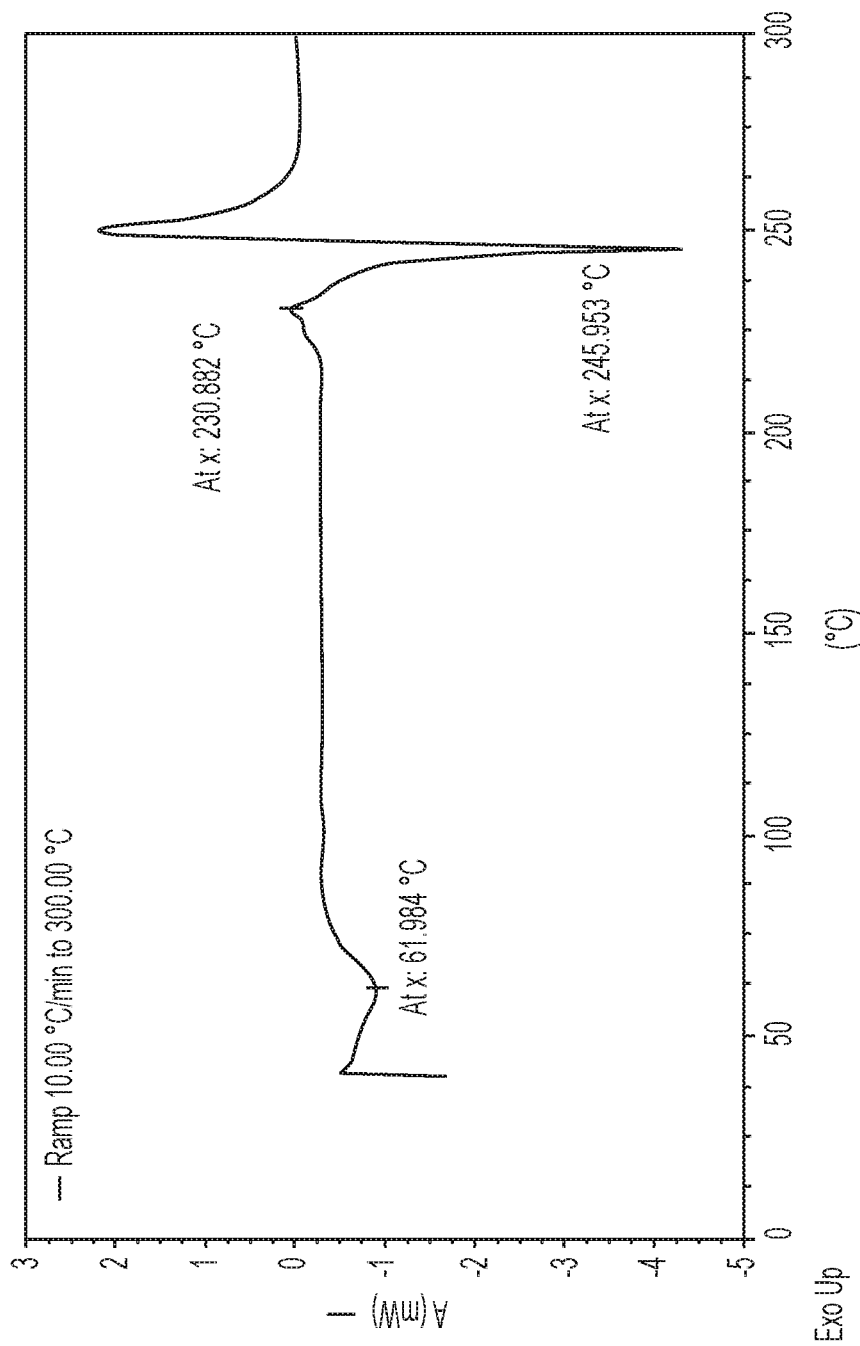
FIG. 13 depicts a DSC thermogram of Form C of Compound 1.
Figure 23:
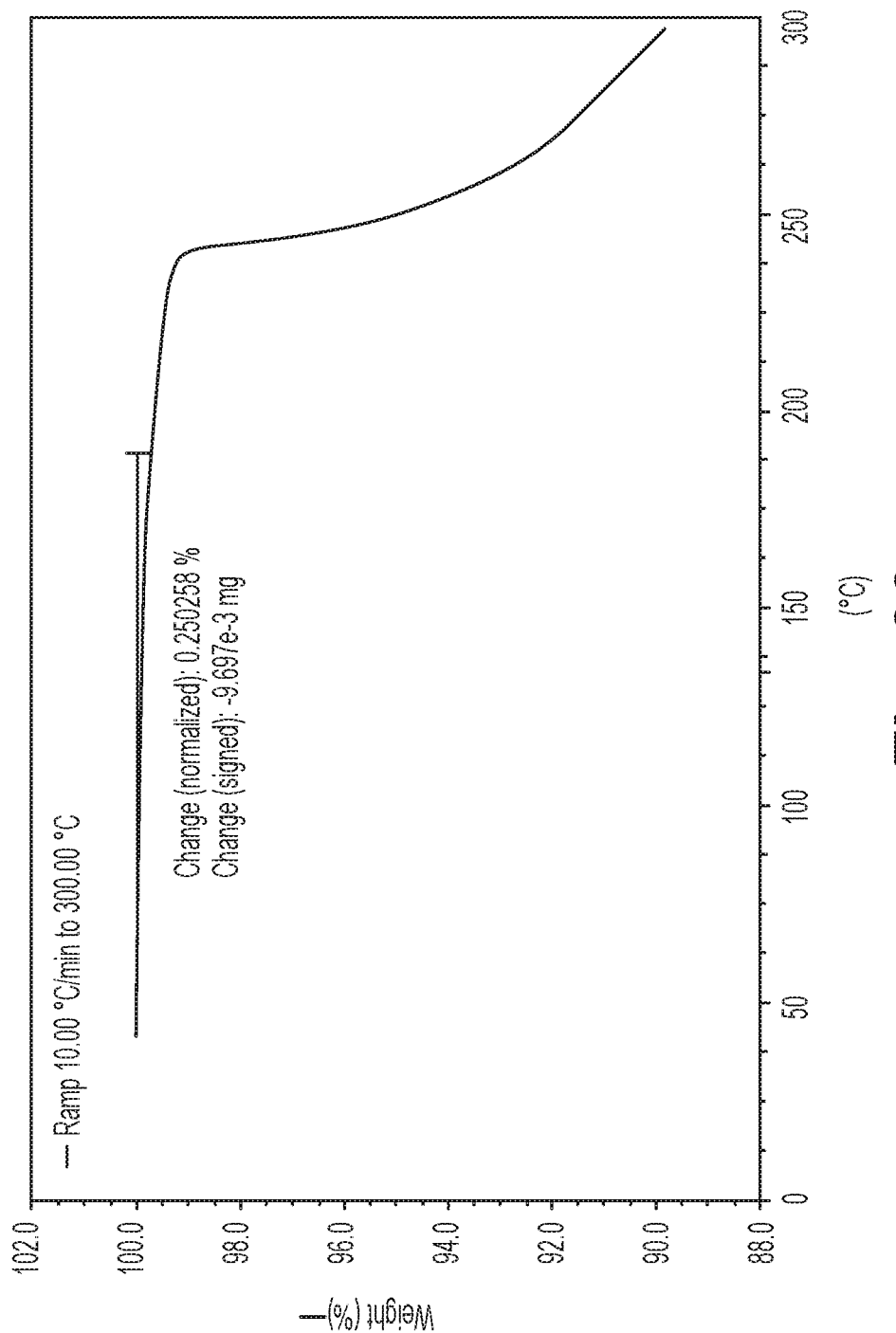
FIG. 23 depicts a TGA thermogram of Form C of Compound 1.
Figure 30:
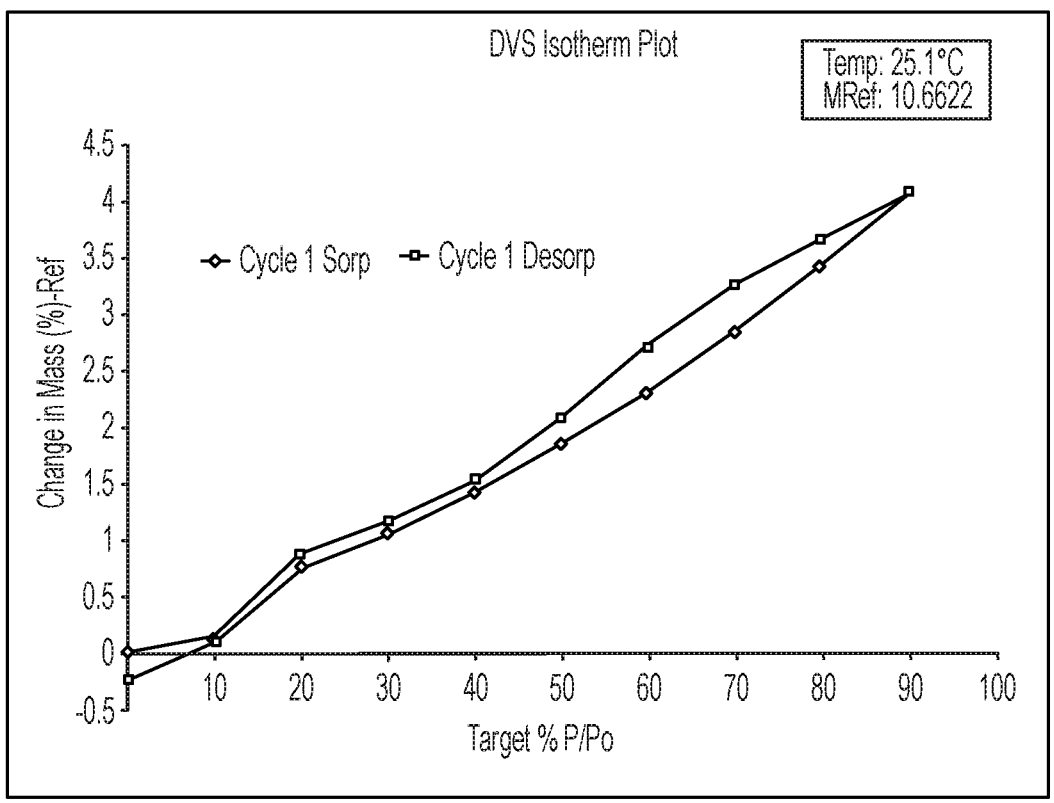
FIG. 30 depicts a DVS isotherm plot of Form C of Compound 1.
Figure 36:
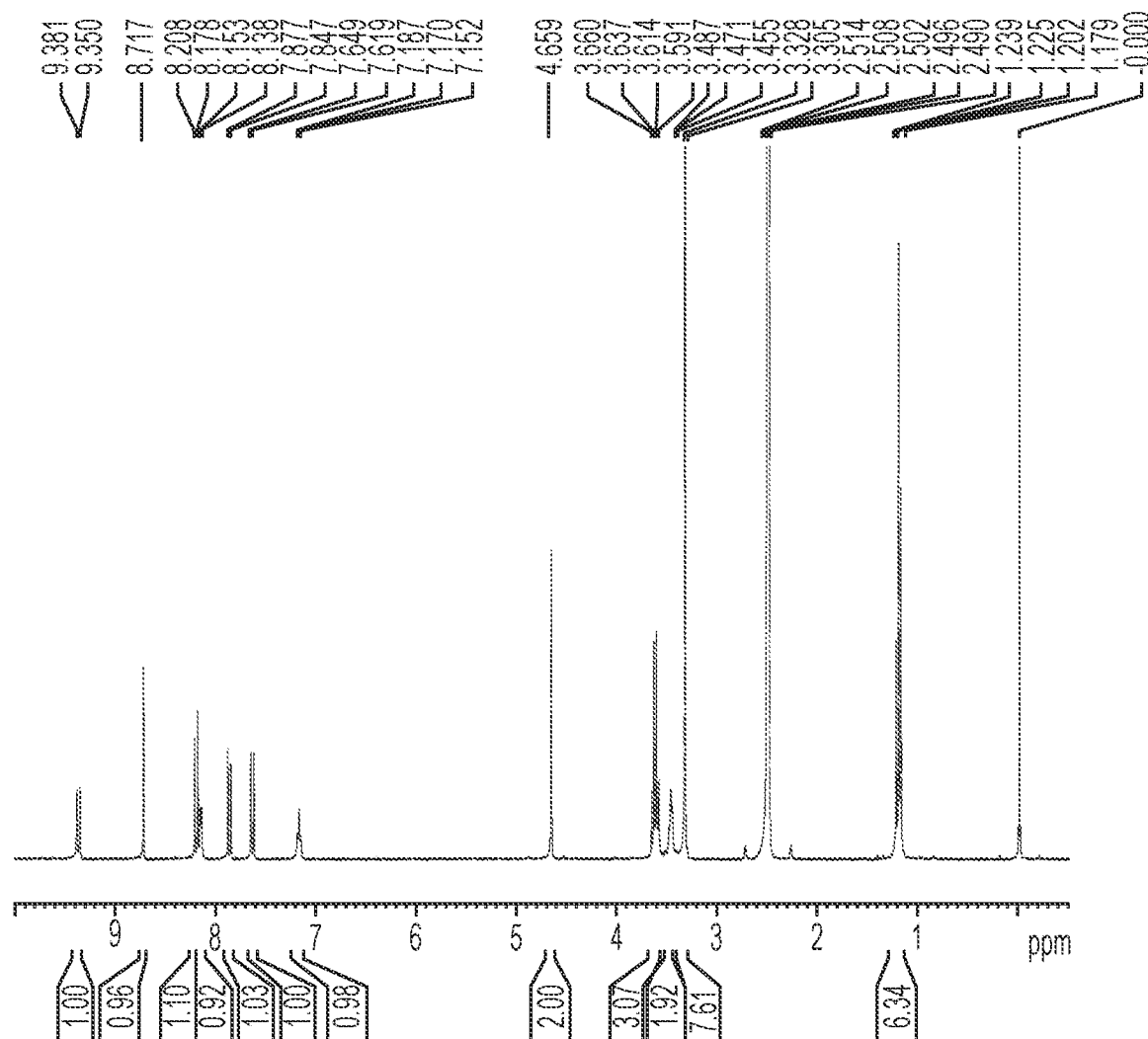
FIG. 36 depicts a $^1$H NMR spectrum of Form C of Compound 1.

The DSC and TGA thermograms of Form C are shown in FIG. 13 and FIG. 23, respectively. About 0.3% TGA weight loss was observed up to 190° C. The DSC thermogram showed several thermal events. A small endotherm around 62° C. was attributed to loss of water. The exothermic peak around 231° C. was most likely attributed to recrystallization of the dehydrated material into Form A which melted at 246° C. The KF result for Form C showed about 1.4% of water. No significant degradation or residual solvent was observed by $^1$H NMR (FIG. 36). The DVS isothermal plot of Form C is shown in FIG. 30. Form C is hygroscopic, with approximately 4.1 wt % water uptake observed between 0 and 90% RH. These observations suggested that Form C is a channel hydrate.

Figure 44A:
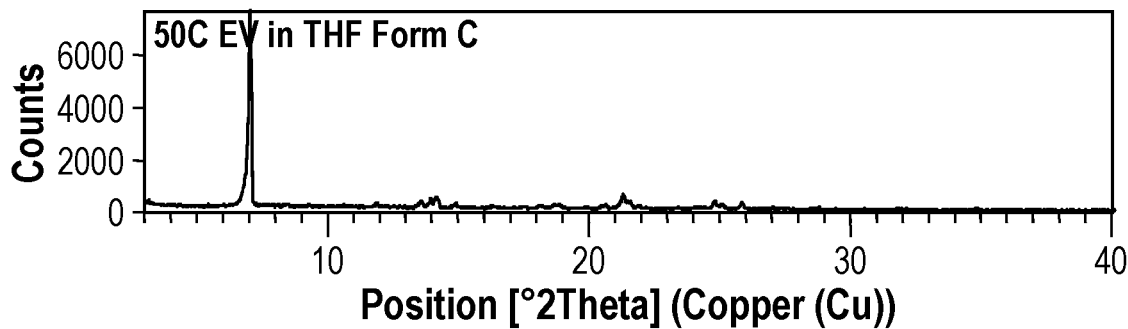
FIG. 44 depicts a comparison of XRPD patterns of Form C of Compound 1 (a) as-is, (b) after DVS, (c) after compression at 2000 psi, and (d) after heating at 190° C.
Figure 44B:
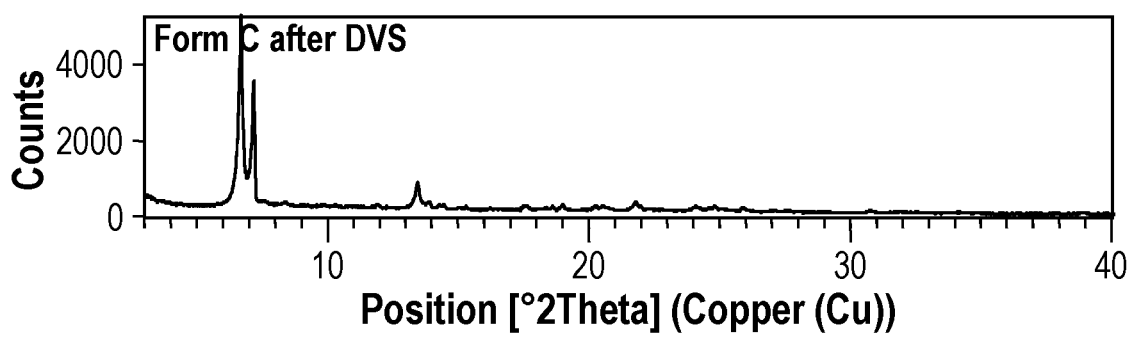
Figure 44C:
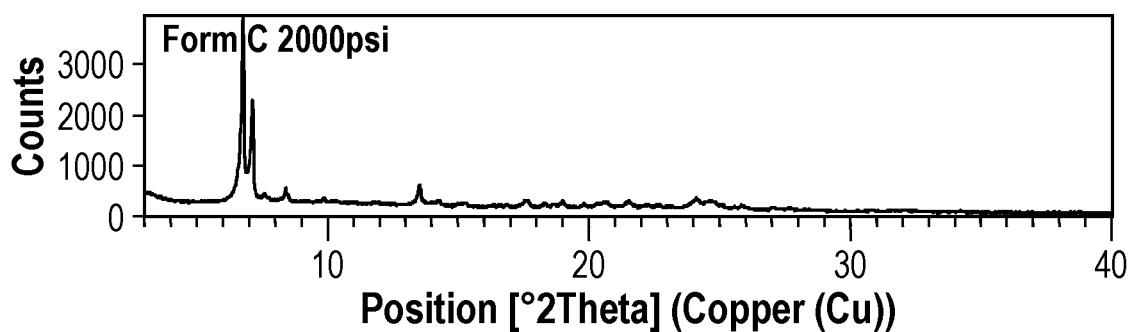
Figure 44D:
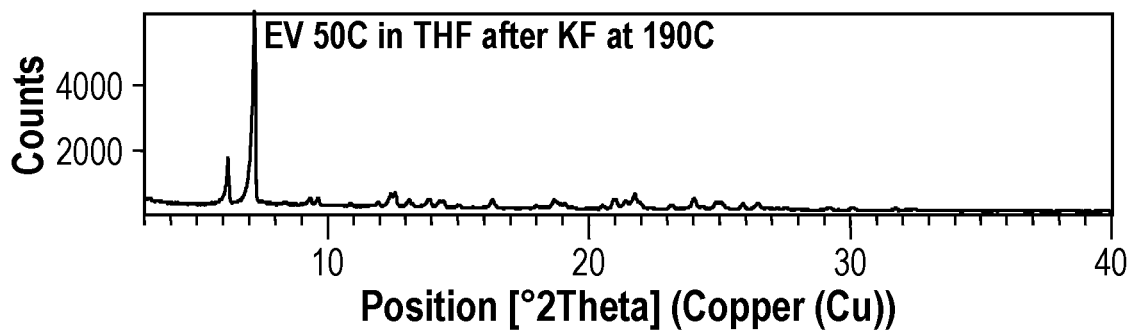

The stability of Form C was further characterized by compression test and form transfer experiments (Table 6). Upon application of 2000-psi pressure for about 1 minute, Form C seemed to partially convert to Form E (FIG. 44(c)). The XRPD pattern also contained some additional peaks, which might be attributed to another metastable form that was not discovered by other experiments in this study. Similar form change was observed for solids recovered after DVS experiment (FIG. 44(b)). The solid obtained upon heating Form C in the KF oven at 190° C. was a mixture of Form A and Form C with diffraction peaks of Form C shifting to higher 2θ angles (FIG. 44(d)). Form C was also observed to convert to Form E upon slurry in THF/water (5:95). These results suggested that Form C is a metastable hydrate.

Form D.

Figure 4:
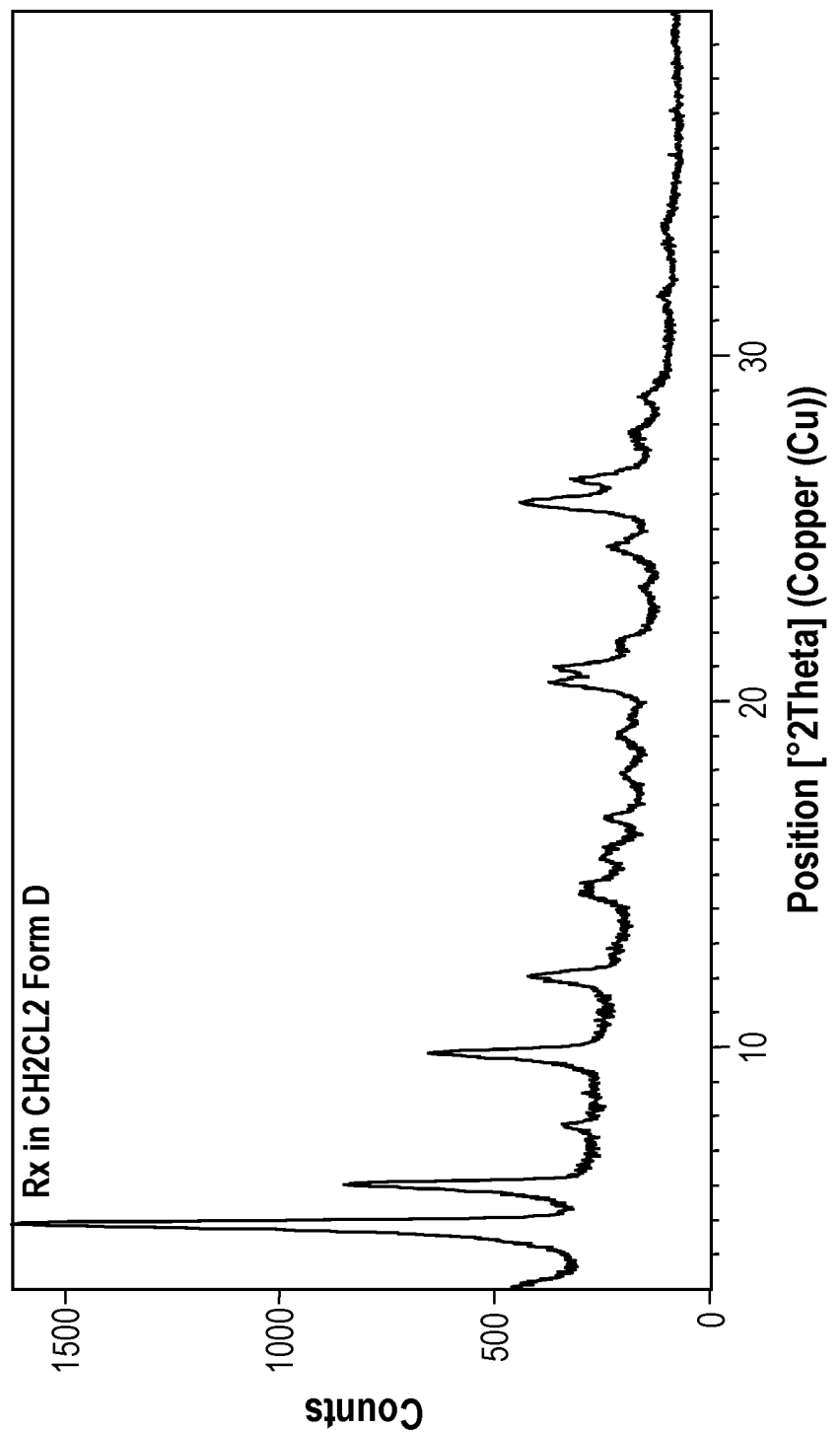
FIG. 4 depicts an XRPD pattern of Form D of Compound 1.

Form D was generated by evaporation or recrystallization experiment in DCM at room temperature or 50° C. Form D has a crystalline XRPD pattern as shown in FIG. 4.

TABLE 11

Form D XRPD Peak List

| Position [°2θ] | d-spacing [Å] | Relative Intensity [%] |
|---|---|---|
| 4.89 | 18.0774 | 100.0 |
| 6.01 | 14.6968 | 43.3 |
| 6.10 | 14.4888 | 34.3 |
| 7.73 | 11.4313 | 5.5 |
| 9.83 | 8.9996 | 31.2 |
| 12.06 | 7.3416 | 15.8 |
| 14.44 | 6.1322 | 8.1 |
| 16.64 | 5.3280 | 5.9 |
| 20.55 | 4.3230 | 17.1 |
| 20.98 | 4.2353 | 16.1 |
| 21.69 | 4.0973 | 5.8 |
| 24.49 | 3.6346 | 7.6 |
| 25.75 | 3.4593 | 23.1 |
| 26.42 | 3.3731 | 13.6 |

Figure 14:
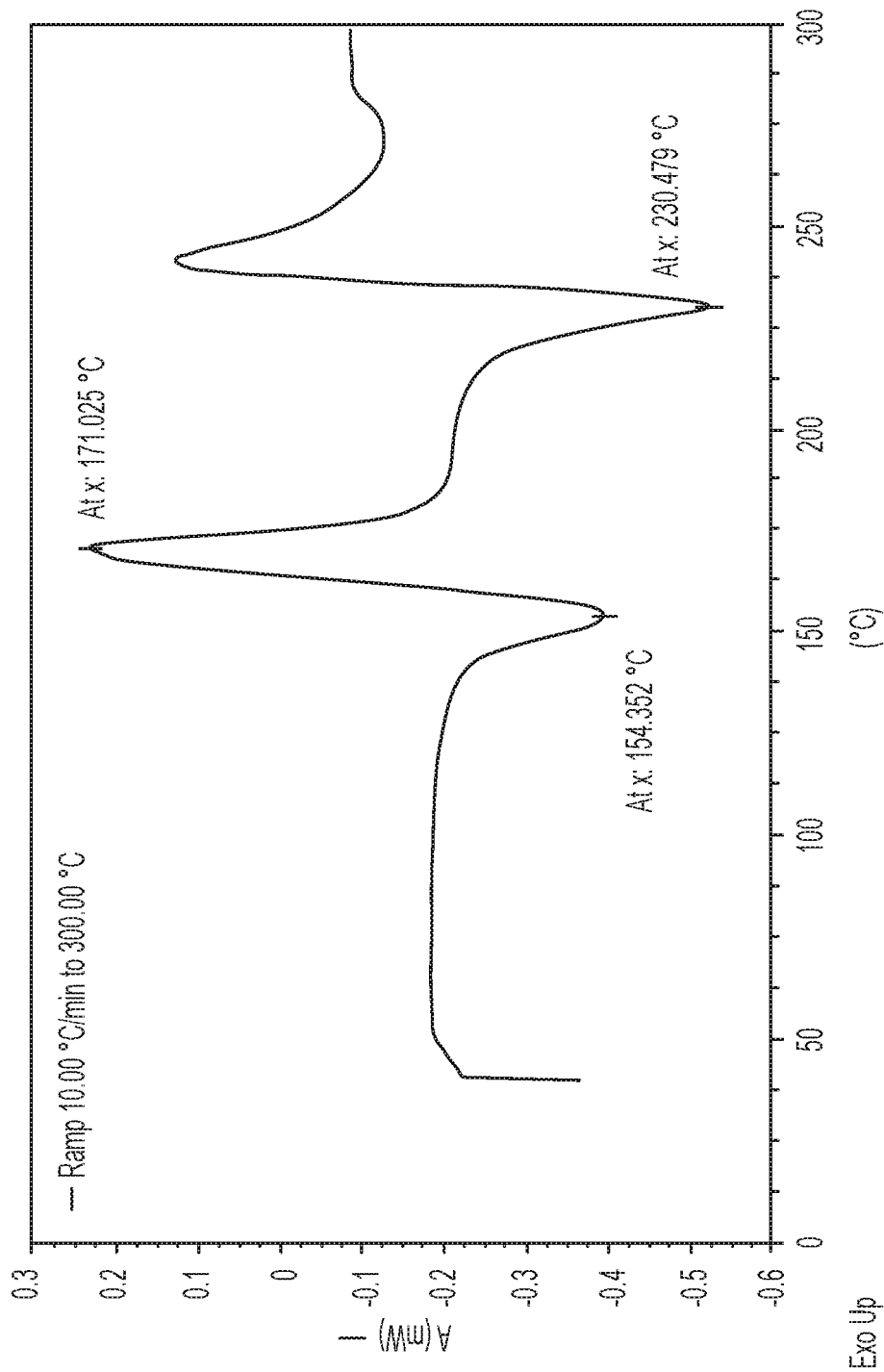
FIG. 14 depicts a DSC thermogram of Form D of Compound 1.
Figure 24:
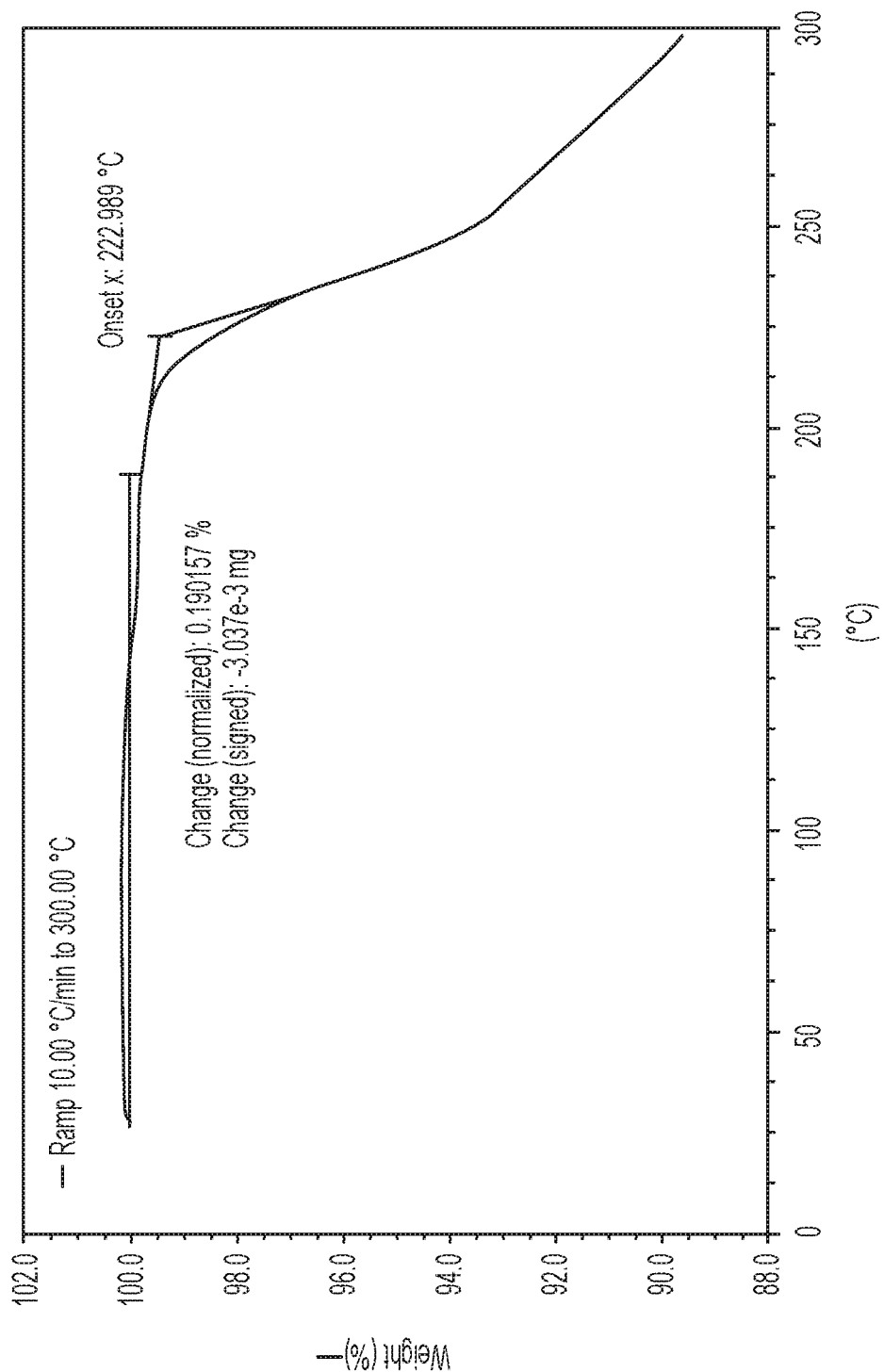
FIG. 24 depicts a TGA thermogram of Form D of Compound 1.
Figure 31:
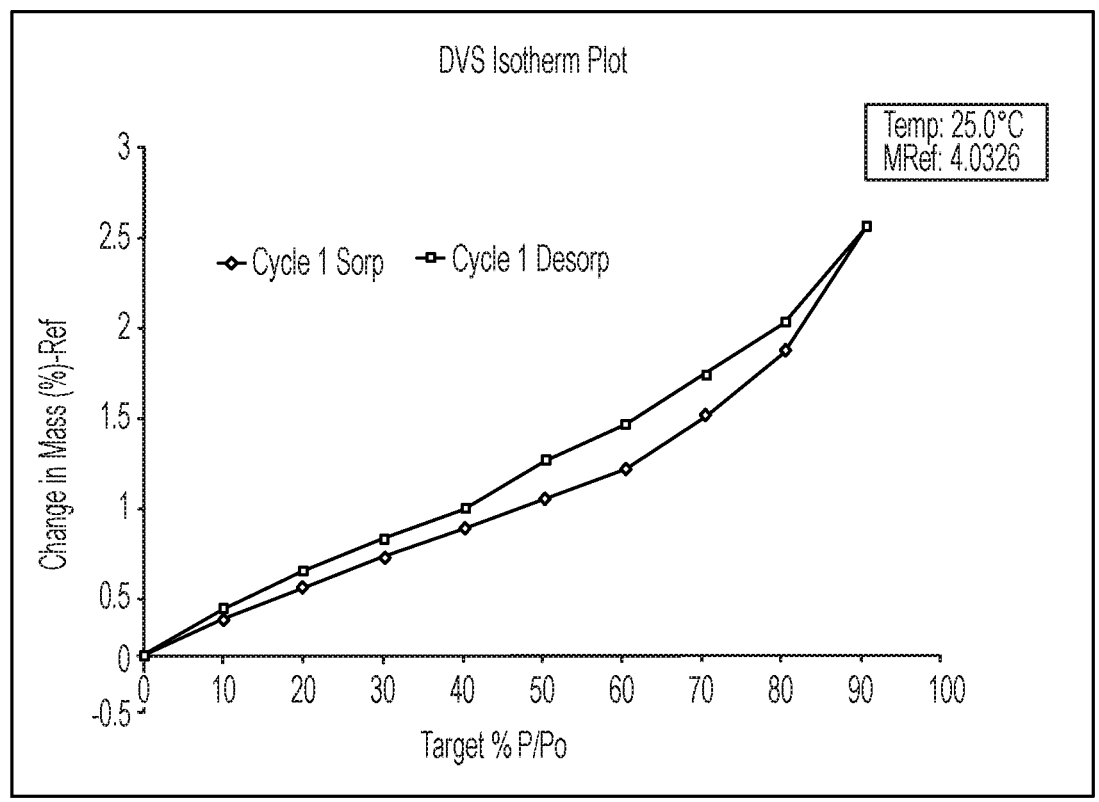
FIG. 31 depicts a DVS isotherm plot of Form D of Compound 1.
Figure 32:
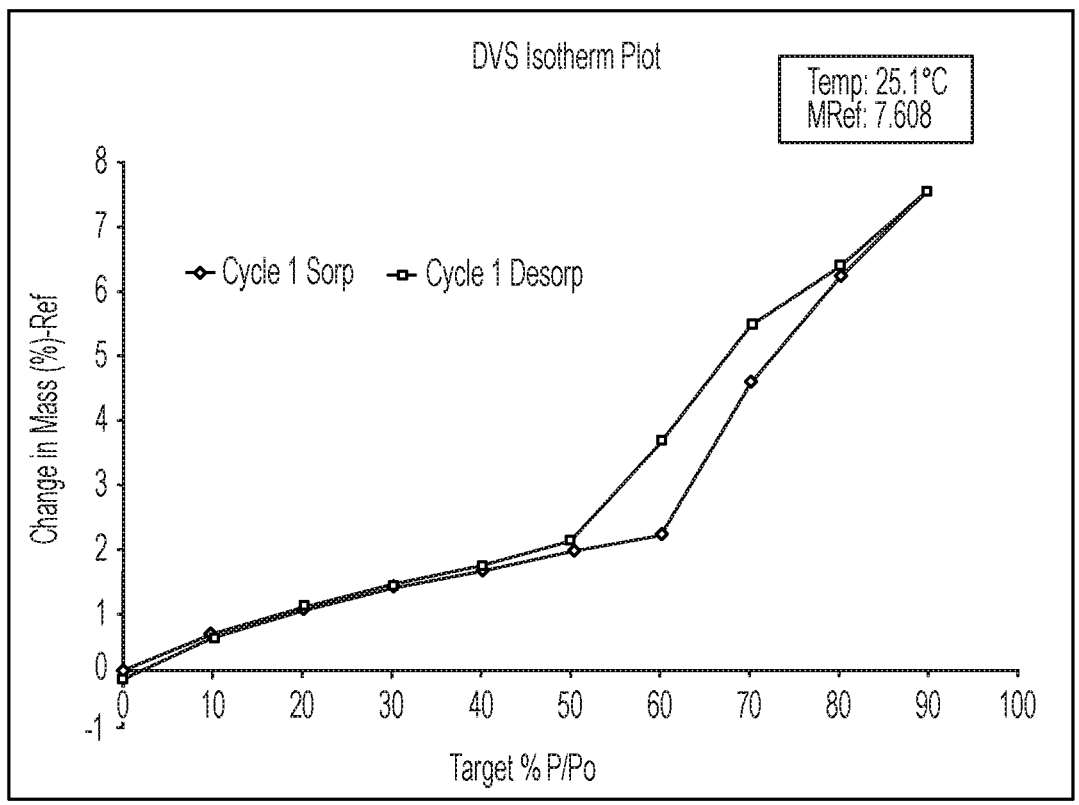
FIG. 32 depicts a DVS isotherm plot of Form E of Compound 1.
Figure 33:
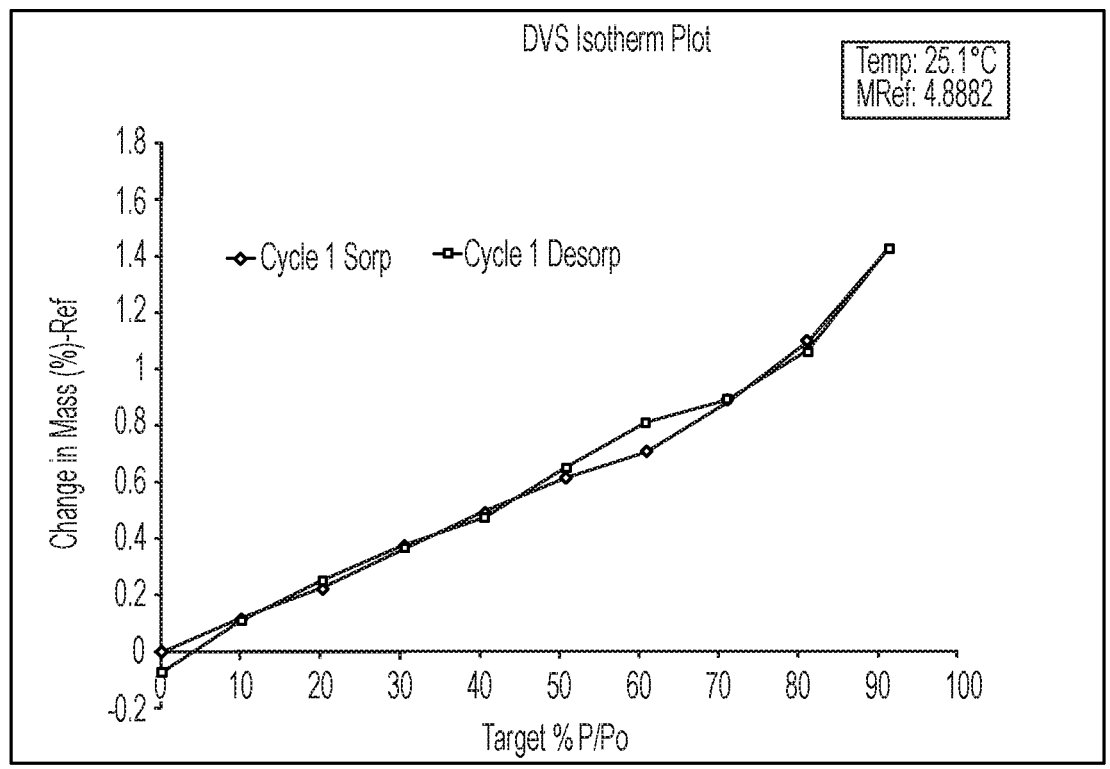
FIG. 33 depicts a DVS isotherm plot of Form I of Compound 1.
Figure 37:
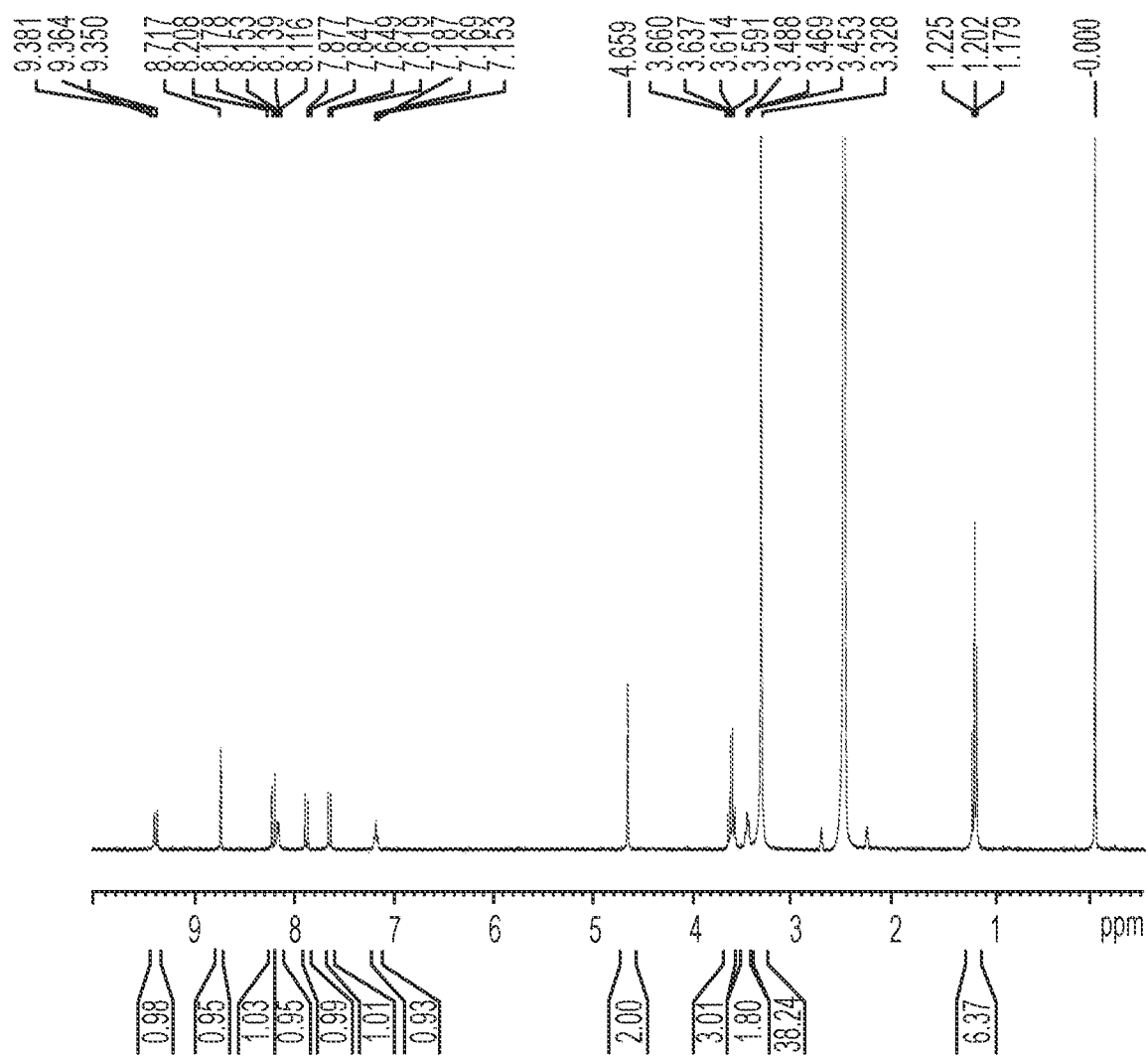
FIG. 37 depicts a $^1$H NMR spectrum of Form D of Compound 1.
Figure 45A:
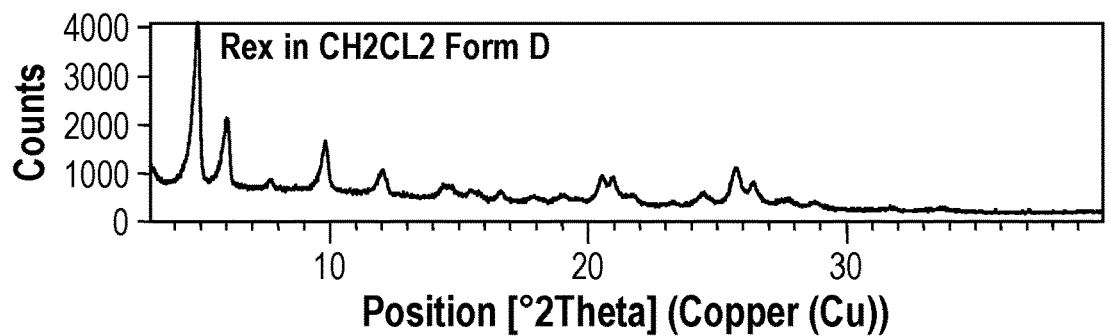
FIG. 45 depicts a comparison of XRPD patterns of Form D of Compound 1 (a) as-is, (b) after compression at 2000 psi, (c) after heating at 190° C., and (d) after DVS.
Figure 45B:
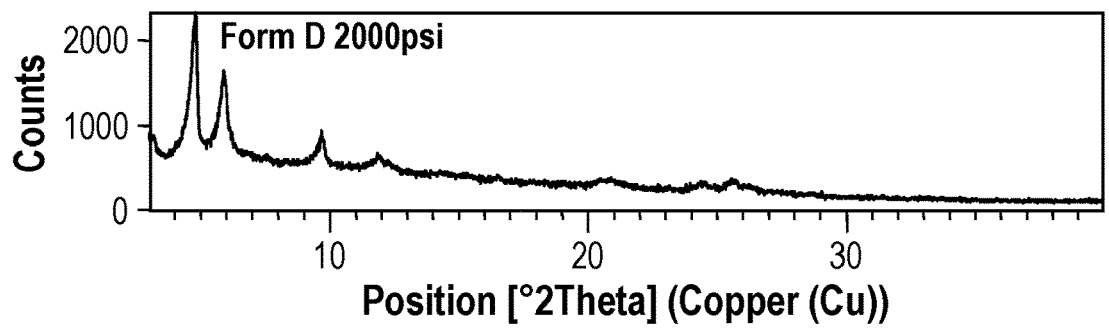
Figure 45C:
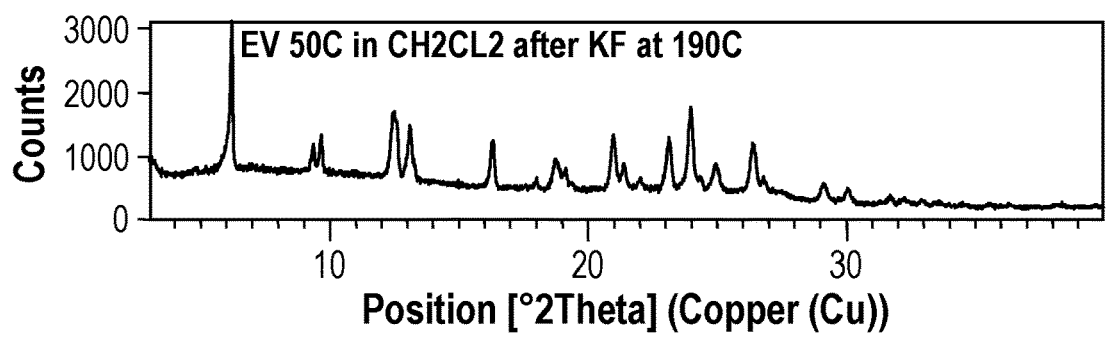
Figure 45D:
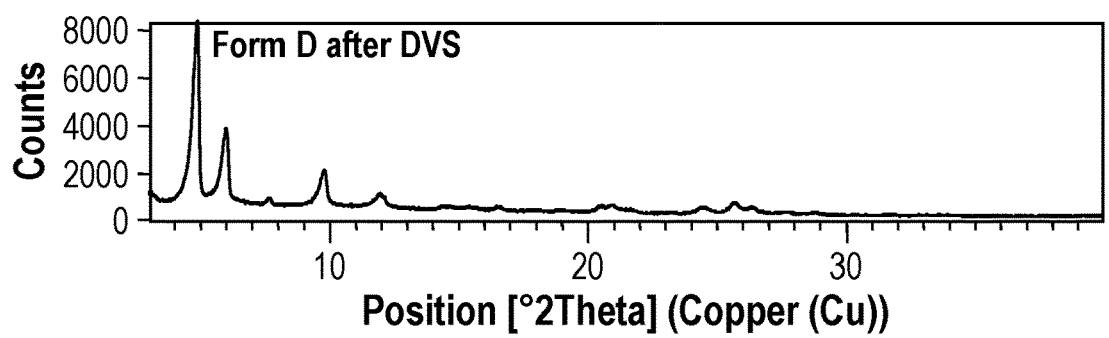
Figure 46A:
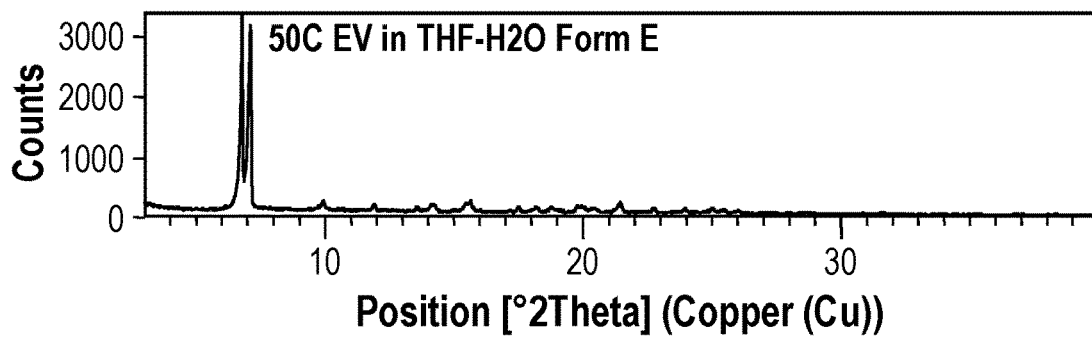
FIG. 46 depicts a comparison of XRPD patterns of Form E of Compound 1 (a) as-is, (b) after compression at 2000 psi, (c) after heating at 190° C., and (d) after DVS.
Figure 46B:
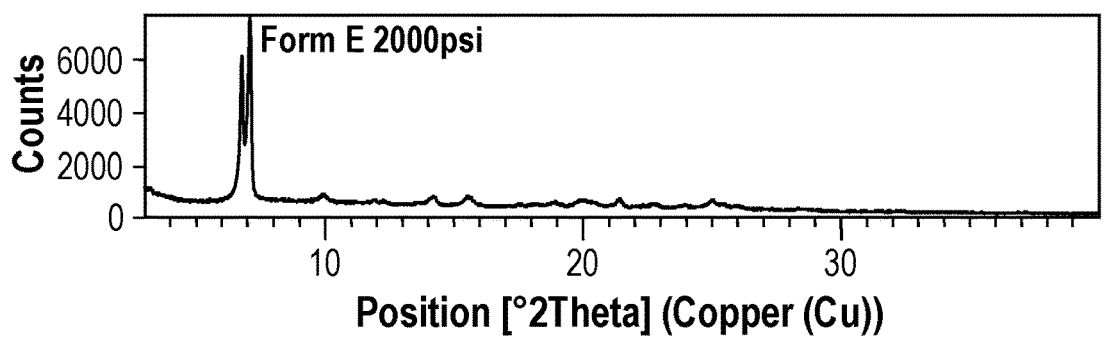
Figure 46C:
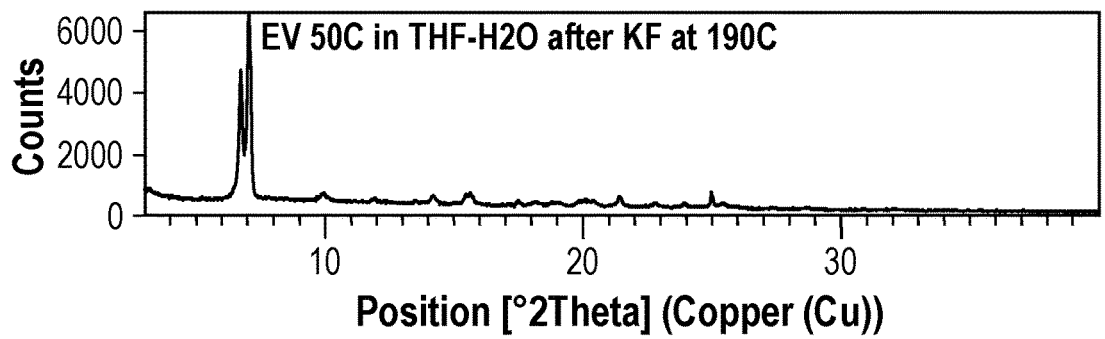
Figure 46D:
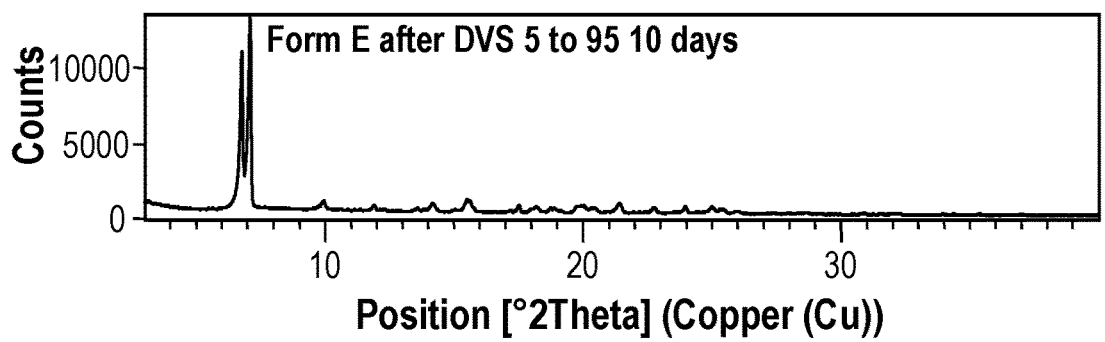

DSC and TGA thermograms of Form D are shown in FIG. 14 and FIG. 24, respectively. The DSC thermogram showed a melting/recrystallization event at 154-171° C. (peak to peak), followed by a melting/decomposition event with a peak temperature of 230° C. About 0.2% TGA weight loss was observed up to 190° C. The decomposition onset temperature was approximately 223° C. No significant degradation or residual solvent was observed for the Form D sample by $^1$H NMR (FIG. 37). The DVS isothermal plot of Form D is shown in FIG. 31. Form D is slightly hygroscopic, with about 2.6 wt % water uptake between 0 and 90% RH. No form change was observed by XRPD after DVS experiment (FIG. 45(d)). The KF result for Form D showed about 0.4 wt % of water. These observations confirm that Form D is an anhydrate.

The stability of Form D was further characterized by compression test and form transfer experiments (Table 6). Upon application of 2000-psi pressure for about 1 minute, the material was shown to be mainly Form D (FIG. 45(b)). A small amount of Form A may also be present in the compressed sample, but can't be definitely determined due to broad diffraction peaks. The solid obtained upon heating Form D in the KF oven at 190° C. was confirmed to be Form A (FIG. 45(*c*)). These results along with the solvent mediated transformation experiment confirmed that Form D is a metastable anhydrate.

Form E.

Figure 5:
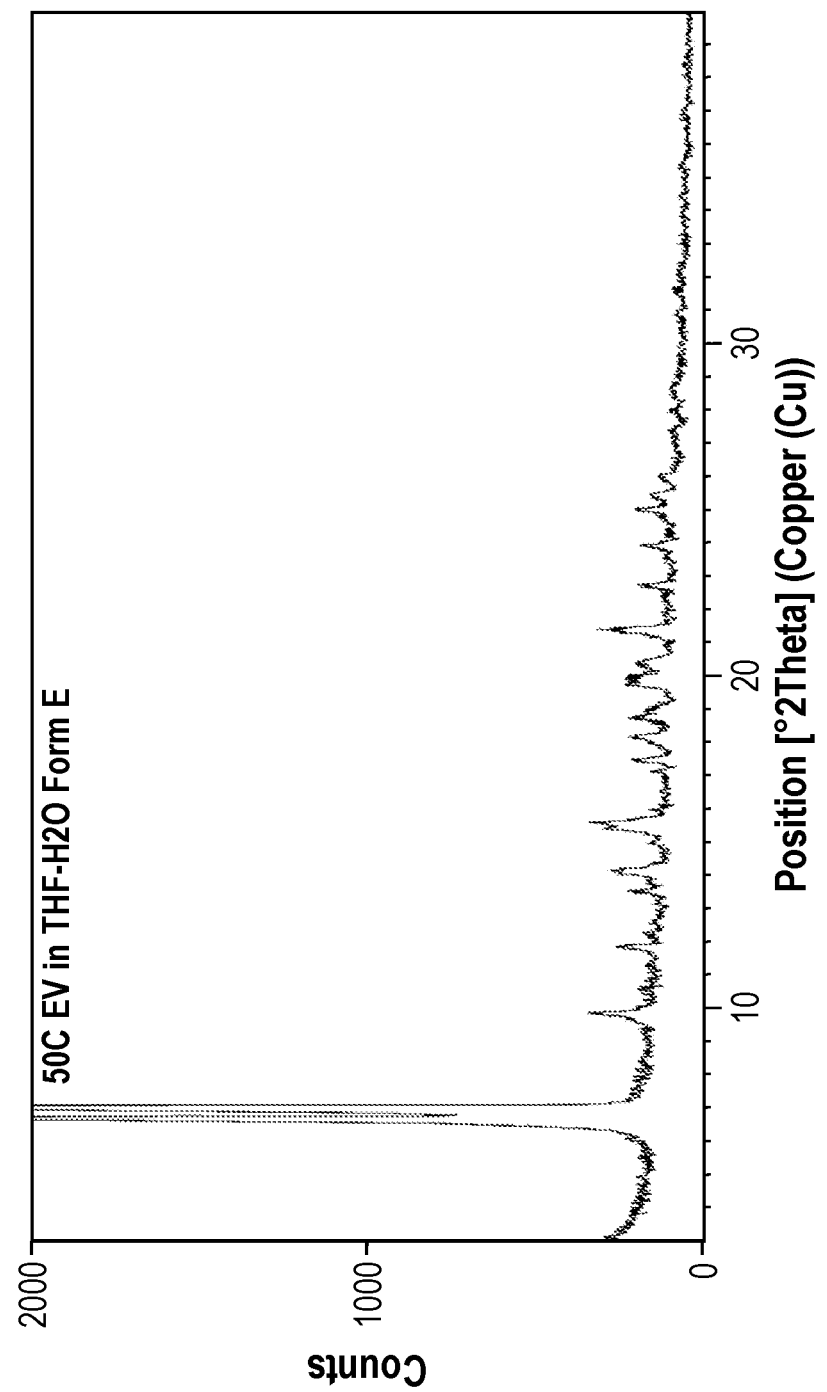
FIG. 5 depicts an XRPD pattern of Form E of Compound 1.

Form E was generated by evaporation experiment in THF/water (1:1) at 50° C. Form E has a crystalline XRPD pattern as shown in FIG. 5.

TABLE 12

Form E XRPD Peak List

| Position [°2θ] | d-spacing [Å] | Relative Intensity [%] |
|---|---|---|
| 6.80 | 12.9949 | 100.0 |
| 7.13 | 12.4033 | 94.5 |
| 9.95 | 8.8927 | 5.1 |
| 14.21 | 6.2339 | 4.0 |
| 15.48 | 5.7228 | 4.7 |
| 15.64 | 5.6656 | 5.4 |
| 19.80 | 4.4838 | 3.5 |
| 21.44 | 4.1447 | 5.2 |
| 25.04 | 3.5567 | 3.2 |

Figure 15:
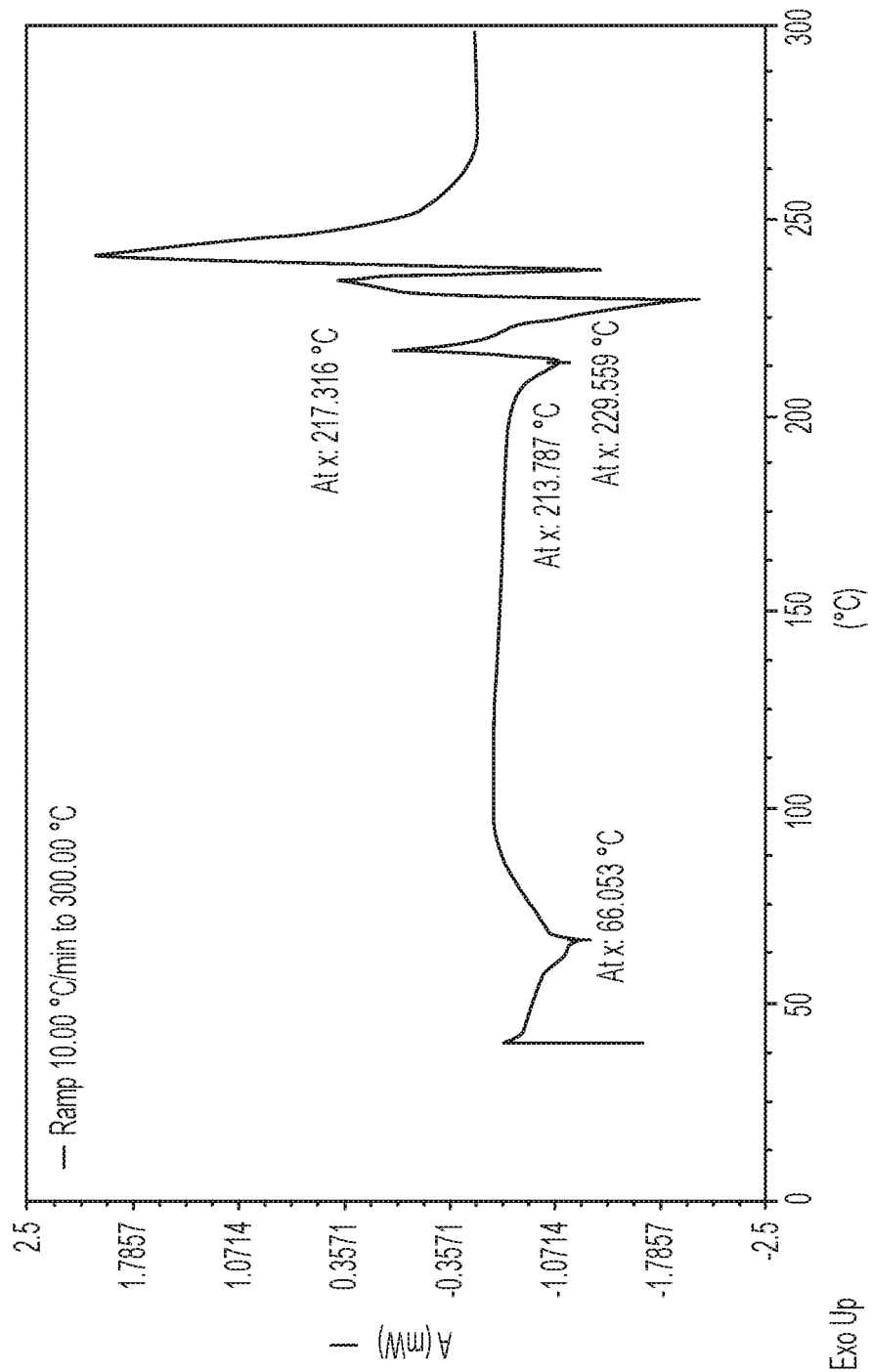
FIG. 15 depicts a DSC thermogram of Form E of Compound 1.
Figure 25:
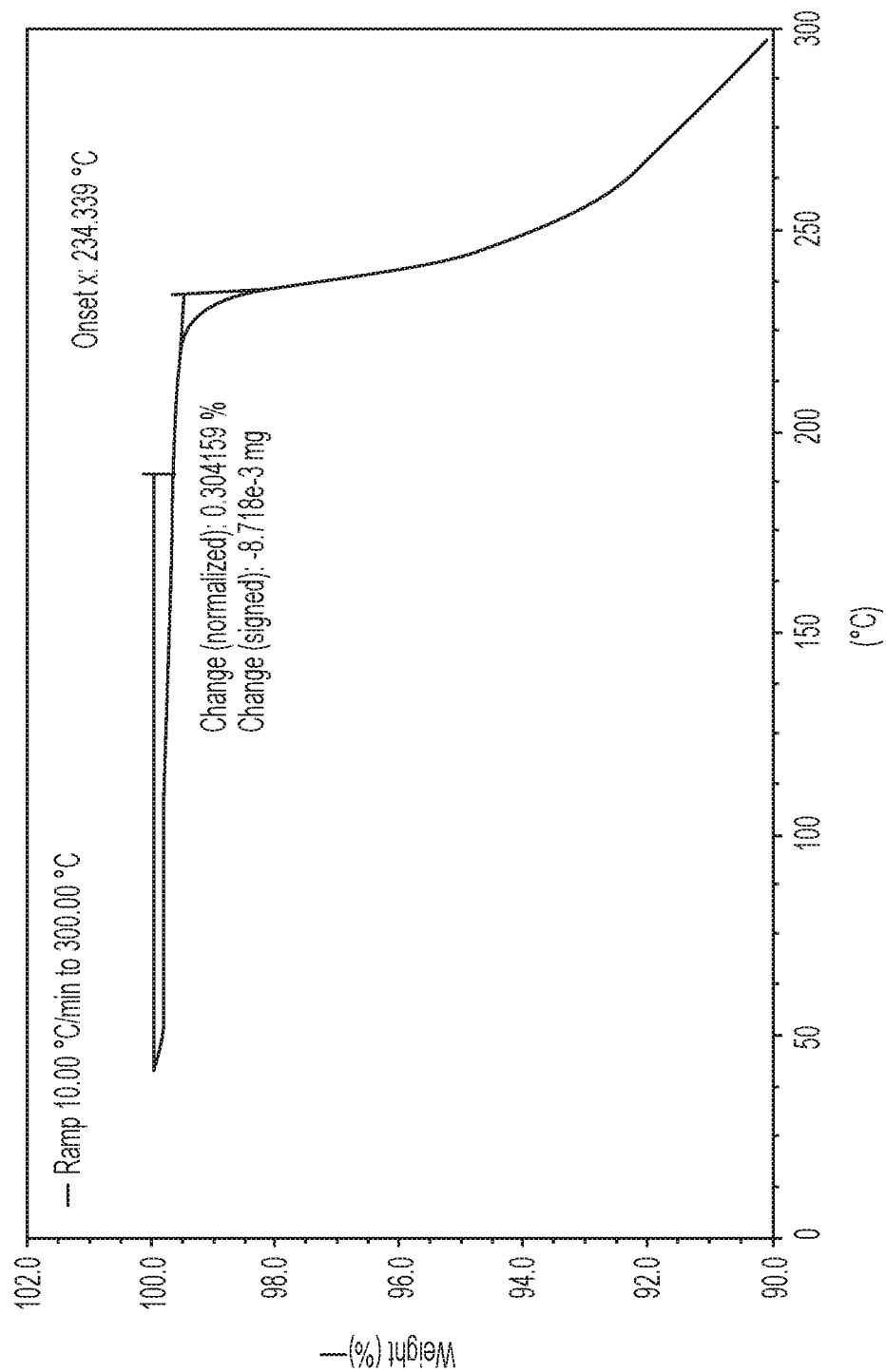
FIG. 25 depicts a TGA thermogram of Form E of Compound 1.
Figure 38:
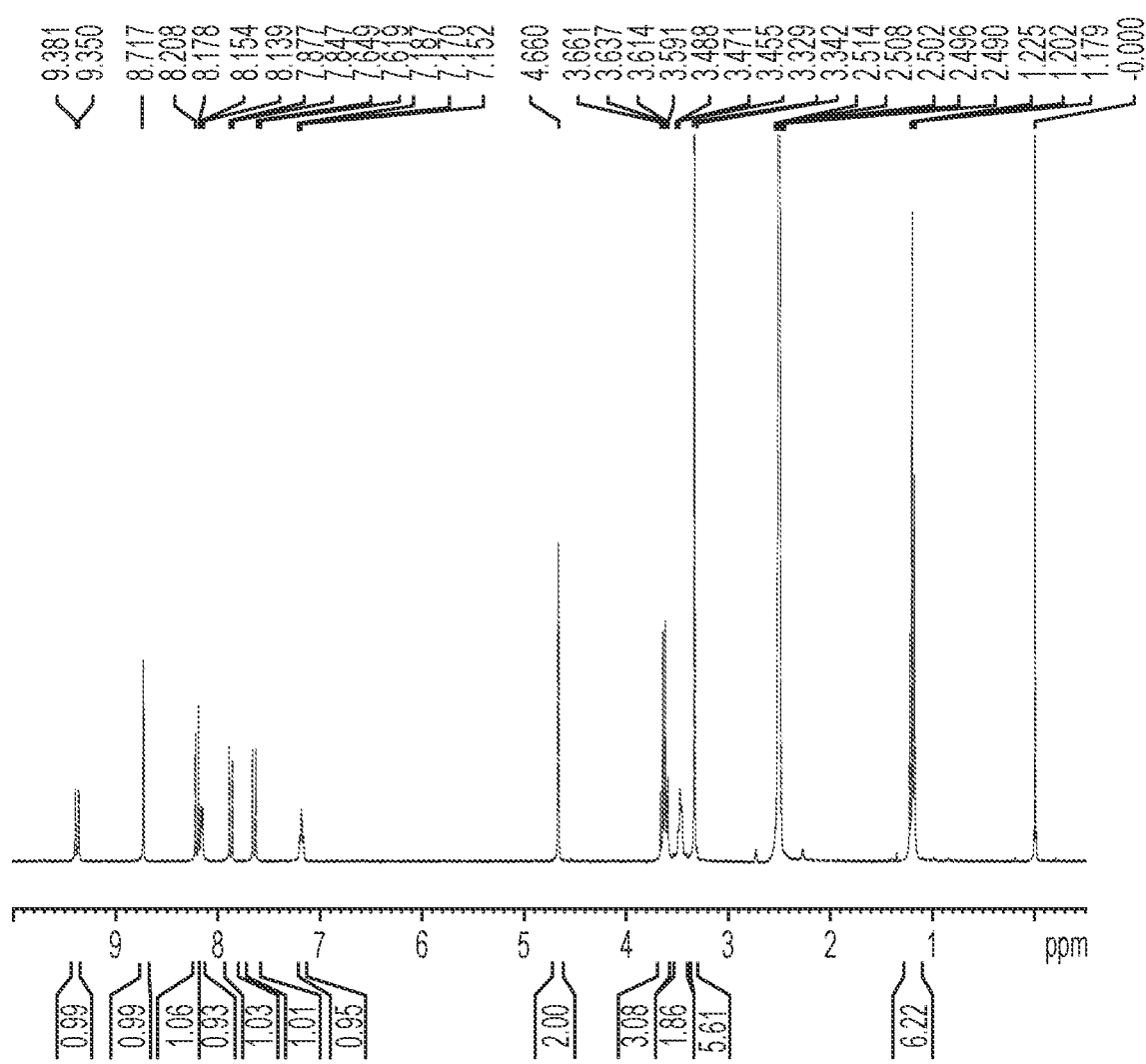
FIG. 38 depicts a $^1$H NMR spectrum of Form E of Compound 1.
Figure 39:
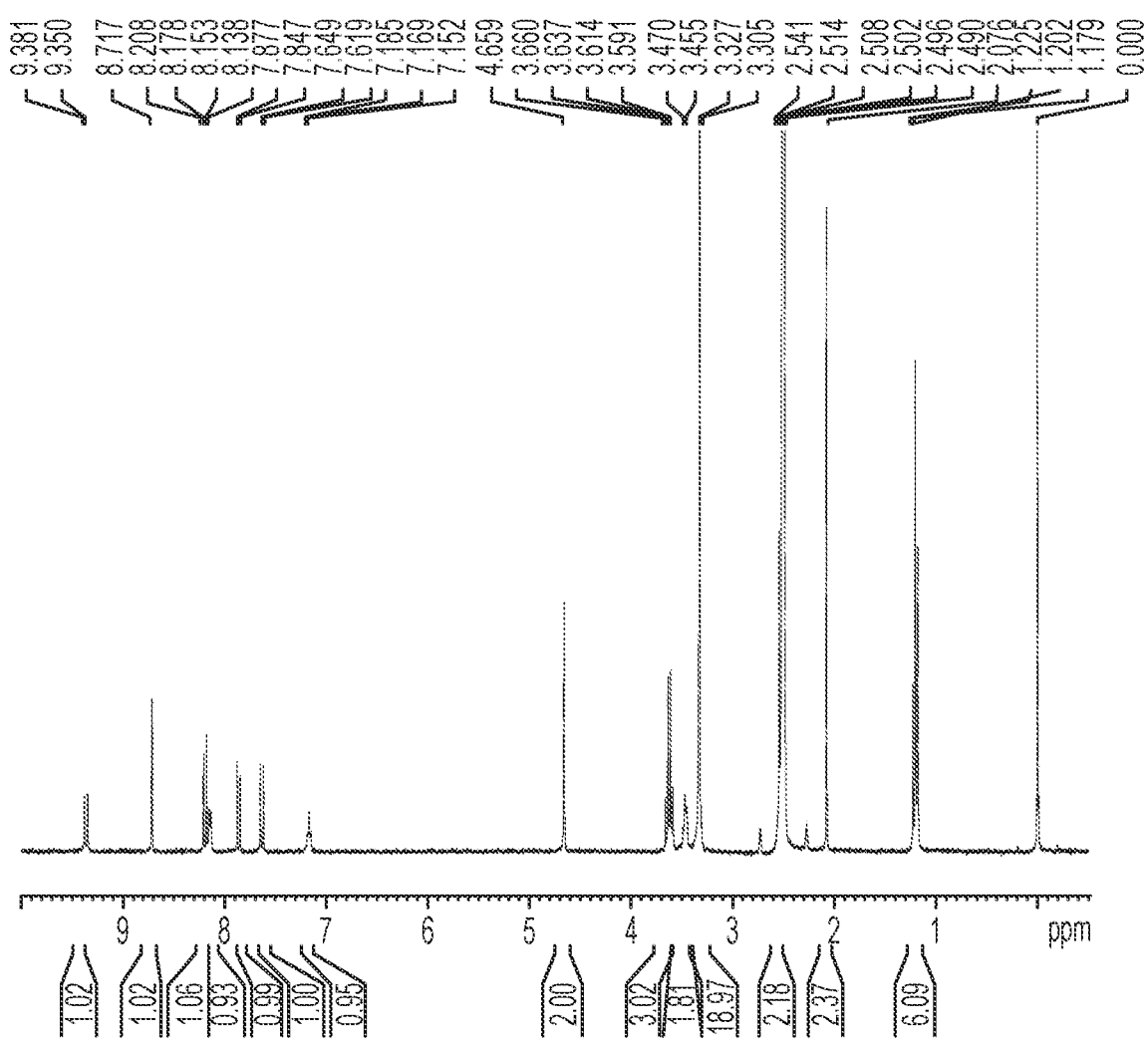
FIG. 39 depicts a $^1$H NMR spectrum of Form F of Compound 1.
Figure 40:
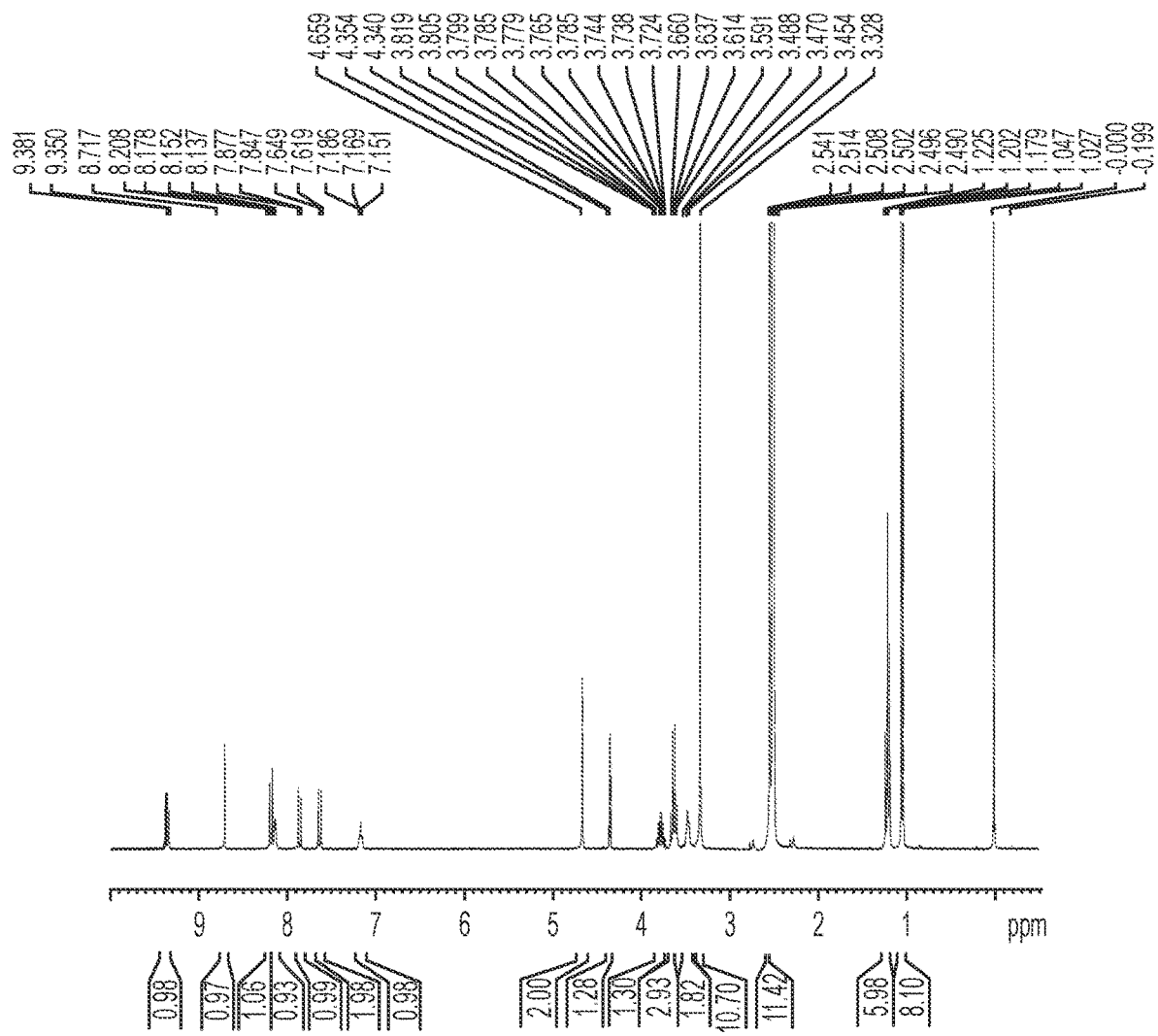
FIG. 40 depicts a $^1$H NMR spectrum of Form G of Compound 1.
Figure 41:
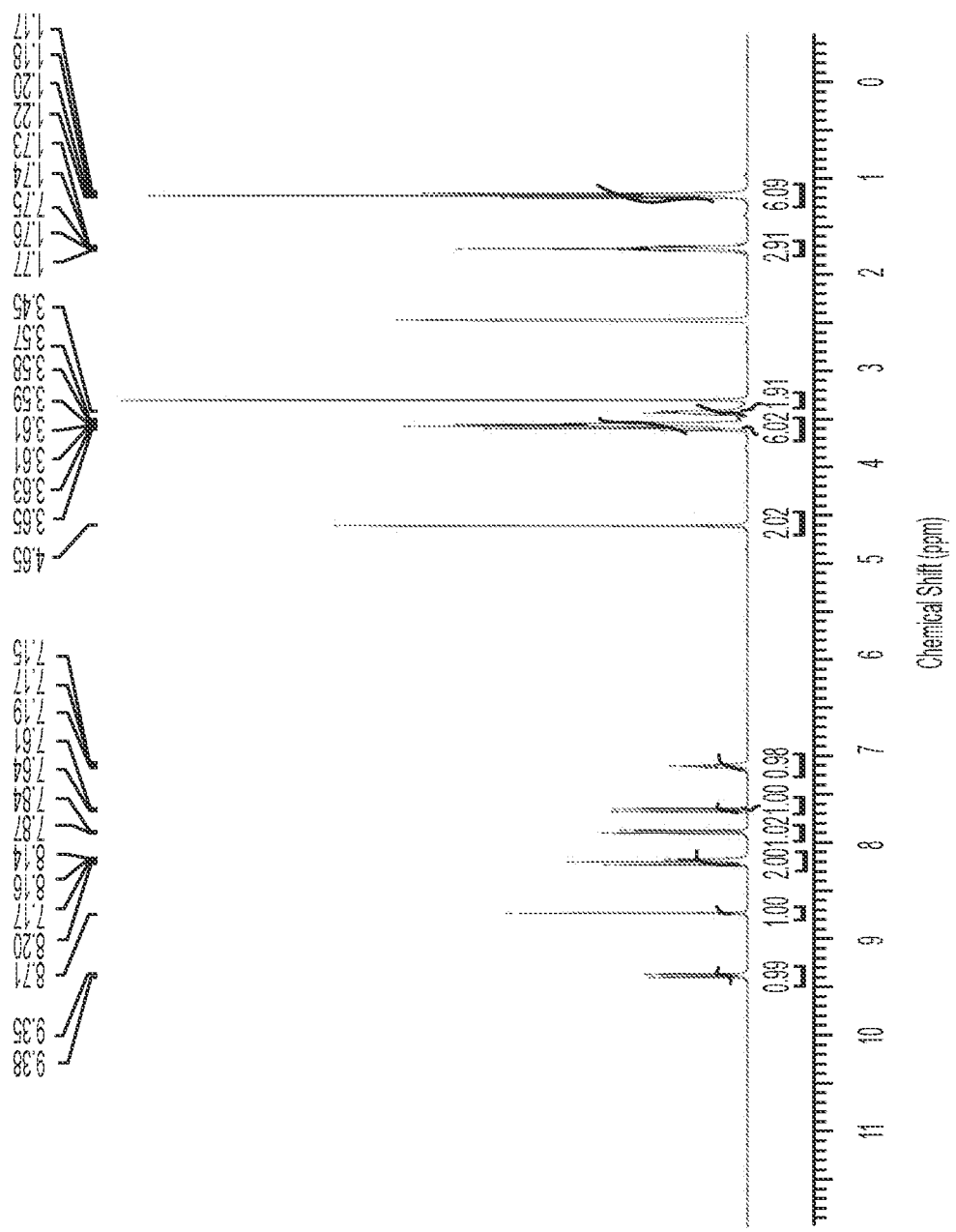
FIG. 41 depicts a $^1$H NMR spectrum of Form I of Compound 1 obtained from recrystallization of Compound 1 in THF/water.

DSC and TGA thermograms of Form E are shown in FIG. 15 and FIG. 25, respectively. The DSC thermogram showed several thermal events. Small endothermic peaks around 66° C. were attributed to loss of water. The endo-exothermic peaks at 214-217° C. (peak to peak) were attributed to lattice collapse and rearrangement of the dehydrated Form E material. Finally, the recrystallized material went through a melting/decomposition with a peak temperature of 230° C. About 0.3% TGA weight loss was observed up to 190° C. The decomposition onset temperature was approximately 234° C. No significant degradation or residual solvent was observed by $^1$H NMR (FIG. 38). The DVS isothermal plot of Form E in shown in FIG. 32. The water uptake was about 2.2 wt % between 0 and 60% RH, followed by steep increase to 7.5 wt % at 90% RH. Slight hysteresis was observed between 80 to 50% RH upon desorption. No form change was observed by XRPD after DVS experiment (FIG. 46(*d*)). The KF result for Form E showed about 1.2 wt % of water. These observations suggested that Form E is a hydrate, and a metastable hydrate with higher water content may exist.

The stability of Form E was further characterized by compression test and form transfer experiments (Table 6). Upon application of 2000-psi pressure for about 1 minute, the material was still Form E (FIG. 46(*b*)). The solid obtained upon heating Form E in the KF oven at 190° C. was confirmed to be Form E (FIG. 46(*c*)). The solvent mediated transformation experiment showed that Form E converts to Form A upon slurry in acetone. Form E also converted to Form A in THF/water (5/95) upon long periods of equilibration.

Form F.

Figure 6:
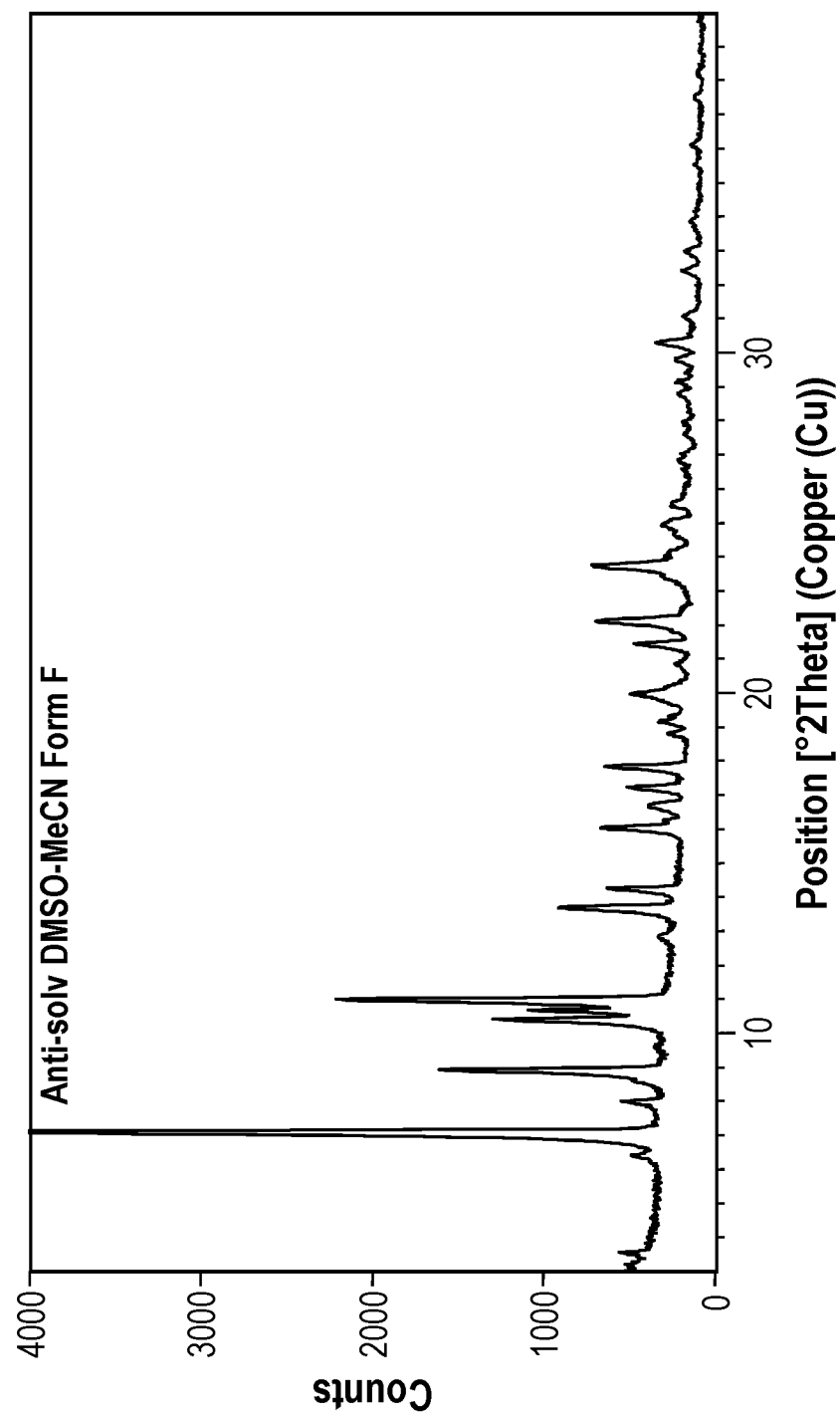
FIG. 6 depicts an XRPD pattern of Form F of Compound 1.

Form F was generated by anti-solvent recrystallization experiment in DMSO/ACN. Form F has a crystalline XRPD pattern as shown in FIG. 6.

TABLE 13

Form F XRPD Peak List

| Position [°2θ] | d-spacing [Å] | Relative Intensity [%] |
|---|---|---|
| 7.11 | 12.4324 | 100.0 |
| 8.00 | 11.0538 | 4.1 |
| 8.92 | 9.9089 | 22.2 |
| 10.41 | 8.4984 | 16.9 |

TABLE 13-continued

Form F XRPD Peak List

| Position [°2θ] | d-spacing [Å] | Relative Intensity [%] |
|---|---|---|
| 10.68 | 8.2860 | 13.8 |
| 11.00 | 8.0462 | 32.4 |
| 13.70 | 6.4641 | 11.6 |
| 14.25 | 6.2138 | 6.9 |
| 16.04 | 5.5241 | 8.0 |
| 17.23 | 5.1454 | 5.6 |
| 17.84 | 4.9716 | 8.0 |
| 19.97 | 4.4452 | 5.6 |
| 21.45 | 4.1432 | 5.0 |
| 22.11 | 4.0201 | 9.2 |
| 23.73 | 3.7491 | 9.2 |
| 30.30 | 2.9500 | 4.0 |

Figure 16:
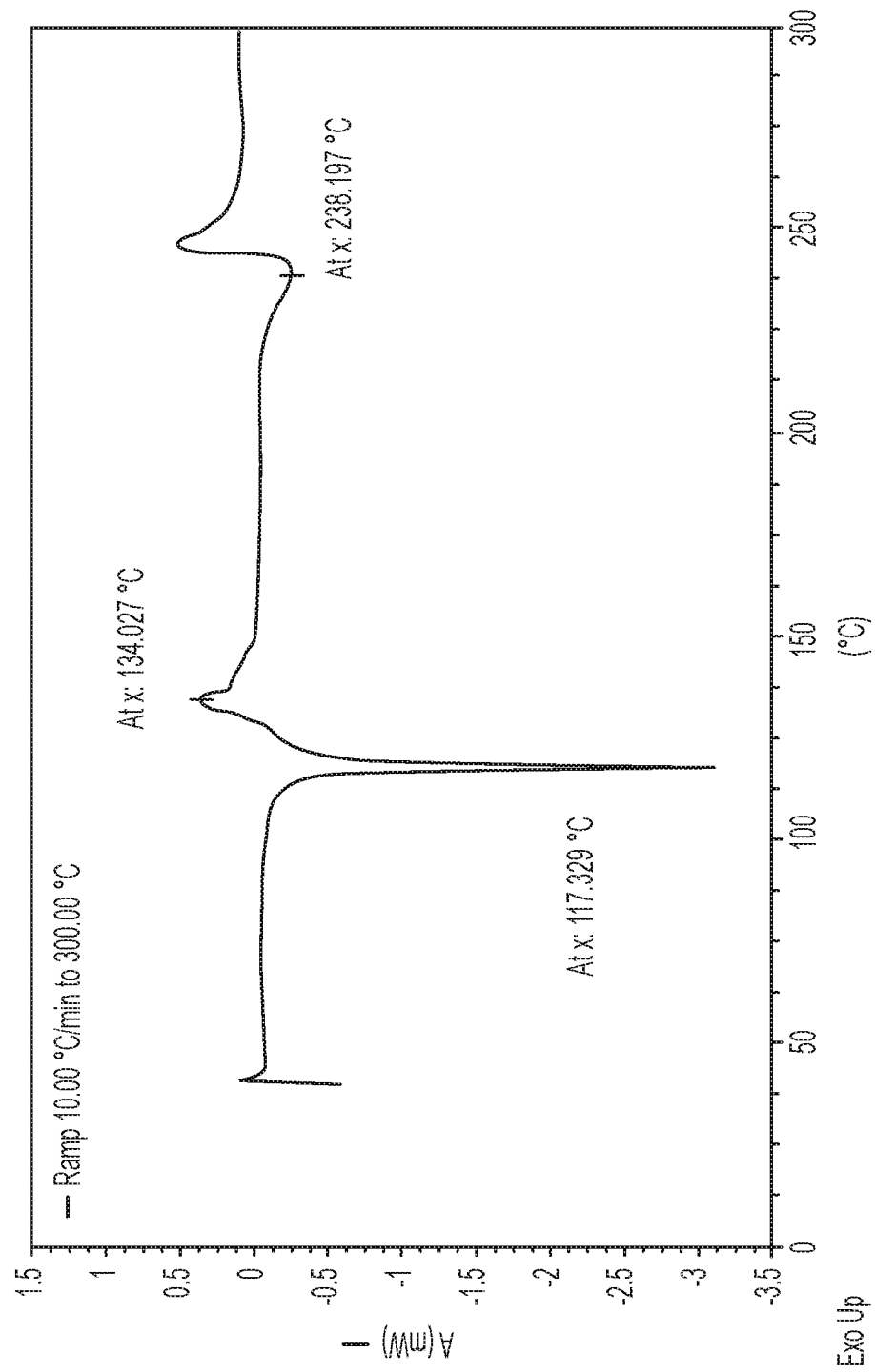
FIG. 16 depicts a DSC thermogram of Form F of Compound 1.

The DSC thermogram of Form F is shown in FIG. 16. The DSC thermogram showed an endothermic peak around 117° C., followed by an exothermic peak around 134° C., and finally a major endothermic peak around 238° C. No significant degradation was observed by $^1$H NMR (FIG. 39), but residual DMSO and about 6.5 wt % of ACN were observed. Based on the available information, Form F is a solvate.

Form G.

Figure 7:
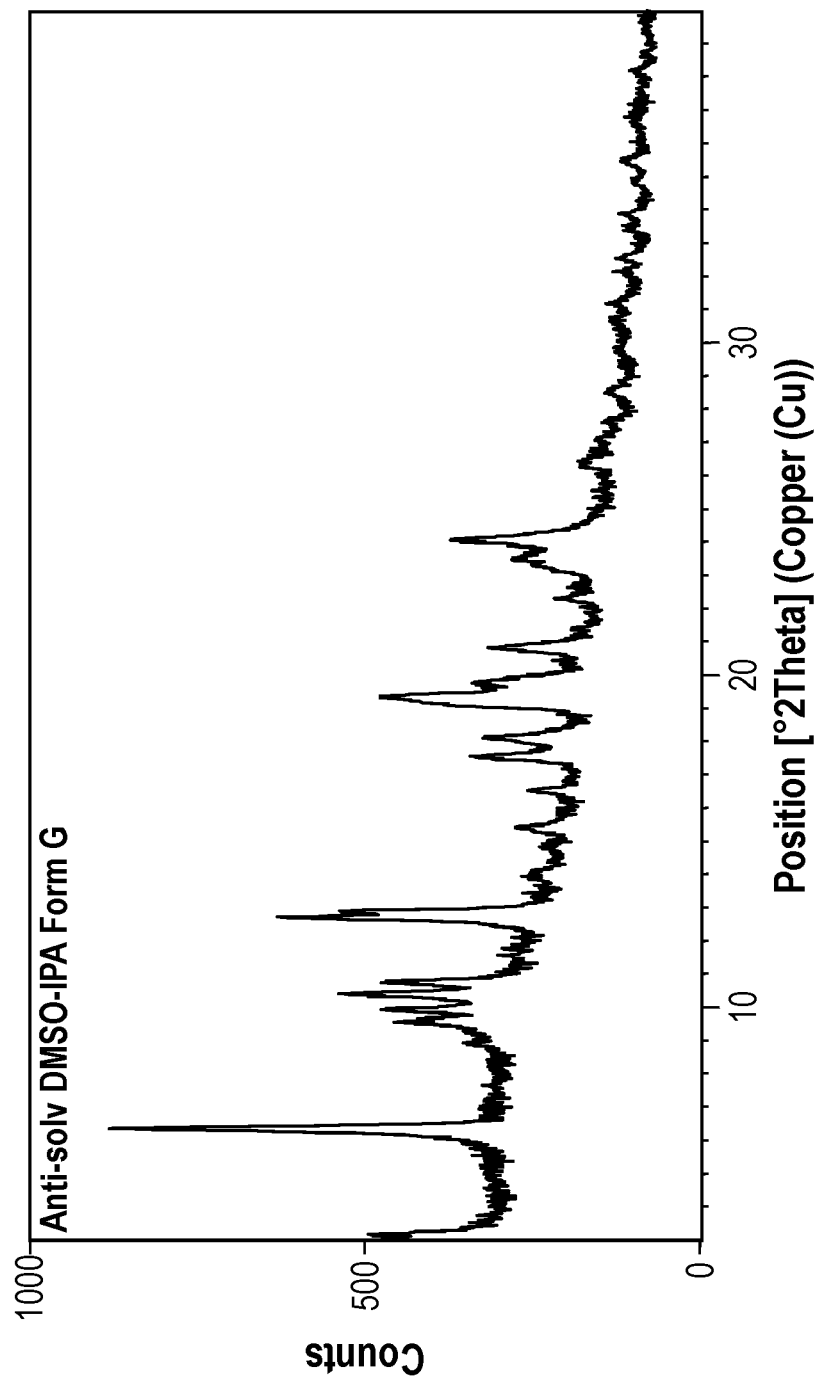
FIG. 7 depicts an XRPD pattern of Form G of Compound 1.

Form G was generated by anti-solvent recrystallization experiment in DMSO/IPA. Form G has a crystalline XRPD pattern as shown in FIG. 7.

TABLE 14

Form G XRPD Peak List

| Position [°2θ] | d-spacing [Å] | Relative Intensity [%] |
|---|---|---|
| 6.36 | 13.8918 | 100.0 |
| 9.56 | 9.2509 | 30.2 |
| 9.94 | 8.8976 | 33.6 |
| 10.41 | 8.4973 | 44.9 |
| 10.77 | 8.2159 | 33.5 |
| 12.71 | 6.9634 | 65.6 |
| 12.89 | 6.8706 | 48.5 |
| 13.96 | 6.3428 | 5.3 |
| 15.41 | 5.7515 | 12.9 |
| 16.53 | 5.3626 | 11.7 |
| 17.56 | 5.0511 | 26.2 |
| 18.12 | 4.8966 | 24.4 |
| 19.09 | 4.6503 | 33.1 |
| 19.35 | 4.5884 | 51.6 |
| 19.74 | 4.4968 | 27.5 |
| 20.83 | 4.2655 | 25.0 |
| 22.31 | 3.9852 | 10.5 |
| 23.49 | 3.7873 | 20.9 |
| 24.08 | 3.6955 | 37.1 |
| 26.36 | 3.3817 | 9.5 |
| 28.54 | 3.1279 | 7.1 |
| 31.16 | 2.8700 | 6.7 |
| 32.56 | 2.7498 | 6.2 |
| 33.86 | 2.6471 | 5.5 |
| 35.47 | 2.5309 | 6.0 |

Figure 17:
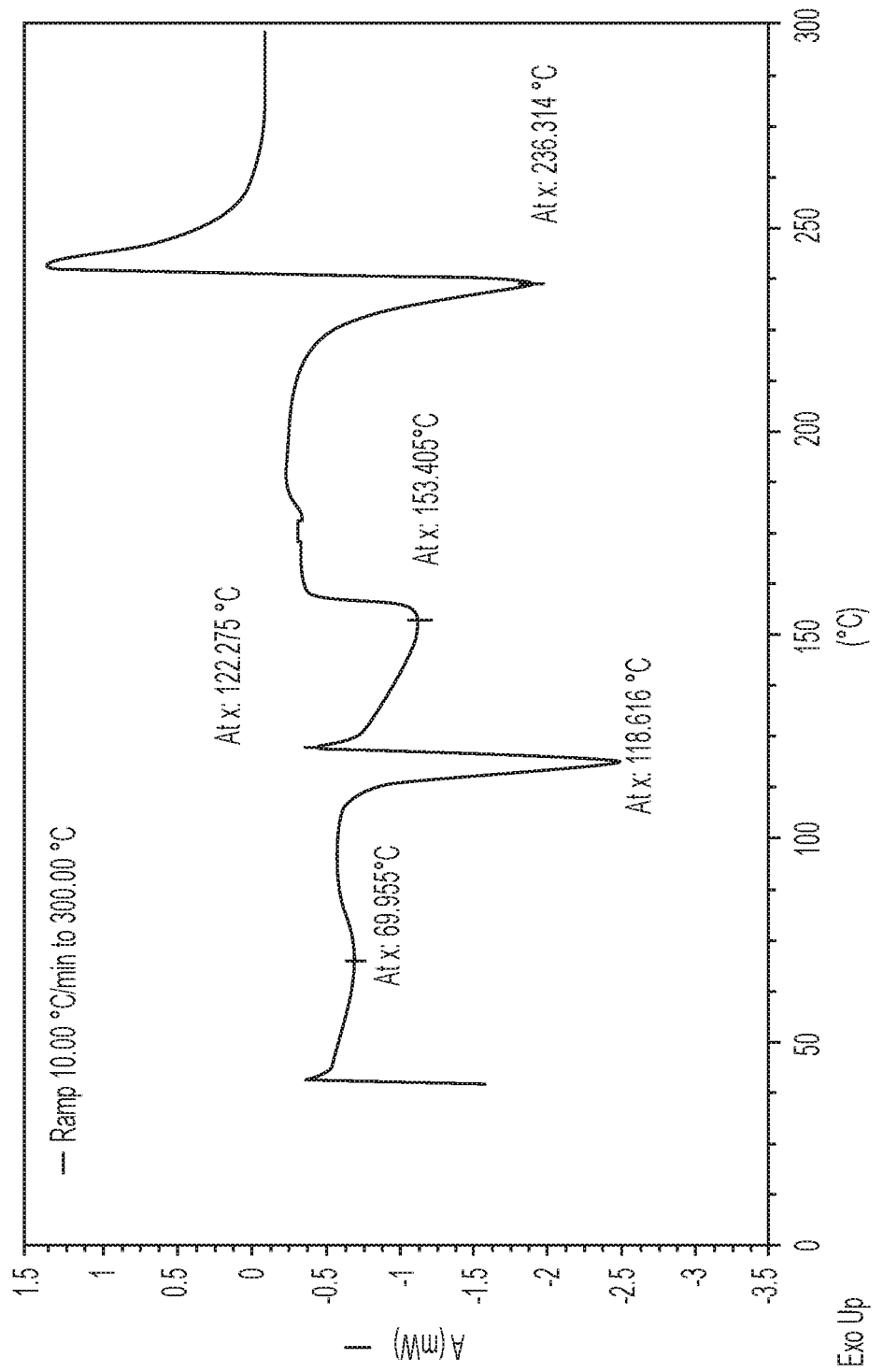
FIG. 17 depicts a DSC thermogram of Form G of Compound 1.

The DSC thermogram of Form G is shown in FIG. 17. The DSC thermogram showed multiple events, including endothermic peaks around 70 and 119° C., an exothermic peak around 122° C., additional endothermic peak around 153° C., and finally a major endothermic peak around 236° C. No significant degradation was observed by $^1$H NMR (FIG. 40), but residual DMSO and about 14.3 wt % of IPA were observed. Based on the available information, Form G is most likely a solvate.

Form H.

Figure 8:
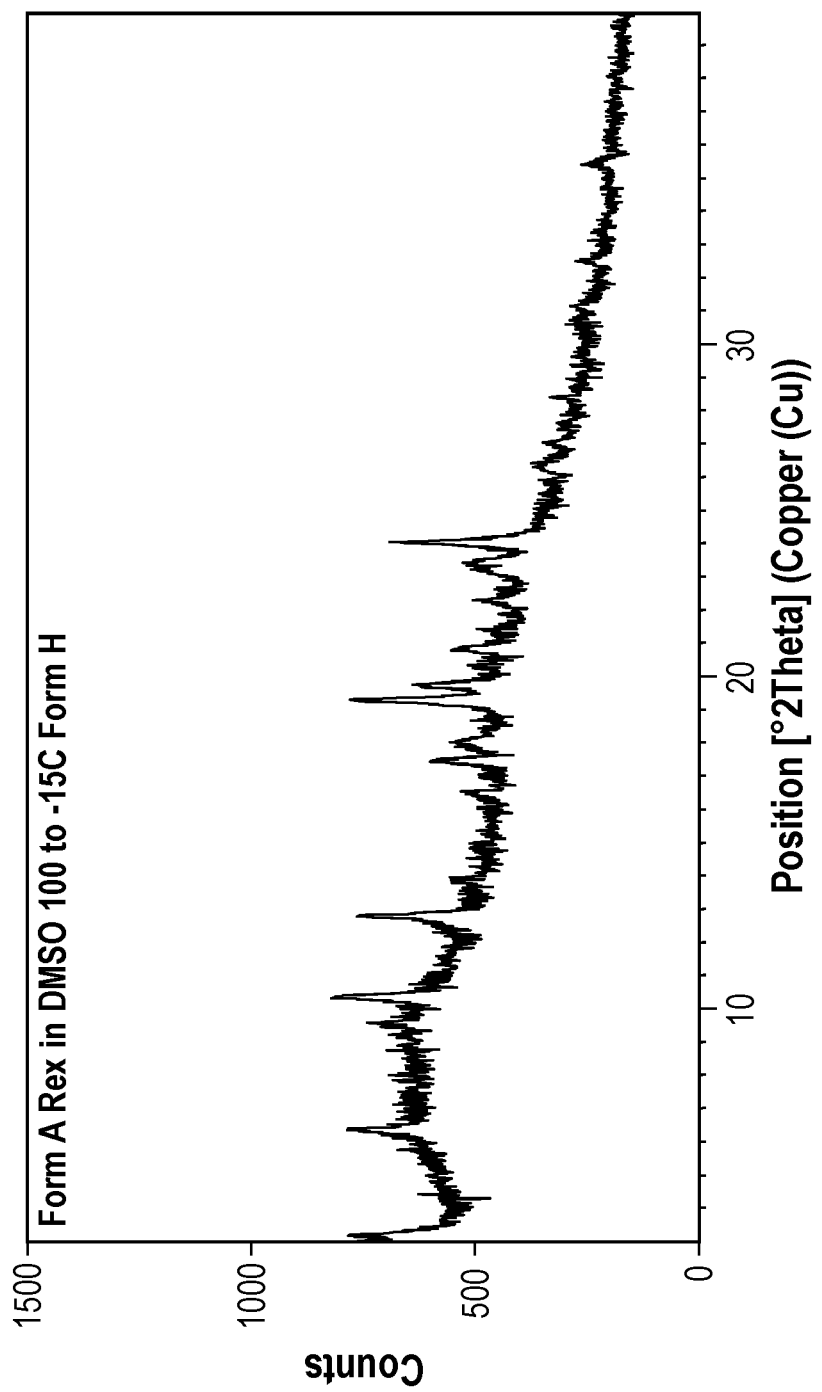
FIG. 8 depicts an XRPD pattern of Form H of Compound 1.

Form H was generated by cooling recrystallization in DMSO from 100 to −15° C. Form H has a semi-crystalline XRPD pattern as shown in FIG. 8.

TABLE 15

Form H XRPD Peak List

| Position [°2θ] | d-spacing [Å] | Relative Intensity [%] |
|---|---|---|
| 6.37 | 13.8804 | 58.9 |
| 9.54 | 9.2667 | 44.7 |
| 10.37 | 8.5341 | 78.8 |
| 12.81 | 6.9123 | 77.6 |
| 13.81 | 6.4116 | 19.3 |
| 16.51 | 5.3690 | 20.9 |
| 17.48 | 5.0737 | 44.0 |
| 18.03 | 4.9206 | 33.7 |
| 19.31 | 4.5967 | 100.0 |
| 19.75 | 4.4954 | 60.8 |
| 20.85 | 4.2614 | 40.3 |
| 22.29 | 3.9886 | 29.4 |
| 23.44 | 3.7950 | 43.3 |
| 24.06 | 3.6989 | 97.3 |
| 26.34 | 3.3839 | 17.7 |
| 27.04 | 3.2974 | 17.1 |
| 28.42 | 3.1404 | 20.1 |
| 31.08 | 2.8772 | 18.0 |
| 32.52 | 2.7537 | 16.8 |
| 35.46 | 2.5315 | 18.0 |

Figure 18:
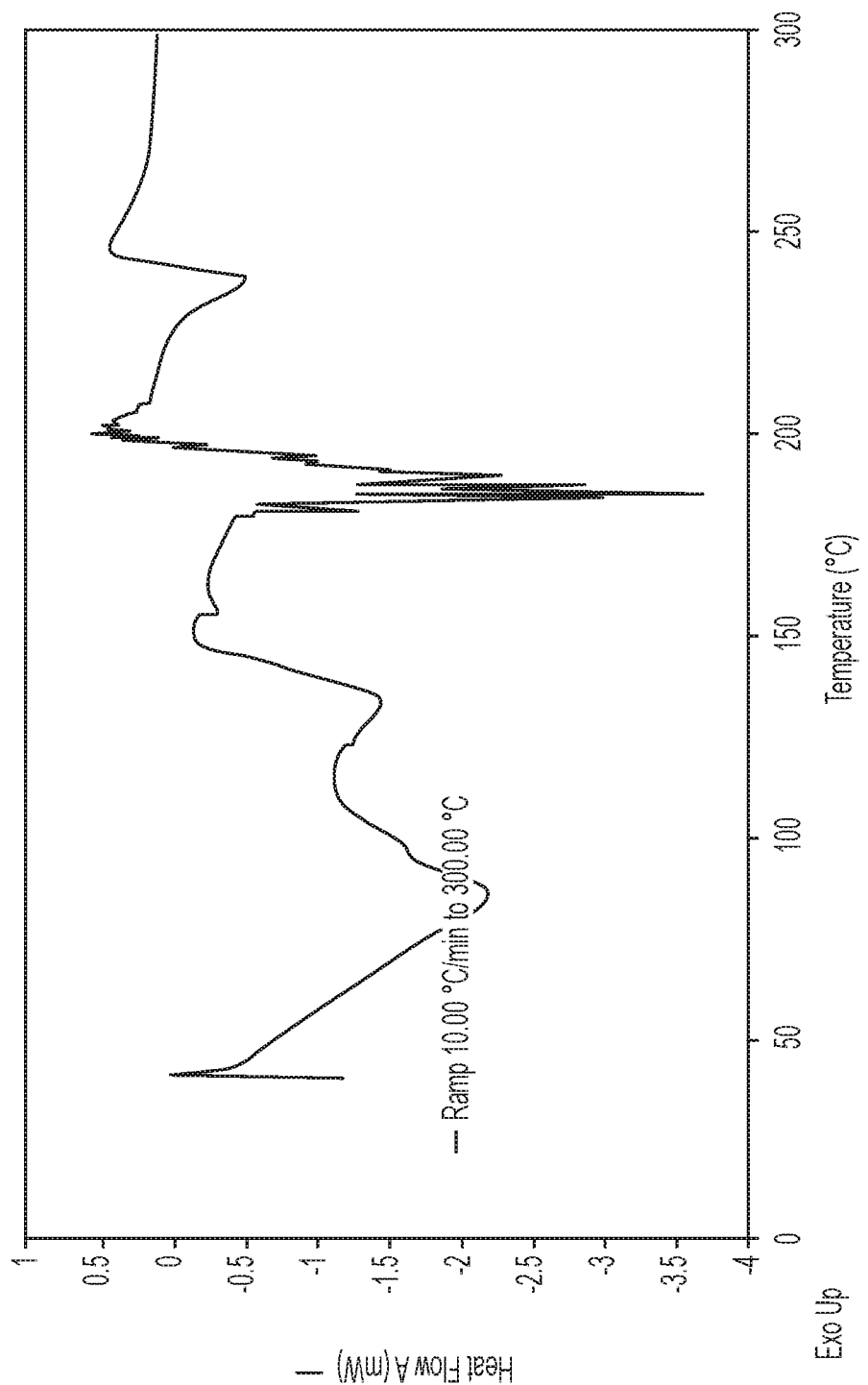
FIG. 18 depicts a DSC thermogram Form H of Compound 1.
Figure 26:
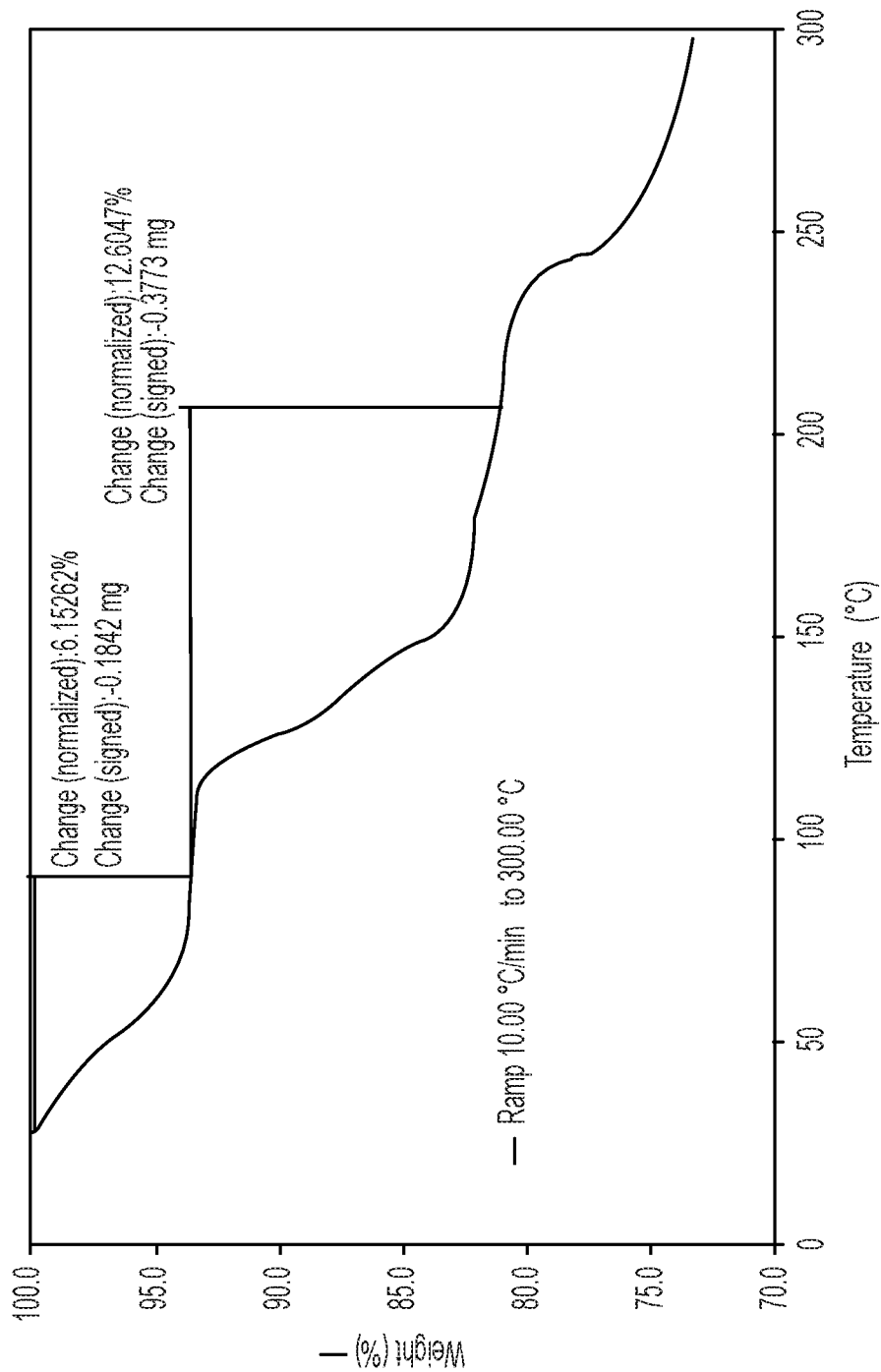
FIG. 26 depicts a TGA thermogram of Form H of Compound 1.

DSC and TGA thermograms of Form H are shown in FIG. 18 and FIG. 26, respectively. The DSC thermogram showed multiple endothermic events. Approximately 6.1% TGA weight loss was observed up to 100° C., with additional 12.6% weight loss observed up to about 200° C. Form H was not further characterized due to semi-crystalline nature of the material. Form H was further slurried in water and generated Form I, as discussed below. Based on the available information, Form H is likely a solvate or hydrate.

Form I.

Figure 9:
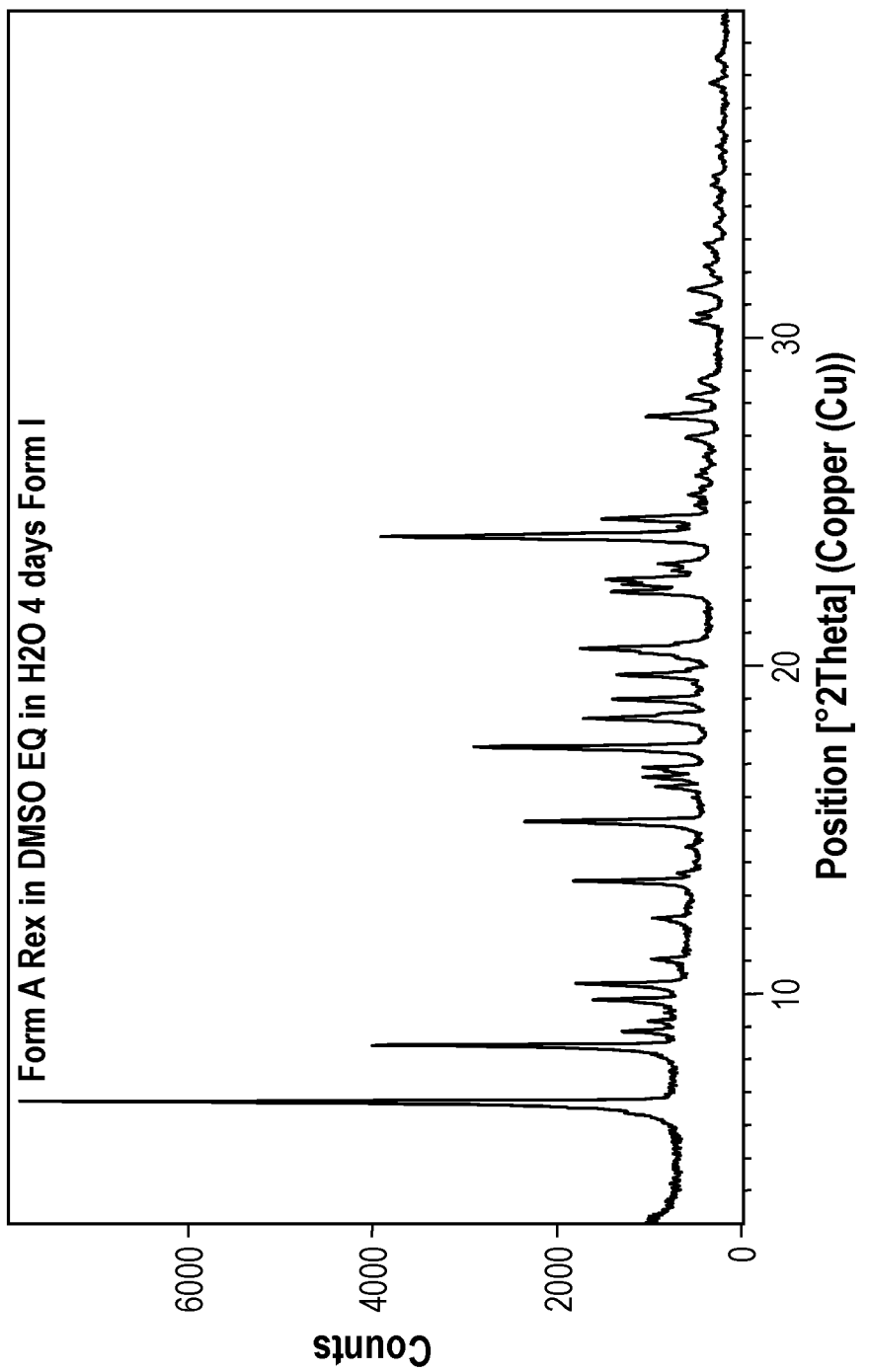
FIG. 9 depicts an XRPD pattern of Form I of Compound 1.

Form I was generated by equilibration of Form H in water for 4 days. Form I has a crystalline XRPD pattern as shown in FIG. 9.

TABLE 16

Form I XRPD Peak List

| Position [°2θ] | d-spacing [Å] | Relative Intensity [%] |
|---|---|---|
| 6.73 | 13.1420 | 100.0 |
| 8.44 | 10.4774 | 46.5 |
| 8.87 | 9.9732 | 9.1 |
| 9.83 | 8.9980 | 13.7 |
| 10.32 | 8.5718 | 16.8 |
| 11.07 | 7.9920 | 5.5 |
| 12.32 | 7.1855 | 6.0 |
| 13.45 | 6.5817 | 18.7 |
| 15.27 | 5.8035 | 26.7 |
| 16.33 | 5.4289 | 6.8 |
| 16.62 | 5.3357 | 8.8 |
| 16.90 | 5.2455 | 9.0 |
| 17.53 | 5.0587 | 34.7 |
| 18.41 | 4.8200 | 18.5 |
| 18.99 | 4.6733 | 14.3 |
| 19.73 | 4.5000 | 13.8 |
| 20.54 | 4.3244 | 19.2 |
| 22.27 | 3.9922 | 14.9 |
| 22.50 | 3.9520 | 13.3 |
| 22.64 | 3.9275 | 15.3 |
| 22.92 | 3.8810 | 5.7 |

TABLE 16-continued

Form I XRPD Peak List

| Position [°2θ] | d-spacing [Å] | Relative Intensity [%] |
|---|---|---|
| 23.12 | 3.8475 | 8.0 |
| 23.95 | 3.7160 | 50.0 |
| 24.49 | 3.6346 | 16.8 |
| 27.62 | 3.2298 | 10.6 |

Figure 19:
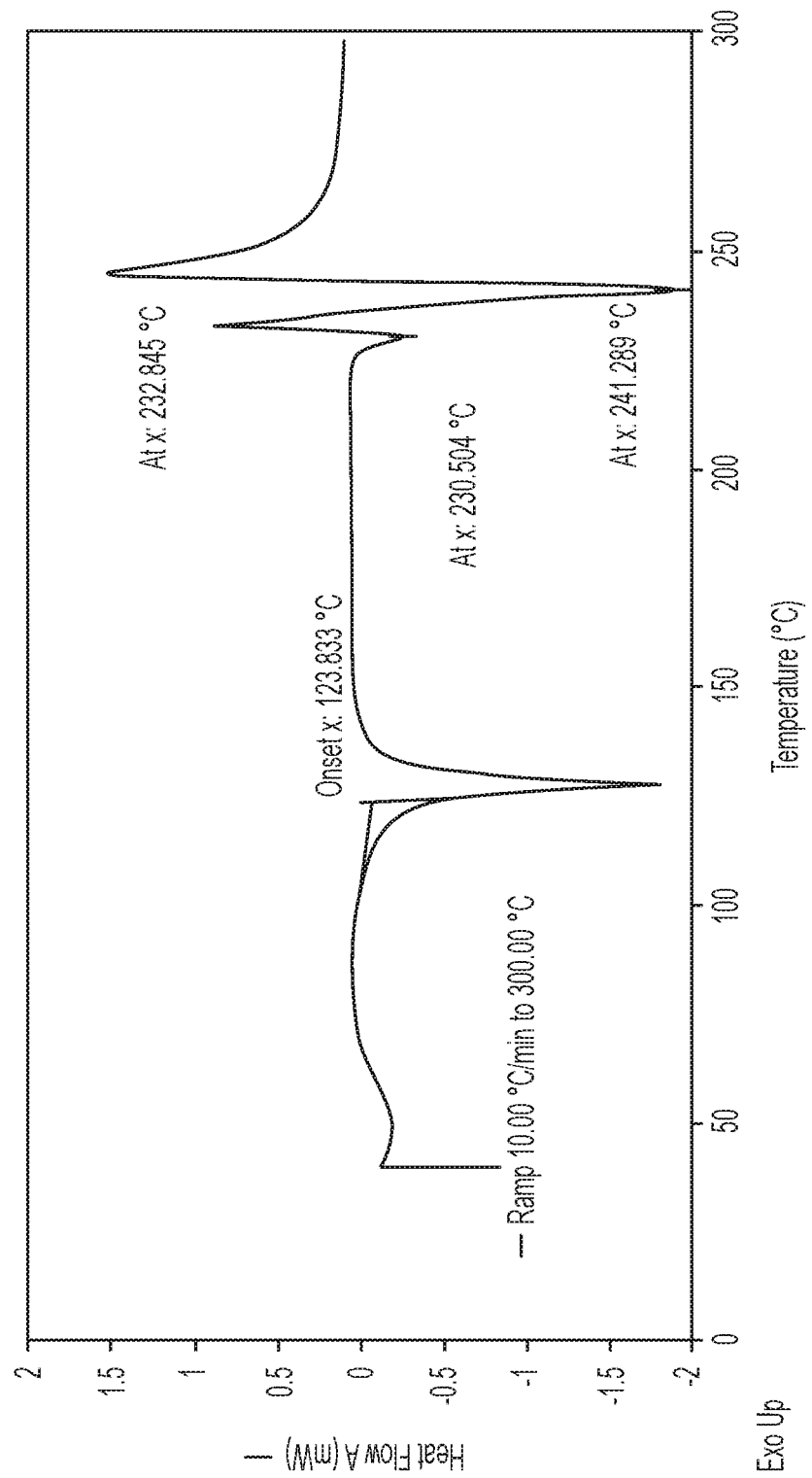
FIG. 19 depicts a DSC thermogram of Form I of Compound 1 obtained from a slurry of Form H in water.
Figure 27:
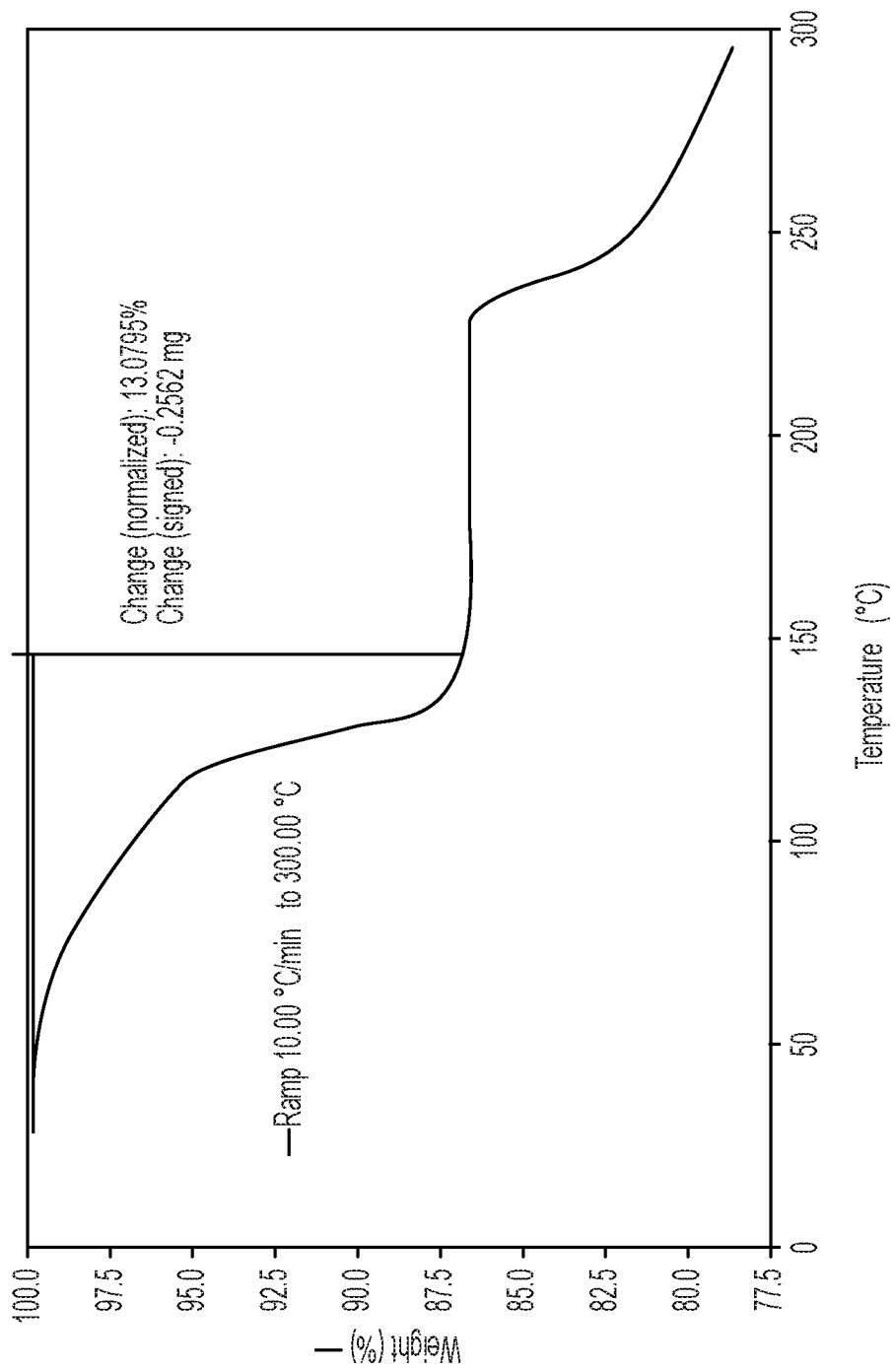
FIG. 27 depicts a TGA thermogram of Form I of Compound 1 obtained from a slurry of Form H in water.
Figure 47A:
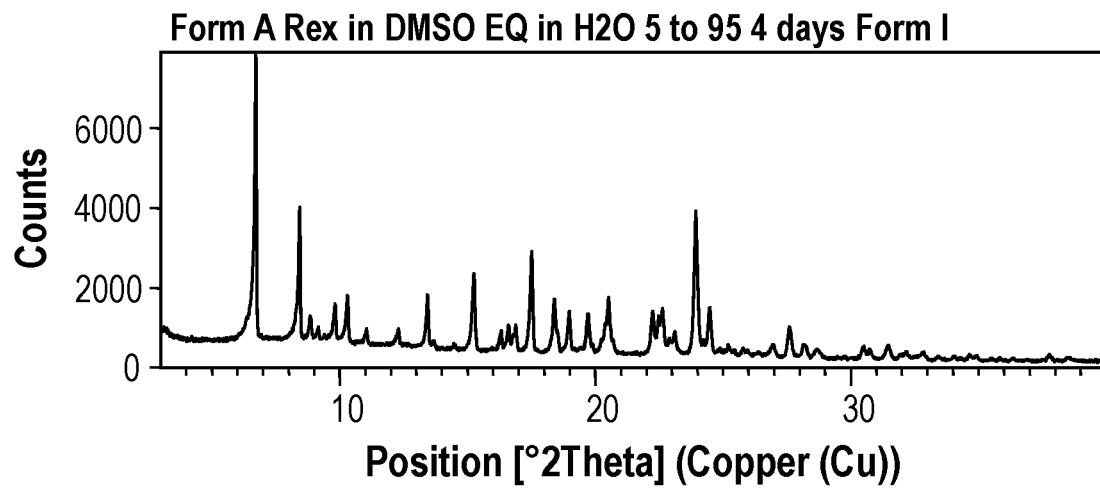
FIG. 47 depicts a comparison of XRPD patterns of Form I of Compound 1 obtained from slurry of Form H in water (a) as-is and (b) after DVS.
Figure 47B:
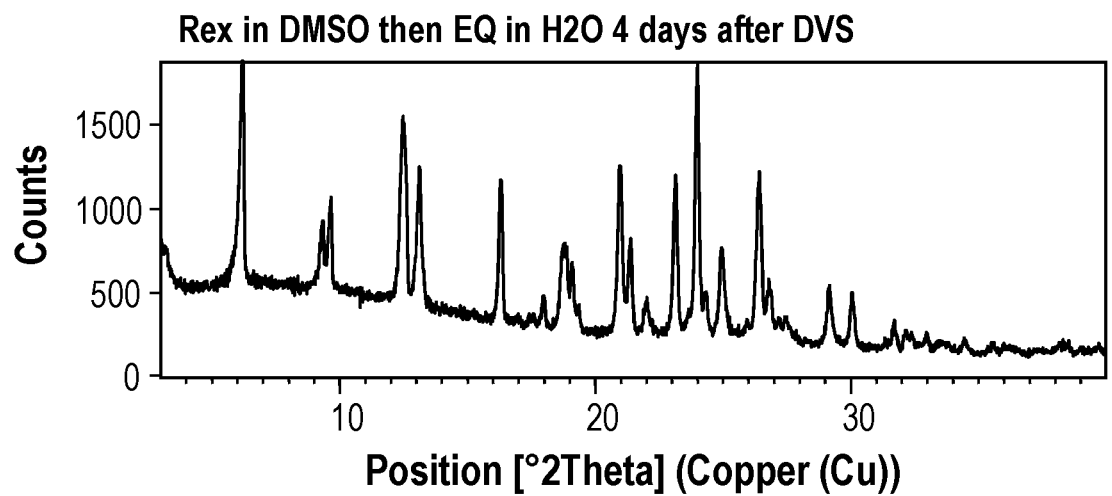

DSC and TGA thermograms of Form I are shown in FIG. 19 and FIG. 27, respectively. The DSC thermogram showed multiple events, including an endothermic peak around 124° C., followed by endo-/exothermic peaks around 230° C., and finally a major endothermic peak around 241° C. About 13.1% TGA weight loss was observed up to 150° C. The DVS isothermal plot of Form I in shown in FIG. 33. Approximately 1.5 wt % water uptake was observed between 0 and 90% RH and the solid obtained after DVS was found to change to Form A (FIG. 47(*b*)). The DVS observation doesn't seem to correspond to the large weight loss observed by TGA. It was suspected that the Form I sample was unstable and converted to Form A before or during DVS experiments. Based on the characterization data, Form I is a hydrate or a hydrate/solvate.

Figure 10:
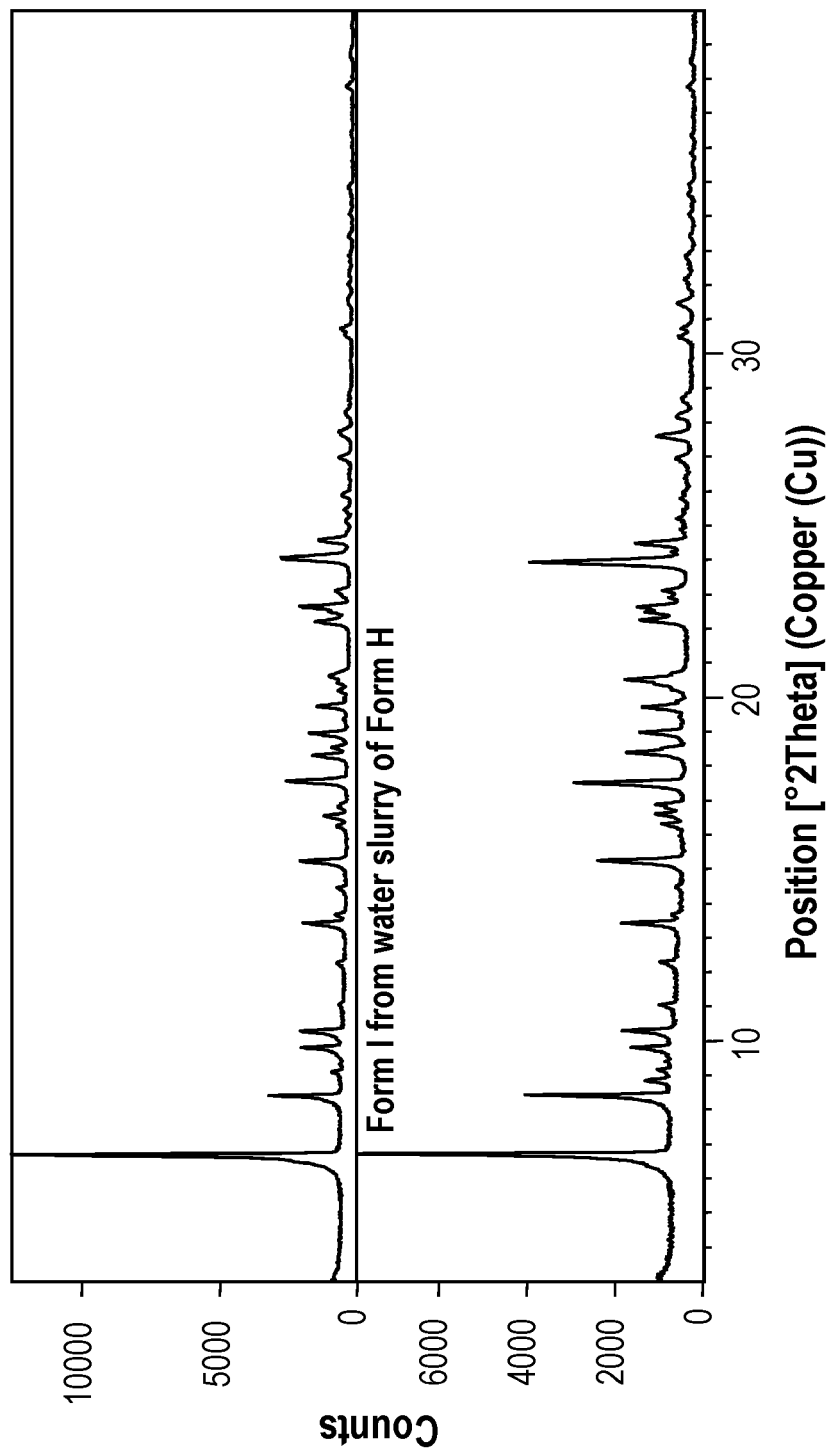
FIG. 10 depicts a comparison of XRPD patterns of Form I of Compound 1 obtained from recrystallization of Compound 1 in THF/water (top) and Form I of Compound 1 obtained from slurry of Form H in water (bottom).
Figure 20:
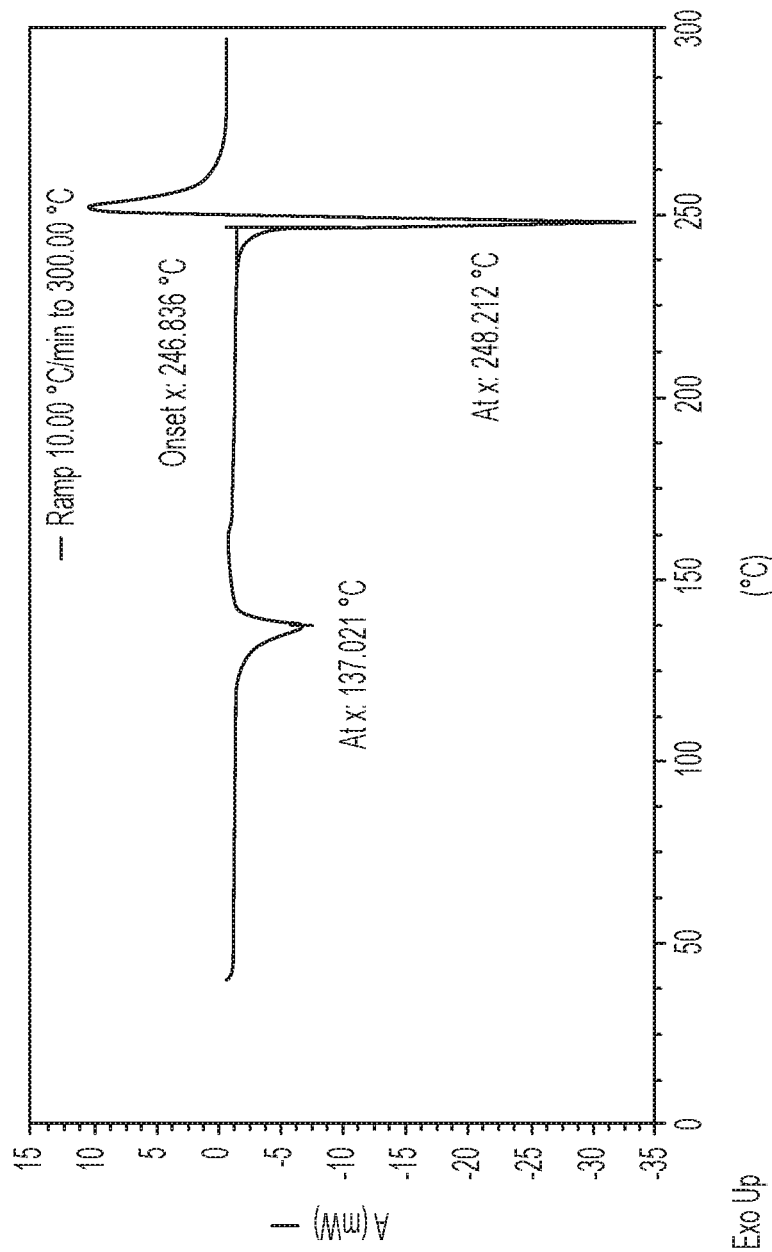
FIG. 20 depicts a DSC thermogram of Form I of Compound 1 obtained from recrystallization of Compound 1 in THF/water.
Figure 28:
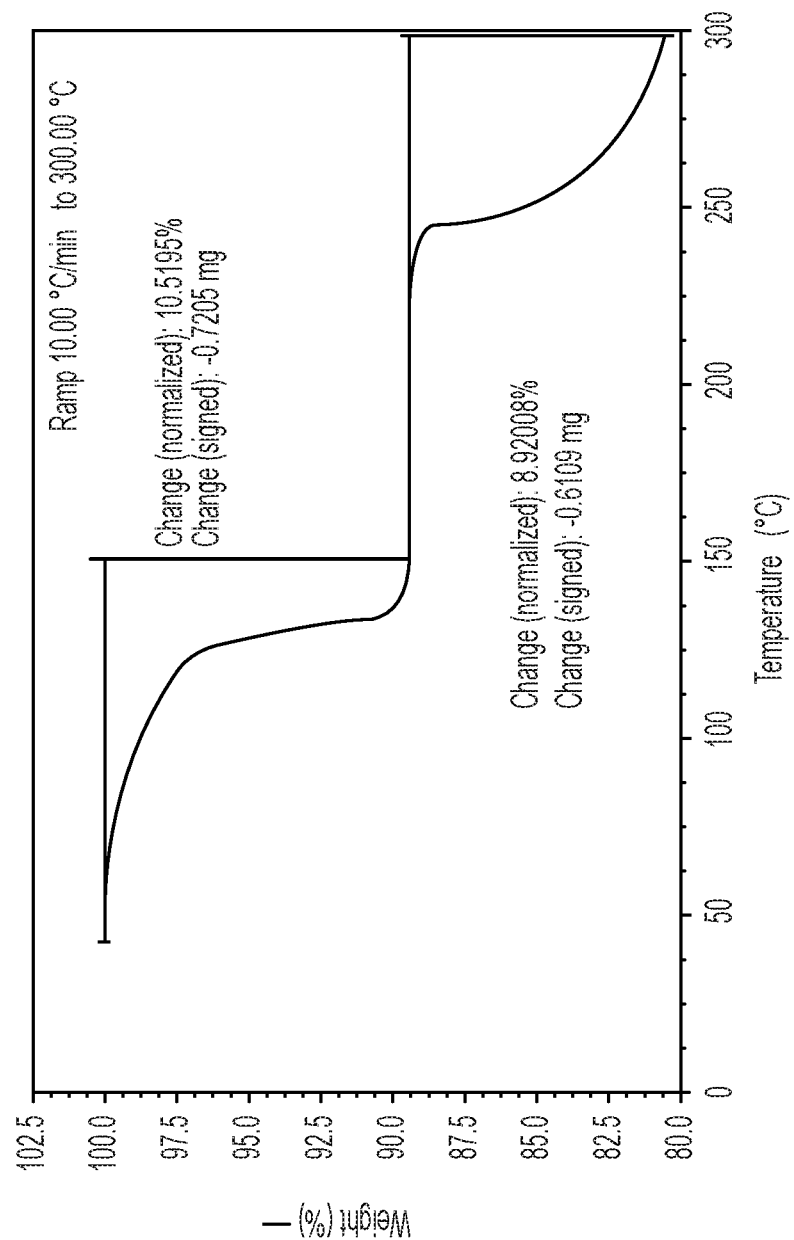
FIG. 28 depicts a TGA thermogram of Form I of Compound 1 obtained from recrystallization of Compound 1 in THF/water.
Figure 29:
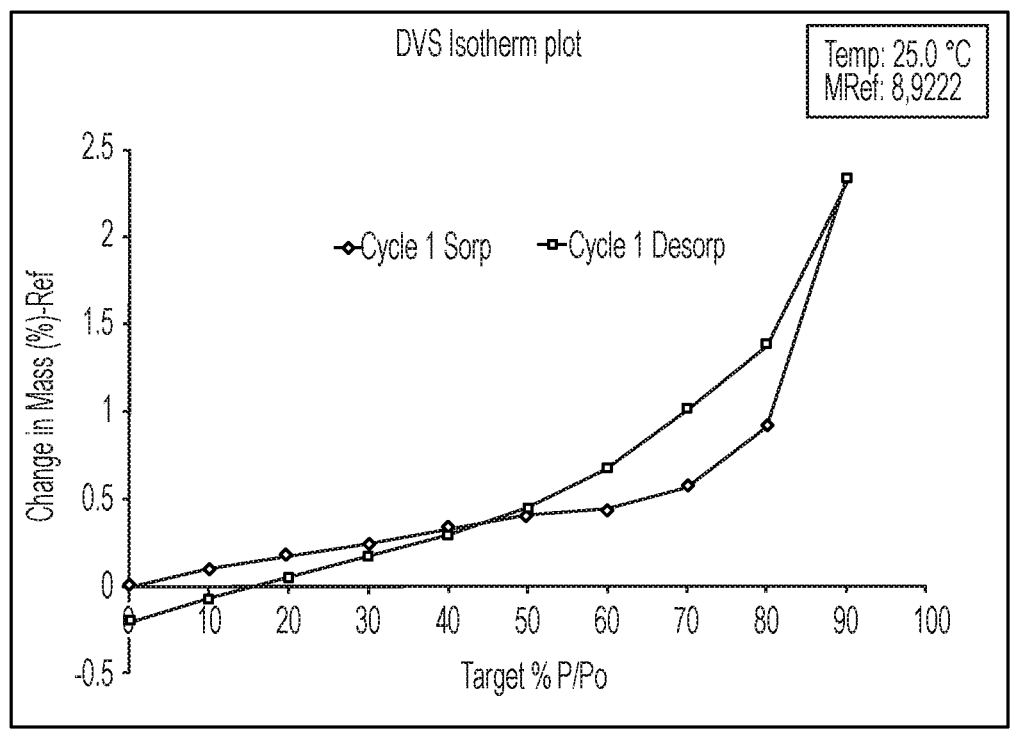
FIG. 29 depicts a DVS isotherm plot of Form A of Compound 1.

Form I was also observed when Compound 1 was recrystallized in THF/water. The XRPD pattern of Form I obtained from recrystallization in THF/water in comparison to the XRPD of Form I obtained from a slurry of Form H in water is shown in FIG. 10. The DSC and TGA thermograms are shown in FIG. 20 and FIG. 28, respectively. About 10.5% TGA weight loss was observed up to 150° C. The DSC thermogram showed a small endothermic peak around 137° C., and a major endothermic peak with an onset temperature of 247° C. The $^1$H NMR spectrum of Form I obtained from recrystallization in THF/water (FIG. 41) showed about 0.73 molar equivalent of THF, consistent with the TGA weight loss observed. Based on these data, Form I obtained from recrystallization in THF/water is likely a THF solvate or solvate/hydrate.

The two Form I samples observed, which were obtained from different solvent systems, suggests that Form I is an isostructural solvate/hydrate.

Example 2. Salt and Co-Crystal Screen of Compound 1

A salt/co-crystal screen was performed to identify a form with better aqueous solubility. A crystalline form of Compound 1, designated as Form A, was mixed with co-formers under various conditions in attempts to generate salts and/or co-crystals.

X-ray Powder Diffraction (XRPD): The Rigaku SmartLab X-ray diffraction system was configured for reflection Bragg-Brentano geometry using a line source X-ray beam. The x-ray source is a Cu Long Fine Focus tube that was operated at 40 kV and 44 ma. That source provides an incident beam profile at the sample that changes from a narrow line at high angles to a broad rectangle at low angles. Beam conditioning slits are used on the line X-ray source to ensure that the maximum beam size is less than 10 mm both along the line and normal to the line. The Bragg-Brentano geometry is a para-focusing geometry controlled by passive divergence and receiving slits with the sample itself acting as the focusing component for the optics. The inherent resolution of Bragg-Brentano geometry is governed in part by the diffractometer radius and the width of the receiving slit used. Typically, the Rigaku Smart-Lab is operated to give peak widths of 0.1 °2θ or less. The axial divergence of the X-ray beam is controlled by 5.0-degree Soller slits in both the incident and diffracted beam paths.

Powder samples were prepared in a low background Si holder using light manual pressure to keep the sample surfaces flat and level with the reference surface of the sample holder. Each sample was analyzed from 2 to 40 °2θ using a continuous scan of 6 °2θ per minute with an effective step size of 0.02 °2θ.

Differential Scanning Calorimetry (DSC):

DSC analyses were carried out using a TA Instruments Q2000 instrument. The instrument temperature calibration was performed using indium. The DSC cell was kept under a nitrogen purge of ~50 mL per minute during each analysis. The sample was placed in a standard, crimped, aluminum pan and was heated from 25° C. to 350° C. at a rate of 10° C. per minute.

Thermogravimetric (TG) Analysis:

The TG analysis was carried out using a TA Instruments Q50 instrument. The instrument balance was calibrated using class M weights and the temperature calibration was performed using alumel. The nitrogen purge was ~40 mL per minute at the balance and ~60 mL per minute at the furnace. Each sample was placed into a pre-tared platinum pan and heated from 20° C. to 350° C. at a rate of 10° C. per minute.

Nuclear Magnetic Resonance (NMR) Spectroscopy:

The $^1$H NMR spectra were acquired on a Bruker DRX-500 spectrometer located at the Chemistry Department of Purdue University. Samples were prepared by dissolving material in DMSO-$d_6$. The solutions were filtered and placed into individual 5-mm NMR tubes for subsequent spectral acquisition. The temperature controlled (298 K)$^1$H NMR spectra acquired on the DRX-500 utilized a 5-mm cryoprobe operating at an observing frequency of 499.89 MHz.

Typical Cooling Experiment:

A vial was charged with 16.6 mg of Compound 1 (Form A). Acetone was added until the solid dissolved; about 6 mL was used. Another vial was charged with 4.2 mg of phosphoric acid. Acetone (about ½ mL) was added and mixed. The acid solution was transferred to the API solution and mixed. The resulting solution was placed in a freezer (about −15° C.) for two days, during which time crystallization occurred. The solvent was decanted and the solid dried in the air.

Typical Evaporation Experiment:

A solution of 15.0 mg of Compound 1 (Form A) and 5.5 mg of L-ascorbic acid in about 4 mL of tetrahydrofuran was placed in an open vial in a fume hood overnight. THF was allowed to evaporate, resulting in a solid.

Typical Milling Experiment:

A mixture of 17.9 mg of Compound 1 (Form A) and 7.2 mg of p-toluenesulfonic acid was placed in a PEEK grinding cup with 10 µL of methanol and one steel ball. The sample was placed on a Retsch mill and milled at 100% power for 20 minutes. The resulting solid was allowed to dry in the air.

Typical Slurry Experiment:

A vial was charged with 17.8 mg of Compound 1 (Form A), 5.6 mg of L-lysine, and approximately 500 µL of a 1:1 stoichiometric solution of both API and co-former in methanol. A magnetic stir bar was placed in the vial and it was placed on a stir plate at room temperature for about 7 days. The solids were isolated by centrifugation.

Results are shown in Table 17:

TABLE 17

Preliminary Results - Salt/Co-Crystal Screen

| Co-former | Conditions$^a$ | XRPD Pattern |
|---|---|---|
| acetic acid | evaporation from THF at RT | Compound 1^ |
|  | grinding in MeOH, ~20 min | Form A |
| t-aconitic acid | evaporation from THF at RT | New Form + non-crystalline material |
|  | grinding in MeOH, ~20 min | New Form + Form A |
|  | slurried in acetone, 7 days | New Form + co-former |
| adipic acid | evaporation from THF at RT | Form A + Compound 1^ + co-former |
|  | grinding in MeOH, ~20 min | Form A + co-former |
|  | slurried in acetone, 7 days | Form A + co-former |
| L-ascorbic acid | evaporation from THF at RT | New Form |
|  | grinding in MeOH, ~20 min | Form A + co-former |
|  | slurried in acetone, 7 days | Form A + co-former |
| aspartic acid | evaporation from THF at RT | New Form + co-former |
|  | grinding in MeOH, ~20 min | Form A + acid |
|  | slurried in MeOH, 7 days | Form A + co-former |
| benzenesulfonic acid | evaporation from THF at RT | non-crystalline material |
|  | acetone, 60° C. cooled to −15° C.: no solid formed | Form A |
|  | evaporation from acetone at RT |  |
| benzoic acid | evaporation from THF at RT | New Form + Form A + co-former |
|  | grinding in MeOH, ~20 min | Form A + co-former |
|  | slurried in 1:1 THF/hexanes, 7 days | New Form + co-former |
| camphoric acid | evaporation from THF at RT | Form A + co-former |
|  | grinding in MeOH, ~20 min | Form A + co-former |
|  | slurried in 1:1 THF/hexanes, 7 days | Form A + co-former |
| caprylic acid | evaporation from THF at RT | Form A |
|  | grinding in MeOH, ~20 min | Form A |
|  | slurried in 1:1 THF/hexnes, 7 days: no solid formed (gel) triturated in Et$_2$O | Form A |
| citric acid | evaporation from THF at RT | non-crystalline material |
|  | grinding in MeOH, ~20 min | Form A + co-former |
|  | slurried in 10:1 THF/hexanes, 7 days | New Form + co-former |
| cyclamic acid | evaporation from THF at RT | non-crystalline material |
|  | acetone, 60° C. cooled to −15° C.: no solid formed | Form A + co-former |
|  | evaporation from acetone at RT |  |
| dodecyl-sulfuric acid | evaporation from THF at RT | non-crystalline material |
|  | acetone, 60° C. cooled to −15° C.: no solid formed | Form A + co-former |
|  | evaporation from acetone at RT |  |
| ethanesulfonic acid | evaporation from THF at RT | Compound 1^ + non-crystalline material |
|  | acetone, 60° C. cooled to −15° C. | Compound 1^ +non-crystalline material |
| D-fructose | evaporation from THF at RT | Compound 1^ +co-former |
|  | grinding in MeOH, ~20 min | Form A + co-former |
|  | slurried in MeOH, 7 days | Form A + co-former |
| fumaric acid | evaporation from THF at RT | Form A + Compound 1^ + co-former |
|  | grinding in MeOH, ~20 min | Form A + co-former |
|  | slurried in acetone, 7 days | Form A + co-former |
| galactaric (mucic) acid | evaporation from THF at RT | Form A + co-former |
|  | grinding in MeOH, ~20 min | Form A + co-former |
|  | slurried in MeOH, 7 days | Form A + co-former |
| gentisic acid | evaporation from THF at RT | Form A |
|  | grinding in MeOH, ~20 min | New Form |
|  | slurried in 1:1 THF/hexanes, 7 days | New Form 2 + co-former |

TABLE 17-continued

Preliminary Results - Salt/Co-Crystal Screen

| Co-former | Conditions[a] | XRPD Pattern |
|---|---|---|
| D-gluconic acid | evaporation from THF at RT | Compound 1^ |
| | grinding in MeOH, ~20 min | Form A |
| L-glutamic acid | evaporation from THF at RT | Form A + co-former |
| | grinding in MeOH, ~20 min | Form A + co-former |
| | slurried in MeOH, 7 days | Form A + co-former |
| glutaric acid | evaporation from THF at RT | Form A |
| | grinding in MeOH, ~20 min | Form A + co-former |
| | slurried in 1:1 THF/hexanes, 7 days | New Form + co-former |
| glycolic acid | evaporation from THF at RT | Form A |
| | grinding in MeOH, ~20 min | Form A |
| | slurried in 1:1 THF/hexanes, 7 days | Form A |
| hippuric acid | evaporation from THF at RT | Compound 1^ + co-former |
| | grinding in MeOH, ~20 min | Form A + co-former |
| | slurried in acetone, 7 days | Form A + co-former |
| hydrochloric acid | evaporation from THF at RT | non-crystalline material |
| | acetone, 60° C. cooled to −15° C.: no solid formed; evaporation from acetone at RT | Form A |
| 1-hydroxy-2-naphthoic acid | evaporation from THF at RT | New Form |
| | grinding in MeOH, ~20 min | Form A + New Form |
| | grinding in MeOH, ~20 min (1:2) | New Form 2 |
| | slurried in 1:1 THF/hexanes, 7 days | New Form 2 + co-former |
| isethionic acid | evaporation from THF at RT | New Form + non-crystalline material |
| | acetone, 60° C. cooled to −15° C.: no solid formed evaporation from acetone at RT | Form A |
| ketoglutaric acid | evaporation from THF at RT | Form A + Compound 1^ |
| | grinding in MeOH, ~20 min | Form A + co-former |
| | slurried in 1:1 THF/hexanes, 7 days | New Form + co-former |
| L-lactic acid | evaporation from THF at RT | Form A |
| | grinding in MeOH, ~20 min: gel triturated in Et2O | Form A |
| | slurried in 1:1 THF/hexanes, 7 days | Form A |
| lauric acid | evaporation from THF at RT | Form A + co-former |
| | grinding in MeOH, ~20 min | Form A + co-former |
| | slurried in MeOH, 7 days | Form A + co-former |
| L-lysine | evaporation from THF at RT | Compound 1^ |
| | grinding in MeOH, ~20 min | Form A + co-former |
| | slurried in MeOH, 7 days | New Form |
| maleic acid | evaporation from THF at RT | Form A + Compound 1^ |
| | grinding in MeOH, ~20 min | New Form |
| | slurried in acetone, 7 days | New Form + co-former |
| | acetone/hexanes, reflux cooled to RT | Form A |
| | THF/hexanes, reflux cooled to RT | Compound 1^ |
| L-malic acid | evaporation from THF at RT | Form A |
| | grinding in MeOH, ~20 min | Form A |
| | slurried in 1:1 THF/hexanes, 7 days: no solid formed (gel) triturated in Et2O: no solid formed (gel) | — |
| malonic acid | evaporation from THF at RT | New Form + Form A |
| | grinding in MeOH, ~20 min | Form A |
| | slurried in 1:1 THF/hexanes, 7 days | New Form + co-former |
| methanesulfonic acid | evaporation from THF at RT | Compound 1^ + non-crystalline material |
| | acetone, 60° C. cooled to −15° C.: no solid formed evaporation from acetone at RT | Form A + Compound 1^ |
| | slow evaporation from acetone at 60° C. cooled to RT | New Form |
| naphthalene-1,5-disulfonic acid | evaporation from THF at RT | New Form + Compound 1^ |
| | grinding in MeOH, ~20 min | Form A + non-crystalline material |
| | slurried in acetone, RT | non-crystalline material |
| naphthalene-2-sulfonic acid | evaporation from THF at RT | non-crystalline material |
| | grinding in MeOH, ~20 min | Form A + non-crystalline material |
| | acetone, RT cooled to −15 ° C.; no solid formed evaporation from acetone at RT | non-crystalline |
| nicotinamide | evaporation from THF at RT | Form A + Compound 1^ + co-former |
| | grinding in MeOH, ~20 min | Form A + co-former |
| | slurried in MeOH, 7 days | Form A + co-former |
| nicotinic acid | evaporation from THF at RT | Compound 1^ + co-former |
| | grinding in MeOH, ~20 min | Form A + co-former |
| | slurried in MeOH, 7 days | Form A + co-former |
| oleic acid | evaporation from THF at RT: no solid formed (gel) triturated in Et2O | Form A |
| | grinding in MeOH, ~20 min: no solid formed (gel) triturated in Et2O | Form A + non-crystalline material |
| | slurried in MeOH, 7 days: no solid formed (gel) triturated in Et2O | Form A |
| orotic acid | evaporation from THF at RT | Compound 1^ |
| | grinding in MeOH, ~20 min | Form A + co-former |
| | slurried in MeOH, 7 days | Form A + co-former |
| oxalic acid | evaporation from THF at RT | Form A + Compound 1^ |
| | slurried in 1:1 THF/hexanes, 7 days | New Form + co-former |
| palmitic acid | evaporation from THF at RT | Compound 1^ + co-former |
| | grinding in MeOH, ~20 min | Form A + co-former |
| | slurried in MeOH, 7 days | Form A + co-former |
| pamoic acid | evaporation from THF at RT | non-crystalline material + co-former |
| | grinding in MeOH, ~20 min | Form A + co-former |
| | slurried in MeOH, 7 days | Form A + co-former |
| phosphoric acid | evaporation from THF at RT | New Form + non-crystalline material |
| | acetone, 60° C. cooled to −15° C. | New Form + Form A |
| | slow evaporation from THF at RT | New Form + non-crystalline material |
| L-proline | evaporation from THF at RT | Compound 1^ + co-former |
| | grinding in MeOH, ~20 min | Form A + co-former |
| | slurried in MeOH, 7 days | Form A + co-former |
| L-pyroglutamic acid | evaporation from THF at RT | Form A + co-former |
| | grinding in MeOH, ~20 min | Form A + co-former |
| | slurried in acetone, 7 days | Form A + co-former |
| saccharin | evaporation from THF at RT | New Form |
| | grinding in MeOH, ~20 min | Form A + co-former |
| | slurried in MeOH, 7 days | Form A + co-former |
| sebacic acid | evaporation from THF at RT | Form A + co-former |
| | grinding in MeOH, ~20 min | Form A + co-former |
| | slurried in MeOH, 7 days | Form A + co-former |
| sorbic acid | evaporation from THF at RT | Form A + Compound 1^ + co-former |
| | grinding in MeOH, ~20 min | Form A + co-former |
| | slurried in 1:1 THF/hexanes, 7 days | Form A + co-former |
| stearic acid | evaporation from THF at RT | Compound 1^ + co-former |
| | grinding in MeOH, ~20 min | Form A + co-former |
| | slurried in MeOH, 7 days | Form A + co-former |
| succinic acid | evaporation from THF at RT | Form A + co-former |
| | grinding in MeOH, ~20 min | Form A + co-former |
| | slurried in acetone, 7 days | Form A + co-former |

TABLE 17-continued

Preliminary Results - Salt/Co-Crystal Screen

| Co-former | Conditions[a] | XRPD Pattern |
|---|---|---|
| sulfuric acid | evaporation from THF | Compound 1^ + non-crystalline material |
| | acetone, 60° C. cooled to −15° C.: no solid formed | Form A + Compound 1^ |
| | evaporation from acetone at RT | |
| L-tartaric acid | evaporation from THF at RT | non-crystalline material |
| | grinding in MeOH, ~20 min | Form A + co-former |
| | slurried in acetone, 7 days | Form A + co-former |
| thiocyanic acid | evaporation from THF at RT | New Form + non-crystalline material |
| | acetone, 60° C. cooled to −15° C. | New Form + Form A |
| p-toluene-sulfonic acid | evaporation from THF at RT | non-crystalline material |
| | grinding in MeOH, ~20 min | New Form |
| | acetone, 60° C. cooled to −15° C.: no solid formed | non-crystalline material |
| | evaporation from acetone at RT | |
| vanillic acid | evaporation from THF at RT | Form A + Compound 1^ + co-former |
| | grinding in MeOH, ~20 min | Form A + co-former |
| | slurried in acetone, 7 days | Form A + co-former |
| vanillin | evaporation from THF at RT | Form A + Compound 1^ |
| | grinding in MeOH, ~20 min | Form A + co-former |
| | slurried in acetone, 7 days | New Form + Form A |

[a]ACN = acetonitrile, EtOH = ethanol, Et$_2$O = diethyl ether, hex = hexanes, MeOH = methanol, P = precipitation, THF = tetrahydrofuran, RT = room temperature.
^unknown freebase crystal form Based on this primary salt/co-crystal screen, twenty one potential co-crystals were identified: t-aconitic acid, L-ascorbic acid, aspartic acid, benzoic acid, citric acid, gentisic acid, glutaric acid, 1-hydroxy-2-naphthoic acid, isethionic acid, ketoglutaric acid, L-lysine, maleic acid, malonic acid, methanesulfonic acid, naphthalene-1,5-disulphonic acid, oxalic acid, phosphoric acid, saccharin, thiocyanic acid, p-toluenesulfonic acid, and vanillin. Peak lists are set forth in Tables 18-40.

TABLE 18 t-Aconitic Acid.

| Position [°2θ] | d-spacing [Å] | Relative Intensity [%] |
|---|---|---|
| 3.91 | 22.57 | 43.05 |
| 6.21 | 14.21 | 8.43 |
| 7.81 | 11.31 | 17.42 |
| 10.98 | 8.05 | 17.71 |
| 12.52 | 7.07 | 61.86 |
| 12.62 | 7.01 | 37.92 |
| 13.00 | 6.80 | 64.44 |
| 13.25 | 6.68 | 31.13 |
| 14.10 | 6.27 | 7.62 |
| 15.70 | 5.64 | 5.70 |
| 16.40 | 5.40 | 15.45 |
| 18.56 | 4.78 | 45.52 |
| 19.05 | 4.65 | 18.96 |
| 19.58 | 4.53 | 8.23 |
| 20.09 | 4.42 | 12.29 |
| 20.67 | 4.29 | 7.02 |
| 20.99 | 4.23 | 7.78 |
| 21.64 | 4.10 | 30.43 |
| 23.58 | 3.77 | 100.00 |
| 23.90 | 3.72 | 51.38 |
| 24.54 | 3.62 | 52.22 |
| 25.17 | 3.54 | 44.83 |
| 26.01 | 3.42 | 34.95 |
| 26.37 | 3.38 | 13.94 |
| 26.86 | 3.32 | 7.46 |

TABLE 18-continued t-Aconitic Acid.

| Position [°2θ] | d-spacing [Å] | Relative Intensity [%] |
|---|---|---|
| 28.20 | 3.16 | 5.37 |
| 30.90 | 2.89 | 22.49 |
| 32.08 | 2.79 | 5.62 |
| 33.96 | 2.64 | 5.90 |
| 38.14 | 2.36 | 6.30 |

TABLE 19

L-Ascorbic Acid.

| Position [°2θ] | d-spacing [Å] | Relative Intensity [%] |
|---|---|---|
| 6.79 | 13.00 | 100.00 |
| 9.51 | 9.29 | 7.95 |
| 11.89 | 7.44 | 5.85 |
| 13.55 | 6.53 | 9.00 |
| 14.06 | 6.29 | 22.26 |
| 18.03 | 4.92 | 7.77 |
| 18.29 | 4.85 | 6.12 |
| 18.85 | 4.70 | 13.15 |
| 19.99 | 4.44 | 17.50 |
| 21.98 | 4.04 | 8.11 |
| 24.76 | 3.59 | 45.91 |
| 25.68 | 3.47 | 46.88 |
| 27.25 | 3.27 | 4.94 |
| 31.24 | 2.86 | 10.71 |

TABLE 20

Aspartic Acid.

| Position [°2θ] | d-spacing [Å] | Relative Intensity [%] |
|---|---|---|
| 6.48 | 13.63 | 13.91 |
| 6.71 | 13.17 | 19.68 |
| 6.81 | 12.97 | 57.32 |
| 6.97 | 12.67 | 100.00 |
| 11.77 | 7.51 | 12.96 |
| 13.63 | 6.49 | 7.02 |
| 13.94 | 6.35 | 10.32 |
| 14.17 | 6.25 | 11.25 |
| 15.21 | 5.82 | 7.46 |
| 15.61 | 5.67 | 16.24 |
| 17.54 | 5.05 | 7.31 |
| 18.68 | 4.75 | 5.18 |
| 19.68 | 4.51 | 5.17 |
| 19.96 | 4.44 | 5.93 |
| 20.48 | 4.33 | 7.22 |
| 20.97 | 4.23 | 17.93 |
| 21.64 | 4.10 | 7.24 |
| 22.78 | 3.90 | 16.57 |
| 23.63 | 3.76 | 21.45 |
| 23.71 | 3.75 | 14.42 |
| 24.03 | 3.70 | 11.88 |
| 24.72 | 3.60 | 9.76 |
| 24.91 | 3.57 | 5.62 |
| 25.41 | 3.50 | 19.78 |
| 25.89 | 3.44 | 6.10 |
| 26.13 | 3.41 | 6.78 |
| 28.16 | 3.17 | 12.05 |
| 31.07 | 2.88 | 6.65 |
| 37.21 | 2.41 | 5.96 |
| 39.37 | 2.29 | 8.36 |

TABLE 21

| Benzoic Acid. | | |
|---|---|---|
| Position [°2θ] | d-spacing [Å] | Relative Intensity [%] |
| 6.22 | 14.20 | 35.52 |
| 8.12 | 10.88 | 36.69 |
| 9.37 | 9.43 | 9.30 |
| 9.67 | 9.14 | 13.41 |
| 9.94 | 8.89 | 22.42 |
| 10.55 | 8.38 | 11.80 |
| 12.46 | 7.10 | 26.30 |
| 12.62 | 7.01 | 28.63 |
| 13.08 | 6.76 | 18.51 |
| 14.91 | 5.94 | 28.94 |
| 16.28 | 5.44 | 36.24 |
| 17.21 | 5.15 | 15.40 |
| 18.75 | 4.73 | 32.47 |
| 19.09 | 4.64 | 8.55 |
| 19.90 | 4.46 | 34.56 |
| 20.38 | 4.35 | 7.35 |
| 20.97 | 4.23 | 30.30 |
| 21.39 | 4.15 | 15.62 |
| 21.88 | 4.06 | 12.61 |
| 23.10 | 3.85 | 25.78 |
| 23.72 | 3.75 | 35.37 |
| 23.99 | 3.71 | 100.00 |
| 24.38 | 3.65 | 10.76 |
| 24.92 | 3.57 | 14.32 |
| 25.57 | 3.48 | 20.23 |
| 25.88 | 3.44 | 17.71 |
| 26.38 | 3.38 | 31.89 |
| 26.83 | 3.32 | 7.79 |
| 27.75 | 3.21 | 40.17 |
| 29.12 | 3.06 | 13.12 |
| 30.10 | 2.97 | 20.82 |
| 31.70 | 2.82 | 6.94 |
| 32.15 | 2.78 | 14.42 |

TABLE 22

| Citric Acid. | | |
|---|---|---|
| Position [°2θ] | d-spacing [Å] | Relative Intensity [%] |
| 2.00 | 44.16 | 31.07 |
| 5.84 | 15.12 | 19.69 |
| 7.85 | 11.25 | 14.90 |
| 9.18 | 9.63 | 6.51 |
| 11.07 | 7.99 | 15.14 |
| 12.30 | 7.19 | 27.31 |
| 12.97 | 6.82 | 44.99 |
| 13.92 | 6.36 | 11.20 |
| 14.21 | 6.23 | 9.42 |
| 14.52 | 6.10 | 34.09 |
| 15.58 | 5.68 | 14.18 |
| 17.46 | 5.07 | 31.04 |
| 17.88 | 4.96 | 12.77 |
| 18.21 | 4.87 | 25.73 |
| 18.49 | 4.79 | 11.49 |
| 19.54 | 4.54 | 12.92 |
| 19.77 | 4.49 | 5.13 |
| 21.30 | 4.17 | 37.66 |
| 22.10 | 4.02 | 26.73 |
| 23.79 | 3.74 | 100.00 |
| 24.09 | 3.69 | 65.52 |
| 25.16 | 3.54 | 8.60 |
| 26.18 | 3.40 | 31.51 |
| 26.57 | 3.35 | 13.71 |
| 27.68 | 3.22 | 24.65 |
| 27.91 | 3.19 | 6.47 |
| 28.90 | 3.09 | 14.85 |
| 29.18 | 3.06 | 5.12 |
| 30.01 | 2.98 | 6.46 |
| 31.34 | 2.85 | 11.91 |
| 32.61 | 2.74 | 5.23 |
| 33.65 | 2.66 | 11.92 |
| 34.39 | 2.61 | 6.33 |

TABLE 22-continued

| Citric Acid. | | |
|---|---|---|
| Position [°2θ] | d-spacing [Å] | Relative Intensity [%] |
| 36.14 | 2.48 | 7.95 |
| 36.75 | 2.44 | 7.33 |
| 37.68 | 2.39 | 7.93 |
| 39.40 | 2.28 | 5.36 |

TABLE 23

| Form 1 Gentisic Acid. | | |
|---|---|---|
| Position [°2θ] | d-spacing [Å] | Relative Intensity [%] |
| 4.29 | 20.60 | 10.04 |
| 6.65 | 13.27 | 59.06 |
| 7.36 | 12.00 | 14.53 |
| 8.16 | 10.83 | 5.36 |
| 11.47 | 7.71 | 7.07 |
| 11.86 | 7.46 | 9.52 |
| 13.10 | 6.75 | 11.10 |
| 13.30 | 6.65 | 14.16 |
| 13.49 | 6.56 | 8.11 |
| 14.01 | 6.32 | 22.77 |
| 14.96 | 5.92 | 28.48 |
| 16.10 | 5.50 | 5.91 |
| 17.79 | 4.98 | 5.59 |
| 18.25 | 4.86 | 12.55 |
| 18.58 | 4.77 | 19.45 |
| 19.65 | 4.51 | 7.09 |
| 20.03 | 4.43 | 47.62 |
| 20.73 | 4.28 | 13.51 |
| 21.32 | 4.16 | 13.37 |
| 23.89 | 3.72 | 76.55 |
| 24.61 | 3.61 | 19.80 |
| 24.79 | 3.59 | 66.33 |
| 25.63 | 3.47 | 100.00 |
| 26.03 | 3.42 | 27.22 |
| 26.74 | 3.33 | 33.46 |
| 27.25 | 3.27 | 35.79 |
| 28.02 | 3.18 | 7.42 |
| 30.98 | 2.88 | 11.86 |
| 31.94 | 2.80 | 5.00 |
| 32.38 | 2.76 | 9.10 |
| 34.65 | 2.59 | 7.52 |

TABLE 24

| Form 2 Gentisic Acid. | | |
|---|---|---|
| Position [°2θ] | d-spacing [Å] | Relative Intensity [%] |
| 4.35 | 20.29 | 10.41 |
| 7.52 | 11.74 | 20.05 |
| 8.42 | 10.50 | 57.45 |
| 9.80 | 9.02 | 36.67 |
| 10.39 | 8.51 | 12.01 |
| 12.12 | 7.30 | 5.83 |
| 14.06 | 6.29 | 13.99 |
| 16.05 | 5.52 | 50.82 |
| 16.33 | 5.42 | 28.49 |
| 16.88 | 5.25 | 4.96 |
| 17.75 | 4.99 | 18.93 |
| 18.41 | 4.82 | 8.62 |
| 19.59 | 4.53 | 14.82 |
| 19.76 | 4.49 | 81.38 |
| 20.80 | 4.27 | 9.74 |
| 21.31 | 4.17 | 13.25 |
| 22.66 | 3.92 | 5.29 |
| 23.56 | 3.77 | 61.11 |
| 24.74 | 3.60 | 100.00 |
| 25.19 | 3.53 | 9.60 |
| 25.41 | 3.50 | 37.30 |
| 25.60 | 3.48 | 33.27 |

TABLE 24-continued

Form 2 Gentisic Acid.

| Position [°2θ] | d-spacing [Å] | Relative Intensity [%] |
|---|---|---|
| 26.32 | 3.38 | 13.78 |
| 26.91 | 3.31 | 53.49 |
| 27.60 | 3.23 | 31.93 |
| 28.84 | 3.09 | 22.83 |
| 31.13 | 2.87 | 12.96 |
| 33.02 | 2.71 | 8.04 |
| 36.83 | 2.44 | 10.01 |
| 39.66 | 2.27 | 5.79 |

TABLE 25

Glutaric Acid.

| Position [°2θ] | d-spacing [Å] | Relative Intensity [%] |
|---|---|---|
| 7.15 | 12.36 | 5.31 |
| 11.97 | 7.39 | 6.92 |
| 16.78 | 5.28 | 6.30 |
| 19.67 | 4.51 | 16.15 |
| 22.01 | 4.03 | 34.26 |
| 24.06 | 3.70 | 100.00 |
| 27.31 | 3.26 | 51.84 |

TABLE 26

Form 1 1-Hydroxy-2-Naphthoic Acid.

| Position [°2θ] | d-spacing [Å] | Relative Intensity [%] |
|---|---|---|
| 6.74 | 13.10 | 12.51 |
| 7.40 | 11.94 | 20.88 |
| 9.53 | 9.27 | 15.35 |
| 10.26 | 8.61 | 47.90 |
| 11.18 | 7.91 | 14.55 |
| 12.07 | 7.33 | 7.25 |
| 12.33 | 7.17 | 5.60 |
| 12.80 | 6.91 | 6.34 |
| 13.99 | 6.33 | 7.77 |
| 14.27 | 6.20 | 12.37 |
| 14.97 | 5.91 | 9.82 |
| 15.25 | 5.81 | 5.87 |
| 15.59 | 5.68 | 9.69 |
| 16.71 | 5.30 | 10.85 |
| 17.24 | 5.14 | 54.25 |
| 18.42 | 4.81 | 13.43 |
| 19.07 | 4.65 | 18.61 |
| 21.42 | 4.15 | 6.94 |
| 22.46 | 3.95 | 57.41 |
| 23.37 | 3.80 | 48.34 |
| 23.85 | 3.73 | 41.68 |
| 24.42 | 3.64 | 19.76 |
| 25.99 | 3.43 | 100.00 |
| 26.44 | 3.37 | 27.80 |
| 27.98 | 3.19 | 16.87 |
| 28.93 | 3.08 | 8.86 |
| 29.48 | 3.03 | 12.50 |
| 30.40 | 2.94 | 12.67 |
| 31.56 | 2.83 | 8.62 |
| 34.18 | 2.62 | 5.12 |
| 35.65 | 2.52 | 5.16 |

TABLE 27

Form 2 1-Hydroxy-2-Naphthoic Acid.

| Position [°2θ] | d-spacing [Å] | Relative Intensity [%] |
|---|---|---|
| 2.58 | 34.23 | 26.79 |
| 5.09 | 17.36 | 15.90 |

TABLE 27-continued

Form 2 1-Hydroxy-2-Naphthoic Acid.

| Position [°2θ] | d-spacing [Å] | Relative Intensity [%] |
|---|---|---|
| 7.62 | 11.60 | 17.41 |
| 10.15 | 8.71 | 21.63 |
| 12.12 | 7.30 | 38.83 |
| 12.37 | 7.15 | 69.28 |
| 13.22 | 6.69 | 7.45 |
| 13.98 | 6.33 | 22.08 |
| 14.31 | 6.19 | 26.79 |
| 15.30 | 5.79 | 18.15 |
| 16.92 | 5.24 | 7.00 |
| 17.46 | 5.07 | 20.09 |
| 19.46 | 4.56 | 35.11 |
| 21.74 | 4.09 | 11.64 |
| 22.88 | 3.88 | 10.30 |
| 23.57 | 3.77 | 7.35 |
| 24.04 | 3.70 | 100.00 |
| 24.37 | 3.65 | 21.99 |
| 24.88 | 3.58 | 8.22 |
| 25.21 | 3.53 | 12.20 |
| 26.16 | 3.40 | 92.92 |
| 26.65 | 3.34 | 62.82 |
| 28.30 | 3.15 | 6.24 |
| 29.59 | 3.02 | 19.17 |
| 30.62 | 2.92 | 16.41 |
| 33.13 | 2.70 | 6.08 |
| 33.62 | 2.66 | 8.96 |

TABLE 28

Isethionic Acid.

| Position [°2θ] | d-spacing [Å] | Relative Intensity [%] |
|---|---|---|
| 5.07 | 17.42 | 47.77 |
| 5.77 | 15.31 | 11.53 |
| 6.84 | 12.92 | 35.10 |
| 18.24 | 4.86 | 18.03 |
| 24.11 | 3.69 | 7.51 |
| 26.72 | 3.33 | 100.00 |
| 27.35 | 3.26 | 21.12 |
| 29.58 | 3.02 | 5.20 |

TABLE 29

Ketoglutaric Acid.

| Position [°2θ] | d-spacing [Å] | Relative Intensity [%] |
|---|---|---|
| 8.31 | 10.63 | 15.04 |
| 9.25 | 9.55 | 16.96 |
| 11.23 | 7.87 | 27.48 |
| 11.58 | 7.64 | 10.51 |
| 14.26 | 6.20 | 6.21 |
| 14.87 | 5.95 | 7.06 |
| 15.99 | 5.54 | 11.70 |
| 16.30 | 5.43 | 5.33 |
| 16.65 | 5.32 | 10.76 |
| 17.92 | 4.95 | 7.79 |
| 19.19 | 4.62 | 7.92 |
| 20.08 | 4.42 | 17.83 |
| 20.54 | 4.32 | 5.44 |
| 21.31 | 4.17 | 18.92 |
| 21.64 | 4.10 | 70.22 |
| 22.32 | 3.98 | 97.45 |
| 22.56 | 3.94 | 31.45 |
| 23.23 | 3.83 | 24.72 |
| 23.57 | 3.77 | 8.31 |
| 24.46 | 3.64 | 47.30 |
| 25.50 | 3.49 | 100.00 |
| 25.84 | 3.45 | 36.10 |
| 27.16 | 3.28 | 8.50 |
| 27.96 | 3.19 | 75.21 |

TABLE 29-continued

Ketoglutaric Acid.

| Position [°2θ] | d-spacing [Å] | Relative Intensity [%] |
|---|---|---|
| 31.04 | 2.88 | 10.17 |
| 31.29 | 2.86 | 10.09 |
| 32.44 | 2.76 | 33.68 |
| 32.64 | 2.74 | 10.53 |
| 33.12 | 2.70 | 20.82 |
| 33.74 | 2.65 | 17.81 |
| 34.62 | 2.59 | 5.51 |
| 35.57 | 2.52 | 16.39 |
| 37.04 | 2.42 | 6.13 |
| 37.75 | 2.38 | 33.27 |

TABLE 30

L-Lysine.

| Position [°2θ] | d-spacing [Å] | Relative Intensity [%] |
|---|---|---|
| 7.04 | 12.54 | 30.29 |
| 7.64 | 11.56 | 100.00 |
| 8.77 | 10.08 | 16.63 |
| 9.79 | 9.02 | 35.43 |
| 12.34 | 7.16 | 5.25 |
| 14.05 | 6.30 | 45.72 |
| 15.33 | 5.77 | 14.84 |
| 15.74 | 5.63 | 12.14 |
| 19.00 | 4.67 | 22.16 |
| 19.54 | 4.54 | 60.18 |
| 19.93 | 4.45 | 17.86 |
| 20.33 | 4.36 | 9.03 |
| 21.23 | 4.18 | 42.57 |
| 21.69 | 4.09 | 6.16 |
| 22.69 | 3.92 | 33.02 |
| 23.71 | 3.75 | 23.50 |
| 24.58 | 3.62 | 25.30 |
| 25.27 | 3.52 | 13.30 |
| 25.80 | 3.45 | 46.06 |
| 27.52 | 3.24 | 30.07 |
| 28.41 | 3.14 | 18.70 |
| 29.09 | 3.07 | 5.82 |
| 30.19 | 2.96 | 15.77 |
| 31.87 | 2.81 | 8.32 |
| 32.95 | 2.72 | 14.09 |
| 35.43 | 2.53 | 6.76 |

TABLE 31

Maleic Acid.

| Position [°2θ] | d-spacing [Å] | Relative Intensity [%] |
|---|---|---|
| 8.37 | 10.56 | 13.72 |
| 10.54 | 8.39 | 7.50 |
| 12.07 | 7.33 | 23.47 |
| 13.01 | 6.80 | 29.64 |
| 13.81 | 6.41 | 11.14 |
| 14.20 | 6.23 | 7.91 |
| 14.84 | 5.97 | 9.20 |
| 18.10 | 4.90 | 7.57 |
| 18.87 | 4.70 | 19.14 |
| 19.31 | 4.59 | 37.67 |
| 20.96 | 4.23 | 7.28 |
| 21.11 | 4.20 | 10.36 |
| 21.65 | 4.10 | 6.00 |
| 24.15 | 3.68 | 10.56 |
| 24.76 | 3.59 | 100.00 |
| 25.27 | 3.52 | 24.31 |
| 27.73 | 3.21 | 12.89 |
| 28.37 | 3.14 | 13.90 |
| 29.13 | 3.06 | 6.39 |
| 29.45 | 3.03 | 10.62 |

TABLE 32

Malonic Acid.

| Position [°2θ] | d-spacing [Å] | Relative Intensity [%] |
|---|---|---|
| 6.20 | 14.26 | 30.75 |
| 7.26 | 12.16 | 9.48 |
| 8.51 | 10.38 | 29.17 |
| 9.27 | 9.53 | 29.91 |
| 9.64 | 9.17 | 9.60 |
| 10.65 | 8.30 | 16.07 |
| 11.63 | 7.60 | 14.99 |
| 12.44 | 7.11 | 19.49 |
| 12.58 | 7.03 | 5.42 |
| 13.11 | 6.75 | 20.09 |
| 14.17 | 6.25 | 5.27 |
| 14.52 | 6.09 | 19.85 |
| 15.52 | 5.70 | 10.07 |
| 15.82 | 5.60 | 9.19 |
| 16.28 | 5.44 | 14.11 |
| 17.04 | 5.20 | 12.54 |
| 18.13 | 4.89 | 5.28 |
| 18.53 | 4.79 | 55.17 |
| 19.08 | 4.65 | 14.34 |
| 19.71 | 4.50 | 41.23 |
| 20.96 | 4.24 | 21.87 |
| 21.38 | 4.15 | 28.34 |
| 21.86 | 4.06 | 19.58 |
| 22.73 | 3.91 | 8.38 |
| 23.10 | 3.85 | 60.60 |
| 23.38 | 3.80 | 38.17 |
| 23.96 | 3.71 | 48.01 |
| 24.65 | 3.61 | 17.47 |
| 24.87 | 3.58 | 100.00 |
| 25.17 | 3.54 | 53.95 |
| 26.41 | 3.37 | 45.55 |
| 26.83 | 3.32 | 5.07 |
| 27.98 | 3.19 | 35.31 |
| 28.60 | 3.12 | 17.37 |
| 29.12 | 3.06 | 9.77 |
| 29.48 | 3.03 | 7.52 |
| 30.02 | 2.97 | 12.50 |
| 32.32 | 2.77 | 14.27 |
| 32.91 | 2.72 | 5.29 |
| 38.24 | 2.35 | 8.19 |

TABLE 33

Methanesulfonic Acid.

| Position [°2θ] | d-spacing [Å] | Relative Intensity [%] |
|---|---|---|
| 5.04 | 17.53 | 61.63 |
| 5.90 | 14.97 | 24.03 |
| 6.97 | 12.67 | 41.87 |
| 11.68 | 7.57 | 33.42 |
| 11.98 | 7.38 | 10.48 |
| 13.08 | 6.76 | 55.69 |
| 13.42 | 6.59 | 10.08 |
| 14.13 | 6.26 | 44.29 |
| 15.69 | 5.64 | 18.45 |
| 16.13 | 5.49 | 29.81 |
| 17.77 | 4.99 | 35.32 |
| 18.67 | 4.75 | 74.18 |
| 19.86 | 4.47 | 25.64 |
| 20.11 | 4.41 | 20.67 |
| 21.00 | 4.23 | 17.32 |
| 21.22 | 4.18 | 77.02 |
| 21.83 | 4.07 | 79.76 |
| 23.14 | 3.84 | 36.78 |
| 23.46 | 3.79 | 100.00 |
| 23.72 | 3.75 | 22.23 |
| 24.08 | 3.69 | 75.06 |
| 25.02 | 3.56 | 11.86 |
| 25.34 | 3.51 | 14.87 |
| 26.02 | 3.42 | 60.11 |
| 26.52 | 3.36 | 82.61 |
| 26.96 | 3.30 | 44.55 |

TABLE 33-continued

Methanesulfonic Acid.

| Position [°2θ] | d-spacing [Å] | Relative Intensity [%] |
| --- | --- | --- |
| 27.48 | 3.24 | 56.61 |
| 27.98 | 3.19 | 29.57 |
| 29.99 | 2.98 | 28.27 |
| 32.10 | 2.79 | 13.08 |
| 32.71 | 2.74 | 13.38 |
| 33.94 | 2.64 | 6.40 |
| 35.87 | 2.50 | 5.60 |
| 36.48 | 2.46 | 11.85 |
| 38.28 | 2.35 | 9.44 |

TABLE 34

Naphthalene-1,5-Disulphonic Acid.

| Position [°2θ] | d-spacing [Å] | Relative Intensity [%] |
| --- | --- | --- |
| 5.05 | 17.49 | 100.00 |
| 7.14 | 12.38 | 73.33 |
| 7.55 | 11.70 | 17.49 |
| 10.59 | 8.35 | 8.49 |
| 12.02 | 7.36 | 24.13 |
| 14.25 | 6.21 | 30.60 |
| 14.55 | 6.08 | 24.06 |
| 15.11 | 5.86 | 19.00 |
| 15.79 | 5.61 | 21.43 |
| 18.43 | 4.81 | 31.15 |
| 18.73 | 4.73 | 10.18 |
| 20.61 | 4.31 | 27.60 |
| 20.98 | 4.23 | 67.09 |
| 21.25 | 4.18 | 48.21 |
| 22.49 | 3.95 | 43.49 |
| 23.57 | 3.77 | 23.69 |
| 24.39 | 3.65 | 72.28 |
| 26.60 | 3.35 | 98.26 |
| 27.36 | 3.26 | 57.68 |
| 29.22 | 3.05 | 32.18 |
| 30.59 | 2.92 | 25.63 |
| 36.76 | 2.44 | 16.88 |

TABLE 35

Oxalic Acid.

| Position [°2θ] | d-spacing [Å] | Relative Intensity [%] |
| --- | --- | --- |
| 4.96 | 17.80 | 9.65 |
| 6.33 | 13.95 | 6.18 |
| 7.93 | 11.14 | 9.07 |
| 11.14 | 7.94 | 36.38 |
| 14.02 | 6.31 | 8.36 |
| 14.85 | 5.96 | 25.99 |
| 16.22 | 5.46 | 6.82 |
| 17.38 | 5.10 | 21.23 |
| 17.57 | 5.04 | 9.42 |
| 18.11 | 4.89 | 29.02 |
| 18.74 | 4.73 | 20.39 |
| 20.52 | 4.33 | 10.65 |
| 21.22 | 4.18 | 8.45 |
| 23.13 | 3.84 | 57.79 |
| 23.73 | 3.75 | 12.06 |
| 24.08 | 3.69 | 52.03 |
| 24.67 | 3.61 | 32.92 |
| 25.21 | 3.53 | 27.09 |
| 25.49 | 3.49 | 13.51 |
| 25.78 | 3.45 | 23.18 |
| 28.82 | 3.09 | 7.08 |
| 28.97 | 3.08 | 100.00 |
| 30.37 | 2.94 | 9.36 |
| 31.06 | 2.88 | 13.17 |
| 32.62 | 2.74 | 7.44 |
| 34.95 | 2.57 | 5.31 |

TABLE 35-continued

Oxalic Acid.

| Position [°2θ] | d-spacing [Å] | Relative Intensity [%] |
| --- | --- | --- |
| 36.93 | 2.43 | 25.44 |
| 37.50 | 2.40 | 14.71 |
| 38.01 | 2.37 | 15.23 |
| 39.47 | 2.28 | 10.67 |
| 39.86 | 2.26 | 5.22 |

TABLE 36

Phosphoric Acid.

| Position [°2θ] | d-spacing [Å] | Relative Intensity [%] |
| --- | --- | --- |
| 5.15 | 17.13 | 28.64 |
| 6.19 | 14.26 | 70.79 |
| 6.79 | 13.01 | 100.00 |
| 7.08 | 12.47 | 96.70 |
| 7.39 | 11.95 | 69.06 |
| 9.33 | 9.47 | 12.75 |
| 9.63 | 9.18 | 14.82 |
| 9.93 | 8.90 | 19.14 |
| 11.95 | 7.40 | 32.35 |
| 12.41 | 7.13 | 28.58 |
| 12.59 | 7.03 | 50.70 |
| 13.10 | 6.75 | 31.89 |
| 13.55 | 6.53 | 16.06 |
| 14.18 | 6.24 | 48.63 |
| 14.88 | 5.95 | 50.69 |
| 16.30 | 5.43 | 27.49 |
| 17.98 | 4.93 | 39.23 |
| 18.71 | 4.74 | 88.14 |
| 19.09 | 4.65 | 29.71 |
| 20.96 | 4.23 | 95.71 |
| 21.34 | 4.16 | 57.66 |
| 21.92 | 4.05 | 69.16 |
| 23.12 | 3.84 | 20.21 |
| 23.98 | 3.71 | 44.16 |
| 24.36 | 3.65 | 27.15 |
| 24.88 | 3.58 | 93.45 |
| 25.74 | 3.46 | 53.06 |
| 26.40 | 3.37 | 39.92 |
| 26.79 | 3.32 | 19.62 |
| 29.12 | 3.06 | 27.22 |
| 30.02 | 2.97 | 26.18 |
| 38.18 | 2.36 | 11.38 |

TABLE 37

Saccharin.

| Position [°2θ] | d-spacing [Å] | Relative Intensity [%] |
| --- | --- | --- |
| 6.82 | 12.95 | 100.00 |
| 9.40 | 9.40 | 3.30 |
| 10.24 | 8.63 | 54.26 |
| 11.70 | 7.56 | 8.36 |
| 11.89 | 7.44 | 15.96 |
| 13.65 | 6.48 | 17.37 |
| 14.02 | 6.31 | 7.66 |
| 15.92 | 5.56 | 17.27 |
| 16.87 | 5.25 | 6.68 |
| 17.19 | 5.15 | 6.66 |
| 18.11 | 4.89 | 12.04 |
| 18.40 | 4.82 | 12.07 |
| 19.03 | 4.66 | 23.26 |
| 20.00 | 4.44 | 7.48 |
| 20.53 | 4.32 | 65.51 |
| 21.67 | 4.10 | 8.18 |
| 22.20 | 4.00 | 6.24 |
| 22.74 | 3.91 | 6.47 |
| 24.09 | 3.69 | 39.30 |
| 24.63 | 3.61 | 66.80 |

TABLE 37-continued

Saccharin.

| Position [°2θ] | d-spacing [Å] | Relative Intensity [%] |
|---|---|---|
| 25.02 | 3.56 | 24.34 |
| 25.37 | 3.51 | 9.35 |
| 25.59 | 3.48 | 11.85 |
| 27.06 | 3.29 | 8.08 |
| 27.49 | 3.24 | 7.55 |
| 28.40 | 3.14 | 6.51 |
| 31.22 | 2.86 | 6.95 |
| 35.49 | 2.53 | 5.12 |

TABLE 38

Thiocyanic Acid.

| Position [°2θ] | d-spacing [Å] | Relative Intensity [%] |
|---|---|---|
| 6.86 | 12.87 | 100.00 |
| 6.95 | 12.71 | 20.77 |
| 13.72 | 6.45 | 16.48 |
| 14.17 | 6.24 | 10.80 |
| 14.93 | 5.93 | 6.52 |
| 16.71 | 5.30 | 5.11 |
| 18.18 | 4.88 | 9.81 |
| 18.84 | 4.71 | 6.30 |
| 20.39 | 4.35 | 8.97 |
| 20.77 | 4.27 | 24.53 |
| 22.69 | 3.92 | 8.91 |
| 24.87 | 3.58 | 21.27 |
| 25.09 | 3.55 | 13.88 |
| 25.80 | 3.45 | 24.81 |
| 31.72 | 2.82 | 8.18 |

TABLE 39 p-Toluenesulfonic Acid.

| Position [°2θ] | d-spacing [Å] | Relative Intensity [%] |
|---|---|---|
| 6.49 | 13.60 | 100.00 |
| 9.65 | 9.16 | 19.03 |
| 10.00 | 8.84 | 18.29 |
| 11.98 | 7.38 | 10.11 |
| 12.62 | 7.01 | 9.06 |
| 13.22 | 6.69 | 31.26 |
| 15.02 | 5.89 | 8.95 |
| 15.24 | 5.81 | 19.96 |
| 16.30 | 5.43 | 9.99 |
| 16.54 | 5.36 | 11.74 |
| 17.60 | 5.03 | 5.85 |
| 18.09 | 4.90 | 15.00 |
| 19.99 | 4.44 | 25.97 |
| 20.73 | 4.28 | 18.53 |
| 21.53 | 4.12 | 10.90 |
| 22.24 | 3.99 | 13.21 |
| 23.34 | 3.81 | 21.67 |
| 23.55 | 3.78 | 87.01 |
| 23.79 | 3.74 | 59.51 |
| 24.71 | 3.60 | 49.75 |
| 26.36 | 3.38 | 21.87 |
| 26.70 | 3.34 | 17.35 |
| 27.15 | 3.28 | 7.73 |
| 27.56 | 3.23 | 39.77 |
| 29.54 | 3.02 | 8.48 |
| 30.07 | 2.97 | 6.00 |
| 30.73 | 2.91 | 6.32 |
| 31.98 | 2.80 | 8.89 |
| 33.82 | 2.65 | 5.94 |
| 35.43 | 2.53 | 5.55 |

TABLE 40

Vanillin.

| Position [°2θ] | d-spacing [Å] | Relative Intensity [%] |
|---|---|---|
| 2.74 | 32.26 | 42.30 |
| 6.22 | 14.21 | 18.04 |
| 9.66 | 9.15 | 6.38 |
| 10.93 | 8.09 | 9.13 |
| 11.43 | 7.74 | 11.48 |
| 11.58 | 7.64 | 13.94 |
| 12.22 | 7.24 | 13.79 |
| 12.58 | 7.03 | 25.30 |
| 13.24 | 6.68 | 100.00 |
| 14.42 | 6.14 | 12.44 |
| 15.45 | 5.73 | 83.47 |
| 16.33 | 5.42 | 10.41 |
| 17.28 | 5.13 | 23.92 |
| 18.77 | 4.72 | 19.15 |
| 19.12 | 4.64 | 5.25 |
| 19.32 | 4.59 | 12.08 |
| 20.99 | 4.23 | 22.41 |
| 21.41 | 4.15 | 23.54 |
| 21.56 | 4.12 | 28.26 |
| 22.89 | 3.88 | 18.01 |
| 23.20 | 3.83 | 40.78 |
| 23.53 | 3.78 | 40.30 |
| 23.77 | 3.74 | 23.32 |
| 24.06 | 3.70 | 43.79 |
| 24.80 | 3.59 | 17.00 |
| 25.42 | 3.50 | 32.00 |
| 25.63 | 3.47 | 12.00 |
| 25.91 | 3.44 | 20.81 |
| 26.20 | 3.40 | 29.21 |
| 26.60 | 3.35 | 52.02 |
| 27.10 | 3.29 | 20.22 |
| 27.84 | 3.20 | 5.88 |
| 28.70 | 3.11 | 10.49 |
| 29.09 | 3.07 | 18.59 |
| 29.25 | 3.05 | 12.75 |
| 30.44 | 2.93 | 6.55 |
| 31.71 | 2.82 | 5.43 |
| 32.08 | 2.79 | 7.55 |
| 32.61 | 2.74 | 8.49 |
| 33.01 | 2.71 | 10.70 |
| 33.48 | 2.67 | 13.66 |
| 34.50 | 2.60 | 6.41 |
| 38.16 | 2.36 | 9.90 |

Figure 49:
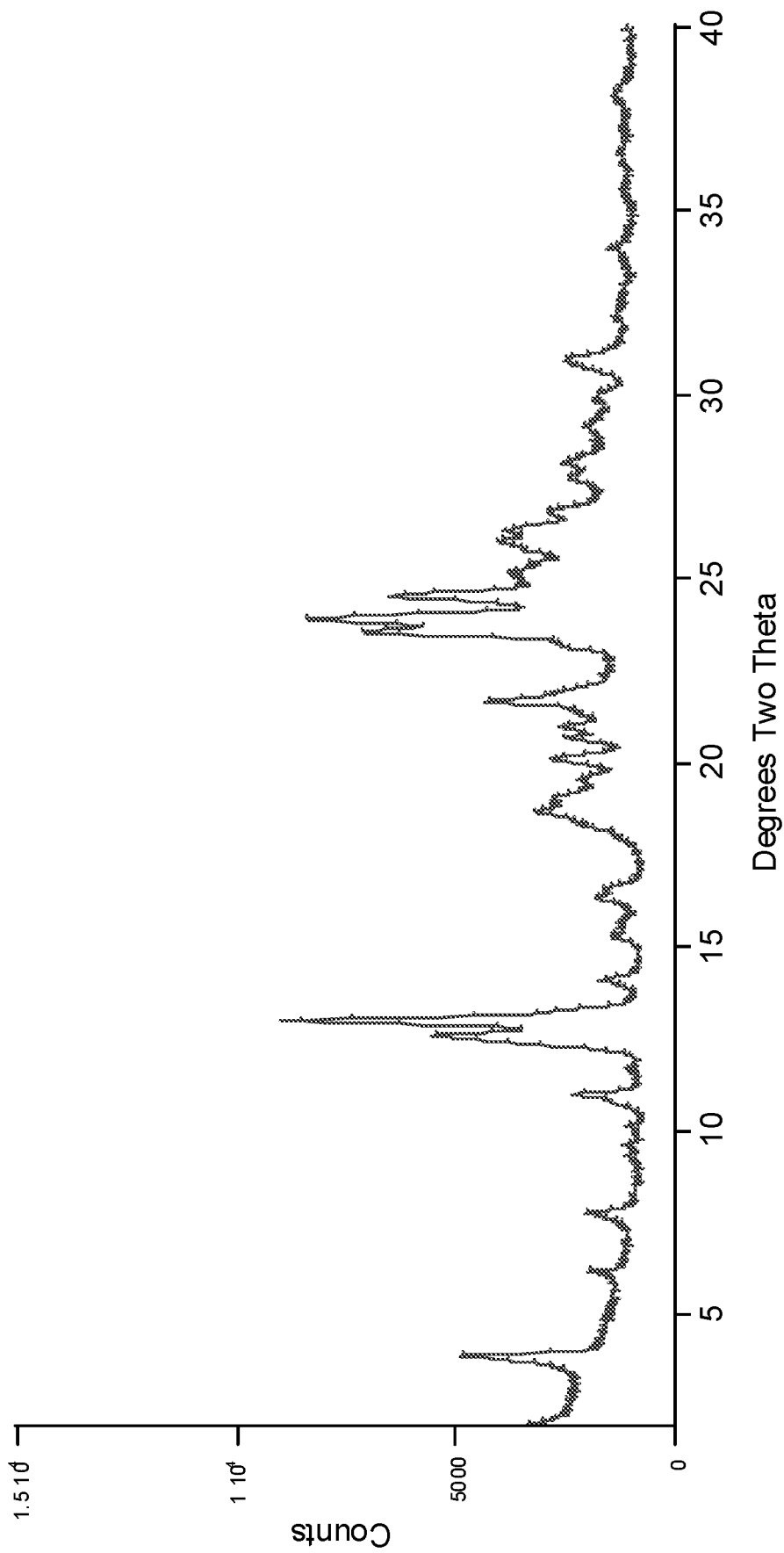
FIG. 49 depicts an XRPD pattern of Compound 1 complex with t-aconitic acid.

FIG. 49 depicts an XRPD pattern of the t-aconitic acid complex.

Figure 50:
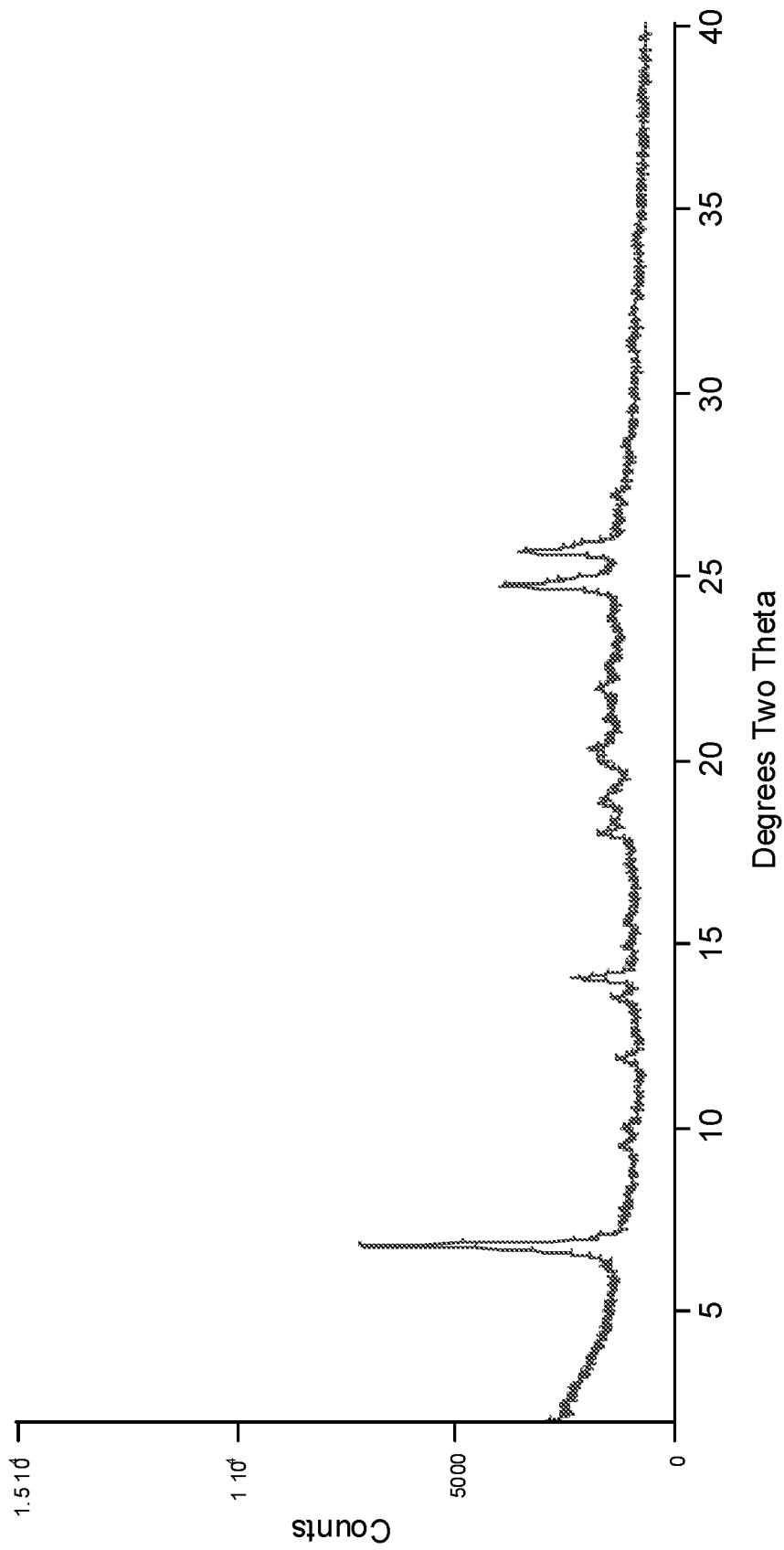
FIG. 50 depicts an XRPD pattern of Compound 1 complex with L-ascorbic acid.

FIG. 50 depicts an XRPD pattern of the L-ascorbic acid complex.

Figure 51:
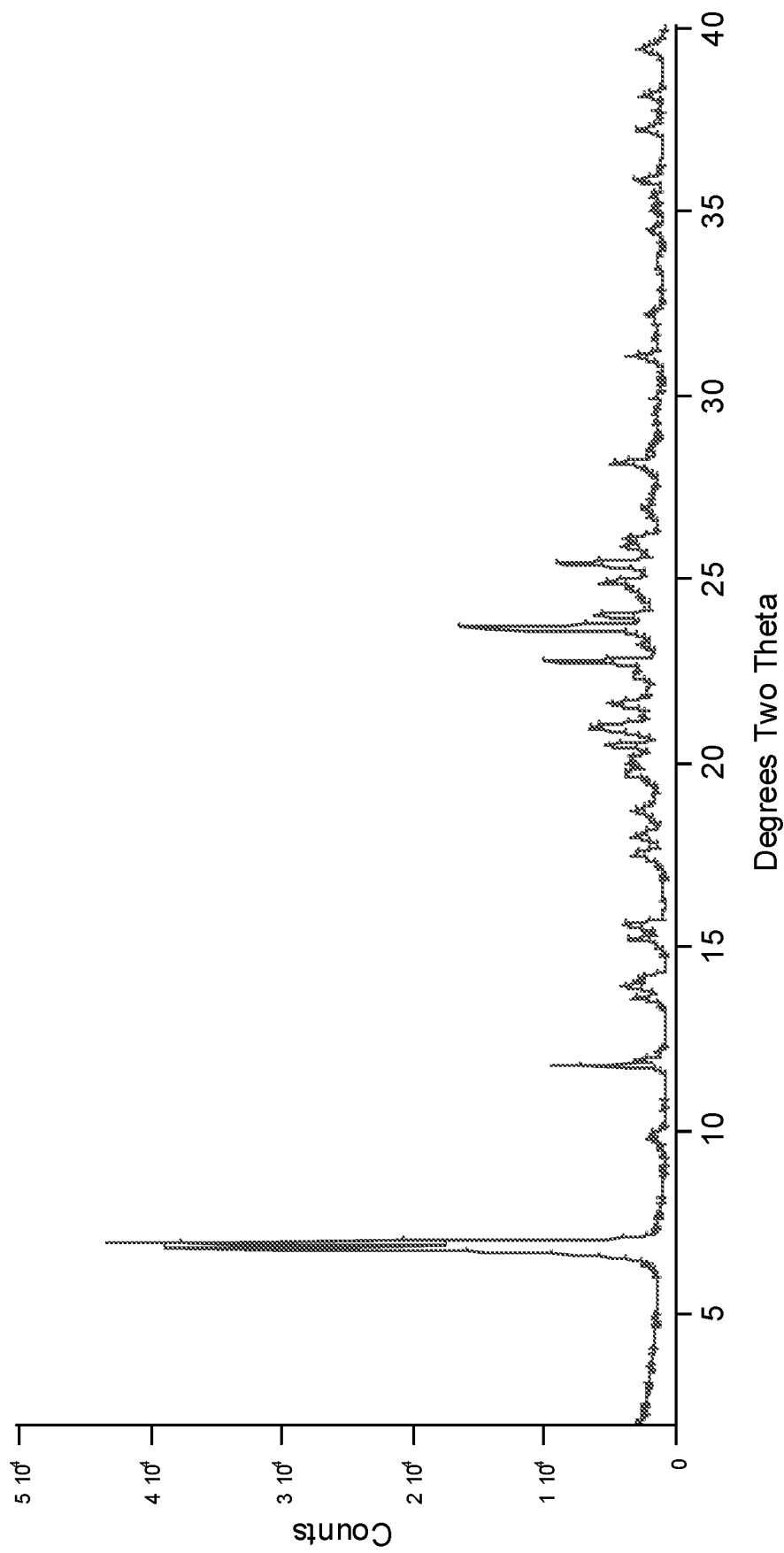
FIG. 51 depicts an XRPD pattern of Compound 1 complex with aspartic acid.

FIG. 51 depicts an XRPD pattern of the aspartic acid complex.

Figure 52:
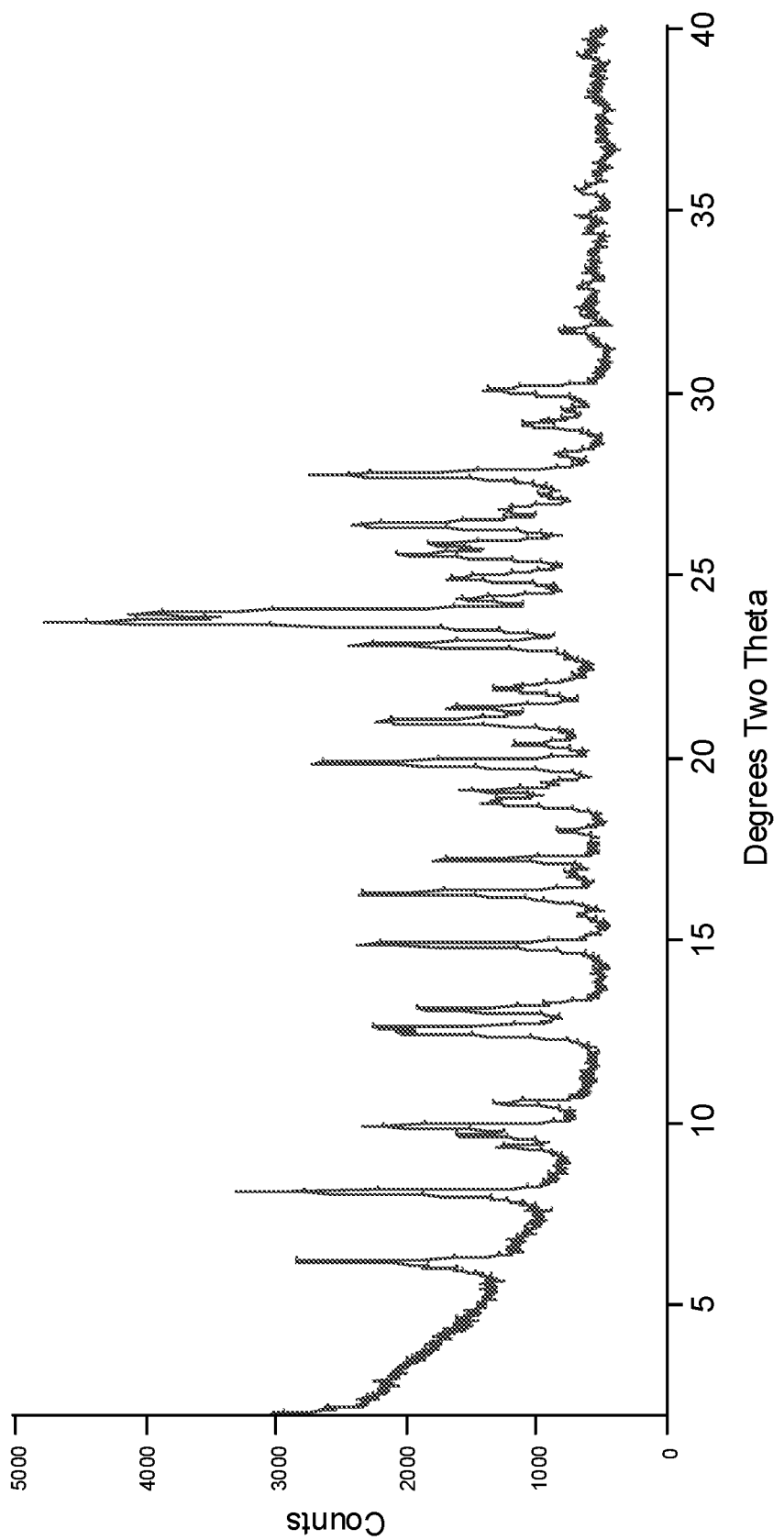
FIG. 52 depicts an XRPD pattern of Compound 1 complex with benzoic acid.

FIG. 52 depicts an XRPD pattern of the benzoic acid complex.

Figure 53:
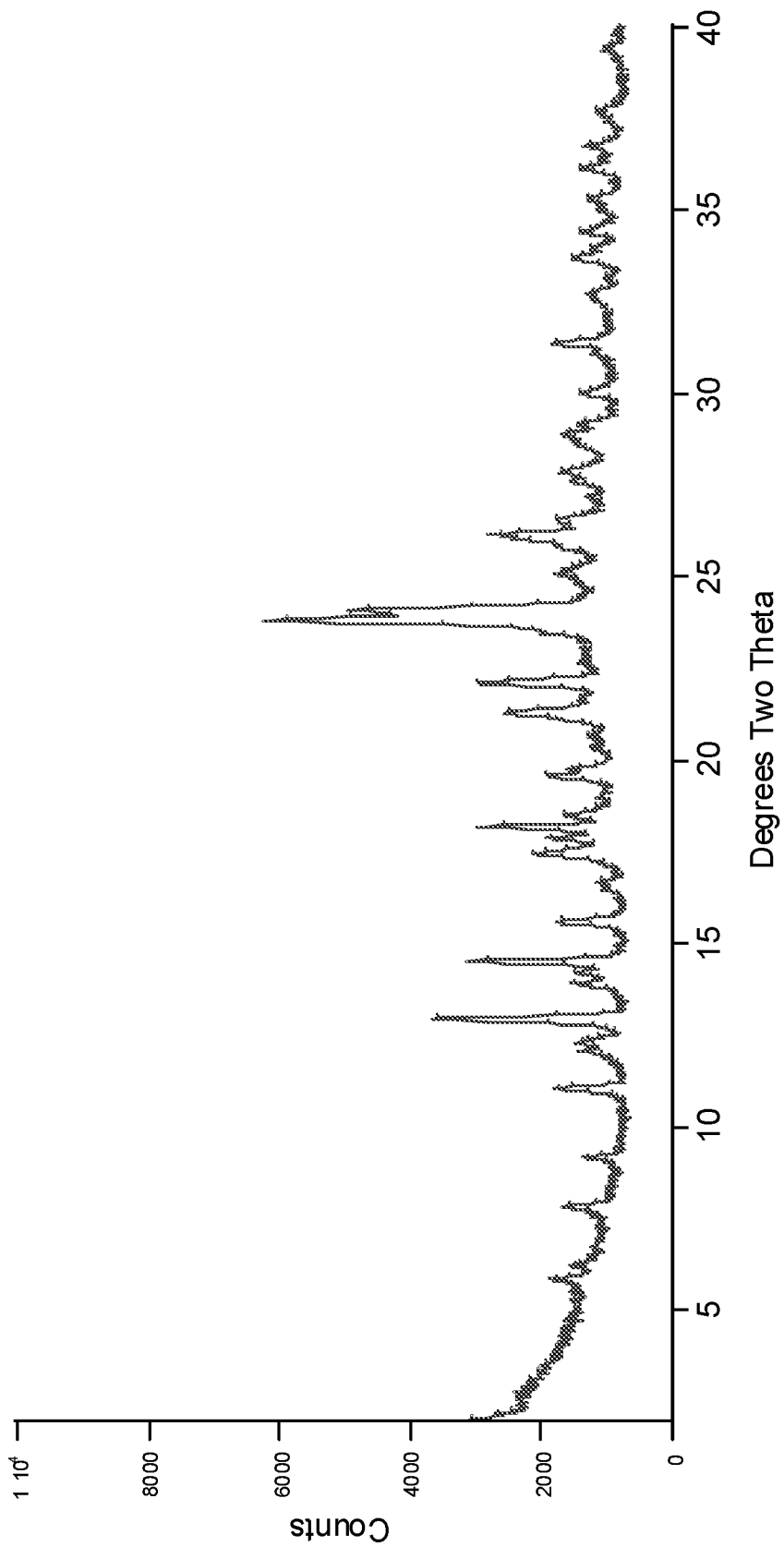
FIG. 53 depicts an XRPD pattern of Compound 1 complex with citric acid.

FIG. 53 depicts an XRPD pattern of the citric acid complex.

Figure 54:
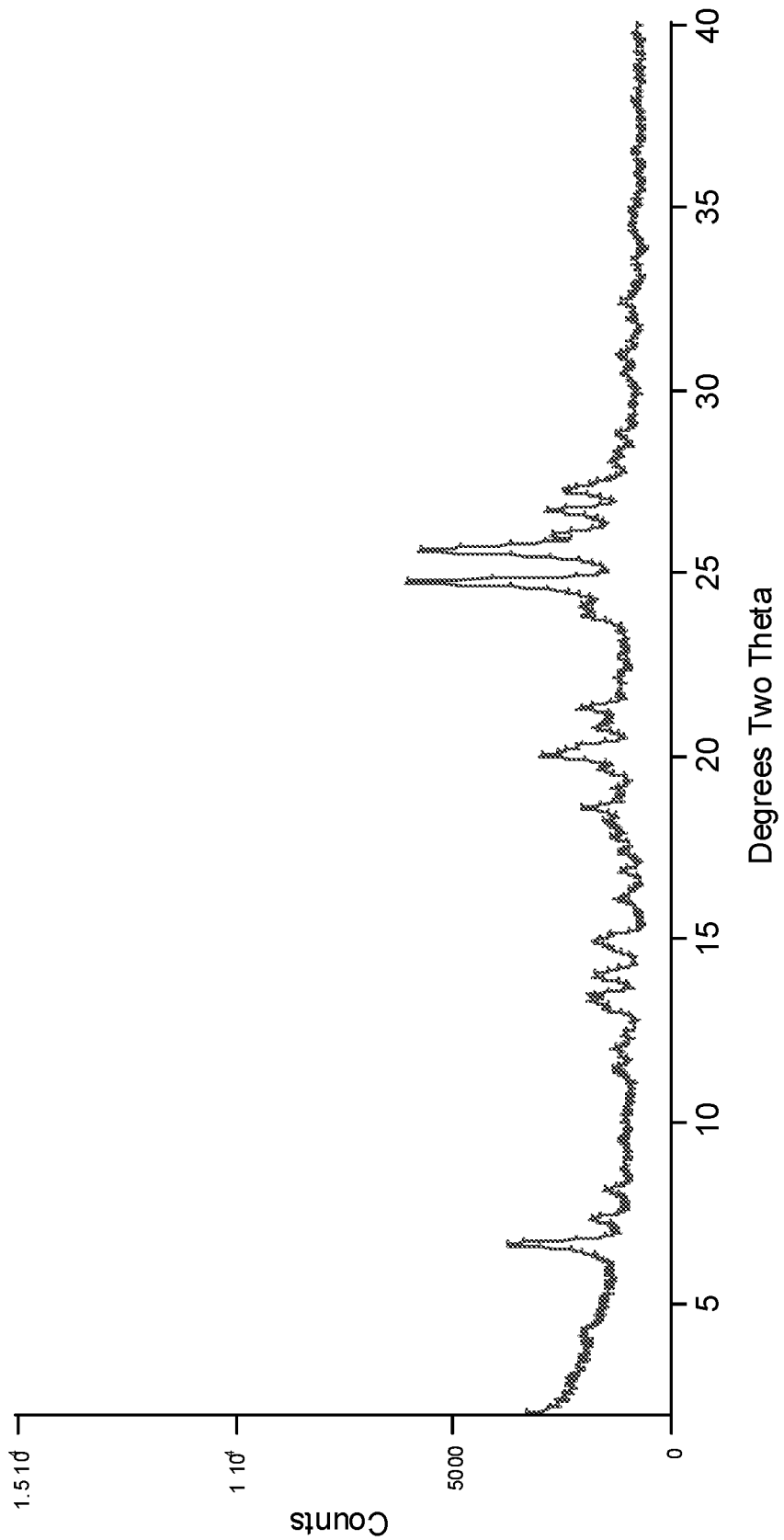
FIG. 54 depicts an XRPD pattern of Form 1 Compound 1 complex with gentisic acid.

FIG. 54 depicts an XRPD pattern of the Form 1 of the gentisic acid complex.

Figure 55:
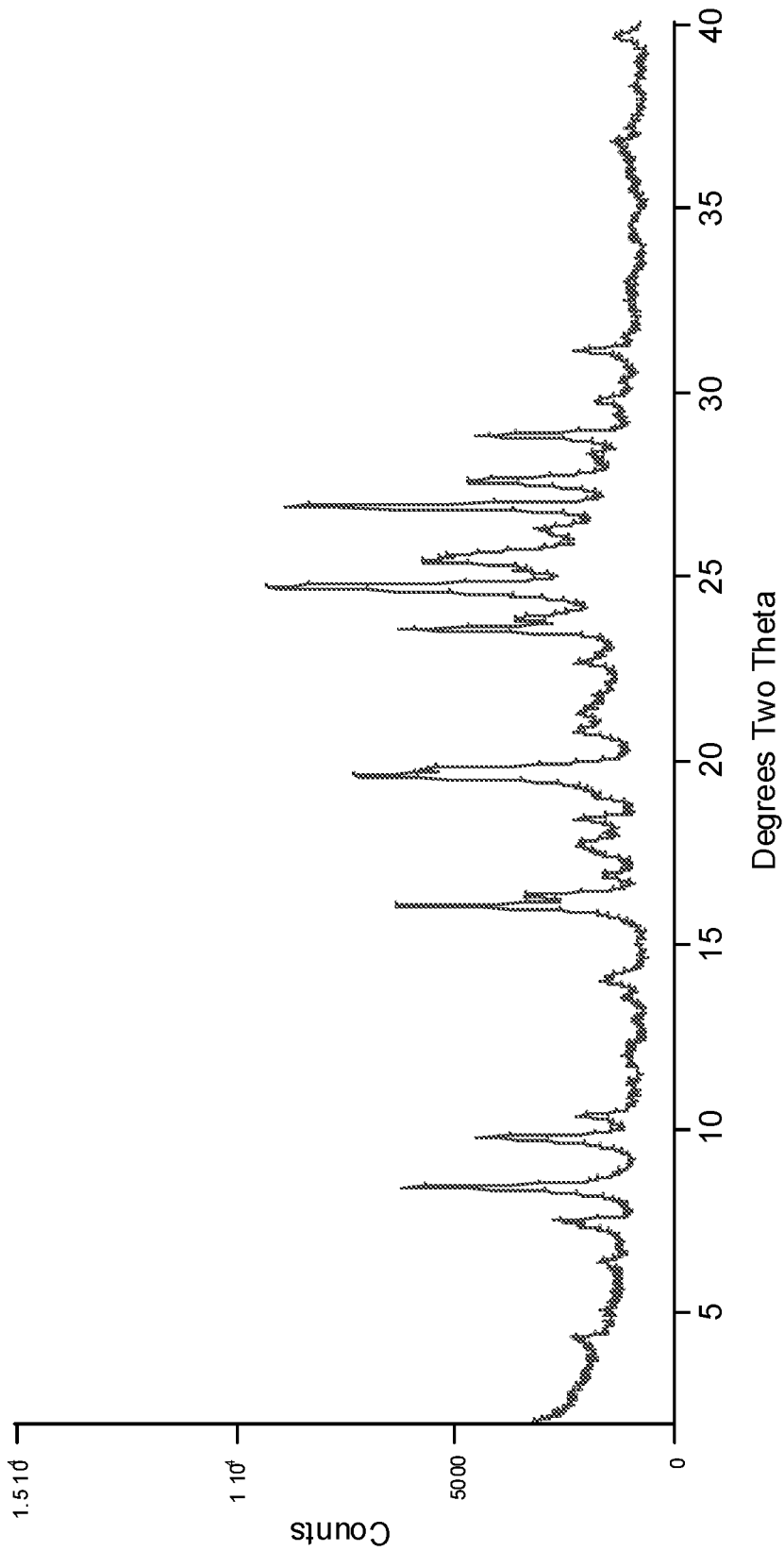
FIG. 55 depicts an XRPD pattern of Form 2 Compound 1 complex with gentisic acid.

FIG. 55 depicts an XRPD pattern of the Form 2 of the gentisic acid complex.

Figure 56:
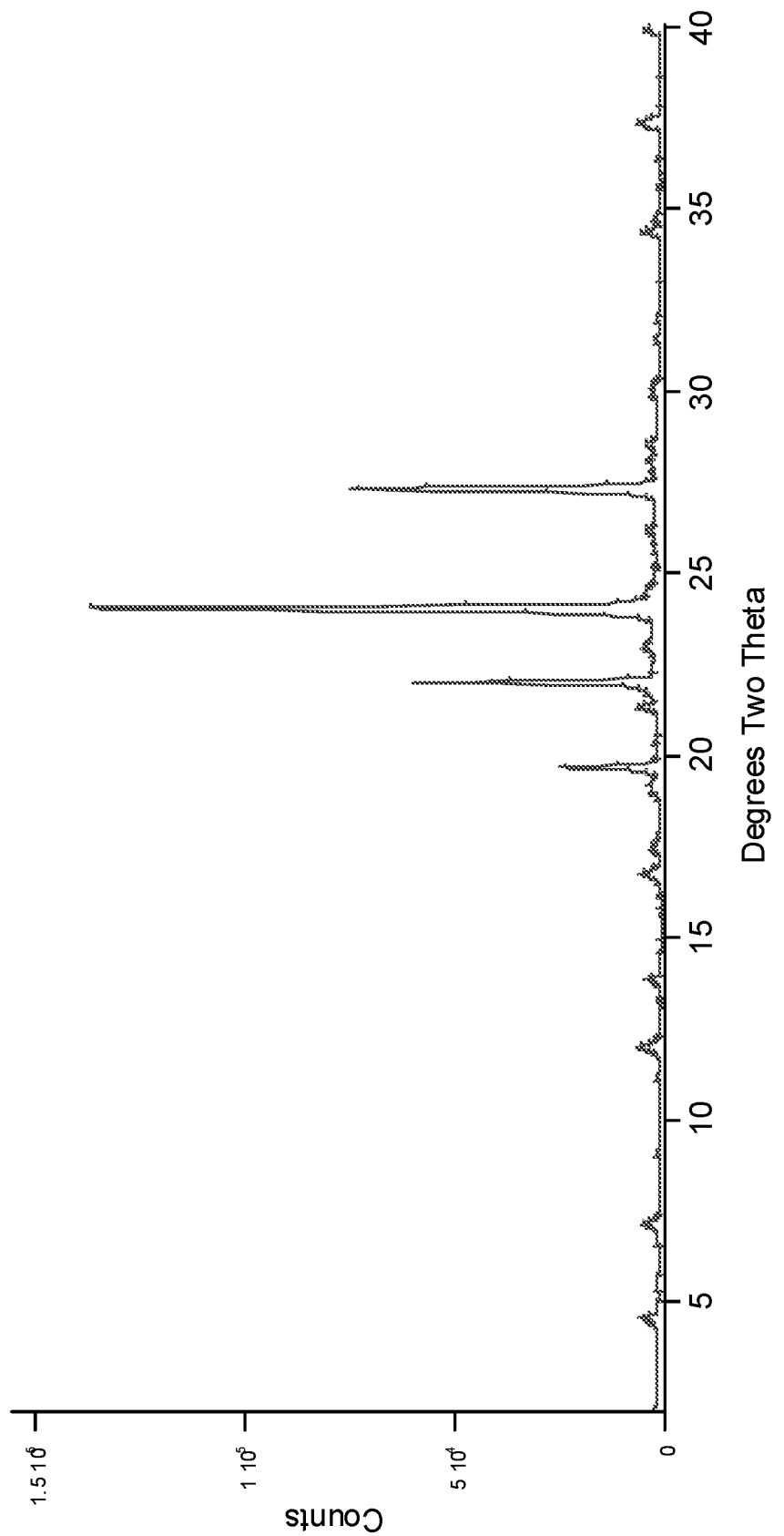
FIG. 56 depicts an XRPD pattern of Compound 1 complex with glutaric acid.

FIG. 56 depicts an XRPD pattern of the glutaric acid complex.

Figure 57:
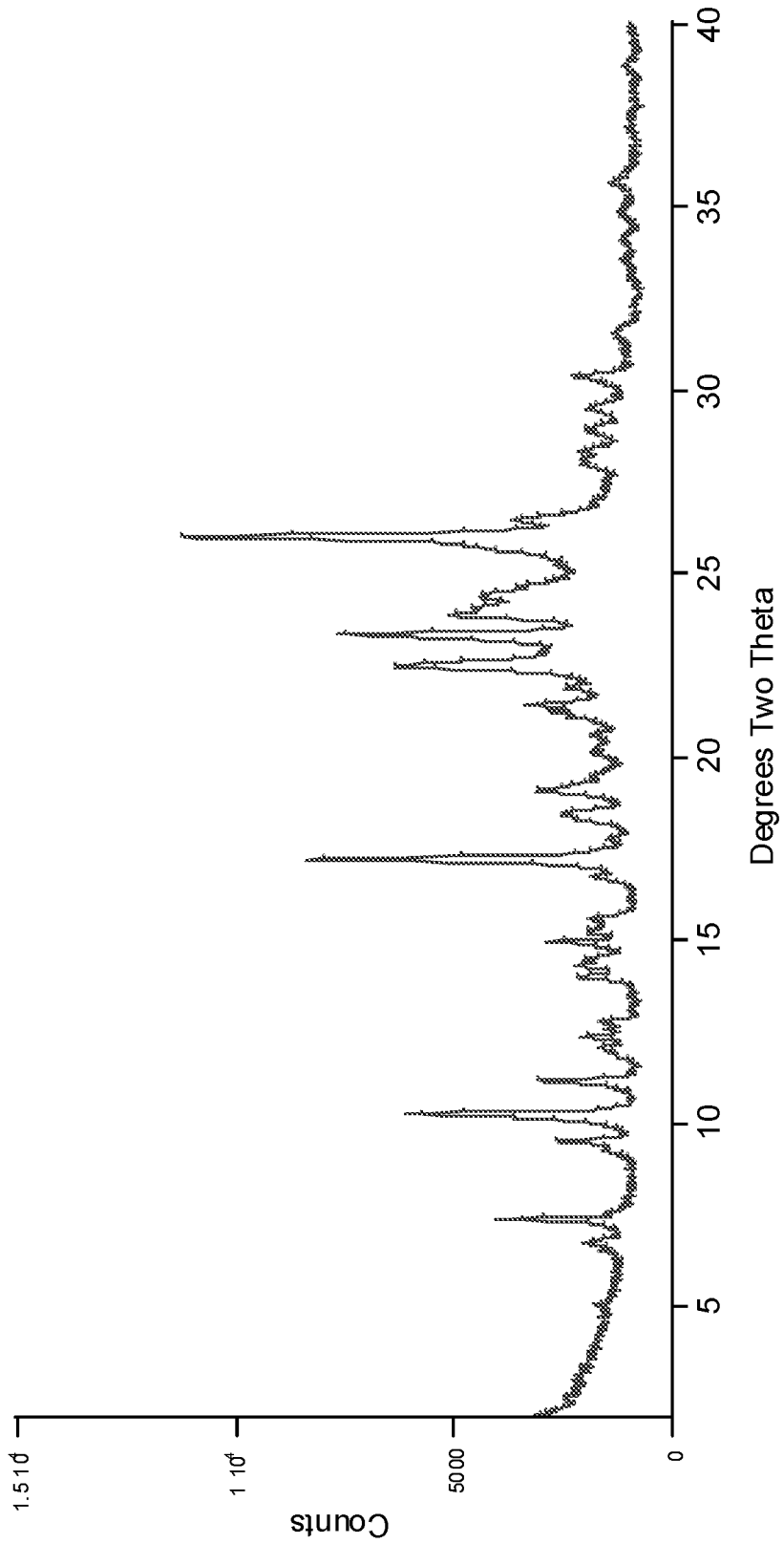
FIG. 57 depicts an XRPD pattern of Form 1 Compound 1 complex with 1-hydroxy-2-naphthoic acid.

FIG. 57 depicts an XRPD pattern of the Form 1 of the 1-hydroxy-2-naphthoic acid complex.

Figure 58:
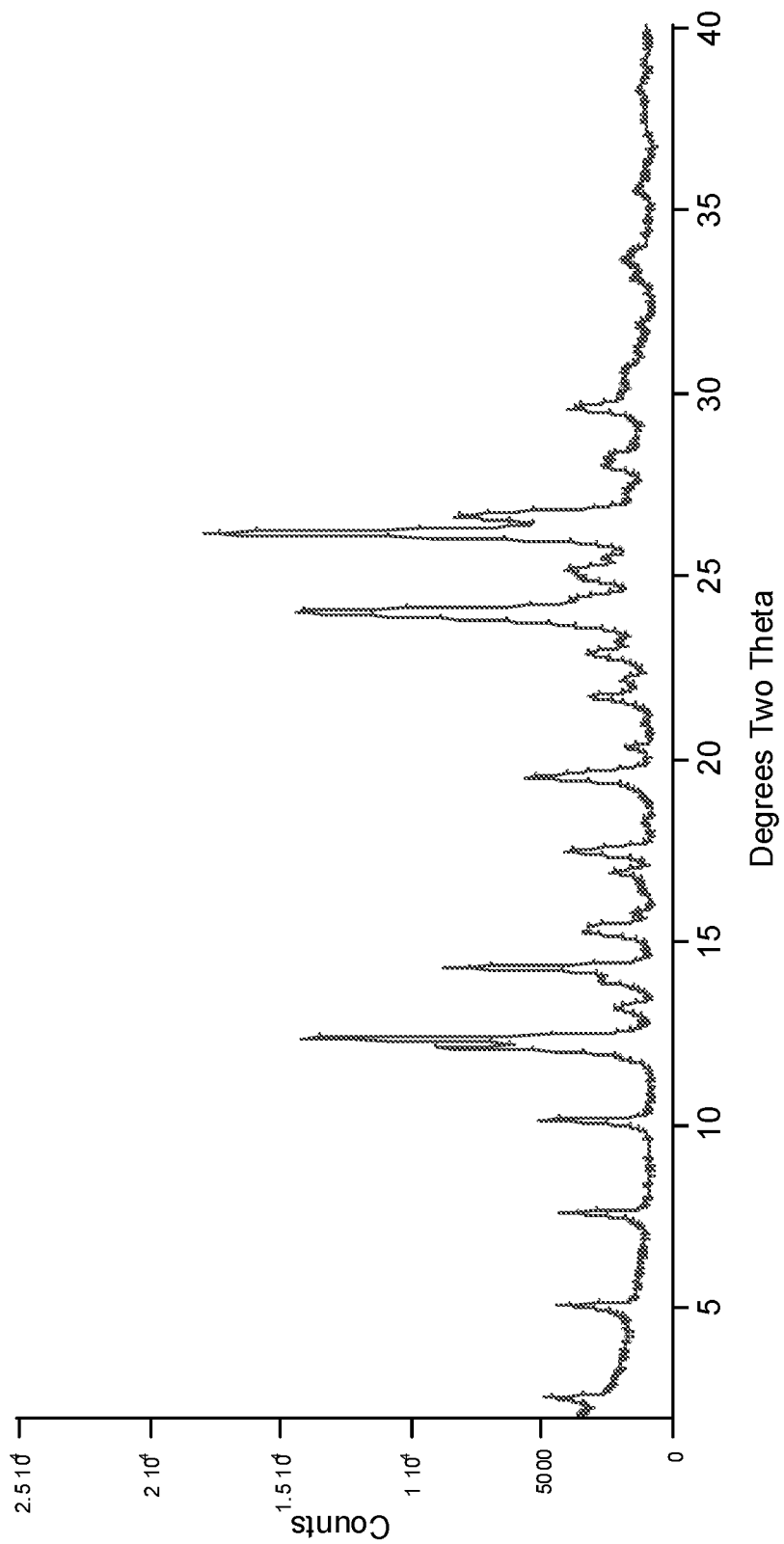
FIG. 58 depicts an XRPD pattern of Form 2 Compound 1 complex with 1-hydroxy-2-naphthoic acid.

FIG. 58 depicts an XRPD pattern of the Form 2 of the 1-hydroxy-2-naphthoic acid complex.

Figure 59:
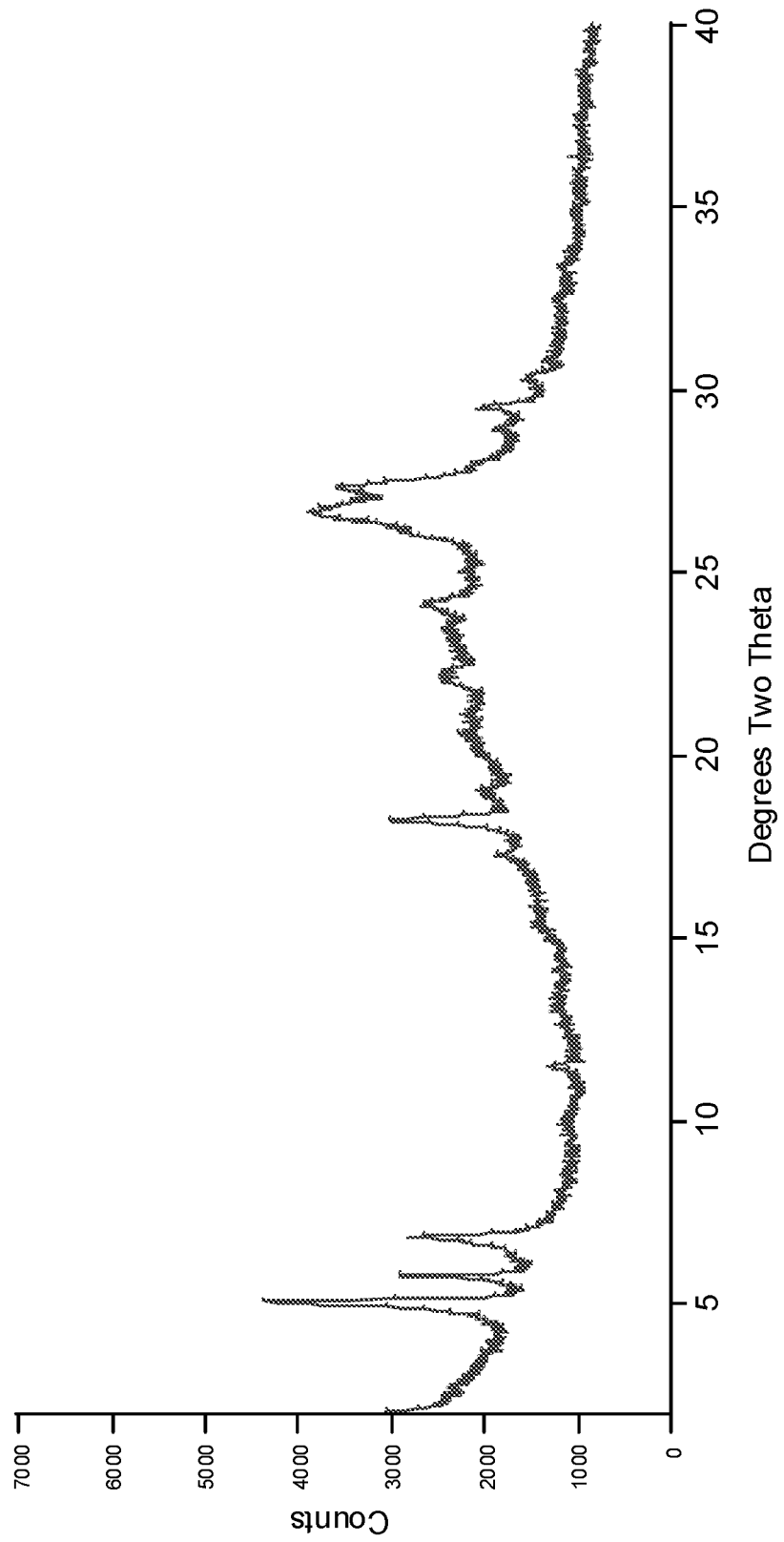
FIG. 59 depicts an XRPD pattern of Compound 1 complex with isethionic acid.

FIG. 59 depicts an XRPD pattern of the isethionic acid complex.

Figure 60:
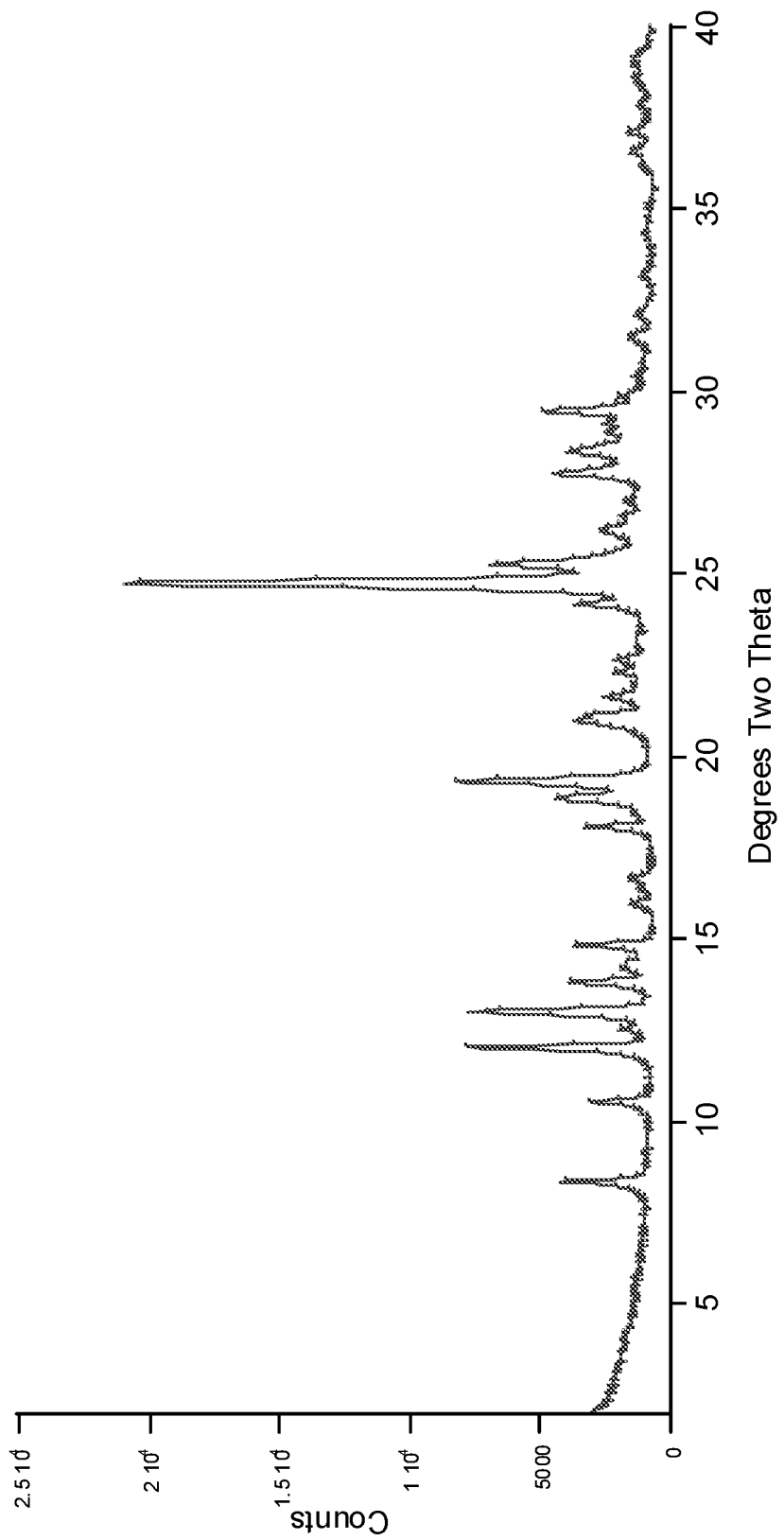
FIG. 60 depicts an XRPD pattern of Compound 1 complex with maleic acid.

FIG. 60 depicts an XRPD pattern of the maleic acid complex.

Figure 61:
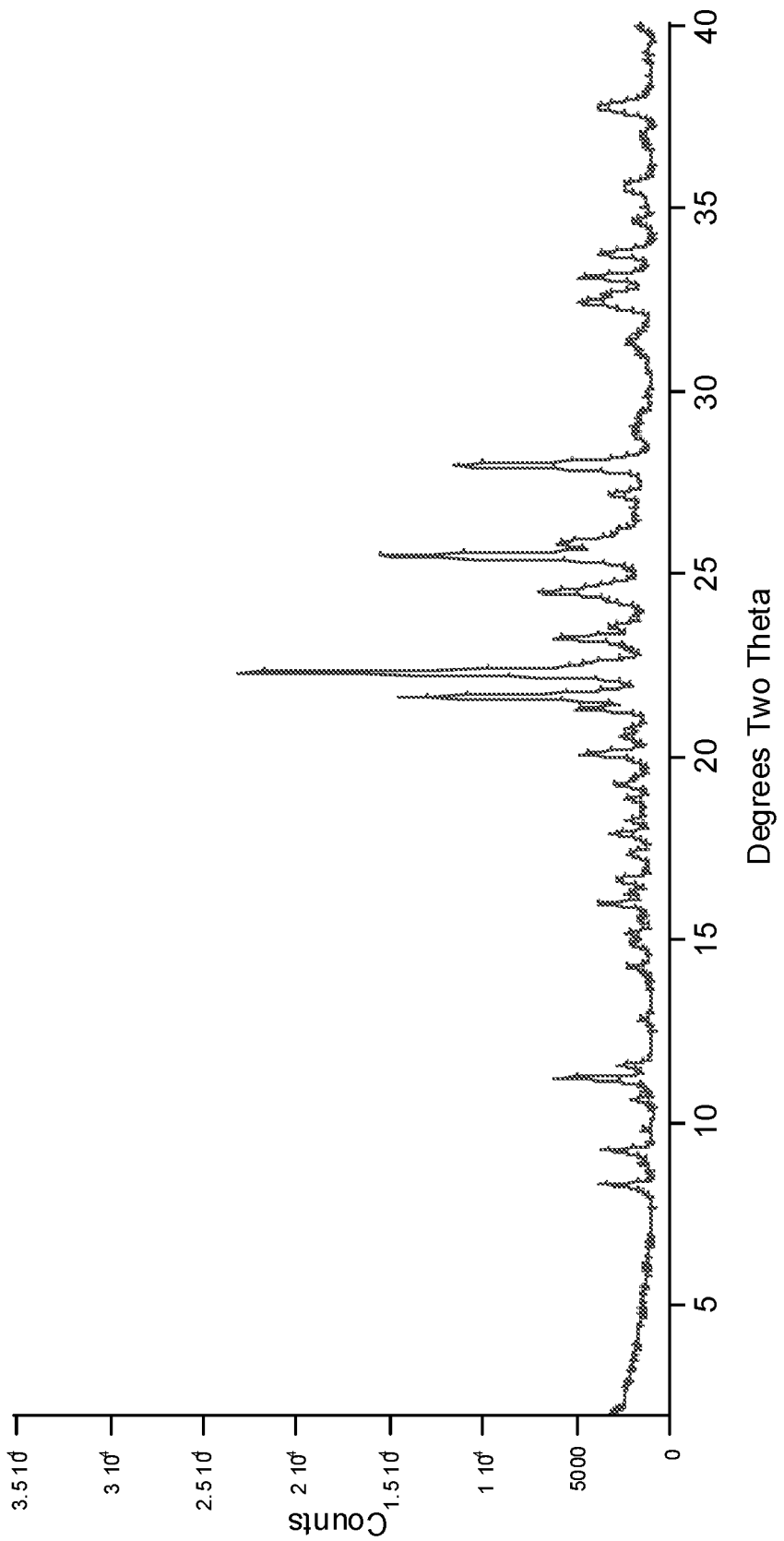
FIG. 61 depicts an XRPD pattern of Compound 1 complex with ketoglutaric acid.

FIG. 61 depicts an XRPD pattern of the ketoglutaric acid complex.

Figure 62:
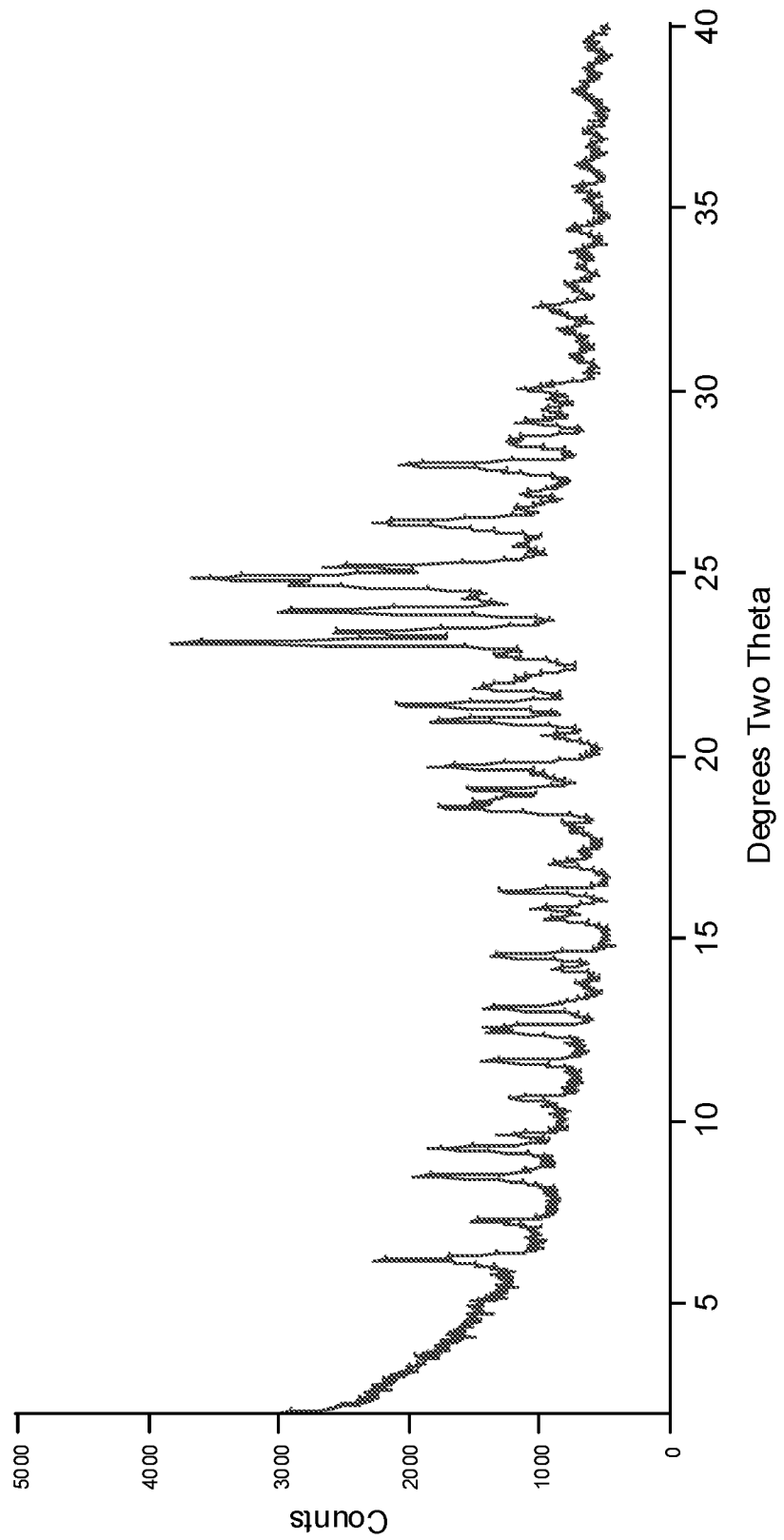
FIG. 62 depicts an XRPD pattern of Compound 1 complex with malonic acid.

FIG. 62 depicts an XRPD pattern of the malonic acid complex.

Figure 63:
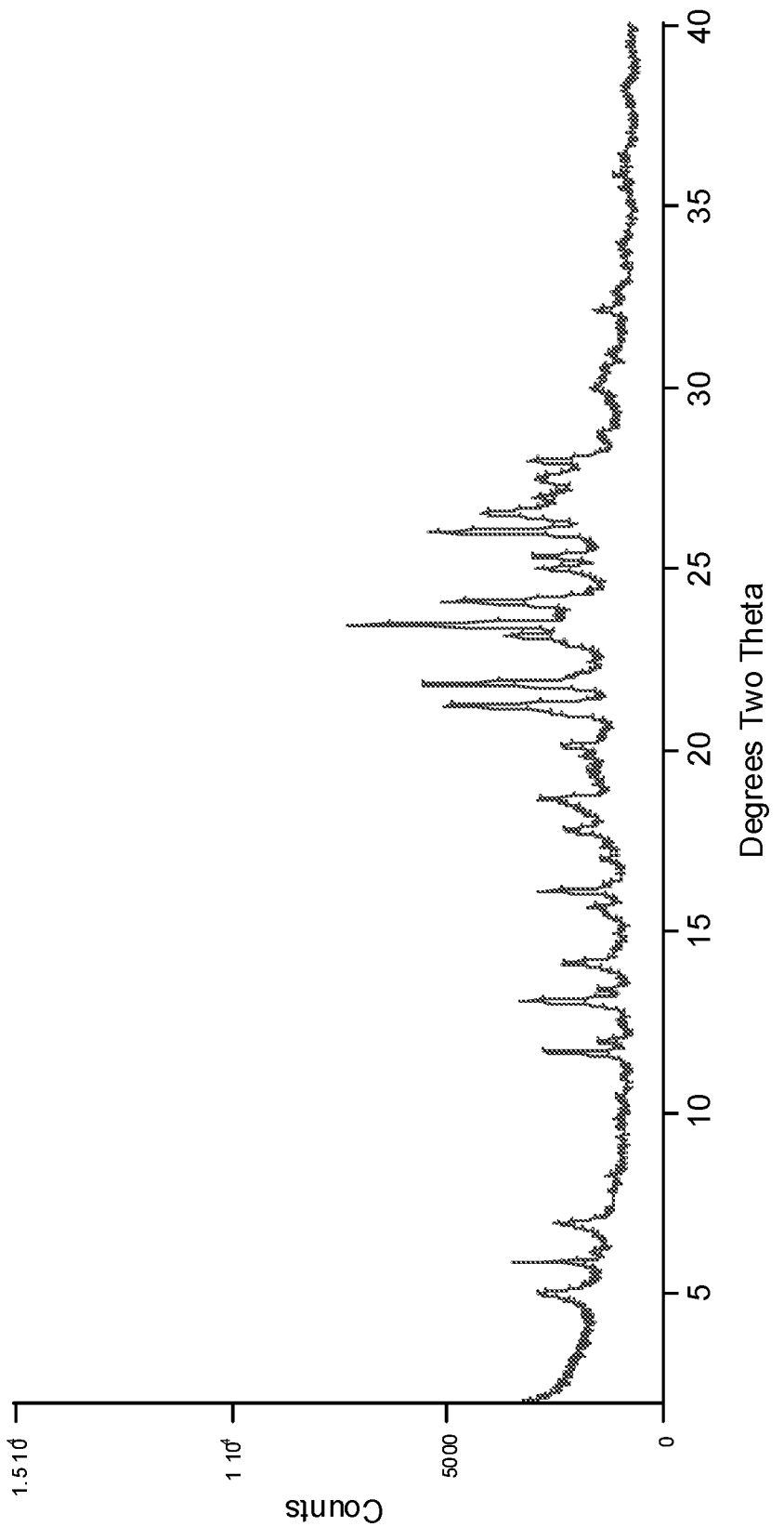
FIG. 63 depicts an XRPD pattern of Compound 1 complex with methanesulfonic acid.

FIG. 63 depicts an XRPD pattern of the methanesulfonic acid complex.

Figure 64:
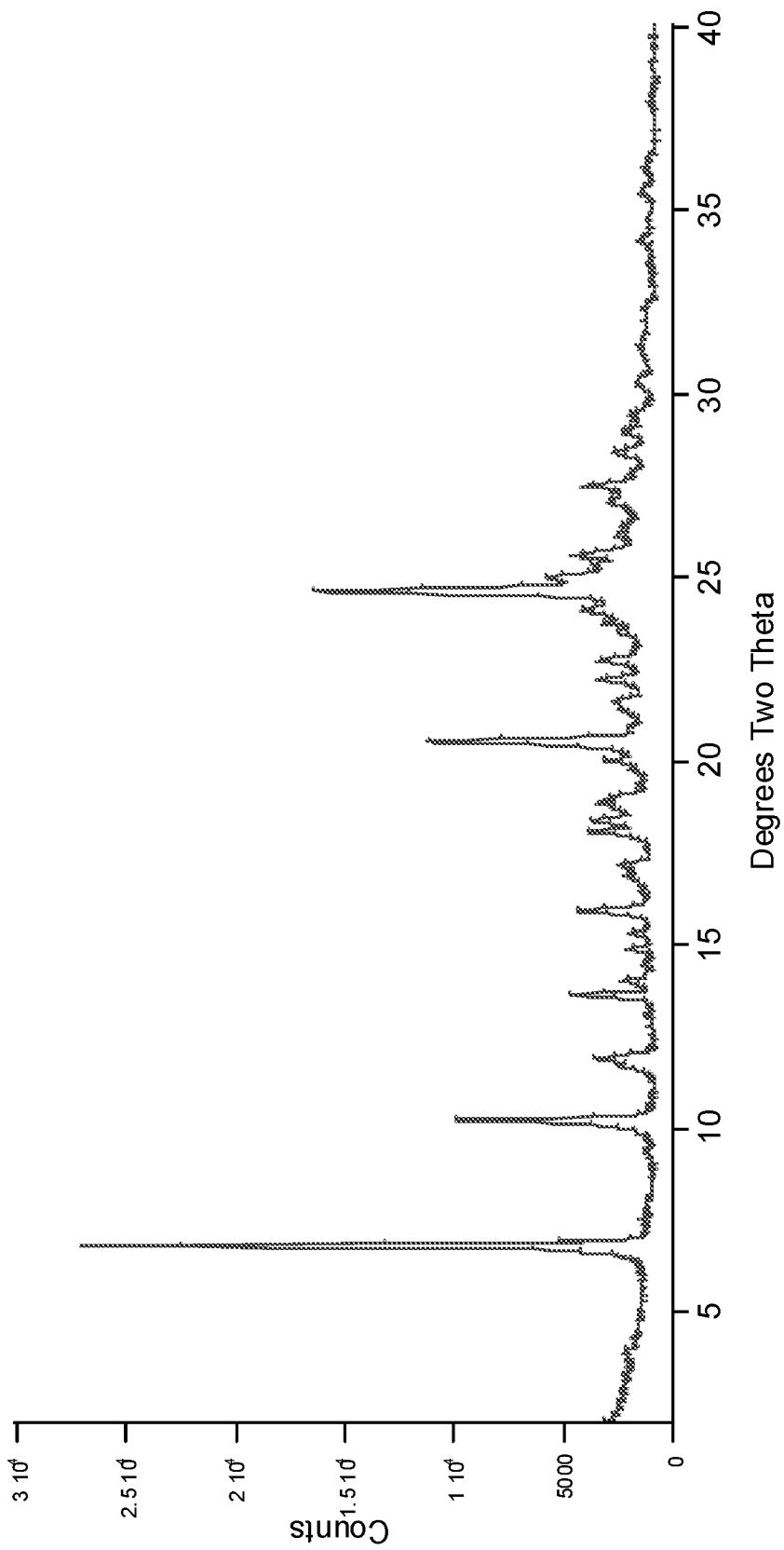
FIG. 64 depicts an XRPD pattern of Compound 1 complex with saccharin.

FIG. 64 depicts an XRPD pattern of the saccharin complex.

Figure 65:
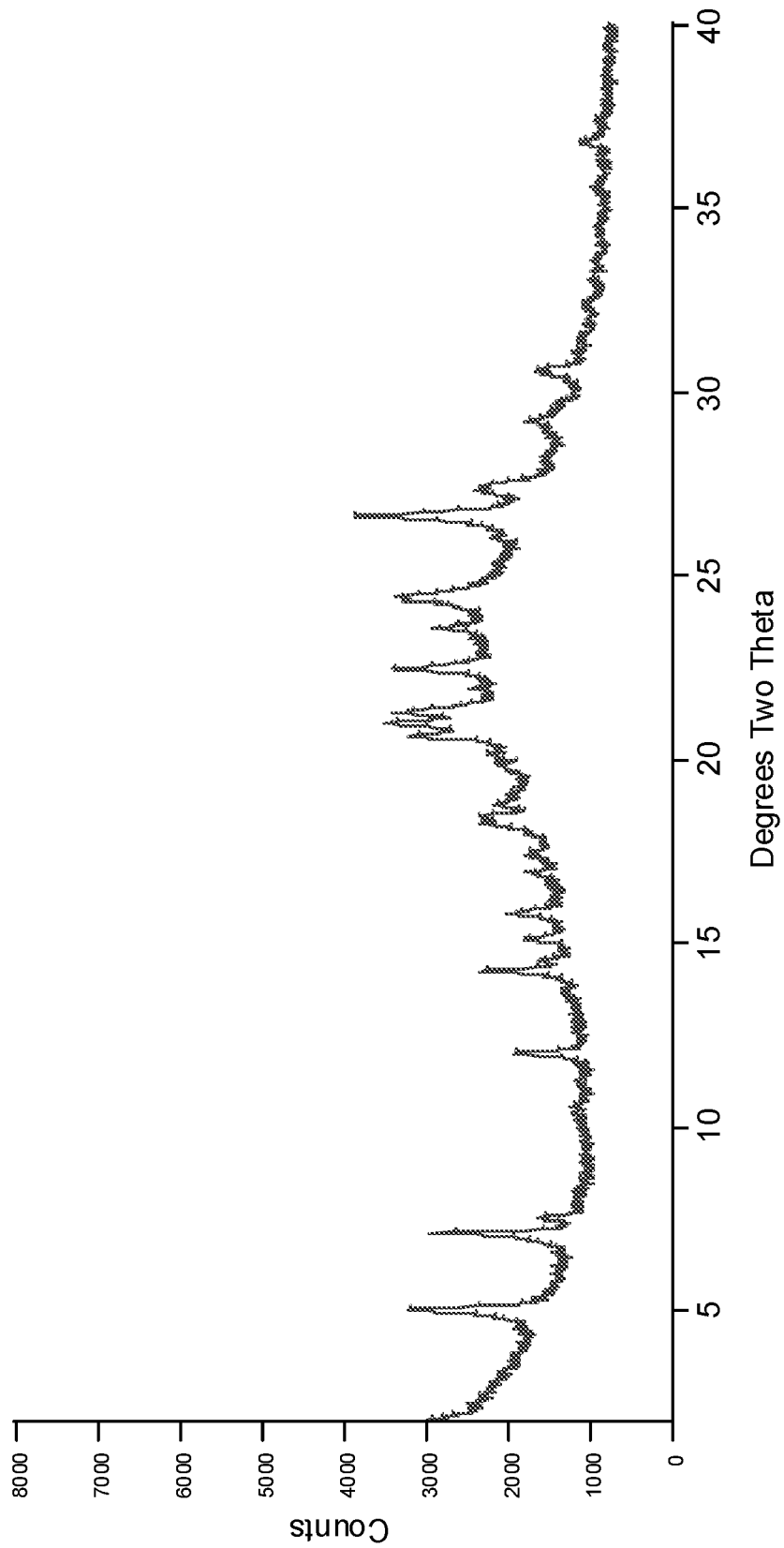
FIG. 65 depicts an XRPD pattern of Compound 1 complex with naphthalene-1,5-disulfonic acid.

FIG. 65 depicts an XRPD pattern of the naphthalene-1,5-disulfonic acid complex.

Figure 66:
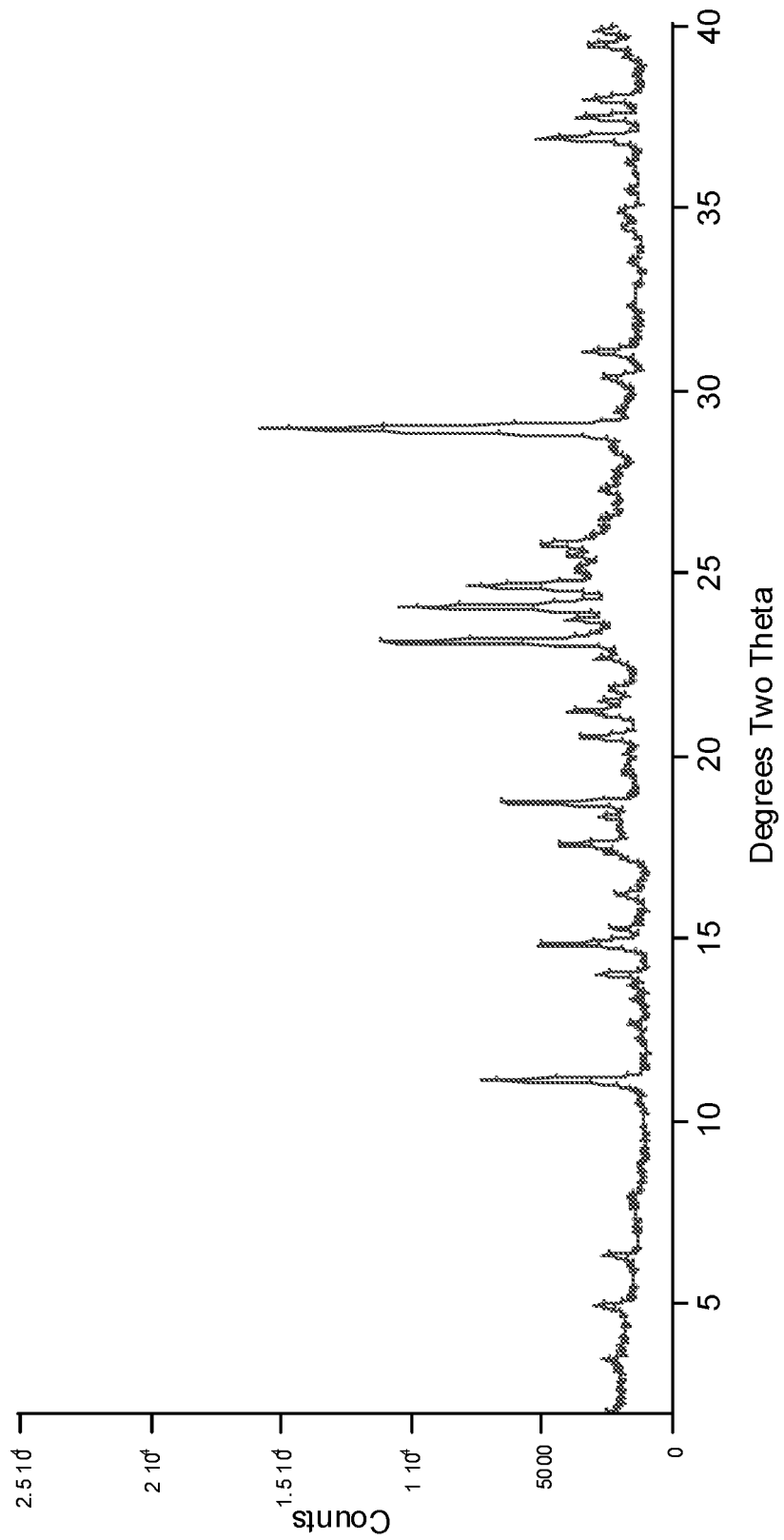
FIG. 66 depicts an XRPD pattern of Compound 1 complex with oxalic acid.

FIG. 66 depicts an XRPD pattern of the oxalic acid complex.

Figure 67:
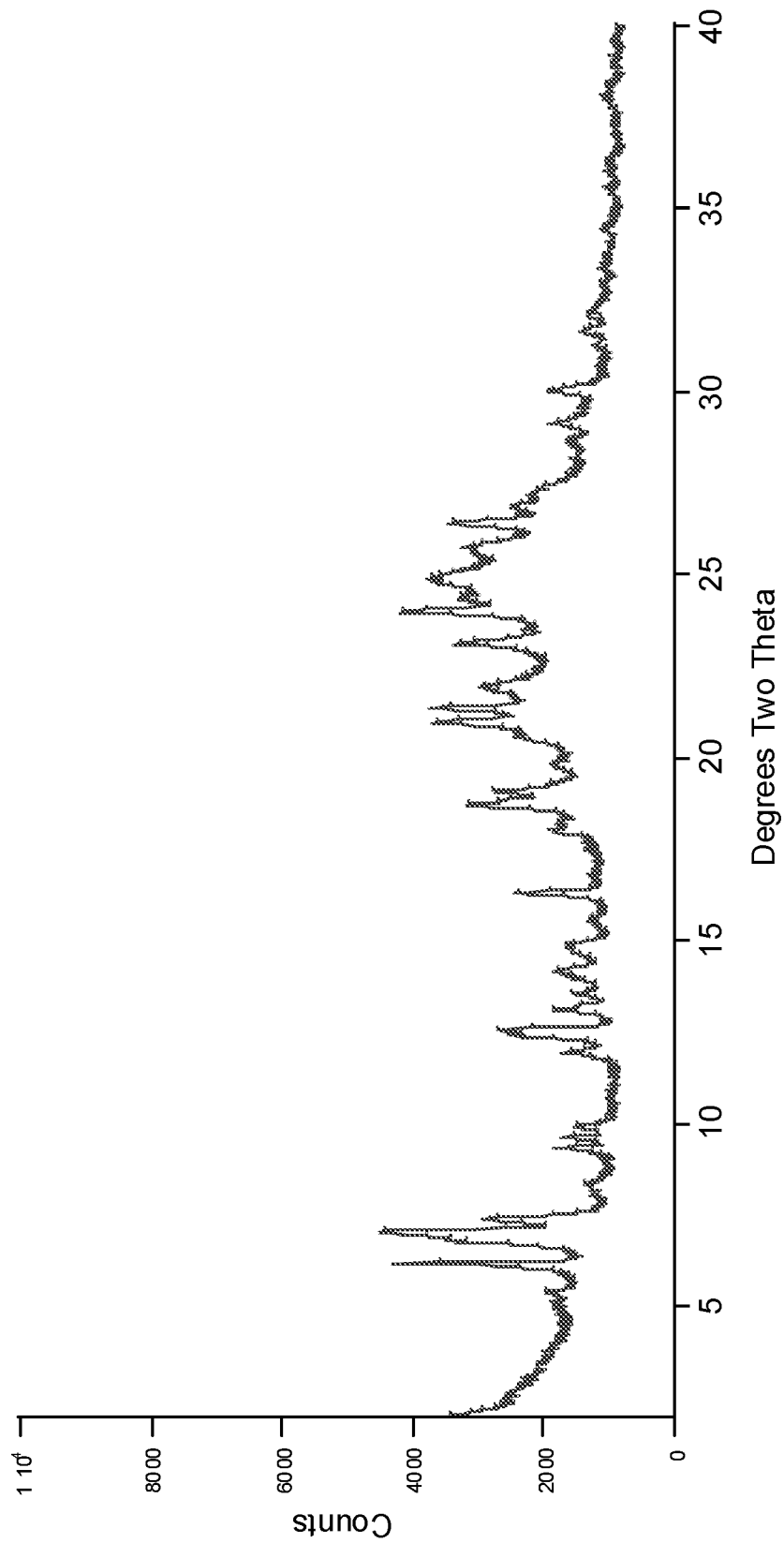
FIG. 67 depicts an XRPD pattern of Compound 1 complex with phosphoric acid.

FIG. 67 depicts an XRPD pattern of the phosphoric acid complex.

Figure 68:
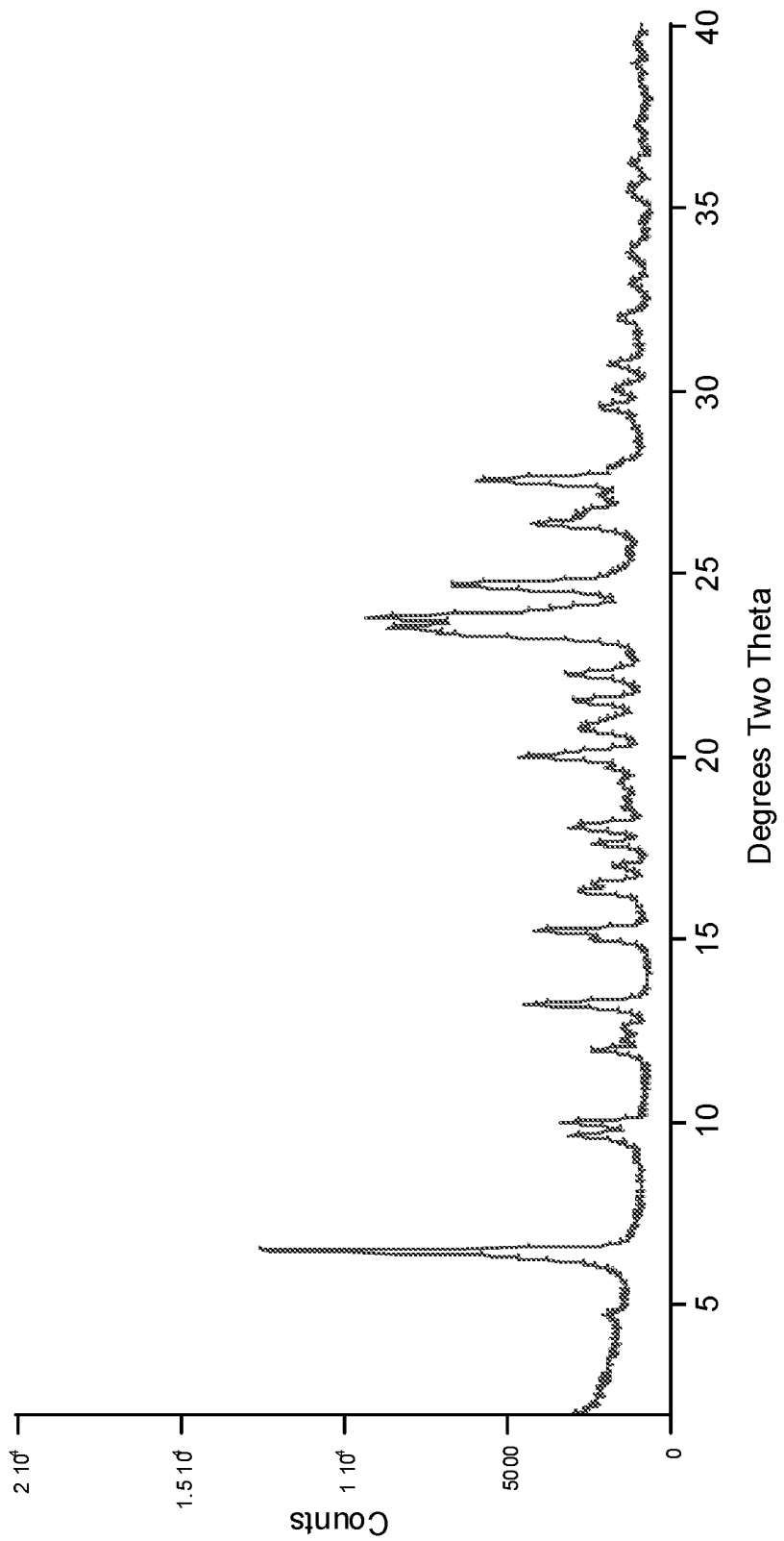
FIG. 68 depicts an XRPD pattern of Compound 1 complex with p-toluenesulfonic acid.

FIG. 68 depicts an XRPD pattern of the p-toluenesulfonic acid complex.

Figure 69:
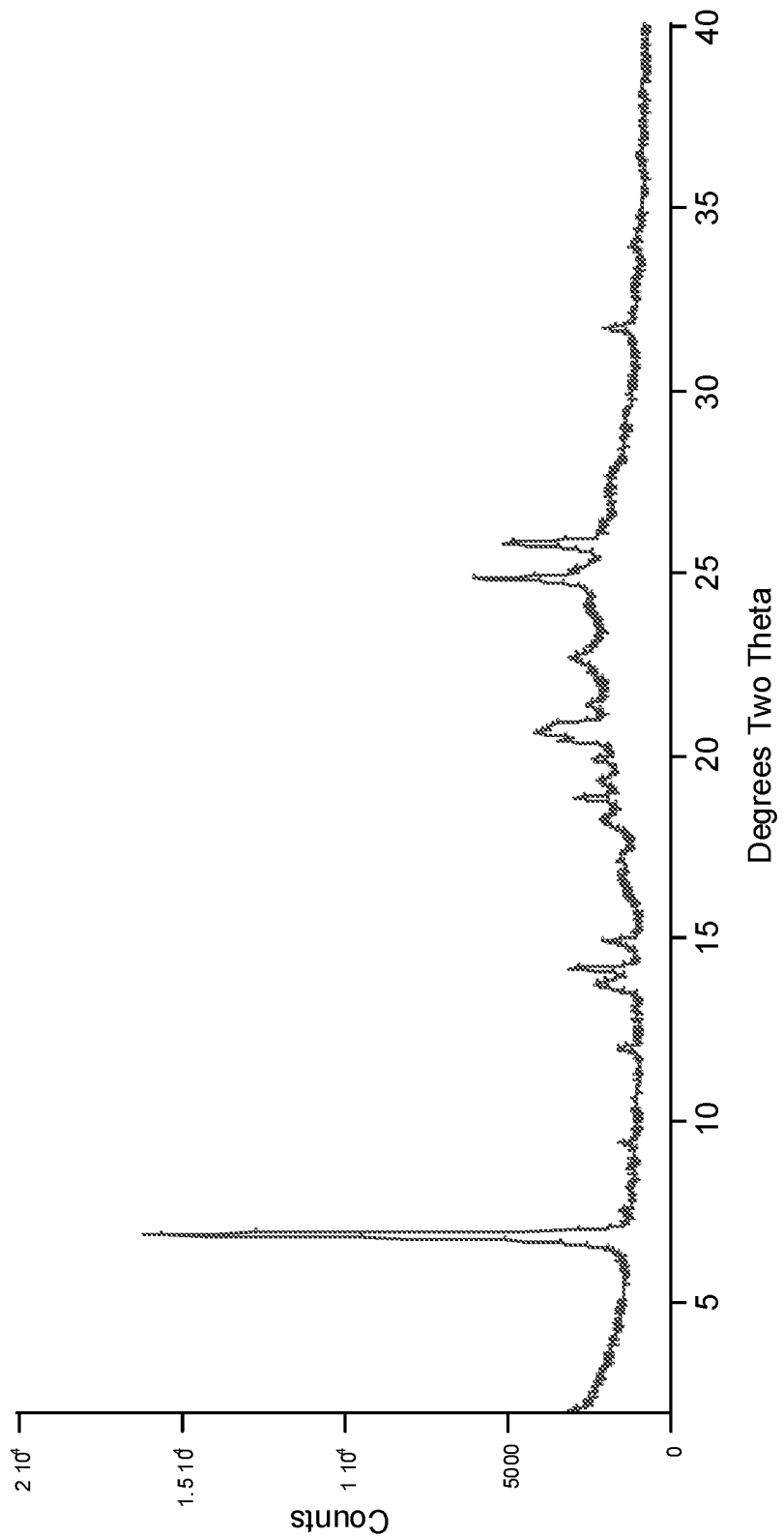
FIG. 69 depicts an XRPD pattern of Compound 1 complex with thiocyanic acid.

FIG. 69 depicts an XRPD pattern of the thiocyanic acid complex.

Figure 70:
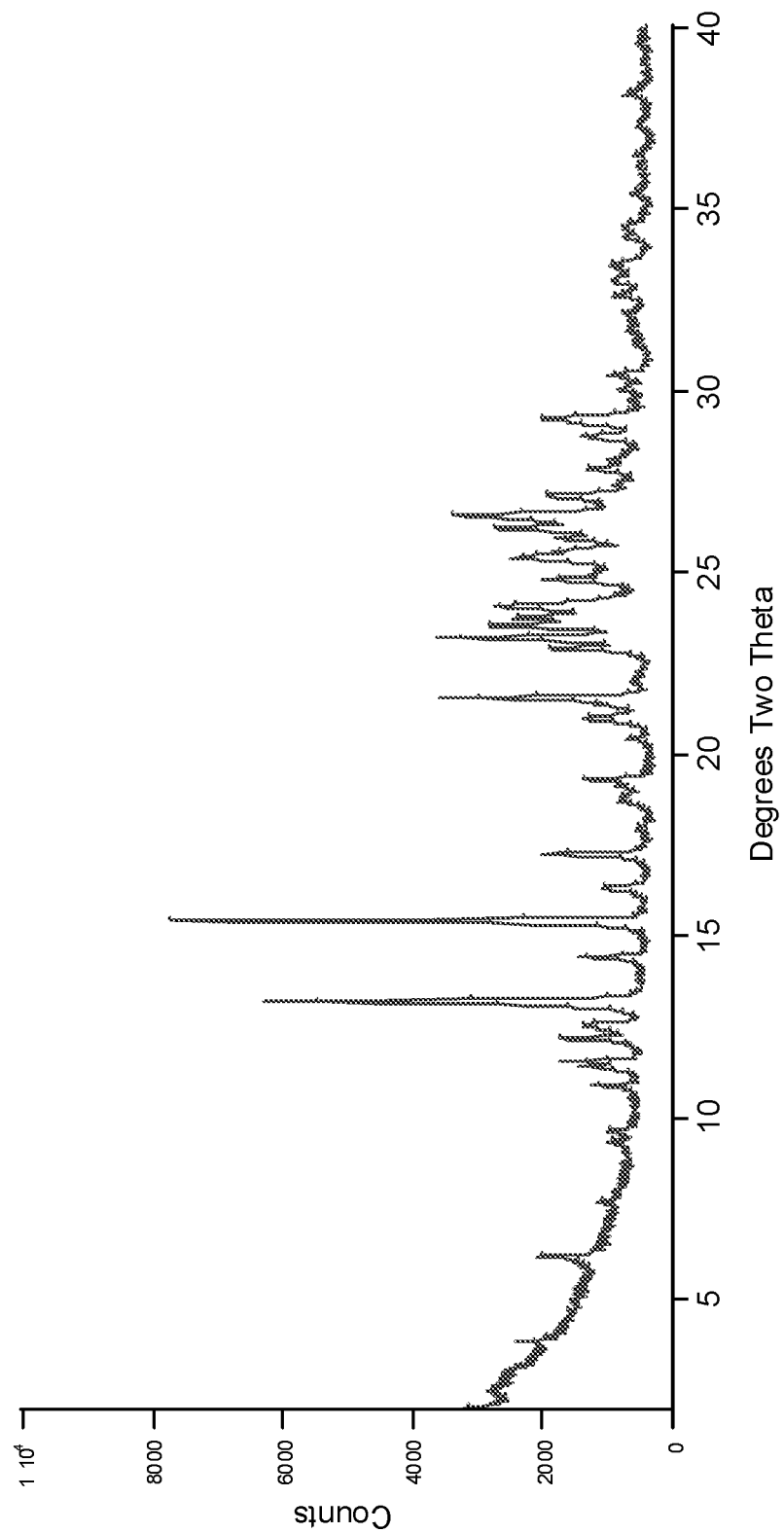
FIG. 70 depicts an XRPD pattern of Compound 1 complex with vanillin.

FIG. 70 depicts an XRPD pattern of the vanillin complex.

Figure 71:
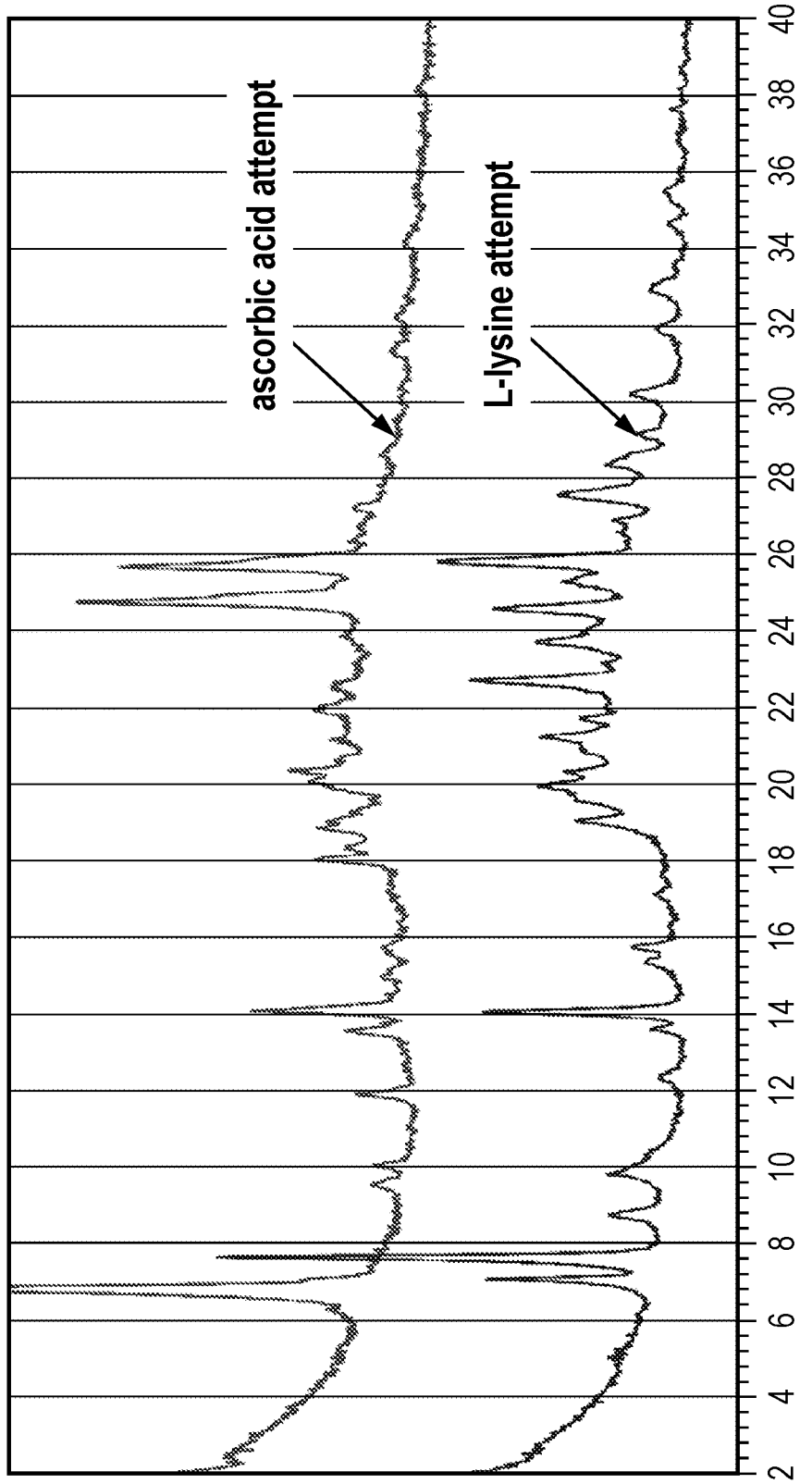
FIG. 71 depicts an overlay of the XRPD spectra for Compound 1 complex with L-ascorbic acid and Compound 1 complex with L-lysine.

FIG. 71 depicts an overlay of the XRPD spectra for the L-ascorbic acid complex and the L-lysine complex.

Figure 72:
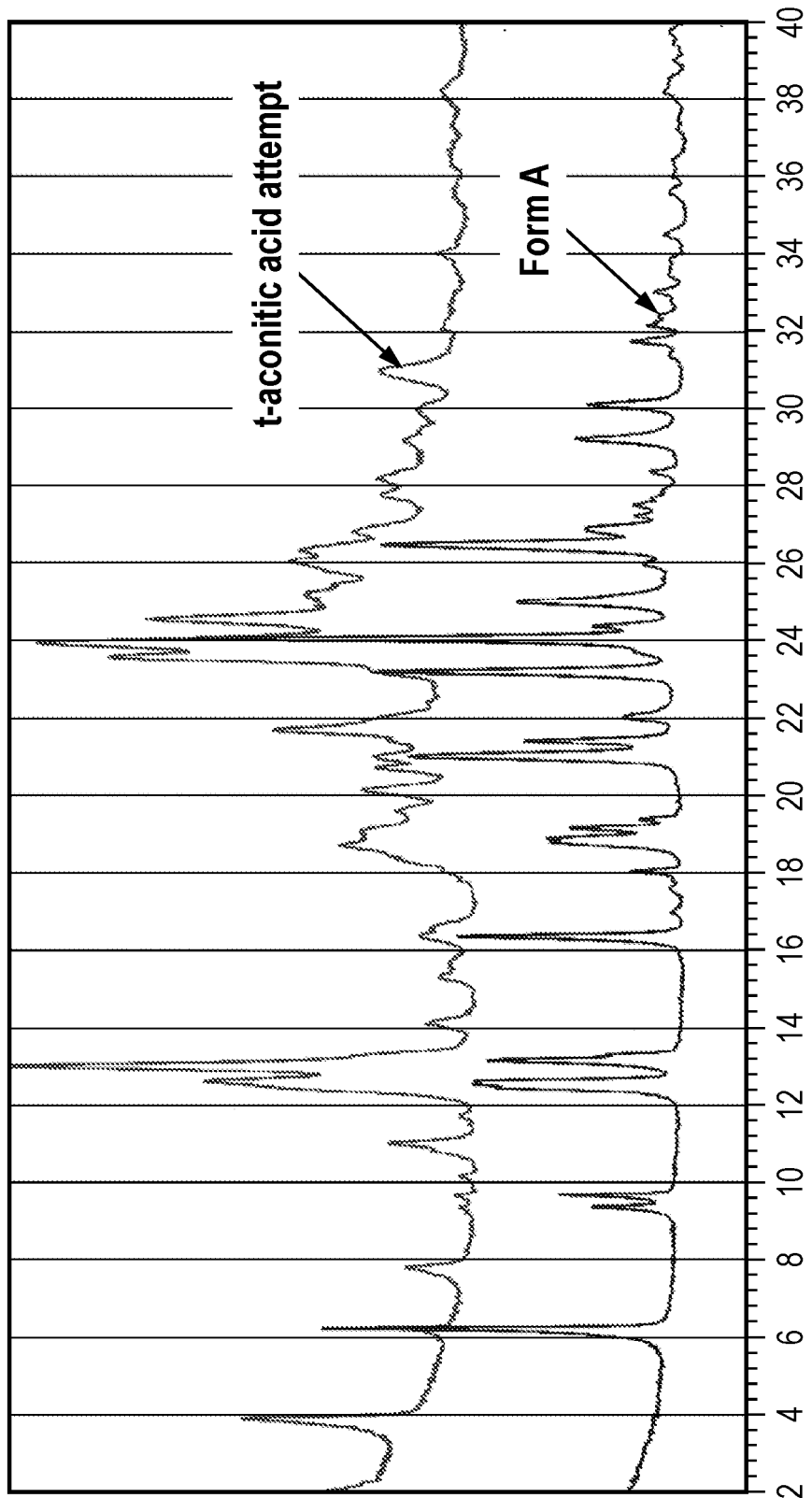
FIG. 72 depicts an overlay of the XRPD spectra for Compound 1 complex with t-aconitic acid and Form A.

FIG. 72 depicts an overlay of the XRPD spectra for the t-aconitic acid complex and Form A.

Figure 73:
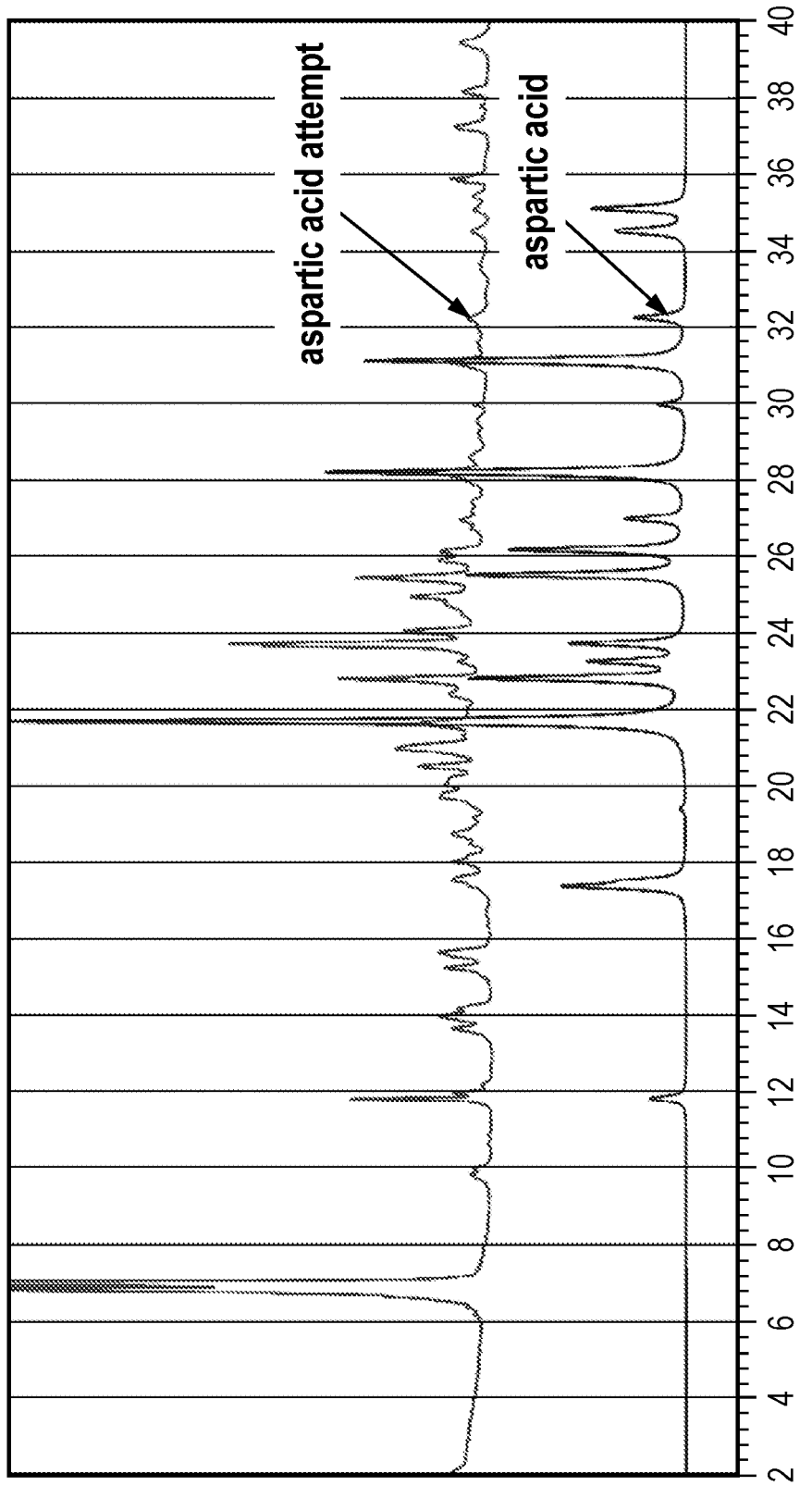
FIG. 73 depicts an overlay of the XRPD spectra for Compound 1 complex with aspartic acid and co-former aspartic acid.

FIG. 73 depicts an overlay of the XRPD spectra for the aspartic acid complex and co-former aspartic acid.

Figure 74:
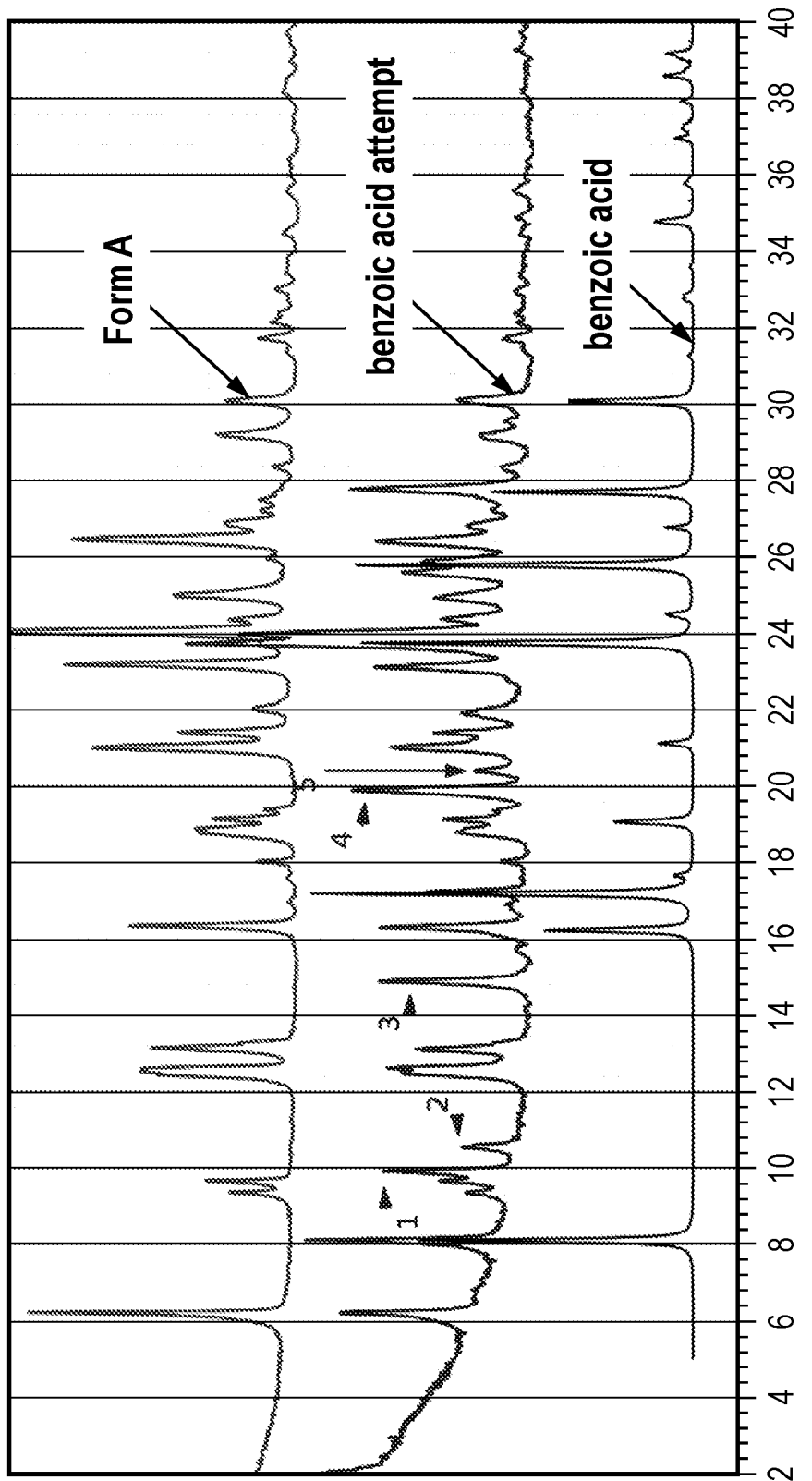
FIG. 74 depicts an overlay of the XRPD spectra for Compound 1 complex with benzoic acid, Form A, and co-former benzoic acid.

FIG. 74 depicts an overlay of the XRPD spectra for the benzoic acid complex, Form A, and co-former benzoic acid.

Figure 75:
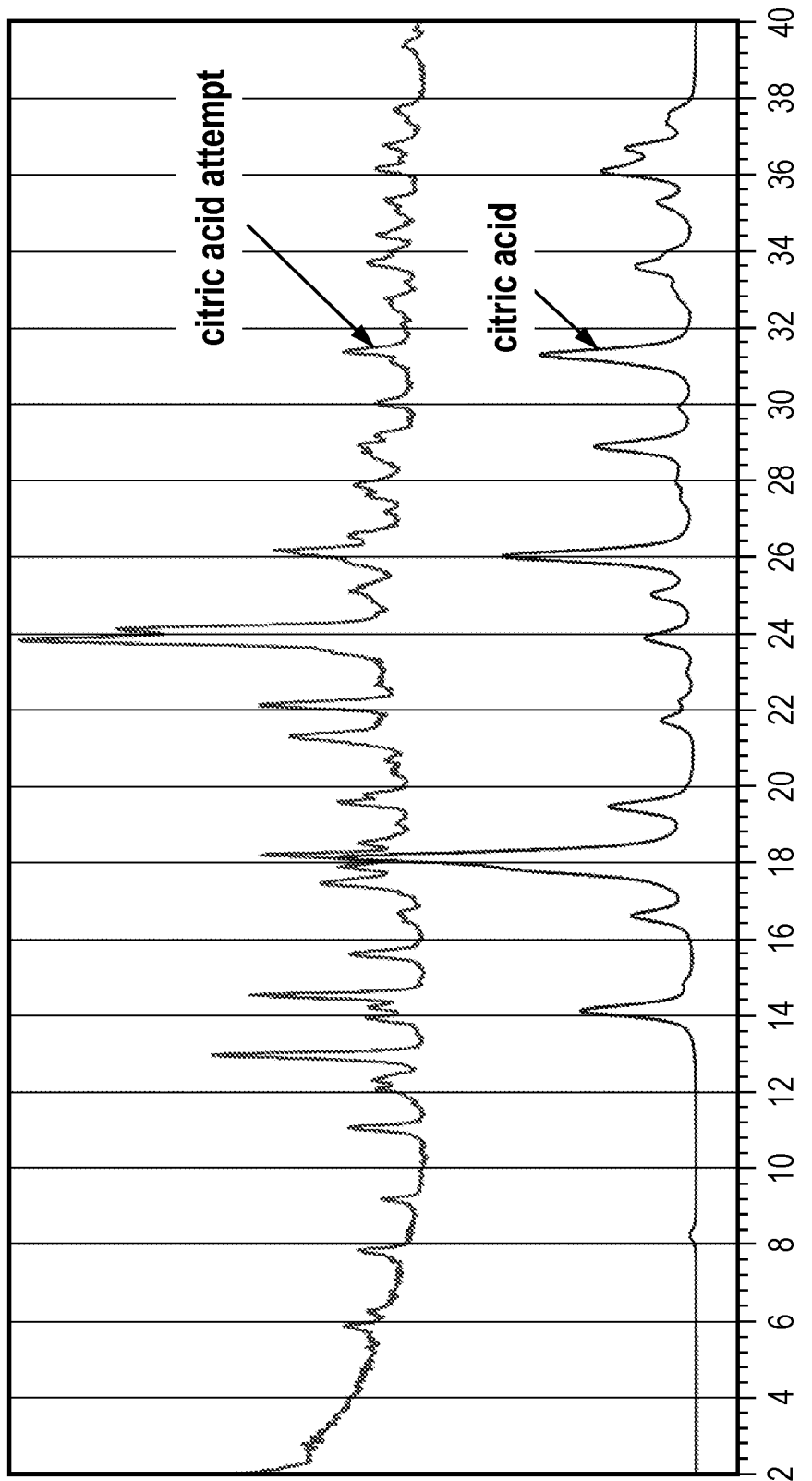
FIG. 75 depicts an overlay of the XRPD spectra for Compound 1 complex with citric acid and co-former citric acid.

FIG. 75 depicts an overlay of the XRPD spectra for the citric acid complex and co-former citric acid.

Figure 76:
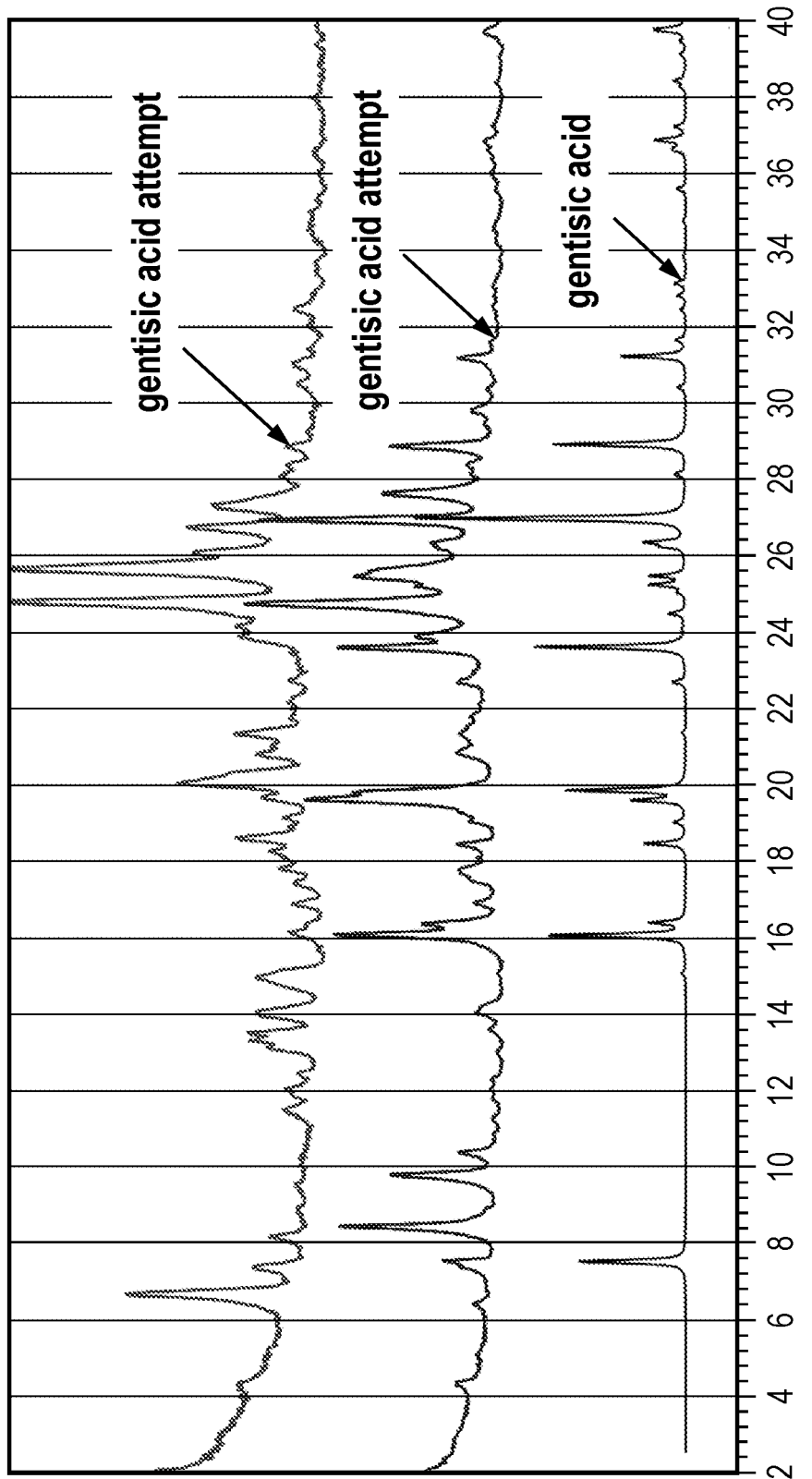
FIG. 76 depicts an overlay of the XRPD spectra for Form 1 Compound 1 complex with gentisic acid, Form 2 Compound 1 complex with gentisic acid, and co-former gentisic acid.

FIG. 76 depicts an overlay of the XRPD spectra for Form 1 of the gentisic acid complex, Form 2 of the gentisic acid complex, and co-former gentisic acid.

Figure 77:
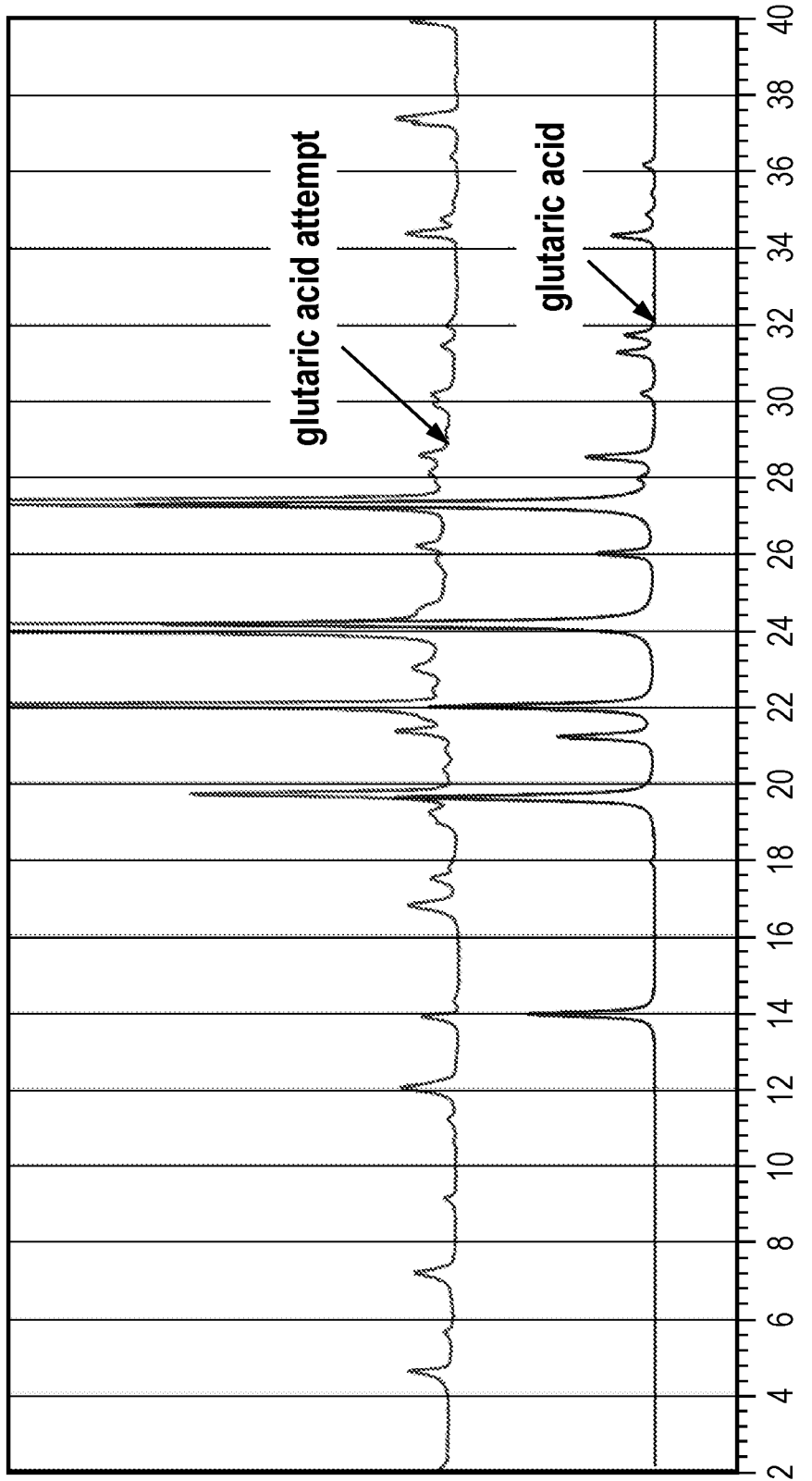
FIG. 77 depicts an overlay of the XRPD spectra for Compound 1 complex with glutaric acid and co-former glutaric acid.

FIG. 77 depicts an overlay of the XRPD spectra for the glutaric acid complex and co-former glutaric acid.

Figure 78:
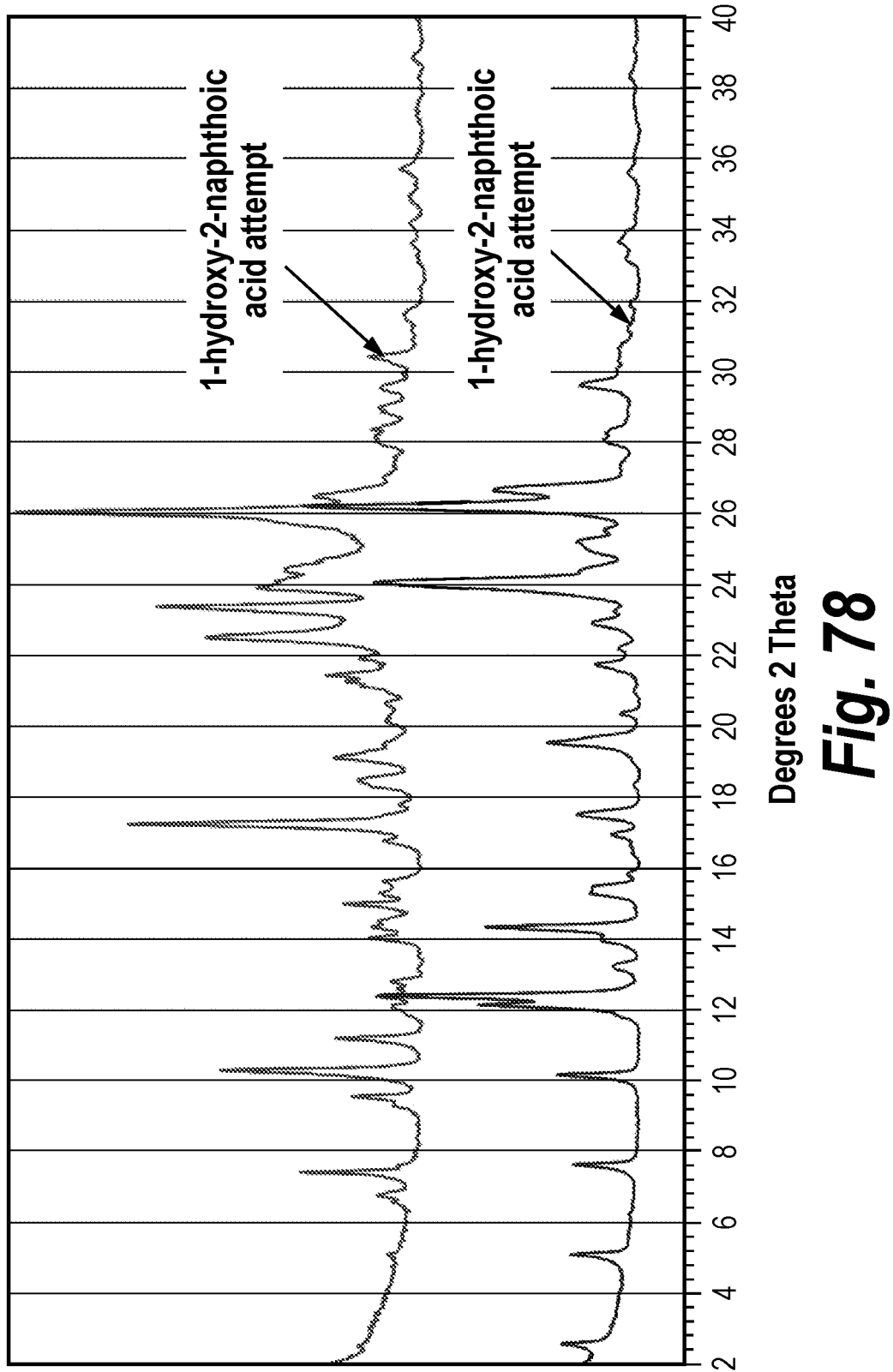
FIG. 78 depicts an overlay of the XRPD spectra for Form 1 Compound 1 complex with 1-hydroxy-2-naphthoic acid and Form 2 Compound 1 complex with 1-hydroxy-2-naphthoic acid.

FIG. 78 depicts an overlay of the XRPD spectra for Form 1 of the 1-hydroxy-2-naphthoic acid complex and Form 2 of the 1-hydroxy-2-naphthoic acid complex.

Figure 79:
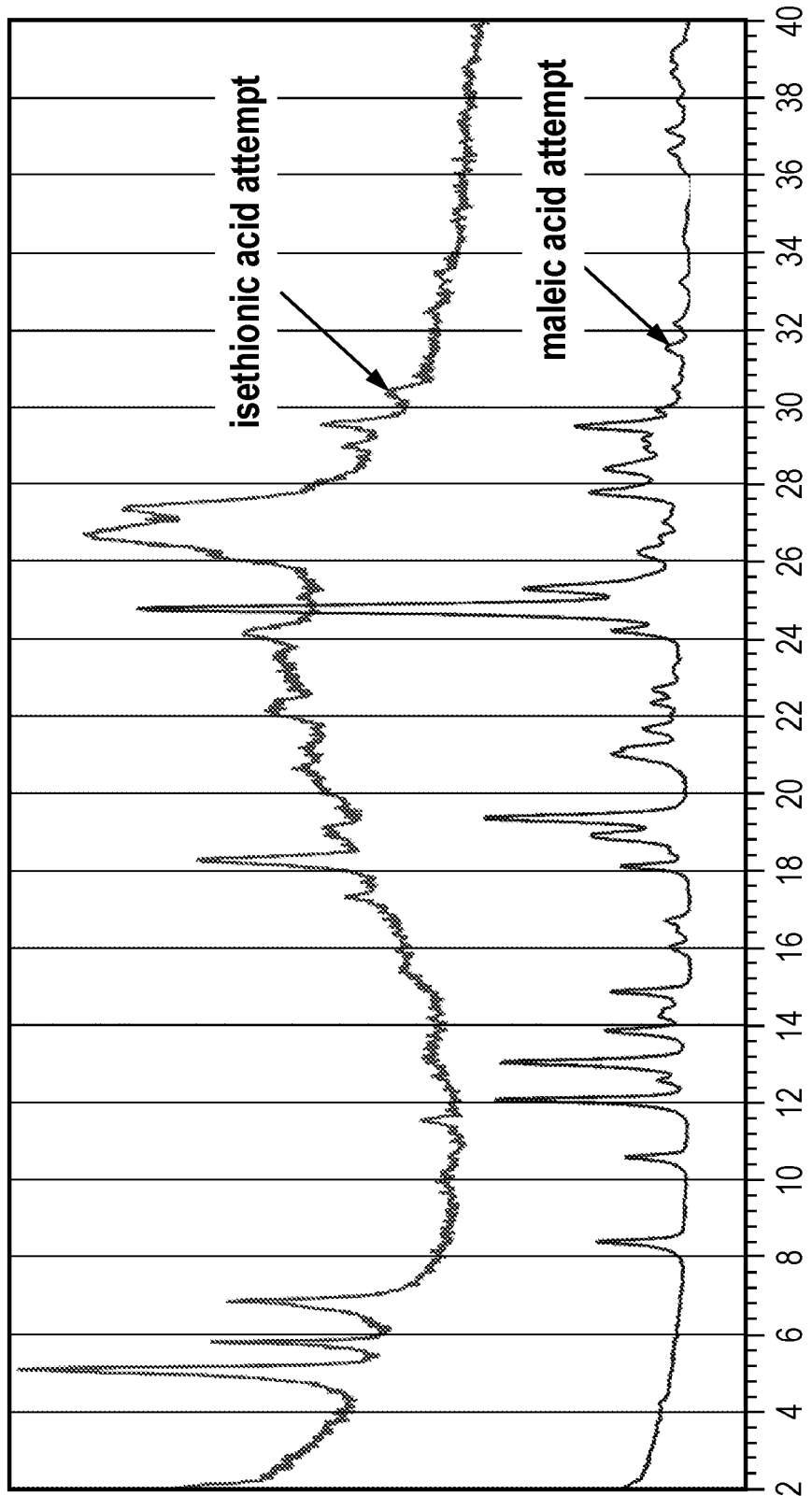
FIG. 79 depicts an overlay of the XRPD spectra for Compound 1 complex with isethionic acid and Compound 1 complex with maleic acid.

FIG. 79 depicts an overlay of the XRPD spectra for the isethionic acid complex and the maleic acid complex.

Figure 80:
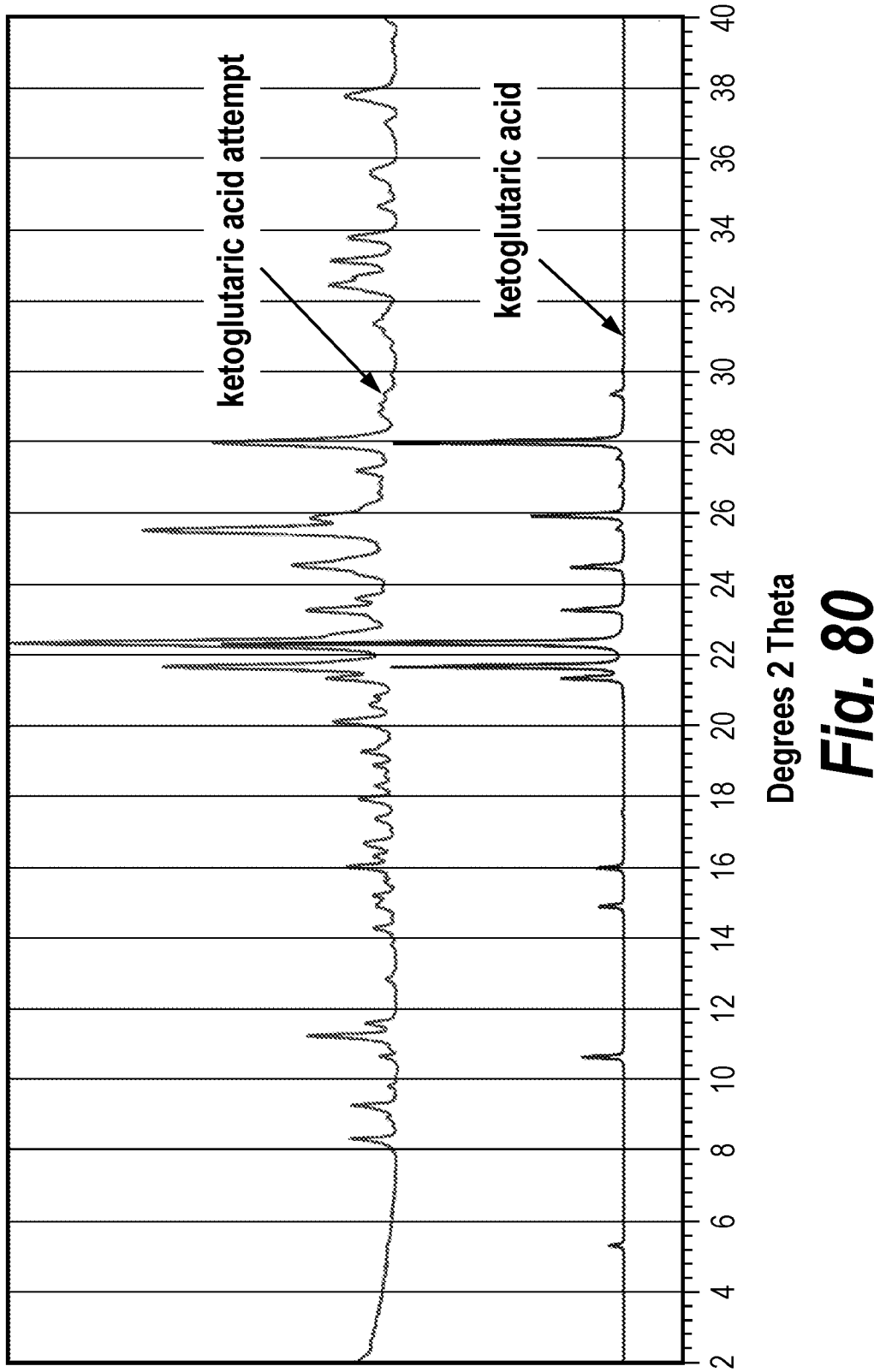
FIG. 80 depicts an overlay of the XRPD spectra for Compound 1 complex with ketoglutaric acid and co-former ketoglutaric acid.

FIG. 80 depicts an overlay of the XRPD spectra for the ketoglutaric acid complex and co-former ketoglutaric acid.

Figure 81:
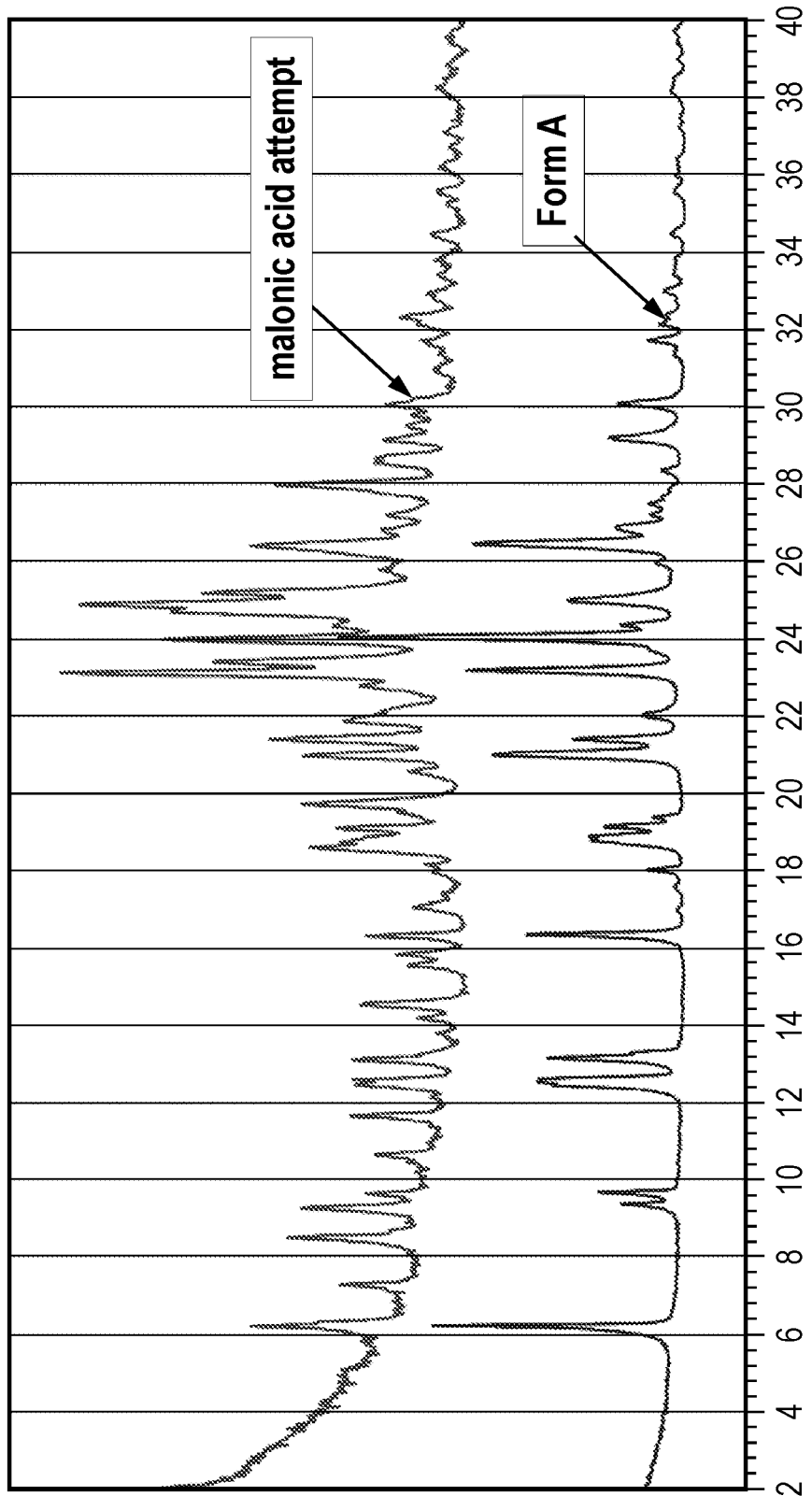
FIG. 81 depicts an overlay of the XRPD spectra for Compound 1 complex with malonic acid and Form A.

FIG. 81 depicts an overlay of the XRPD spectra for the malonic acid complex and Form A.

Figure 82:
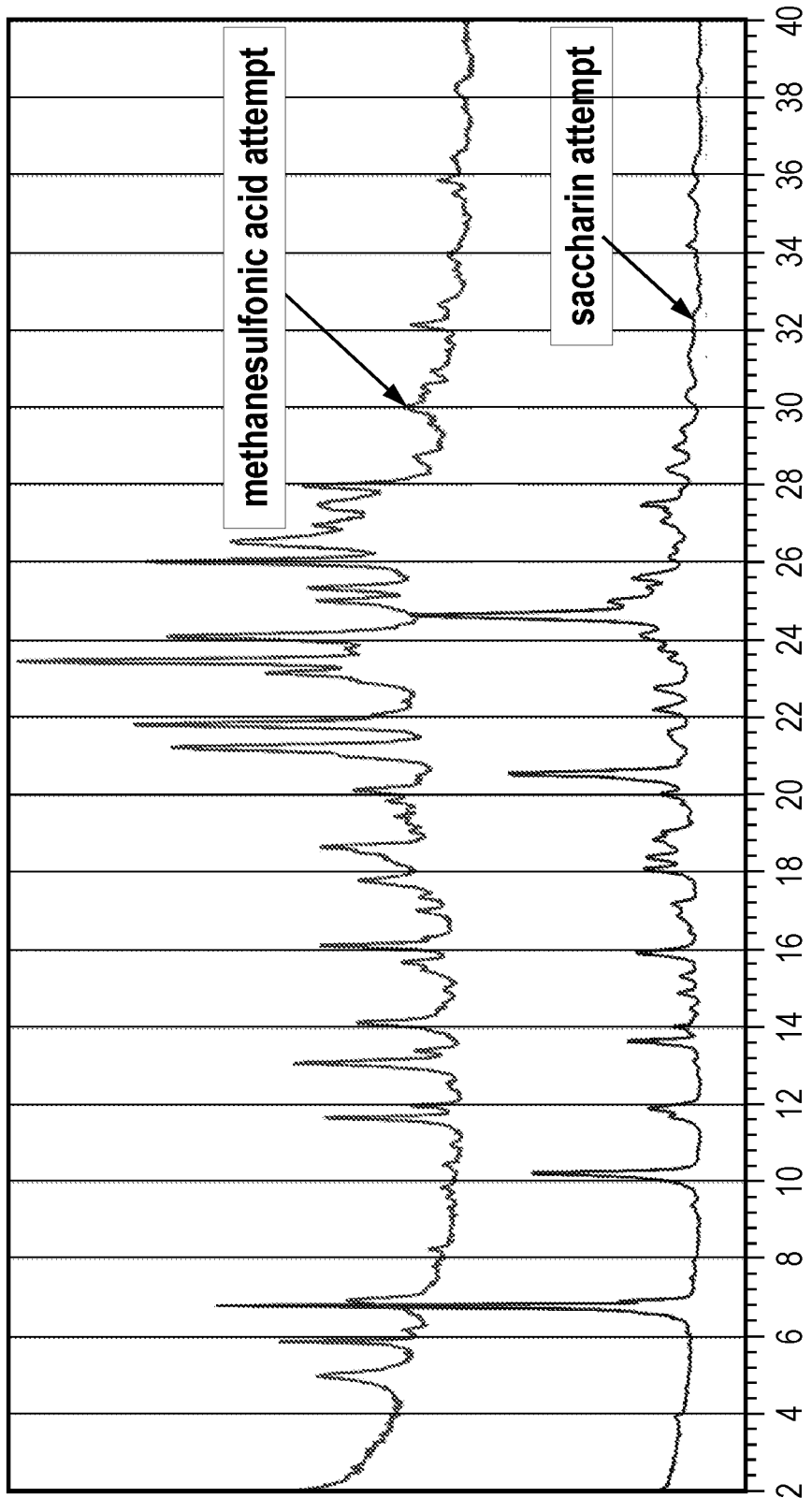
FIG. 82 depicts an overlay of the XRPD spectra for Compound 1 complex with methanesulfonic acid and Compound 1 complex with saccharin.

FIG. 82 depicts an overlay of the XRPD spectra for the methanesulfonic acid complex and the saccharin complex.

Figure 83:
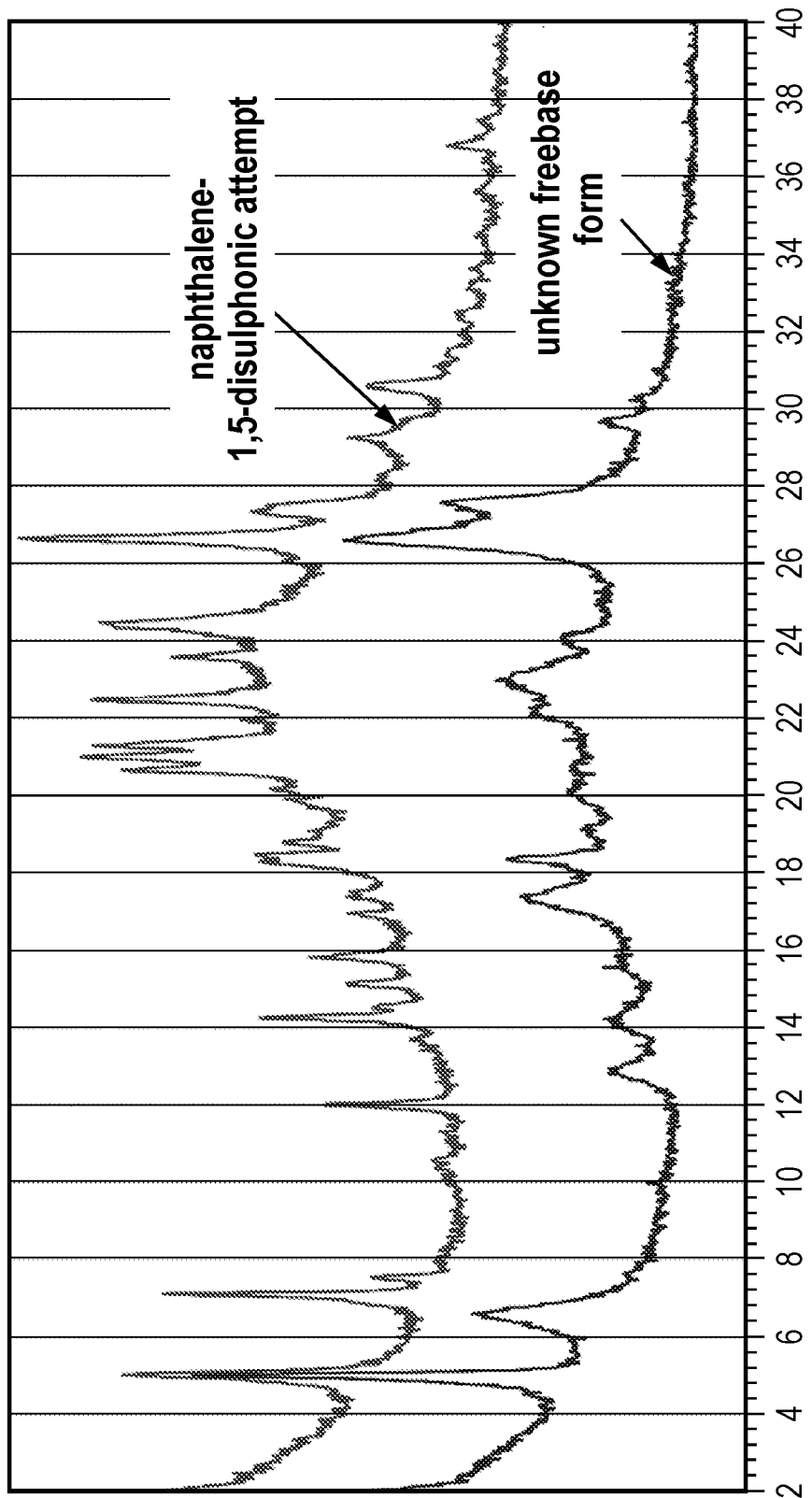
FIG. 83 depicts an overlay of the XRPD spectra for Compound 1 complex with naphthalene-1,5-disulfonic acid and an unknown freebase crystal form.

FIG. 83 depicts an overlay of the XRPD spectra for the naphthalene-1,5-disulfonic acid complex and an unknown freebase polymorph of Compound 1.

Figure 84:
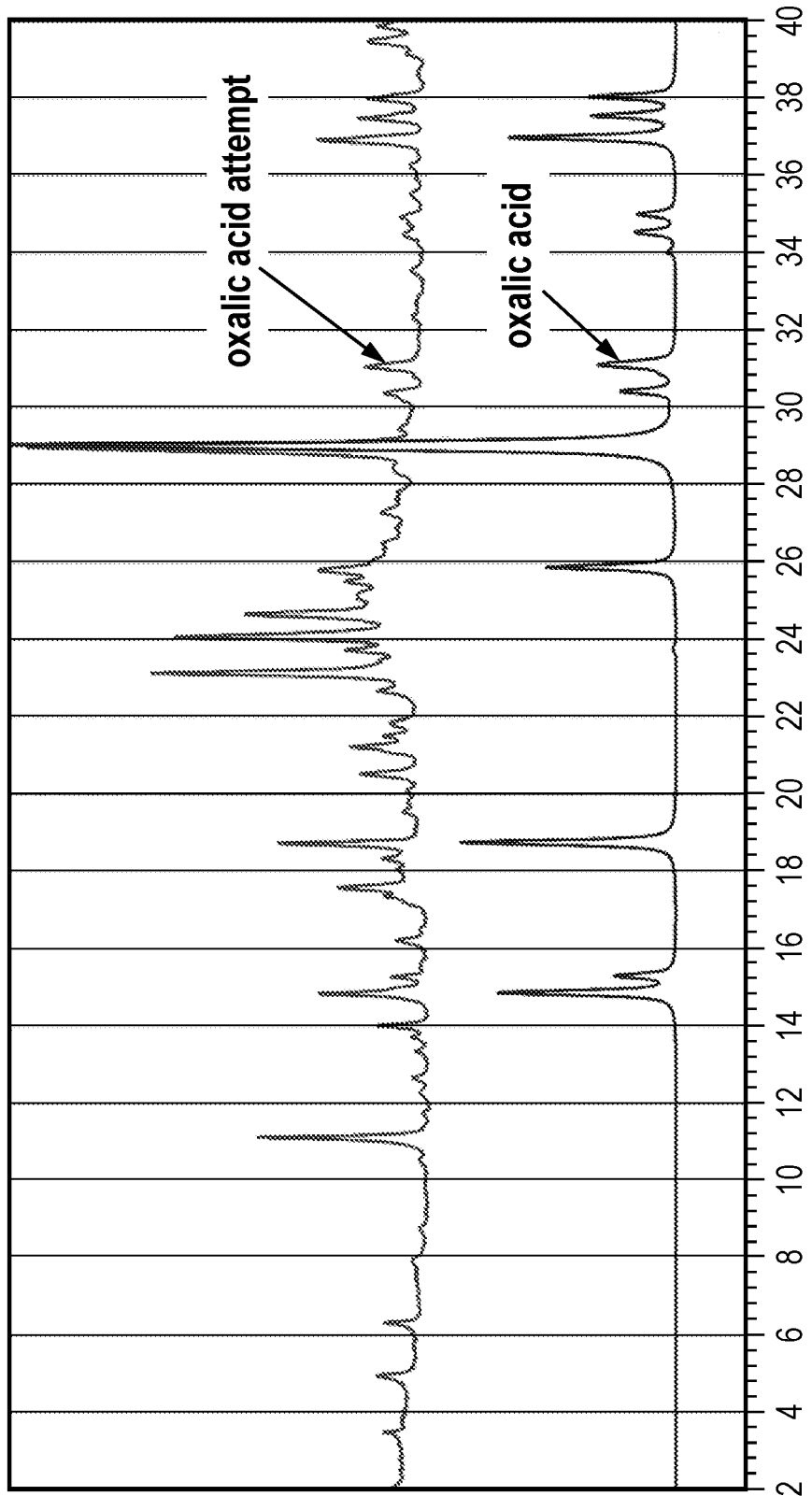
FIG. 84 depicts an overlay of the XRPD spectra for Compound 1 complex with oxalic acid and co-former oxalic acid.

FIG. 84 depicts an overlay of the XRPD spectra for the oxalic acid complex and co-former oxalic acid.

Figure 85:
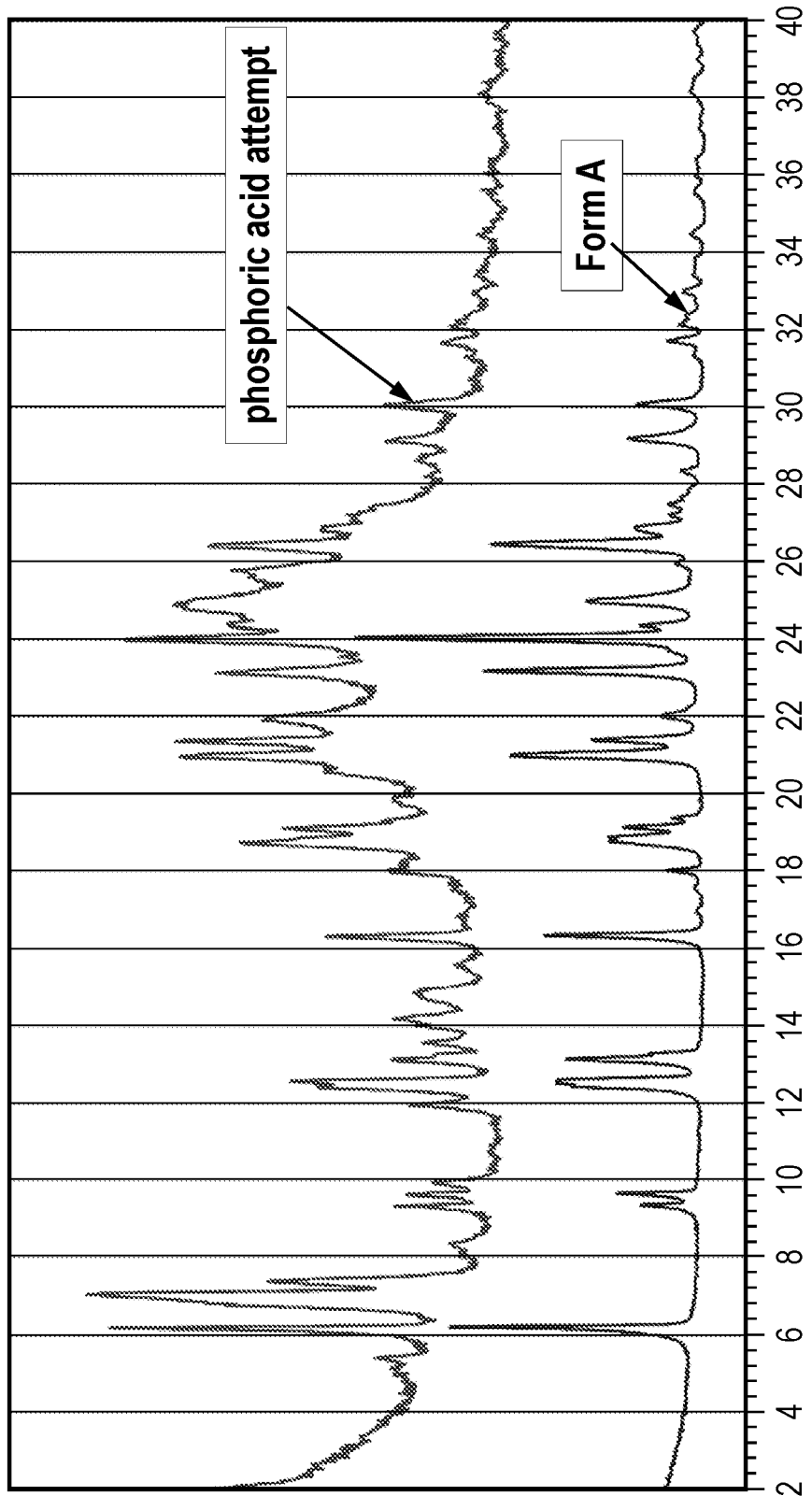
FIG. 85 depicts an overlay of the XRPD spectra for Compound 1 complex with phosphoric acid and Form A.

FIG. 85 depicts an overlay of the XRPD spectra for the phosphoric acid complex and Form A.

Figure 86:
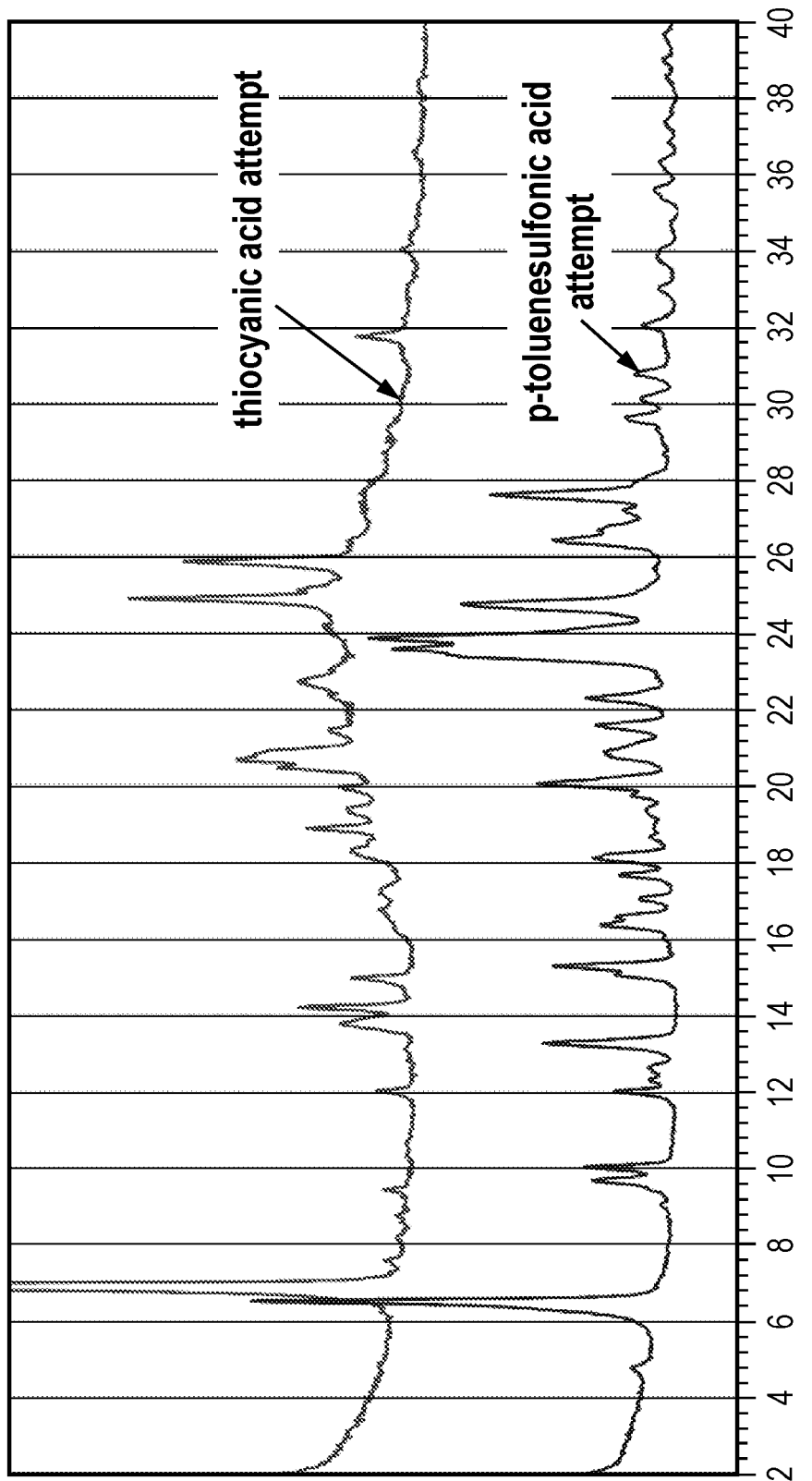
FIG. 86 depicts an overlay of the XRPD spectra for Compound 1 complex with thiocyanic acid and Compound 1 complex with p-toluenesulfonic acid.

FIG. 86 depicts an overlay of the XRPD spectra for the thiocyanic acid complex and the p-toluenesulfonic acid complex.

Figure 87:
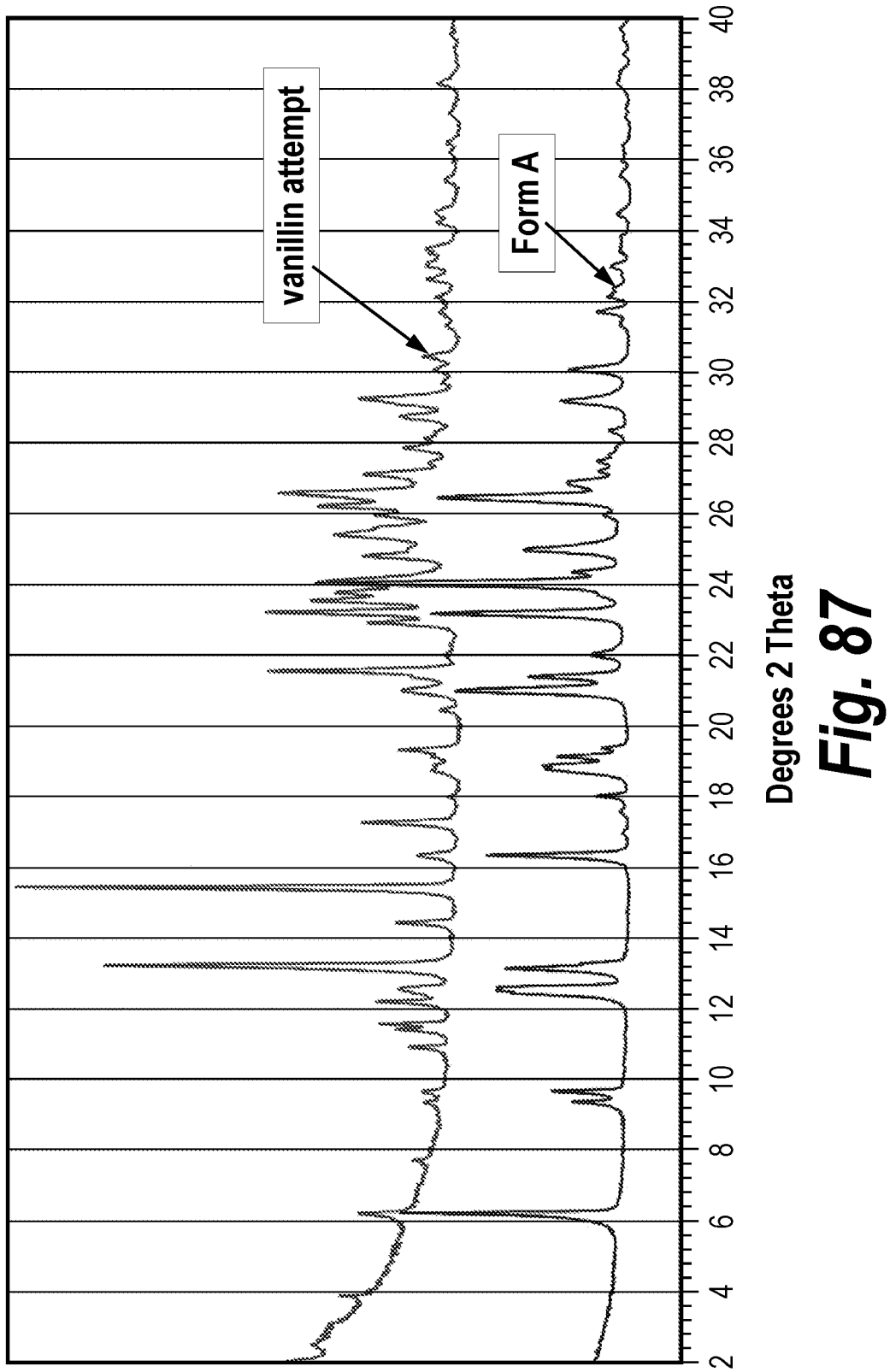
FIG. 87 depicts an overlay of the XRPD spectra for Compound 1 complex with vanillin and Form A.

FIG. 87 depicts an overlay of the XRPD spectra for the vanillin complex and Form A.

Samples having an XRPD pattern suggestive of new phase formation were analyzed by DSC and TGA. The results are summarized in Table 41.

TABLE 41

Thermal Analysis

| Co-former | Results |
| --- | --- |
| L-ascorbic acid | endotherm observed at 88.26° C. 2.55% loss up to 100° C. |

TABLE 41-continued

Thermal Analysis

| Co-former | Results |
| --- | --- |
| gentisic acid | endotherm observed at 115.17° C. 1.69% loss up to 120° C. |
| 1-hydroxy-2-naphthoic acid (Form 1) | endotherms observed at 114.50 and 148.93° C. 10.82% loss up to 150° C. |
| 1-hydroxy-2-naphthoic acid (Form 2) | endotherm observed at 169.60° C. 1.86% loss up to 150° C. |
| L-lysine | endotherms observed at 81.50, 148.49, and 246.20° C. 7.32% loss up to 150° C. 12.61% loss from 150 to 250° C. |
| maleic acid | endotherm observed at 153.89° C. 9.87% loss up to 155° C. |
| methanesulfonic acid | endotherm observed at 157.01° C. 8.28% loss up to 160° C. |
| saccharin | endotherms observed at 62.05 and 161.14° C. 3.70% loss up to 165° C. |
| thiocyanic acid | endotherms observed at 87.75 and 202.18° C. 3.04% loss up to 100° C. 6.54% loss from 100 to 200° C. |
| p-toluenesulfonic acid | endotherms observed at 96.56 and 128.74° C. 3.50% loss up to 130° C. |

Example 3. Scale-Up of Saccharin and Maleic Acid Complexes

Based on the results from the primary salt/co-crystal screen, the maleic acid and saccharin complexes were selected for scale-up and characterization.

| Co-former | Preparation Method | XRPD Pattern |
| --- | --- | --- |
| maleic acid | grinding in MeOH, ~20 minutes | maleic acid co-crystal |
| saccharin | slow evaporation from THF at RT | saccharin co-crystal + unknown freebase crystal form |
| | slurried in THF evaporation from THF at RT | unknown freebase crystal form saccharin co-crystal |

Figure 88:
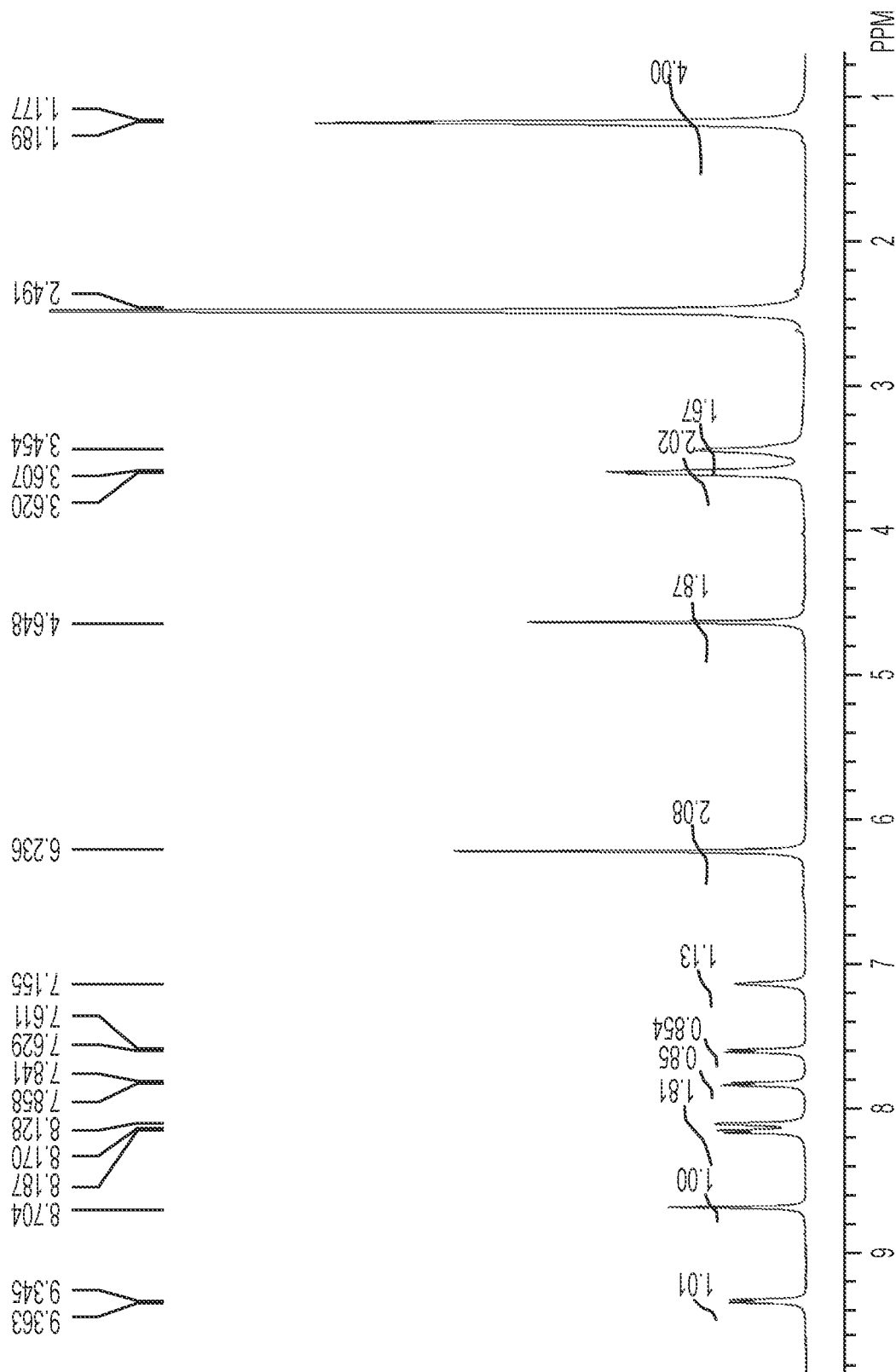
FIG. 88 depicts an $^1$H NMR spectrum of Compound 1 complex with maleic acid.

Characterization data for the maleic acid complex are shown in Table 42. The maleic acid complex appears to be unsolvated. TGA results show 0.50% weight loss below 100° C., and 7.15% weight loss from 100 to 155° C. No solvent is observed in the NMR spectrum. NMR spectroscopy of the maleic acid complex is consistent with an unsolvated complex comprising a 1:1 ratio of Compound 1 to co-former (FIG. 88).

Figure 90:
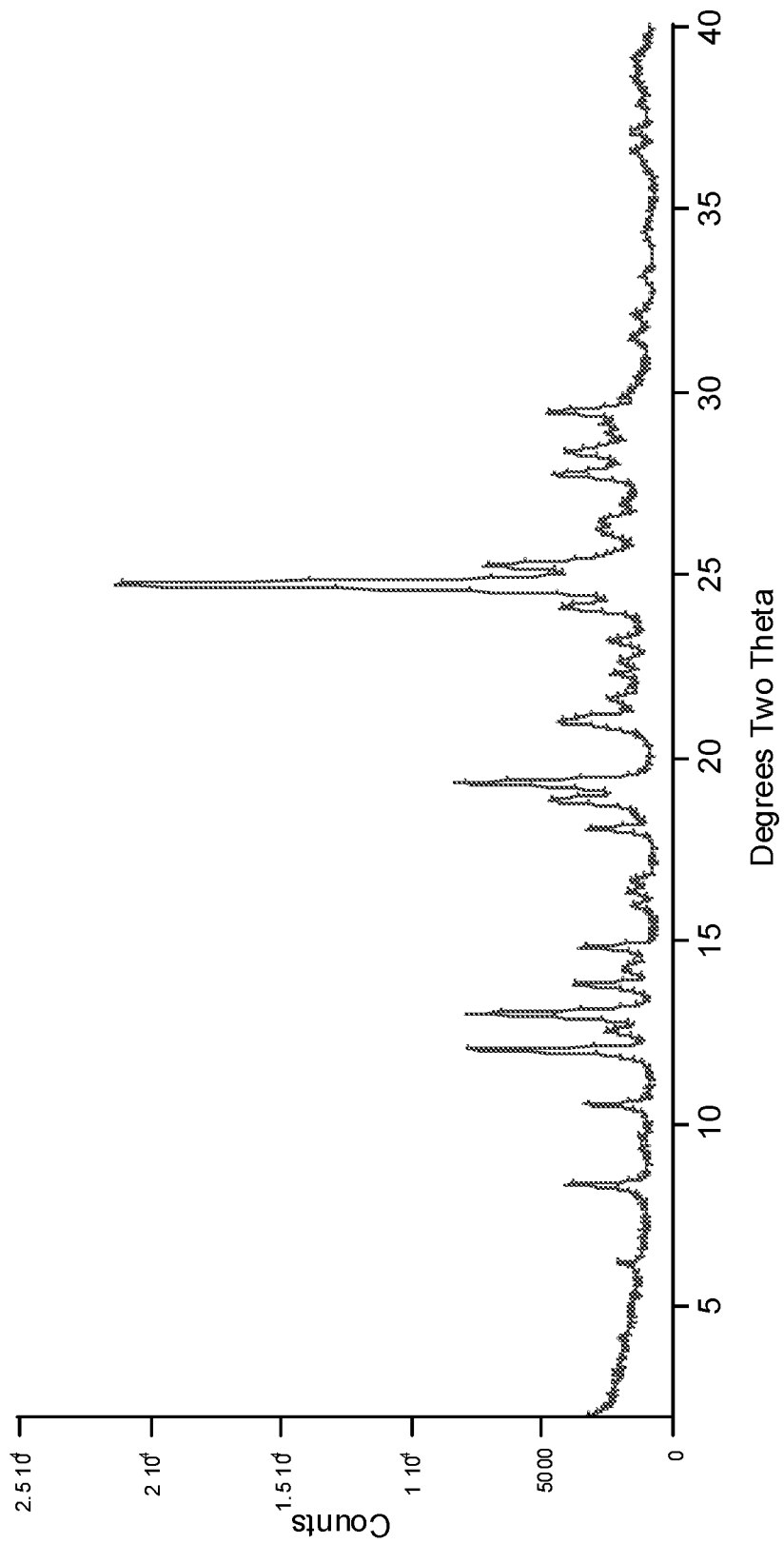
FIG. 90 depicts an XRPD pattern of Compound 1 complex with maleic acid.

The endotherm in the DSC at 155.61° C. is likely melting occurring concurrently with decomposition. FIG. 90 depicts the XRPD spectra for the scale-up of the maleic acid complex.

TABLE 42

Characterization of the Maleic Acid Complex

| Technique | Result |
| --- | --- |
| XRPD | maleic acid complex |
| DSC | endotherm observed at 155.61° C. |
| TG | 0.50% up to 100° C. 7.15% from 100 to 155° C. |
| IR | — |
| NMR | consistent with unsolvated complex comprising a 1:1 ratio of Compound 1 to maleic acid co-former |

Figure 89:
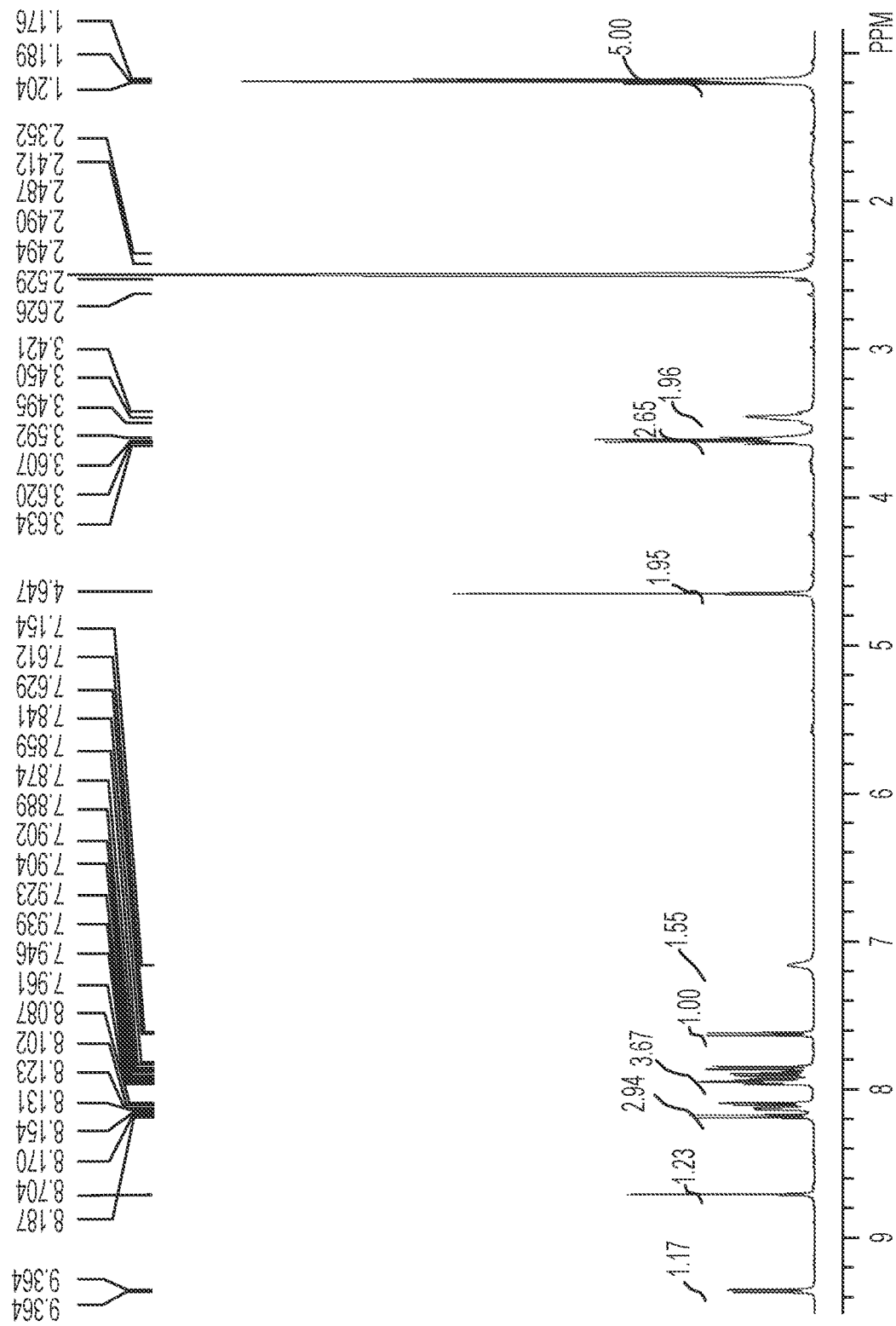
FIG. 89 depicts an $^1$H NMR spectrum of Compound 1 complex with saccharin.

Characterization data for the saccharin complex are shown in Table 43. It may be solvated. TGA results show 7.63% weight loss below 165° C., although no solvent is observed in the NMR spectrum. NMR spectroscopy of the saccharin complex is consistent with an unsolvated complex comprising a 1:1 ratio of Compound 1 to co-former (FIG. 89).

Figure 91:
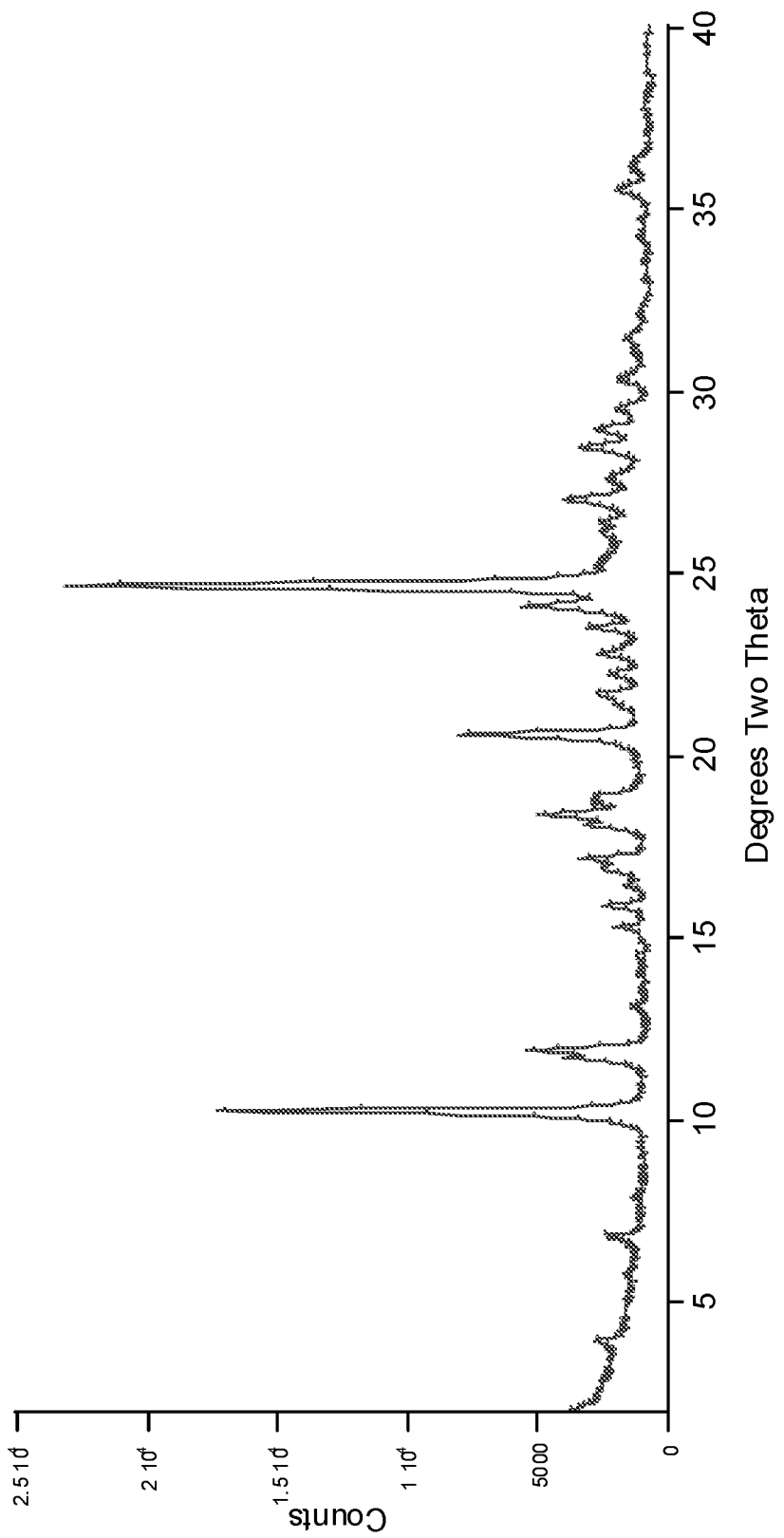
FIG. 91 depicts an XRPD pattern of Compound 1 complex with saccharin.

The endotherm in the DSC at 154.74° C. is likely melting. FIG. 91 depicts the XRPD spectra for the scale-up of the saccharin complex.

TABLE 43

Characterization of the Saccharin Complex

| Technique | Result |
|---|---|
| XRPD | saccharin complex |
| DSC | endotherm observed at 154.74° C. |
| TG | 7.63% up to 165° C. |
| IR | — |
| NMR | consistent with unsolvated complex comprising a 1:1 ratio of Compound 1 to saccharin co-former |

Example 4: Process of Preparing Form a of Compound 1 from Form I of Compound 1

A mixture of Form I of Compound 1 (29.0 g, 54.6 mmol) and acetone (290 mL) was agitated in the presence of Form A of Compound 1 (250 mg, 0.5 mmol) and the resulting mixture was heated to 50-55° C. and agitated at this temperature for 48 h. The mixture was sampled by XRPD to assess conversion to the anhydrate form. Then the batch was cooled to 20-25° C. over 2 h and held at that temperature for 16 h. The batch was filtered and the cake was rinsed with acetone (2×60 mL). The cake was dried under vacuum at 45-55° C. to afford 24.0 g of the Form A of Compound 1 as a yellow solid, in 94% yield.

Enumerated Embodiments

1. A crystalline form of Compound 1:

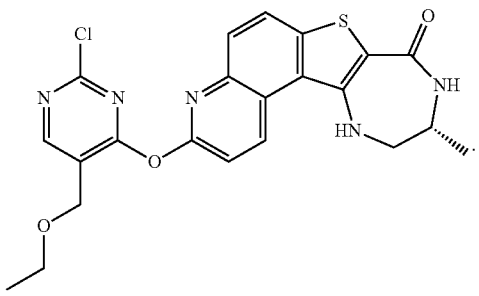 [SMILES: CCOCc1cnc(Cl)nc1Oc1ccc2c(ccc3sc4c(c32)NC[C@@H](C)NC4=O)n1]

2. The crystalline form according to embodiment 1, wherein Compound 1 is unsolvated.
3. The crystalline form according to embodiment 2, wherein the crystalline form is characterized by one or more peaks in its powder X-ray diffraction pattern selected from those at about 6.19, about 9.33, about 9.64, about 12.39, about 12.49, about 12.59, about 13.11, about 13.25, about 16.31, about 18.70, about 18.84, about 19.09, about 20.92, about 21.35, about 23.17, about 24.02, about 24.94, about 26.44, about 29.14, and about 30.04 degrees 2-theta.
4. The crystalline form according to embodiment 3, wherein the crystalline form is characterized by a powder X-ray diffraction pattern having peaks at about 9.33, about 9.64, and about 16.31 degrees 2-theta.
5. The crystalline form according to embodiment 3, wherein the crystalline form is characterized by a powder X-ray diffraction pattern having peaks at about 6.19, about 9.33, about 9.64, and about 16.31 degrees 2-theta.
6. The crystalline form according to embodiment 3, wherein the crystalline form is characterized by a powder X-ray diffraction pattern having peaks at about 6.19, about 9.33, about 9.64, about 16.31, and about 24.02 degrees 2-theta.
7. The crystalline form according to embodiment 3, wherein the crystalline form is characterized by a powder X-ray diffraction pattern having peaks at about 9.64, about 12.39, about 12.49, about 12.59, about 13.11, about 13.25, about 16.31, about 18.70, about 18.84, about 19.09, about 20.92, about 21.35, about 23.17, about 24.02, about 24.94, about 26.44, about 29.14, and about 30.04 degrees 2-theta.
8. The crystalline form according to embodiment 2, wherein the crystalline form is characterized by one or more peaks in its powder X-ray diffraction pattern selected from those at about 6.19, about 7.04, about 9.30, about 9.58, about 9.64, about 12.54, about 18.69, about 19.33, about 21.34, about 27.52, and about 29.18 degrees 2-theta.
9. The crystalline form according to embodiment 8, wherein the crystalline form is characterized by a powder X-ray diffraction pattern having peaks at about 7.04, about 12.54, and about 21.34 degrees 2-theta.
10. The crystalline form according to embodiment 8, wherein the crystalline form is characterized by a powder X-ray diffraction pattern having peaks at about 6.19, about 7.04, about 12.54, and about 21.34 degrees 2-theta.
11. The crystalline form according to embodiment 8, wherein the crystalline form is characterized by a powder X-ray diffraction pattern having peaks at about 6.19, about 7.04, about 9.30, about 9.58, about 9.64, about 12.54, about 18.69, about 19.33, about 21.34, about 27.52, and about 29.18 degrees 2-theta.
12. The crystalline form according to embodiment 2, wherein the crystalline form is characterized by one or more peaks in its powder X-ray diffraction pattern selected from those at about 4.89, about 6.01, about 6.10, about 9.83, about 12.06, about 20.55, about 20.98, about 25.75, and about 26.42 degrees 2-theta.
13. The crystalline form according to embodiment 12, wherein the crystalline form is characterized by a powder X-ray diffraction pattern having peaks at about 4.89, about 6.01, and about 9.83 degrees 2-theta.
14. The crystalline form according to embodiment 12, wherein the crystalline form is characterized by a powder X-ray diffraction pattern having peaks at about 4.89, about 6.01, about 9.83, about 25.75, and about 26.42 degrees 2-theta.
15. The crystalline form according to embodiment 12, wherein the crystalline form is characterized by a powder X-ray diffraction pattern having peaks at about 4.89, about 6.01, about 6.10, about 9.83, about 12.06, about 20.55, about 20.98, about 25.75, and about 26.42 degrees 2-theta.
16. The crystalline form according to embodiment 1, wherein the crystalline form is a hydrate.
17. The crystalline form according to embodiment 16, wherein the crystalline form is characterized by one or more peaks in its powder X-ray diffraction pattern selected from those at about 7.03, about 13.54, about 13.91, about 14.13, about 21.25, about 21.51, about 24.73, and 25.77 degrees 2-theta.

18. The crystalline form according to embodiment 17, wherein the crystalline form is characterized by a powder X-ray diffraction pattern having peaks at about 7.03, about 13.54, about 13.91, and about 14.13 degrees 2-theta.

19. The crystalline form according to embodiment 17, wherein the crystalline form is characterized by a powder X-ray diffraction pattern having peaks at about 7.03, about 13.54, about 13.91, about 14.13, and about 25.77 degrees 2-theta.

20. The crystalline form according to embodiment 17, wherein the crystalline form is characterized by a powder X-ray diffraction pattern having peaks at about 7.03, about 13.54, about 13.91, about 14.13, about 21.25, about 21.51, about 24.73, and 25.77 degrees 2-theta.

21. The crystalline form according to embodiment 16, wherein the crystalline form is characterized by one or more peaks in its powder X-ray diffraction pattern selected from those at about 6.80, about 7.13, about 9.95, about 15.48, about 15.64, and about 21.44 degrees 2-theta.

22. The crystalline form according to embodiment 20, wherein the crystalline form is characterized by a powder X-ray diffraction pattern having peaks at about 6.80 and about 7.13 degrees 2-theta.

23. The crystalline form according to embodiment 21, wherein the crystalline form is characterized by a powder X-ray diffraction pattern having peaks at about 6.80, about 7.13, about 9.95, about 15.48, about 15.64, and about 21.44 degrees 2-theta.

24. The crystalline form according to embodiment 1, wherein the crystalline form is a solvate.

25. The crystalline form according to embodiment 24, wherein the crystalline form is characterized by one or more peaks in its powder X-ray diffraction pattern selected from those at about 7.11, about 8.92, about 10.41, about 10.68, about 11.00, about 13.70, about 22.11, and about 23.73 degrees 2-theta.

26. The crystalline form according to embodiment 25, wherein the crystalline form is characterized by a powder X-ray diffraction pattern having peaks at about 7.11, about 8.92 and about 11.00 degrees 2-theta.

27. The crystalline form according to embodiment 25, wherein the crystalline form is characterized by a powder X-ray diffraction pattern having peaks at about 7.11, about 8.92, about 10.41, about 10.68, about 11.00, about 13.70, about 22.11, and about 23.73 degrees 2-theta.

28. The crystalline form according to embodiment 24, wherein the crystalline form is characterized by one or more peaks in its powder X-ray diffraction pattern selected from those at about 6.36, about 9.56, about 9.94, about 10.41, about 10.77, about 12.71, about 12.89, about 17.56, about 18.12, about 19.09, about 19.35, about 19.74, about 20.83, about 23.49, and about 24.08 degrees 2-theta.

29. The crystalline form according to embodiment 28, wherein the crystalline form is characterized by a powder X-ray diffraction pattern having peaks at about 6.36, about 12.71, and about 12.89 degrees 2-theta.

30. The crystalline form according to embodiment 28, wherein the crystalline form is characterized by a powder X-ray diffraction pattern having peaks at about 6.36, about 9.56, about 9.94, about 10.41, about 10.77, about 12.71, about 12.89, about 17.56, about 18.12, about 19.09, about 19.35, about 19.74, about 20.83, about 23.49, and about 24.08 degrees 2-theta.

31. The crystalline form according to embodiment 24, wherein the crystalline form is characterized by one or more peaks in its powder X-ray diffraction pattern selected from those at about 10.37, about 12.81, about 19.31, about 19.75, and about 24.06 degrees 2-theta.

32. The crystalline form according to embodiment 31, wherein the crystalline form is characterized by a powder X-ray diffraction pattern having peaks at about 12.81, about 19.31, and about 24.06 degrees 2-theta.

33. The crystalline form according to embodiment 31, wherein the crystalline form is characterized by a powder X-ray diffraction pattern having peaks at about 10.37, about 12.81, about 19.31, about 19.75, and about 24.06 degrees 2-theta.

34. The crystalline form according to embodiment 24, wherein the crystalline form is characterized by one or more peaks in its powder X-ray diffraction pattern selected from those at about 6.73, about 8.44, about 13.45, about 15.27, about 17.53, about 20.54, about 23.95, and about 24.49 degrees 2-theta.

35. The crystalline form according to embodiment 34, wherein the crystalline form is characterized by a powder X-ray diffraction pattern having peaks at about 6.73, about 8.44, and about 23.95 degrees 2-theta.

36. The crystalline form according to embodiment 34, wherein the crystalline form is characterized by a powder X-ray diffraction pattern having peaks at about 6.73, about 8.44, about 17.53, and about 23.95 degrees 2-theta.

37. The crystalline form according to embodiment 34, wherein the crystalline form is characterized by a powder X-ray diffraction pattern having peaks at about 6.73, about 8.44, about 15.27, about 17.53, and about 23.95 degrees 2-theta.

38. The crystalline form according to embodiment 34, wherein the crystalline form is characterized by a powder X-ray diffraction pattern having peaks at about 6.73, about 8.44, about 13.45, about 15.27, about 17.53, about 20.54, about 23.95, and about 24.49 degrees 2-theta.

39. A complex comprising Compound 1:

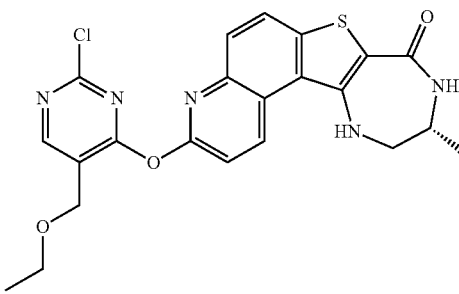

and a co-former X,
wherein X is selected from the group consisting of t-aconitic acid, L-ascorbic acid, aspartic acid, benzoic acid, citric acid, gentisic acid, glutaric acid, 1-hydroxy-2-naphthoic acid, isethionic acid, ketoglutaric acid, L-lysine, maleic acid, malonic acid, methanesulfonic acid, naphthalene-1,5-disulphonic acid, oxalic acid, phosphoric acid, saccharin, thiocyanic acid, p-toluenesulfonic acid, and vanillin.

40. The complex according to embodiment 39, wherein the complex is a crystalline solid form.

41. The complex according to embodiment 39, wherein X is t-aconitic acid.

42. The complex according to embodiment 41, wherein the complex is characterized by one or more peaks in its powder X-ray diffraction pattern selected from those at about 3.91, about 7.81, about 10.98, about 23.58, about 23.90, about 24.54, and about 30.90 degrees 2-theta.

43. The complex according to embodiment 41, wherein the complex is characterized by a powder X-ray diffraction pattern having peaks at about 3.91, about 7.81, about 10.98, and about 30.90 degrees 2-theta.

44. The complex according to embodiment 39, wherein X is L-ascorbic acid.

45. The complex according to embodiment 44, wherein the complex is characterized by one or more peaks in its powder X-ray diffraction pattern selected from those at about 6.79, about 14.06, about 24.76, and about 25.68 degrees 2-theta.

46. The complex according to embodiment 44, wherein the complex is characterized by a powder X-ray diffraction pattern having peaks at about 6.79, about 24.76, and about 25.68 degrees 2-theta.

47. The complex according to embodiment 39, wherein X is aspartic acid.

48. The complex according to embodiment 47, wherein the complex is characterized by one or more peaks in its powder X-ray diffraction pattern selected from those at about 6.81, about 6.97, about 13.63, about 13.94, about 14.17, about 15.21, about 15.61, about 20.97, and about 24.03 degrees 2-theta.

49. The complex according to embodiment 47, wherein the complex is characterized by a powder X-ray diffraction pattern having peaks at about 6.81, about 6.97, about 20.97, and about 24.03 degrees 2-theta.

50. The complex according to embodiment 39, wherein X is benzoic acid.

51. The complex according to embodiment 50, wherein the complex is characterized by one or more peaks in its powder X-ray diffraction pattern selected from those at about 9.94, about 10.55, about 14.91, about 19.90, and about 20.38 degrees 2-theta.

52. The complex according to embodiment 50, wherein the complex is characterized by a powder X-ray diffraction pattern having peaks at about 10.55, about 14.91, and about 19.90 degrees 2-theta.

53. The complex according to embodiment 39, wherein X is citric acid.

54. The complex according to embodiment 53, wherein the complex is characterized by one or more peaks in its powder X-ray diffraction pattern selected from those at about 11.07, about 12.97, about 14.52, about 15.58, about 21.30, about 22.10, about 23.79, and about 24.09 degrees 2-theta.

55. The complex according to embodiment 53, wherein the complex is characterized by a powder X-ray diffraction pattern having peaks at about 11.07, about 12.97, about 15.58, and about 21.30 degrees 2-theta.

56. The complex according to embodiment 53, wherein the complex is characterized by a powder X-ray diffraction pattern having peaks at about 11.07, about 12.97, and about 15.58 degrees 2-theta.

57. The complex according to embodiment 39, wherein X is gentisic acid.

58. The complex according to embodiment 57, wherein the complex is characterized by one or more peaks in its powder X-ray diffraction pattern selected from those at about 6.65, about 13.10, about 13.30, about 13.49, about 14.01, about 14.96, about 20.03, about 24.79, and about 25.63 degrees 2-theta.

59. The complex according to embodiment 57, wherein the complex is characterized by a powder X-ray diffraction pattern having peaks at about 6.65, about 20.03, about 24.79, and about 25.63 degrees 2-theta.

60. The complex according to embodiment 57, wherein the complex is characterized by one or more peaks in its powder X-ray diffraction pattern selected from those at about 8.42, about 9.80, about 24.74, and about 27.60 degrees 2-theta.

61. The complex according to embodiment 57, wherein the complex is characterized by a powder X-ray diffraction pattern having peaks at about 8.42, about 9.80, about 24.74, and about 27.60 degrees 2-theta.

62. The complex according to embodiment 39, wherein X is glutaric acid.

63. The complex according to embodiment 62, wherein the complex is characterized by one or more peaks in its powder X-ray diffraction pattern selected from those at about 4.59, about 7.15, about 11.97, about 16.78, about 17.49, about 37.25, and about 37.39 degrees 2-theta.

64. The complex according to embodiment 62, wherein the complex is characterized by a powder X-ray diffraction pattern having peaks at about 4.59, about 7.15, about 11.97, and about 16.78 degrees 2-theta.

65. The complex according to embodiment 39, wherein X is 1-hydroxy-2-naphthoic acid.

66. The complex according to embodiment 65, wherein the complex is characterized by one or more peaks in its powder X-ray diffraction pattern selected from those at about 7.40, about 9.53, about 11.18, about 17.24, about 22.46, about 23.37, and about 25.99 degrees 2-theta.

67. The complex according to embodiment 65, wherein the complex is characterized by a powder X-ray diffraction pattern having peaks at about 7.40, about 9.53, about 11.18, and about 17.24 degrees 2-theta.

68. The complex according to embodiment 65, wherein the complex is characterized by one or more peaks in its powder X-ray diffraction pattern selected from those at about 5.09, about 7.62, about 10.15, about 12.12, about 12.37, about 17.46, about 19.46, and about 24.04 degrees 2-theta.

69. The complex according to embodiment 65, wherein the complex is characterized by a powder X-ray diffraction pattern having peaks at about 5.09, about 7.62, about 12.12, about 12.37, about 19.46, and about 24.04 degrees 2-theta.

70. The solid form according to embodiment 39, wherein X is isethionic acid.

71. The complex according to embodiment 70, wherein the complex is characterized by one or more peaks in its powder X-ray diffraction pattern selected from those at about 5.07, about 5.77, about 6.84, about 18.24, about 26.72, and about 27.35 degrees 2-theta.

72. The complex according to embodiment 70, wherein the complex is characterized by a powder X-ray diffraction pattern having peaks at about 5.07, about 5.77, about 6.84, about 26.72, and about 27.35 degrees 2-theta.

73. The complex according to embodiment 39, wherein X is ketoglutaric acid.

74. The complex according to embodiment 73, wherein the complex is characterized by one or more peaks in its powder X-ray diffraction pattern selected from those at about 8.31, about 9.25, about 11.23, about 20.08, about 25.50, about 32.44, about 33.12, about 33.74, and about 37.75 degrees 2-theta.

75. The complex according to embodiment 73, wherein the complex is characterized by a powder X-ray diffraction pattern having peaks at about 8.31, about 9.25, about 11.23, and about 20.08 degrees 2-theta.

76. The complex according to embodiment 73, wherein the complex is characterized by a powder X-ray diffraction pattern having peaks at about 8.31, about 9.25, about 11.23, about 20.08, and about 25.50 degrees 2-theta.

77. The complex according to embodiment 39, wherein X is L-lysine.

78. The complex according to embodiment 77, wherein the complex is characterized by one or more peaks in its powder X-ray diffraction pattern selected from those at about 7.04, about 7.64, about 14.05, about 22.69, about 24.58, and about 25.80 degrees 2-theta.

79. The complex according to embodiment 77, wherein the complex is characterized by a powder X-ray diffraction pattern having peaks at about 7.04, about 7.64, and about 22.69 degrees 2-theta.

80. The complex according to embodiment 39, wherein X is maleic acid.

81. The complex according to embodiment 80, wherein the complex is characterized by one or more peaks in its powder X-ray diffraction pattern selected from those at about 8.37, about 10.54, about 12.07, about 13.01, about 13.81, about 14.84, about 19.31, about 24.76, and about 25.27 degrees 2-theta.

82. The complex according to embodiment 80, wherein the complex is characterized by a powder X-ray diffraction pattern having peaks at about 8.37, about 10.54, about 12.07, about 13.01, and about 19.31 degrees 2-theta.

83. The complex according to embodiment 39, wherein X is malonic acid.

84. The complex according to embodiment 83, wherein the complex is characterized by one or more peaks in its powder X-ray diffraction pattern selected from those at about 7.26, about 8.51, about 11.63, about 14.52, about 15.52, about 15.82, about 19.71, about 23.38, and about 27.98 degrees 2-theta.

85. The complex according to embodiment 83, wherein the complex is characterized by a powder X-ray diffraction pattern having peaks at about 7.26, about 8.51, about 11.63, about 14.52, about 15.52, about 15.82, and about 19.71 degrees 2-theta.

86. The complex according to embodiment 39, wherein X is methanesulfonic acid.

87. The complex according to embodiment 86, wherein the complex is characterized by one or more peaks in its powder X-ray diffraction pattern selected from those at about 5.04, about 5.90, about 13.08, about 21.83, about 23.46, about 24.08, and about 26.02 degrees 2-theta.

88. The complex according to embodiment 86, wherein the complex is characterized by a powder X-ray diffraction pattern having peaks at about 5.04, about 5.90, about 13.08, and about 21.83 degrees 2-theta.

89. The complex according to embodiment 39, wherein X is naphthalene-1,5-disulphonic acid.

90. The complex according to embodiment 89, wherein the complex is characterized by one or more peaks in its powder X-ray diffraction pattern selected from those at about 12.02, about 20.61, about 20.98, about 21.25, about 22.49, and about 24.39 degrees 2-theta.

91. The complex according to embodiment 89, wherein the complex is characterized by a powder X-ray diffraction pattern having peaks at about 12.02, about 20.61, about 20.98, and about 21.25 degrees 2-theta.

92. The complex according to embodiment 39, wherein X is oxalic acid.

93. The complex according to embodiment 92, wherein the complex is characterized by one or more peaks in its powder X-ray diffraction pattern selected from those at about 11.14, about 20.52, about 21.22, about 23.13, about 24.08, and about 24.67 degrees 2-theta.

94. The complex according to embodiment 92, wherein the complex is characterized by a powder X-ray diffraction pattern having peaks at about 11.14, about 20.52, about 24.08, and about 24.67 degrees 2-theta.

95. The complex according to embodiment 92, wherein the complex is characterized by a powder X-ray diffraction pattern having peaks at about 11.14, about 24.08, and about 24.67 degrees 2-theta.

96. The complex according to embodiment 39, wherein X is phosphoric acid.

97. The complex according to embodiment 96, wherein the complex is characterized by one or more peaks in its powder X-ray diffraction pattern selected from those at about 6.79, about 7.08, about 7.39, about 9.93, about 11.95, about 14.18, and about 14.88 degrees 2-theta.

98. The complex according to embodiment 96, wherein the complex is characterized by a powder X-ray diffraction pattern having peaks at about 6.79, about 7.08, about 7.39, about 9.93, and about 11.95 degrees 2-theta.

99. The complex according to embodiment 39, wherein X is saccharin.

100. The complex according to embodiment 99, wherein the complex is characterized by one or more peaks in its powder X-ray diffraction pattern selected from those at about 6.82, about 10.24, about 20.53, and about 24.63 degrees 2-theta.

101. The complex according to embodiment 99, wherein the complex is characterized by a powder X-ray diffraction pattern having peaks at about 6.82, about 10.24, and about 20.53 degrees 2-theta.

102. The complex according to embodiment 39, wherein X is thiocyanic acid.

103. The complex according to embodiment 102, wherein the complex is characterized by one or more peaks in its powder X-ray diffraction pattern selected from those at about 6.86, about 6.95, about 14.17, about 25.80 degrees 2-theta.

104. The complex according to embodiment 39, wherein X is p-toluenesulfonic acid.

105. The complex according to embodiment 104, wherein the complex is characterized by one or more peaks in its powder X-ray diffraction pattern selected from those at about 6.49, about 9.65, about 10.00, about 13.22, about 19.99, about 23.55, about 23.79, and about 27.56 degrees 2-theta.

106. The complex according to embodiment 104, wherein the complex is characterized by a powder X-ray diffraction pattern having peaks at about 6.49, about 9.65, about 10.00, and about 13.22 degrees 2-theta.

107. The complex according to embodiment 39, wherein X is vanillin.

108. The complex according to embodiment 107, wherein the complex is characterized by one or more peaks in its powder X-ray diffraction pattern selected from those at about 10.93, about 11.43, about 11.58, about 12.22, about 14.42, about 15.45, about 17.28, about 22.89, about 23.53, and about 23.77 degrees 2-theta.

109. The complex according to embodiment 107, wherein the complex is characterized by a powder X-ray diffraction pattern having peaks at about 10.93, about 11.43, about 11.58, about 14.42, about 15.45, and about 17.28 degrees 2-theta.

110. The complex according to embodiment 107, wherein the complex is characterized by a powder X-ray diffraction pattern having peaks at about 11.43, about 11.58, about 14.42, about 15.45, and about 17.28 degrees 2-theta.

111. A composition comprising a crystalline form according to any of embodiments 1-38.

112. The composition according to embodiment 111, wherein the composition comprises at least about 90% by weight of crystalline Compound 1.

113. The composition according to embodiment 112, wherein the composition comprises at least about 95% by weight of crystalline Compound 1.

114. The composition according to embodiment 111, wherein the composition is substantially free of amorphous Compound 1.

115. A composition comprising a complex according to any of embodiments 39-110.

116. The composition according to embodiment 115, wherein the composition comprises at least about 90% by weight of crystalline complex.

117. The composition according to embodiment 116, wherein the composition comprises at least about 95% by weight of crystalline complex.

118. The composition according to embodiment 115, wherein the composition is substantially free of one or more of amorphous Compound 1, Form A of Compound 1, or co-former X.

119. A method for inhibiting activity of MK2 kinase, or a mutant thereof, in a biological sample comprising the step of contacting said biological sample with a crystalline form according to any of embodiments 1-38 or a complex according to any of embodiments 39-110.

120. A method for inhibiting activity of MK2 kinase, or a mutant thereof, in a patient comprising the step of administering to said patient a crystalline form according to any of embodiments 1-38, a complex according to any of embodiments 39-110, or a composition according to any of embodiments 111-118.

121. The method according to embodiment 120, wherein the activity of the MK2 kinase, or a mutant thereof, is inhibited irreversibly.

122. The method according to embodiment 121, wherein the activity of the MK2 kinase, or a mutant thereof, is inhibited irreversibly by covalently modifying Cys140 of MK2.

123. A method for treating an MK2-mediated disease or disorder in a patient in need thereof, comprising the step of administering to said patient a crystalline form according to any of embodiments 1-38, a co-crystal according to any of embodiments 39-110, or a composition according to any of embodiments 111-118.

124. The method according to embodiment 123, wherein the MK2-mediated disease or disorder is an autoimmune disorder, chronic or acute inflammatory disorder, an auto-inflammatory disorder, a fibrotic disorder, a metabolic disorder, a neoplasia, or a cardiovascular or cerebrovascular disorder.

125. The method according to embodiment 124, wherein the MK2-mediated disease or disorder is an autoimmune disorder, chronic or acute inflammatory disorder, or an auto-inflammatory disorder.

126. The method according to embodiment 125, wherein the autoimmune disorder, chronic or acute inflammatory disorder, and/or auto-inflammatory disorder is selected from the group consisting of inflammatory bowel diseases, ulcerative colitis, Crohn's disease, multiple sclerosis, psoriasis, arthritis, rheumatoid arthritis, osteoarthritis, juvenile arthritis, psoriatic arthritis, reactive arthritis, ankylosing spondylitis, cryopyrin associated periodic syndromes, Muckle-Wells syndrome, familial cold auto-inflammatory syndrome, neonatal-onset multisystem inflammatory disease, TNF receptor associated periodic syndrome, acute and chronic pancreatitis, atherosclerosis, gout, ankylosing spondylitis, fibrotic disorders, hepatic fibrosis, idiopathic pulmonary fibrosis, nephropathy, sarcoidosis, scleroderma, anaphylaxis, diabetes, diabetes mellitus type 1, diabetes mellitus type 2, diabetic retinopathy, Still's disease, vasculitis, sarcoidosis, pulmonary inflammation, acute respiratory distress syndrome, wet and dry age-related macular degeneration, autoimmune hemolytic syndromes, autoimmune and inflammatory hepatitis, autoimmune neuropathy, autoimmune ovarian failure, autoimmune orchitis, autoimmune thrombocytopenia, silicone implant associated autoimmune disease, Sjogren's syndrome, familial Mediterranean fever, systemic lupus erythematosus, vasculitis syndromes, temporal, Takayasu's and giant cell arteritis, Behcet's disease, Wegener's granulomatosis, vitiligo, secondary hematologic manifestation of autoimmune diseases, anemias, drug-induced autoimmunity, Hashimoto's thyroiditis, hypophysitis, idiopathic thrombocytic pupura, metal-induced autoimmunity, myasthenia gravis, pemphigus, autoimmune deafness, Meniere's disease, Goodpasture's syndrome, Graves' disease, HW-related autoimmune syndromes, Gullain-Barre disease, Addison's disease, anti-phospholipid syndrome, asthma, atopic dermatitis, Celiac disease, Cushing's syndrome, dermatomyositis, idiopathic adrenal adrenal atrophy, idiopathic thrombocytopenia, Kawasaki syndrome, Lambert-Eaton Syndrome, pernicious anemia, pollinosis, polyarteritis nodosa, primary biliary cirrhosis, primary sclerosing cholangitis, Raynaud's, Reiter's Syndrome, relapsing polychondritis, Schmidt's syndrome, thyrotoxidosis, sepsis, septic shock, endotoxic shock, exotoxin-induced toxic shock, gram negative sepsis, toxic shock syndrome, glomerulonephritis, peritonitis, interstitial cystitis, hyperoxia-induced inflammations, chronic obstructive pulmonary disease (COPD), vasculitis, graft vs. host reaction, graft vs. host disease, allograft rejections, acute allograft rejection, chronic allograft rejection, early transplantation rejection, acute allograft rejection, reperfusion injury, pain, acute pain, chronic pain, neuropathic pain, fibromyalgia, chronic infections, meningitis, encephalitis, myocarditis, gingivitis, post surgical trauma, tissue injury, traumatic brain injury, enterocolitis, sinusitis, uveitis, ocular inflammation, optic neuritis, gastric ulcers, esophagitis, peritonitis, periodontitis, dermatomyositis, gastritis, myositis, polymyalgia, pneumonia and bronchitis.

127. The method according to embodiment 124, wherein the MK2-mediated disease or disorder is a fibrotic disorder.

128. The method according to embodiment 127, wherein the fibrotic disorder is selected from the group consisting of systemic sclerosis/scleroderma, lupus nephritis, connective tissue disease, wound healing, surgical scarring, spinal cord injury, CNS scarring, acute lung injury, pulmonary fibrosis, idiopathic pulmonary fibrosis, cystic fibrosis, chronic obstructive pulmonary disease, adult respiratory distress syndrome, acute lung injury, drug-induced lung injury, glomerulonephritis, chronic kidney disease, diabetic nephropathy, hypertension-induced nephropathy, alimentary track or gastrointestinal fibrosis, renal fibrosis, hepatic or biliary fibrosis, liver fibrosis, nonalcoholic steatohepatitis, hepatitis C, hepatocellular carcinoma, cirrhosis, primary biliary cirrhosis, cirrhosis due to fatty liver disease cirrhosis due to alcoholic fatty liver disease, cirrhosis due to nonalcoholic steatosis/non-alcoholic fatty liver disease, radiation-induced fibrosis head and neck fibrosis, gastrointestinal fibrosis, pulmonary fibrosis, primary sclerosing cholangitis, restenosis, cardiac fibrosis, endomyocardial fibrosis, atrial fibrosis, opthalmic scarring, fibrosclerosis, fibrotic cancers, fibroids, fibroma, fibroadenomas, fibrosarcomas, transplant arteriopathy, keloid, mediastinal fibrosis, myelofibrosis, retroperitoneal fibrosis, progressive massive fibrosis, and nephrogenic systemic fibrosis.

129. The method according to embodiment 124, wherein the MK2-mediated disease or disorder is a metabolic disorder.

130. The method according to embodiment 129, wherein the metabolic disorder is selected from the group consisting of obesity, steroid-resistance, glucose intolerance, and metabolic syndrome.

131. The method according to embodiment 124, wherein the MK2-mediated disease or disorder is a neoplasia.

132. The method according to embodiment 131, wherein the neoplasia is selected from the group consisting of angiogenesis disorders, multiple myeloma, leukemias, acute lymphocytic leukemia, acute and chronic myelogenous leukemia, chronic lymphocytic leukemia, acute lymphoblastic leukemia, promyelocytic leukemia, lymphomas, B-cell lymphoma, T-cell lymphoma, mantle cell lymphoma, hairy cell lymphoma, Burkitt's lymphoma, mast cell tumors, Hodgkin's disease, non-Hodgkin's disease, myelodysplastic syndrome, fibrosarcoma, rhabdomyosarcoma; astrocytoma, neuroblastoma, glioma, schwannomas, melanoma, seminoma, teratocarcinoma, osteosarcoma, xenoderma pigmentosum, keratoctanthoma, thyroid follicular cancer, Kaposi's sarcoma, melanoma, teratoma, rhabdomyosarcoma, metastatic and bone disorders, cancer of the bone, mouth/pharynx, esophagus, larynx, stomach, intestine, colon, rectum, lung, liver, pancreas, nerve, brain, head and neck, throat, ovary, uterus, prostate, testis, bladder, kidney, breast, gall bladder, cervix, thyroid, prostate, and skin, non-small cell lung cancer, small cell lung cancer, glioma, and glioblastoma multiforme.

133. The method according to embodiment 124, wherein the MK2-mediated disease or disorder is a cardiovascular or cerebrovascular disorder.

134. The method according to embodiment 133, wherein the cardiovascular or cerebrovascular disorder is selected from the group consisting of atherosclerosis, restenosis of an atherosclerotic coronary artery, acute coronary syndrome, myocardial infarction, cardiac-allograft vasculopathy, stroke, central nervous system disorders with an inflammatory or apoptotic component, Alzheimer's disease, Parkinson's disease, Huntington's disease, amyotrophic lateral sclerosis, spinal cord injury, neuronal ischemia and peripheral neuropathy.

The invention claimed is:

1. A crystalline form of Compound 1:

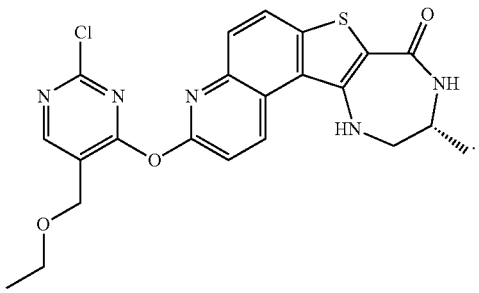 [SMILES: CCOCc1cnc(Cl)nc1Oc1ccc2c(ccc3sc4c(c32)NC[C@@H](C)NC4=O)n1]

2. The crystalline form according to claim 1, wherein Compound 1 is unsolvated.

3. The crystalline form according to claim 2, wherein the crystalline form is characterized by one or more peaks in its powder X-ray diffraction pattern selected from those at about 6.19, about 9.33, about 9.64, about 12.39, about 12.49, about 12.59, about 13.11, about 13.25, about 16.31, about 18.70, about 18.84, about 19.09, about 20.92, about 21.35, about 23.17, about 24.02, about 24.94, about 26.44, about 29.14, and about 30.04 degrees 2-theta.

4. The crystalline form according to claim 3, wherein the crystalline form is characterized by a powder X-ray diffraction pattern having peaks at about 9.33, about 9.64, and about 16.31 degrees 2-theta.

5. The crystalline form according to claim 3, wherein the crystalline form is characterized by a powder X-ray diffraction pattern having peaks at about 6.19, about 9.33, about 9.64, and about 16.31 degrees 2-theta.

6. The crystalline form according to claim 3, wherein the crystalline form is characterized by a powder X-ray diffraction pattern having peaks at about 6.19, about 9.33, about 9.64, about 16.31, and about 24.02 degrees 2-theta.

7. The crystalline form according to claim 3, wherein the crystalline form is characterized by a powder X-ray diffraction pattern having peaks at about 9.64, about 12.39, about 12.49, about 12.59, about 13.11, about 13.25, about 16.31, about 18.70, about 18.84, about 19.09, about 20.92, about 21.35, about 23.17, about 24.02, about 24.94, about 26.44, about 29.14, and about 30.04 degrees 2-theta.

8. The crystalline form according to claim 1, wherein the crystalline form is a hydrate.

9. The crystalline form according to claim 1, wherein the crystalline form is a solvate.

10. The crystalline form according to claim 9, wherein the crystalline form is characterized by one or more peaks in its powder X-ray diffraction pattern selected from those at about 6.73, about 8.44, about 13.45, about 15.27, about 17.53, about 20.54, about 23.95, and about 24.49 degrees 2-theta.

11. The crystalline form according to claim 10, wherein the crystalline form is characterized by a powder X-ray diffraction pattern having peaks at about 6.73, about 8.44, and about 23.95 degrees 2-theta.

12. The crystalline form according to claim 10, wherein the crystalline form is characterized by a powder X-ray diffraction pattern having peaks at about 6.73, about 8.44, about 17.53, and about 23.95 degrees 2-theta.

13. The crystalline form according to claim 10, wherein the crystalline form is characterized by a powder X-ray diffraction pattern having peaks at about 6.73, about 8.44, about 15.27, about 17.53, and about 23.95 degrees 2-theta.

14. The crystalline form according to claim 10, wherein the crystalline form is characterized by a powder X-ray diffraction pattern having peaks at about 6.73, about 8.44, about 13.45, about 15.27, about 17.53, about 20.54, about 23.95, and about 24.49 degrees 2-theta.

15. A complex comprising Compound 1:

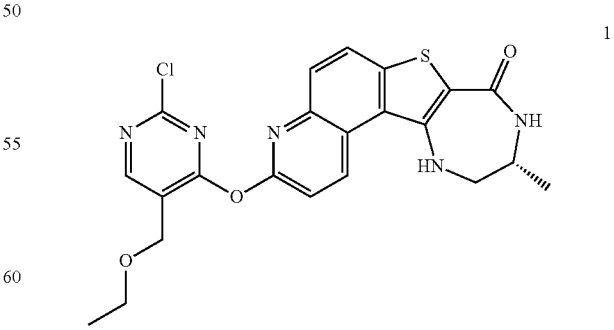

and a co-former X, wherein X is selected from the group consisting of t-aconitic acid, L-ascorbic acid, aspartic acid, benzoic acid, citric acid, gentisic acid, glutaric acid, 1-hydroxy- 2-naphthoic acid, isethionic acid, ketoglutaric acid, L-lysine, maleic acid, malonic acid, methanesulfonic acid, naphthalene-1,5-disulphonic acid, oxalic acid, phosphoric acid, saccharin, thiocyanic acid, p-toluenesulfonic acid, and vanillin.

16. A pharmaceutical composition comprising the crystalline form according to claim 1 and a pharmaceutically acceptable carrier.

17. A pharmaceutical composition comprising the complex according to claim 15 and a pharmaceutically acceptable carrier.

18. The composition according to claim 16, wherein the composition comprises at least about 90% by weight of crystalline Compound 1.

19. The composition according to claim 16, wherein the composition comprises at least about 95% by weight of crystalline Compound 1.

20. The composition according to claim 16, wherein the composition is substantially free of amorphous Compound 1.

21. The composition according to claim 17, wherein the composition comprises at least about 90% by weight of crystalline complex.

22. The composition according to claim 17, wherein the composition comprises at least about 95% by weight of crystalline complex.

23. The composition according to claim 17, wherein the composition is substantially free of one or more of amorphous Compound 1 or co-former X.

* * * * *